United States Patent
Chen (12)

(10) Patent No.: US 12,269,846 B2
(45) Date of Patent: Apr. 8, 2025

(54) CoV-2 (CoV-n) ANTIBODY NEUTRALIZING AND CTL VACCINES USING PROTEIN SCAFFOLDS AND MOLECULAR EVOLUTION

(71) Applicant: Swey-Shen Chen, San Diego, CA (US)

(72) Inventor: Swey-Shen Chen, San Diego, CA (US)

( * ) Notice: Subject to any disclaimer, the term of this patent is extended or adjusted under 35 U.S.C. 154(b) by 642 days.

(21) Appl. No.: 17/191,519

(22) Filed: Mar. 3, 2021

(65) Prior Publication Data
US 2021/0332085 A1 Oct. 28, 2021

Related U.S. Application Data

(60) Provisional application No. 62/985,792, filed on Mar. 5, 2020.

(51) Int. Cl.
| | | |
|---|---|---|
| *A61K 39/215* | (2006.01) | |
| *C07K 14/005* | (2006.01) | |
| *C07K 14/73* | (2006.01) | |
| *C12N 7/00* | (2006.01) | |
| *C12Q 1/02* | (2006.01) | |
| *A61K 39/00* | (2006.01) | |

(52) U.S. Cl.
CPC .......... *C07K 14/005* (2013.01); *A61K 39/215* (2013.01); *C07K 14/70514* (2013.01); *C12N 7/00* (2013.01); *A61K 2039/53* (2013.01); *C07K 2319/00* (2013.01); *C07K 2319/30* (2013.01); *C12N 2770/20022* (2013.01); *C12N 2770/20034* (2013.01)

(58) Field of Classification Search
CPC ......... G01N 2333/165; G01N 2469/20; G01N 33/56983; A61K 39/12; A61K 39/215
See application file for complete search history.

(56) References Cited

FOREIGN PATENT DOCUMENTS

WO    WO2022/104265    *    5/2022

* cited by examiner

*Primary Examiner* — Barry A Chestnut

(57) ABSTRACT

The embodiment of the invention is to conformationally constrain neutralizing B cell epitopes of CoV-2, CoV-n B cell epitopes of the open reading frame proteins, including the membrane S protein, constrained by protein scaffolds, including camelid VHH nanobody in order to elicit neutralizing and blocking antibodies against viral infection. B cell epitopes are molecularly evolved by ribosome display to preempt emerging viral B cell epitopes. Moreover, CTL epitopes are designed from the open reading frame protein for eliciting cell mediated viral protection. Furthermore, mRNA vaccines are prepared for eliciting protective immunity and prevent cytokine storms.

14 Claims, 13 Drawing Sheets

Specification includes a Sequence Listing.

Figure 1B:
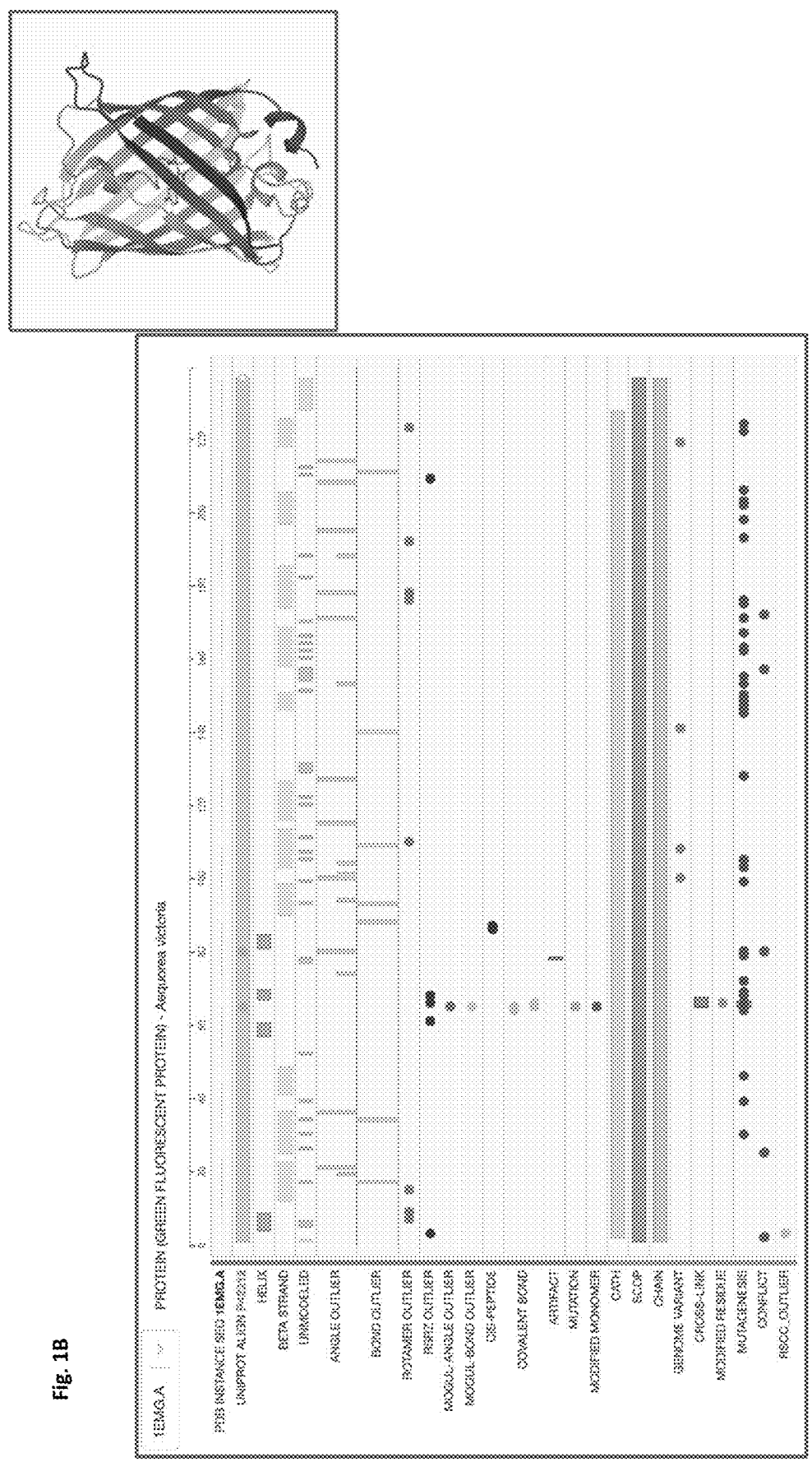

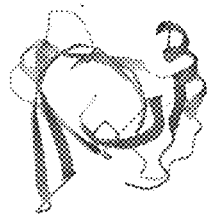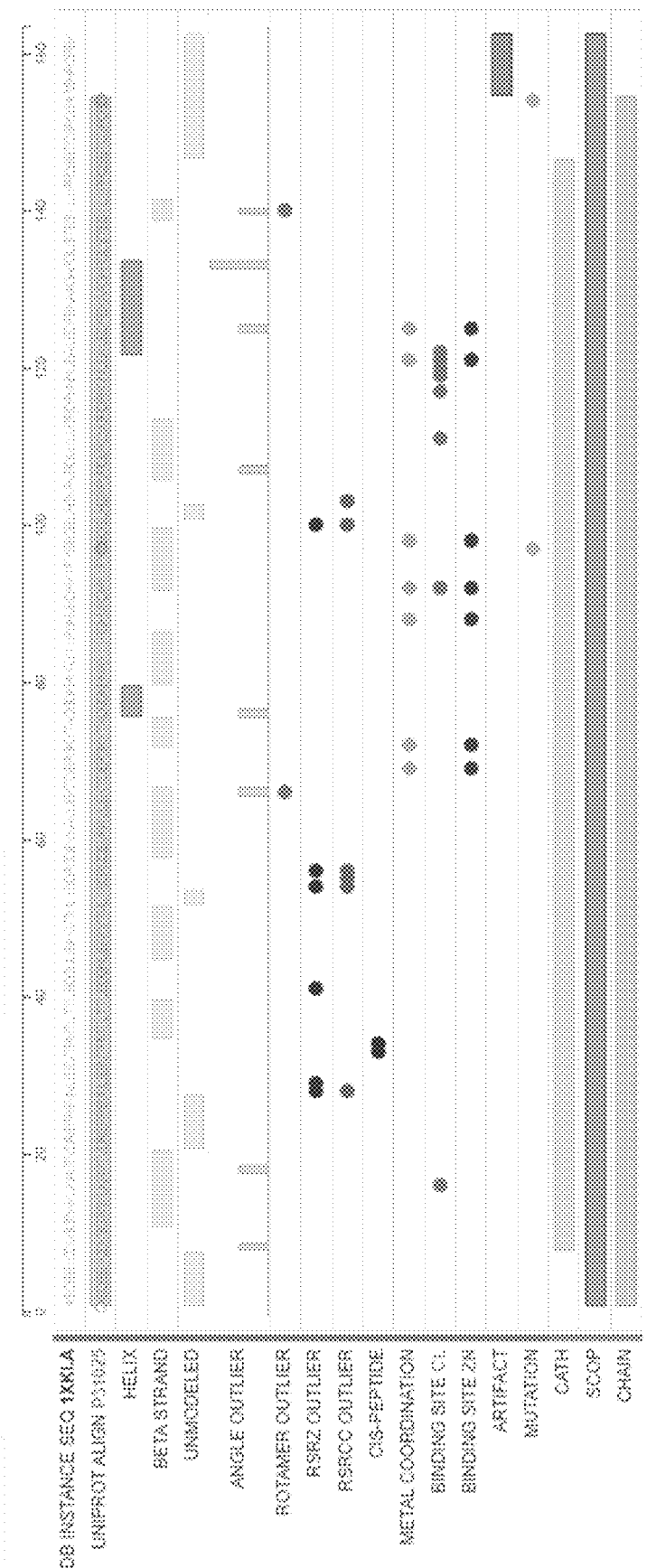
Fig. 1A

Fig. 3 a (domain diagram: NTD, RBD 333–527 (RBM 438–506), SD1, SD2, FP, HR1, HR2, TM, IC; S1 and S2 regions indicated)

b
RVQPTESIVR FPNITNLCPF GEVFNATRFA SVYAWNRKRI SNCVADYSVL
YNSASFSTFK CYGVSPTKLN DLCFTNVYAD SFVIRGDEVR QIAPGQTGKI
ADYNYKLPDD FTGCVIAWNS NNLDSKVGGN YNYLYRLFRK SNLKPFERDI
STEIYQAGST PCNGVEGFNC YFPLQSYGFQ PTNGVGYQPY RVVVLSFELL
HAPATVCGPK STNLVKNKS VNF c 2019-nCoV RBD        2019-nCoV RBD

Fig. 4

Fig. 6

Molecular Clamps of Camelid VHH for CoV-2 S Epitope

Cov 19 fragment

FRKSNLKPFERDISTEIYQAGSTPCN (SEQ ID NO: 1213)
PRRARS (SEQ ID NO: 1207)
RSNNLDSKVGGNYNYLYRL (SEQ ID NO: 1208)
RKTPPIKDFGGFNFSQIL (SEQ ID NO: 1209)

GVEGFNCYFPLQSYGFQPTNGVGYQPYRV (SEQ ID NO: 1214)
SFEIDLLFNKVTLADAGF (SEQ ID NO: 1210)
RSNNLDSKVGGNYNYLYRL (SEQ ID NO: 1208)
YQTQTNSPRRARSVASQSIIAYTNSLG (SEQ ID NO: 1215)
PSKPSKRSFIEDLLFNKVTLADAGFIK (SEQ ID NO: 1216)
RKTPPIKDFGGFNFSQIL (SEQ ID NO: 1209)
AQVKQIYKTPPIKDFGGFNFSQILPDPSKPSKRSF (SEQ ID NO: 1217)

Ncol (856)
CDR2
Camelid
CDR3
Linker
GFP
Xhol (2003)

pET45b+-Camelid-GFP
6300 bp

Fig. 7

| Constructs | CDR2 Domain of Camelid VHH | CDR3 Domain of Camelid VHH | |
|---|---|---|---|
| Camelid-Cov 1-3 | NSNNLDSKVGGNYNYLYRL (SEQ ID NO:1203) | | Asn437 to Leu455 of Cov19 RBD |
| Camelid-Cov 2-3 | | NSNNLDSKVGGNYNYLYRL (SEQ ID NO:1204) | Asn437 to Leu455 of Cov19 RBD |
| Camelid-Cov 3-2 | | YQTQTNSPRRARSVASQSII AYTMSLG (SEQ ID NO:1205) | Tyr674 to Gly699 of Cov19 S1/S2 Furin cleavage site |
| Camelid-Cov 4-2 | | PSKPSKRSFIEDLLFNKVTLA DAGFIK (SEQ ID NO:1206) | Pro808 to Lys835 of Cov19 S2' cleavage site |
| Camelid-Cov 5-3 | IYKTPPIKDFGGFNFSQIL (SEQ ID NO:1207) | | Ile787 to leu805 of Cov19 fusion site |
| Cameldi-Cov 6-1 | | IYKTPPIKDFGGFNFSQIL (SEQ ID NO:1208) | Ile787 to leu805 of Cov19 fusion site |
| Camelid-Cov-Sp1-2 | SPRRARSV (SEQ ID NO:1209) | SFIEDLLFNKVTLADAGF (SEQ ID NO:1210) | Ser679 to Val686 of S1/S2 and Ser815 to Phe822 of S2' cleavage site |
| Camelid-Cov-469 | FRKSNLKPFERDISTEIYQAGS TPCN (SEQ ID NO:1211) | GVEGFNCYEPLQSYGFQPTN GVGYQPYRV (SEQ ID NO:1212) | Phe455 to Val509 of Cov19 RBD; and Phe455 to Asn480 and Gly481 to Val509 |
| Camelid-Cov-Fu-2 | | AQVKQIYKTPPIKDFGGFNF SQILP DPSKPSKRSF (SEQ ID NO:1213) | Ala782 to Phe816 of fusion site |

Fig. 8

Lanes (left to right): Camelid-Cov-1-3, Camelid-Cov-2-3, Camelid-Cov-Fu-2, Camelid-Cov-5-3, Camelid-Cov-6-1, Camelid-Cov-3-2, Camelid-Cov19-GFP Molecular weight markers: 72, 88, 46

Fig. 9

Defined by antigenic loops between b-strands of CoV-2 or Covid-19 (β–β). Pdb: 6VXX

NTD:
HAIHVSGTNGTKRFDWP (β–β) (SEQ ID NO: 2)
TTLDSKTQS (β–β) (SEQ ID NO: 4)
SQPFLMDLEGKQGNFK (β–β) (SEQ ID NO: 6)
LALHRYLTPGDSSSGWTAGAAAAS (β–β) (SEQ ID NO: 9)
PINLVRDLPQGFSAL (β–β) universal (SEQ ID NO: 1214)

RBE (438-506)/RBD (333-527):
The underlined region is the ACE2 receptor-binding domain (RBD);
The bold region is ACE2 receptor binding epitopes (RBE):

RVQPTESIVRFPNITNLCPFG (β1–α1) (SEQ ID NO: 1215)

ATRFASVYAWN (α1–β1) (SEQ ID NO: 1216)

SNCVADYSVLYNSASSFKCYGVSPTKLNDLCFT (β1–β2) (SEQ ID NO: 1217)

GDVARQIAPGQTGKIADYNYKLPDDFTGC (β2–β3) (SEQ ID NO: 1218)

NSNNLDSKVGGNYNYLYRL 434-442 (β3–β4) (SEQ ID NO: 1220)

LFRKSNLKPFERDISTEIYQAGSTPCNGVEGFNCYFPL (β4–β5) (SEQ ID NO: 16)

YGFQPTNGVGYQPYRV 442-496 (β5–β6) ) (SEQ ID NO: 17)

ELLHAPATVCGPKKSTNLVKNKC (β6–β7) (SEQ ID NO: 1228)

*The italics is the S1/S2 junction and S2' of the S2 domain of Covid-19:*

*QTNSPRRARSVASQSIIAY/TMSLG 676-700 Furin cleavage site S1-S2* (SEQ ID NO: 1252)

*PSKPSKR/SFIEDLLFNKVTLADAGFIK 810-828: Furin plus* (SEQ ID NO: 1221)
*PSKPSKR S'2 Furin cleavage site 810-816* (SEQ ID NO: 1222)
*SFIEDLLFNKVTLADAGFIK Fusion peptide 817-836* (SEQ ID NO: 1223)

*Delineated by α–α.*
*FAQVIKQIYKTPPIKDFGGFNFSQILPDPSKPSKRSFI 782-819* (SEQ ID NO: 1253)
*IYKTPPIKDFGGFNFSQILPDPSKPSKR 789-816* (SEQ ID NO: 1254)

HIV-like
Site 1: TNGTKR 71-79 (SEQ ID NO: 1224)
Site 2: HKNNKS 145-150 (SEQ ID NO: 1225)
Site 3: RSYLTPGDSSSG 245-256 (SEQ ID NO: 1226)
Site 4: QTNSPRRA 676-684 (SEQ ID NO: 1227)

The above sequences are subject to trimming and editing from six amino acid residue to 38 amino acid residues. The sequences presented above embody the complete functional regions that can be tested at different length and in the CDR region and at the C-terminus region of a VHH nanobody or N- or C-terminus of GFP and other protein scaffolds

Fig. 10

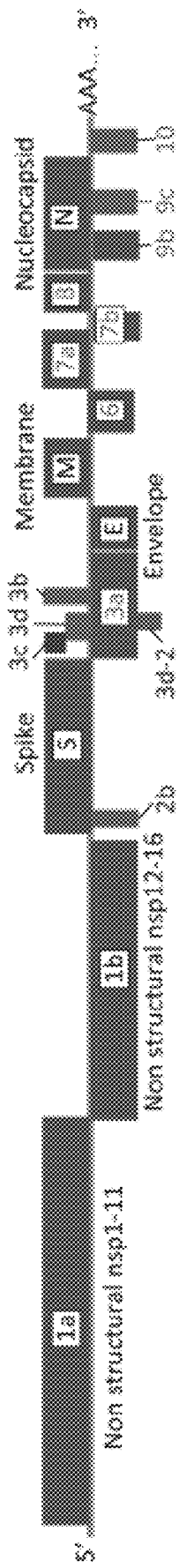

CoV-2 total genomic sequences

Severe acute respiratory syndrome (SARS) CoV-2, complete genome (NCBI Reference Sequence: NC_045512.2), diagram modified upon M. Kellis, Mat Commu #2642, including in the translation frame: ORF1a, ORF-1ab, leader protein (SEQ ID NO: 1228), nsp-2 (SEQ ID NO: 1229), nsp-3 (SEQ ID NO: 1230), nsp-4 (SEQ ID NO: 1231), 3C-like proteinase (SEQ ID NO: 1232), nsp-5 (SEQ ID NO: 1232), nsp-6 (SEQ ID NO: 1233), nsp-7 (SEQ ID NO: 1234), nsp-8 (SEQ ID NO: 1235), nsp-9 (SEQ ID NO: 1236), nsp-10 (SEQ ID NO: 1237), RNA-dependent RNA polymerase (SEQ ID NO: 1238), helicase (SEQ ID NO: 1239), 3→5' exonuclease (SEQ ID NO: 1240), endoRNAse (SEQ ID NO: 1241), 2-O' ribose methyltransferase (SEQ ID NO: 1242), Surface Glycoprotein (S) (SEQ ID NO: 1243), ORF-3a (SEQ ID NO: 1244), E (SEQ ID NO: 1245), M (SEQ ID NO: 1246), ORF-6 (SEQ ID NO: 1251), N (SEQ ID NO: 1247), ORF-7a (SEQ ID NO: 1248), ORF-7b (SEQ ID NO: 1249), ORF-8 (SEQ ID NO: 1250), nucleocapsid (NC) (SEQ ID NO: 1251).

CoV-2 (CoV-n) ANTIBODY NEUTRALIZING AND CTL VACCINES USING PROTEIN SCAFFOLDS AND MOLECULAR EVOLUTION

DOMESTIC PRIORITY

This utility U.S. patent application Ser. No. 17,191,519, filed on Mar. 3, 2021 is based on the US provisional patent, filed on Mar. 6, 2000: App No. 62,985,792 (Confirmation NO: 3480), entitled, "—Coronavirus vaccines (Covid-2, Covid-1) using the protein constrainer to elicit protective antibodies against viral attachment—and other coronaviral proteins—" of Mar. 6, 2020, Thus, the U.S. utility patent application Ser. No. 17/191,519 herein claims the domestic priority date of Mar. 6, 2020 based on prior provisional patents

CROSS-REFERENCES TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Disc Submitted

SEQUENCE LISTINGS

Submitted

BACKGROUND OF THE INVENTION

CoV-2 has become a pandemic infection since 2019. Efforts were made by the pharmaceutical industry focusing mRNA vaccines and spike protein-based vaccines against the Covid 19.

There is a scarcity in focusing on antigenic B cell epitopes and other virion components and cell-mediated immunity during the viral life cycle or emerging variants. The embodiment of the current invention expands the scope of utility of CoV-2, while including spike protein vaccines

DESCRIPTION OF THE RELATED ART

NOT APPLICABLE

BRIEF SUMMARY OF THE INVENTION

The embodiment of the invention employs focused protective B cell epitopes presented on protein scaffolds as an advantage to induce humoral neutralizing antibodies bypassing production of non-protective interfering antibodies, and focuses on the ACE2 receptor binding moieties, N-terminal domain, furin cleavage sites, and RBD while protein display expands vaccines for emerging viral strains. Another embodiment encompasses all the CoV-2 open reading frame proteins. Another embodiment encompasses CTL vaccines to eliminate viral infected foci. Another embodiment encompasses mRNA vaccines to elicit protective immune responses and reduce viral induced inflammation. The chemical engineering involves determination the protective vaccine epitopes, combinatory scaffold constructs, advanced protein display, and bifunctional mRNA utility.

BRIEF DESCRIPTION OF THE SEVERAL VIEWS OF THE DRAWING(S)

Figure 1C:
Figure 1D:
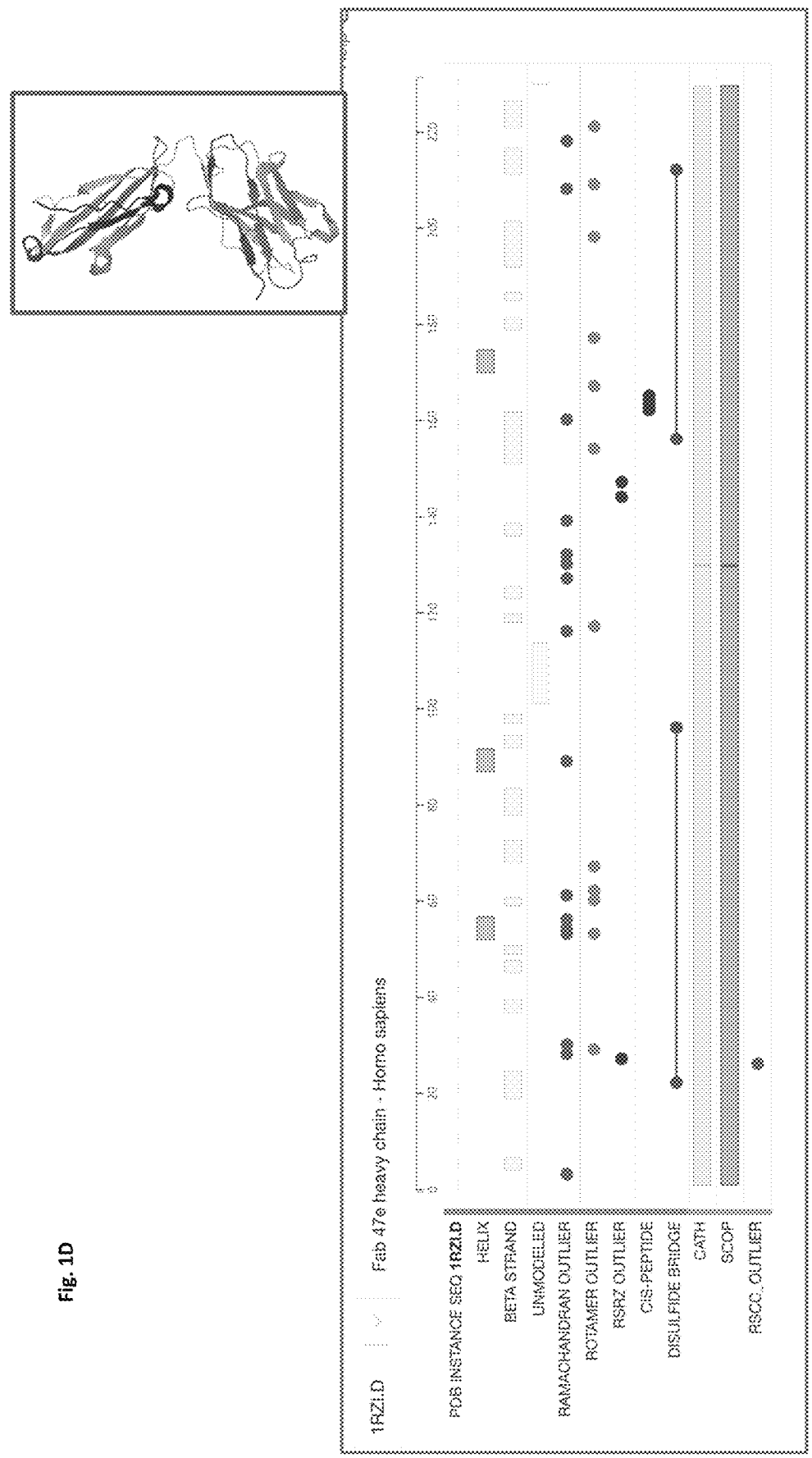

Legend to FIG. 1

The protein folding is dictated by primary sequence and the secondary structure of beta strands or beta (β)-sheet accommodating the loop structures, which assume conformations as an antigenic site, a pharmacophore, or enzymatic sites. The scaffold protein is defined as a candidate protein with such beta (β) strands that can constrain a given loop of protein, or a beta (β) sheet that can accommodate multiple loops in adjacent orientations. Beta (β) strands of FIG. 1A to 1D are colored yellow bar, and the loop sequences are left blank, while the alpha helical sequences are colored. The lipocalins is a family of proteins which transport small hydrophobic molecules such as steroids, retinoids and lipids. They share limited regions of sequence homology and a common tertiary structure architecture. This is an eight stranded antiparallel β barrel with a repeated β sheets topology enclosing an internal ligand binding site. GFP consists of a stable beta (β) barrel consisting of 8 antiparallel beta (β) strands that can accommodate the loop structure wherein. Fibronectin exhibit six beta strands in a barrel. Immunoglobulin heavy and light chain consist of six beta (β) strands in a barrel. The complementarity-determining region (CDR) are typical loop regions scaffolded by the two beta (β)-strands. The invention embodies the replacement of the native loop sequences of immunoglobulin CDRs with loop sequences of CoV-2. These scaffold proteins are embodied to exhibit and conformationally constrained antigenic B cell epitopes of CoV-2, CoV-1 and CoV-n variants, defined as a CoV-2 mutant, or a next generation of CoV-2 with distinct which can be a recombinant with zoonotic origins.

Figure 2:
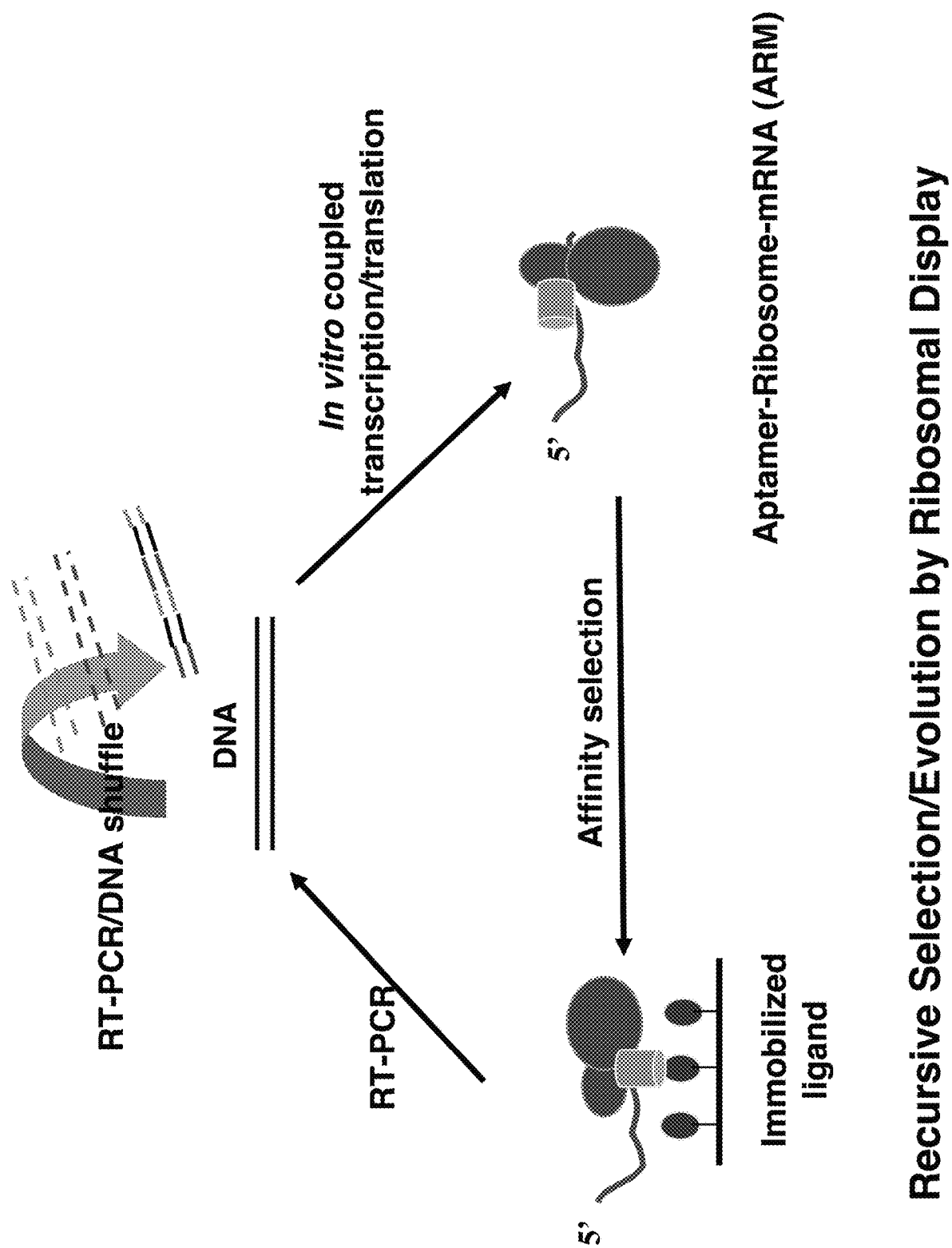

Legend to FIG. 2

Due to selective pressure of CoV-2 facing the herd immunity, mutant CoV-2 ensued according to antibody-mediated immunity against attachment site to host cell receptors such as the cognate interactions between the spike protein and ACE2 receptor. The viral mutant can be predicted a prior by selective binding pressure using ribosome display. Ribosome display (RD) is illustrated as an example for selecting optimized Covid-19 sequences, based on the pre-existing sequences. Other protein displays such as phage display, yeast display are equally applied. RD is a straightforward in vitro phenotype-genotype linked selection. FIG. 2 diagrammatically illustrates the principle of RD as a selection strategy in the laboratory. (i) A highly stable complex of Aptameric or Antibody-Ribosome-Message, i.e., ARM is first formed; (ii) it can be selected on the ligand-coated solid phase; (iii) via RT-PCR, the mRNA can be amplified and undergo molecular evolution at the same time, and improved aptameric protein phenotype is again physically linked to mRNA ready for the next re-iterative round selection. In the embodiment of the invention, RD is used on VHH nanobody platform as well as fibronectin, CTL-A4, GFP and ankyrin repeated (AR) domains as the library scaffold.

Embodiment and Biochemical enablement: The biochemical mechanisms were built into the IgV/VHH, AR, and aforementioned protein scaffolds: (i) Cκ or any protein as a stuffer region rendering this a stalling interaction with the introduction of termination codon in the C-terminus, fused to the viral sequences containing CDRs along with cognate mRNA. (ii) To enable reiteration of phenotype-library linked selection, T7 promoter and the Kozak sequence of the eukaryotic system were built into 5' terminal PCR primer. (iii) The cognate message amplified by RT-PCR and further follow through repeated rounds of selection, and the final product cloned and expressed, and protein purified.

Legend to FIG. 3

Diagram of the spike protein and ACE2 interaction. The spike protein exhibits multiple functions: attachment to ACE2 via the RBD (RBM); and the opening-up or conformational change of the spike protein to reveal the enzymatic furin sites for maturation and finally exposure of the fusion peptides, constrained by the conformationally rearranged HR regions, that permit target cell membrane fusion that facilitate viral entry. The invention embodies eliciting neutralizing antibodies that block all three aspects of the viral life cycles. Moreover, the invention embodies elicitation of CTL against peptide fragment decorated on MHCI that lyse the infected targets. Such CTL targeted peptides are derived from all parts of the spike proteins. FIG. 3c also helps to illustrate the embodiment of the invention producing highly competitive spike protein ACE2 receptor-binding variants; notice four contact regions of the spike protein to the receptors. Mutation can be introduced by error prone PCR an DNA shuffle and the high affinity winning competitors, commensurate with the successfully evolving mutants. High affinity is defined by accessibility of RBE/RBM to ACE2 as well as NTD, e.g., domain N-terminal to RBD/RBM domain permits the conformational flexibility of NTD, and consequently modulate the binding of open form (versus close form inaccessible to the ACE2). Vaccines embodied by this invention, directing the NTD mutants also play an equal important role in defense similar to mutants of RBD/RBE.

Figure 4:
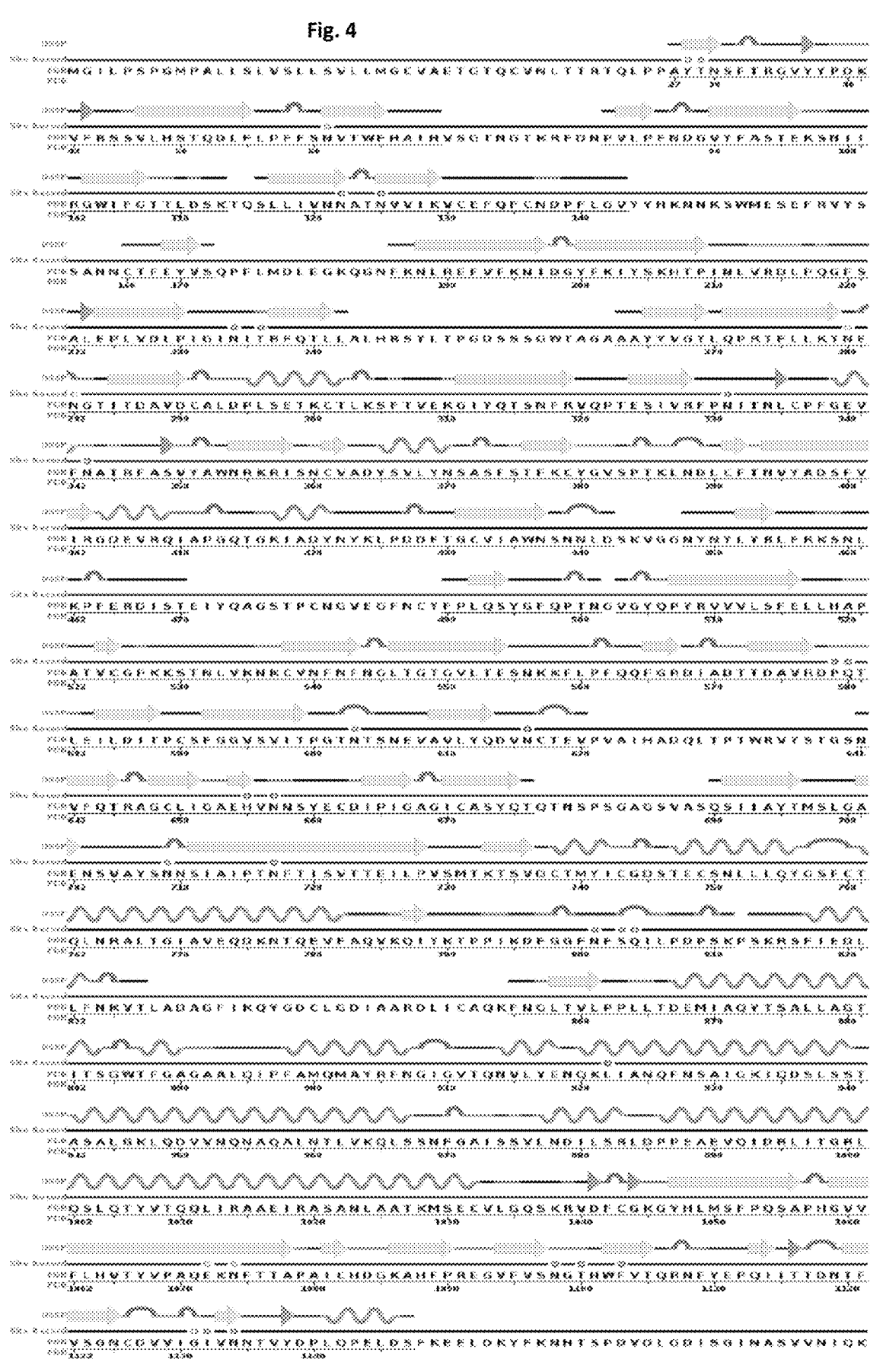

Legend to FIG. 4

Vessler's sequences reports full length of spike protein and is presented herein. As described in FIG. 1, the embodiment of the invention is rendered equivalent pertaining to conformational constraint in that the loop present in the spike protein or any other structural proteins of CoV-2 can be swapped between the beta strands of the four protein scaffolds and replacing the native loop of the scaffold protein. Therefore, the loop in between the beta-beta (β-β) strands, is employed as candidates of antigenic B cell epitopes. Moreover, the invention also embodies the constraining scaffolding principle between the beta strand and an alpha helix; and between alpha helix and alpha helix.

Figure 5:
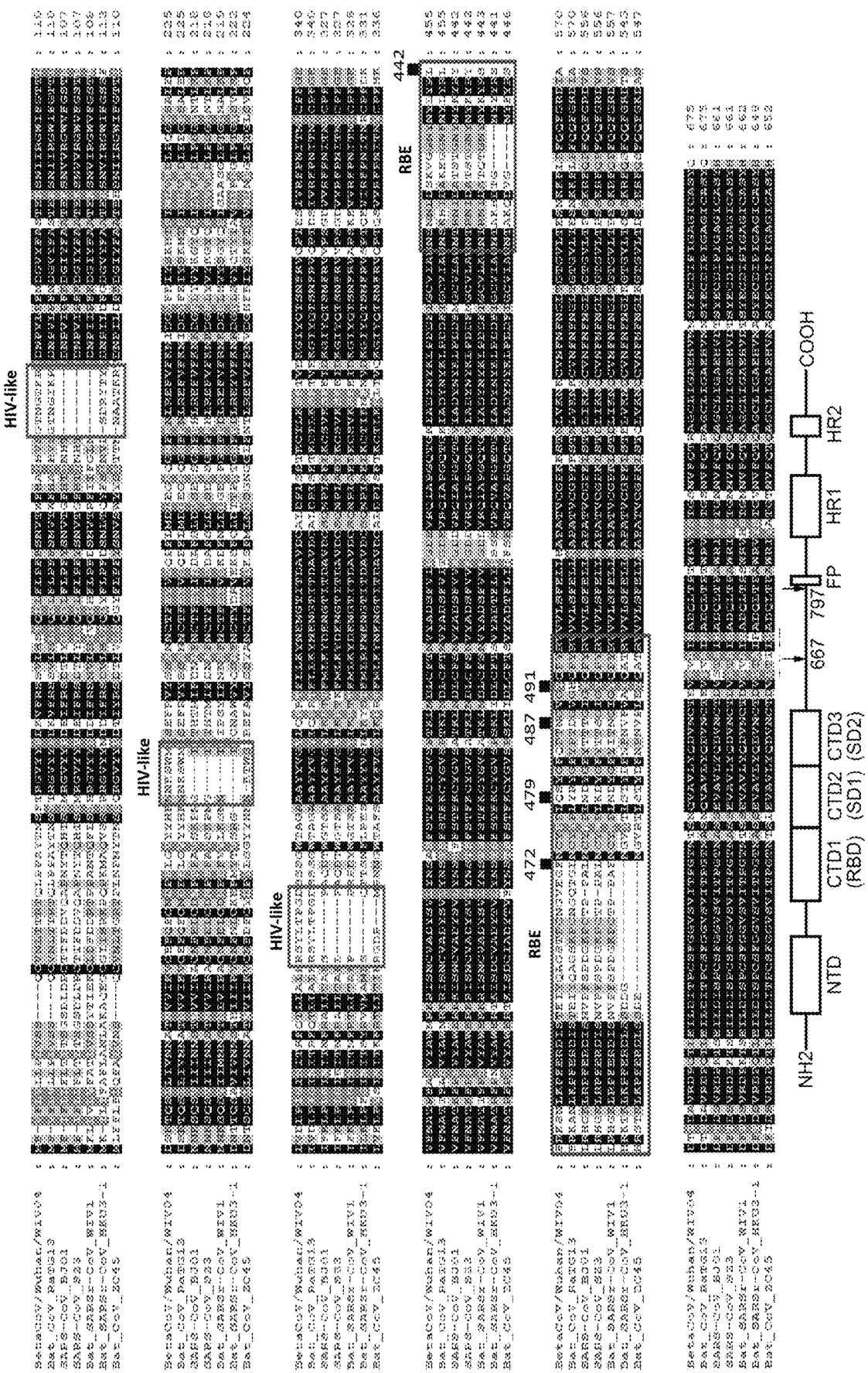

Legend to FIG. 5

Amino acid sequence alignment of the S1 protein of the 2019-nCoV with SARS-CoV and selected bat SARS-CoVs. The receptor-binding motifs of SARS-CoV and the homologous regions of other coronaviruses are indicated by the red box. The key amino acid residues involved in the interaction with human ACE2 are numbered on top of the aligned sequences. The short insertions in the N-terminal domain of the novel coronavirus are indicated by the blue boxes. Bat CoV RaTG13 was identified from *R. affinis* in Yunnan Province. Bat CoV ZC45 was identified from *R. sinicus* in Zhejiang Province.

Legend to FIG. 6

Examples of scaffolding immunoglobulin heavy chain protein scaffold for presenting Cov19 Spike protein fragment: Three firewall precision vaccines constructed in CDRs of camelid VHH in pET45b. Fragments of Cov19 were inserted into CDR2 or CDR3 domain of Camelid-VHH-GFP by using site-directed mutagenesis with primers, attaccaccaaccttagaatcaagattgttagaattgctcaccagttcac (SEQ ID: 1181), tataattacctgtatagattggcaaattatgccggc (SEQ ID NO: 1182) for VHH-Cov1-3. Attaccaccaaccttagaatcaagattgttagaattgctgcgcaataataaac (SEQ ID NO: 1183), tataattacctgtatagattgtggggccagggcacc (SEQ ID NO: 1184) for VHH-Cov2-3. Tccatcattgcctacactatgtcacttggttggggccagggcacc (SEQ ID NO: 1185), ttgactagctacactacgtgcccgccgaggagaattagtctgagtctgatatgctgcgcaataataaac (SEQ ID NO: 1186) for Camelid-Cov-3-2. Aaagtgacacttgcagatgctggcttcatcaaatggggccagggcacc (SEQ ID NO: 1187), gttgaaaagtagatcttcaataaatgacctcttgcttggttttgatggtgctgcgcaataataaac (SEQ ID NO: 1188) for Camelid-Cov-4-2. Aaaaccaccaaaatctttaattggtggtgttttgtaaatgctcaccagttcacattc (SEQ ID NO: 1189), aattttcacaaatattagcaaattatgccggc (SEQ ID NO: 1190) for Camelid-CoV-5-3. Aaaaccaccaaaatctttaattggtggtgttttgtaaattgctgcgcaataataaac (SEQ ID NO: 1191), aattttcacaaatattgggggccagggcacc (SEQ ID NO: 1192) for Camelid-Cov 6-1. Ccgccgaggagagctcaccagttcacattc (SEQ ID NO: 1193), gcacgtagtgtagatggcagtgcaaattatgcc (SEQ ID NO: 1194); and gttgaaaagtagatcttcaataaatgatgctgcgcaataataaacggc (SEQ ID NO: 1195), aaagtgacacttgcagatgctggcttctggggccagggcacccaggttacc (SEQ ID NO: 1196) for Camelid-Cov-S1-2. Ttcagttgaaatatctctctcaaaaggtttgagattagacttcctaaagctcaccagttcaca (SEQ ID NO: 1197), aatatctctctcaaaaggtttgagattagacttcctaaagctcaccagttcacattcttacc (SEQ ID NO: 1198); and ttggaaaccatatgattgtaaaggaaagtaacaattaaaaccttcaacacctgctgcgcaataataaac (SEQ ID NO: 1199), cccactaatggtgttggttaccaaccatacagagtatggggccagggcacccaggttac (SEQ ID NO: 1200) for Camelid-Cov-469. Attaaagatttttggtggtttaattttcacaaatattaccatggggccagggcacc (SEQ ID NO: 1201), aaaatctttaattggtggtgttttgtaaatttgtttgacttgtgctgctgcgcaataataaac (SEQ ID NO: 1202) for Camelid-Cov-Fu-2.

Legend to FIG. 7

The Figure consists of replacing the above RBD regions into the camelid VHH immunoglobulin CDR1, 2, 3. VHH is fused to GFP for protein ribosome display and immunogenicity.

Legend to FIG. 8

Different Vaccine construct data. Although GFP as a fusion protein to the viral vaccine B cell epitope in VHH. The helper CD4 sequences can be any immunogenic carrier protein such as OVA, BSA, KLH, BGG or promiscuous helper T cell determinants PADRE and also promiscuous helper protein of infectious origins of measles viral protein, diphtheria toxin, and tetanus toxin for enhancing antibody responses to Covid-19 spike protein, and other proteins. For example, NSNNLDSKVGGNYNYLYRL (SEQ ID NO:1220), conformationally constrained to the native conformation of the RBD regions, embracing a large contact area of the ACE2 receptor in the spike protein. Since CoV-2 is lethal to patients elicited with CD4 helper T cell epitopes induced cytokine storm, the embodiment of the invention utilizes minimal IgE B cell epitope, which even if can be processed to a CD4 helper epitope, result in minimal CD4 T cell activation.

Legend to FIG. 9

As discussed in the Vessler's sequences, a Table consists of B cell epitopes of a complete spike protein is made wherein; moreover, this Table consists of B cell epitopes from the RBD region of the Vessler's sequences distributed into the CDR1, 2, 3 of VHH and immunoglobulin, and beta sheets scaffolding and N-, C-terminus of the protein scaffolds.

FIG. 10. CoV-2 Total Genomic Sequences

Severe acute respiratory syndrome (SARS) CoV-2, complete genome (NCBI Reference Sequence: NC_045512.2), including in the translation frame: ORF1a, ORF-1ab, leader protein (SEQ ID NO: 1228), nsp-2 (SEQ ID NO: 1229), nsp-3 (SEQ ID NO: 1230), nsp-4 (SEQ ID NO: 1231), 3C-like proteinase (SEQ ID NO: 1232), nsp-5 (SEQ ID NO: 1232), nsp-6 (SEQ ID NO: 1233), nsp-7 (SEQ ID NO: 1234), nsp-8 (SEQ ID NO: 1235), nsp-9 (SEQ ID NO: 1236), nsp-10 (SEQ ID NO: 1237), RNA-dependent RNA polymerase (SEQ ID NO: 1238), helicase (SEQ ID NO: 1239), 3→5' exonuclease (SEQ ID NO: 1240), endoRNAse (SEQ ID NO: 1241), 2-O' ribose methyltransferase (SEQ ID NO: 1242), Surface Glycoprotein (S) (SEQ ID NO: 1243), ORF-3a (SEQ ID NO: 1244), E (SEQ ID NO: 1245), M (SEQ ID NO: 1246), ORF-6 (SEQ ID NO: 1247), N (SEQ ID NO: 1251), ORF-7a (SEQ ID NO: 1248), ORF-7b (SEQ ID NO: 1249), ORF-8 (SEQ ID NO: 1250), nucleocapsid (NC) (SEQ ID NO: 1251).

DETAILED DESCRIPTION OF THE INVENTION

Structure

SARS-CoV-2 or Covid-19 is classified within the subgenus Sarbecovirus of the genus Betacoronavirus of a genome size of ~29,000 ribonucleotides (+ssRNA), comprising six open reading frames with 5'-cap and 3'-poly-A. The first ORF (ORF 1 a/b) about two-thirds of the whole genome, encodes 16 non-structural proteins (NSP 1-16) (Gralinski, L. E., 2020. *Viruses* 12, 135; Forni, D., 2017. *Trends Microbiol* 25, 35-48). ORF near the 3' end encode the four main structure proteins including spike(S) and membrane (M), envelope (E) and nucleocapsid (N) protein (+9 differentially spliced proteins), as well as nonstructural protease, RNA-dependent RNA polymerase complex (RdRp, 5 proteins), as the most complex antigenic (B and T cell epitopes, 34 proteins) viral universe know to date risking cytokine storm. The complete genome is shown in FIG. 10, and all these genes are vaccine candidates for neutralizing antibody vaccines and cytotoxic T lymphocytes (CTL) vaccines.

CoV-2 Total Genomic Sequences:

Severe acute respiratory syndrome (SARS) CoV-2, complete genome (NCBI Reference Sequence: NO_045512.2), including in the translation frame: ORF1a, ORF-1ab, leader protein (SEQ ID: 1228), nsp-2 (SEQ ID: 1229), nsp-3 (SEQ ID: 1230), nsp-4 (SEQ ID: 1231), 3C-like proteinase (SEQ ID: 1232), nsp-5 (SEQ ID: 1232), nsp-6 (SEQ ID: 1233), nsp-7 (SEQ ID: 1234), nsp-8 (SEQ ID: 1235), nsp-9 (SEQ ID: 1236), nsp-10 (SEQ ID: 1237), RNA-dependent RNA polymerase (SEQ ID: 1238), helicase (SEQ ID: 1239), 3→5' exonuclease (SEQ ID: 1240), endoRNAse (SEQ ID: 1241), 2-O' ribose methyltransferase (SEQ ID: 1242), Surface Glycoprotein (S) (SEQ ID: 1243), ORF-3a (SEQ ID: 1244), E (SEQ ID: 1245), M (SEQ ID: 1246), ORF-6 (SEQ ID: 1247), N (SEQ ID: 1251), ORF-7a (SEQ ID: 1248), ORF-7b (SEQ ID: 1249), ORF-8 (SEQ ID: 1250), nucleocapsid (NC) (SEQ ID: 1251).

Origin and Phylogeny 3,713 complete genomic sequences have been deposited (up to Apr. 10, 2020; in NSAID: Zhang at Fudan deposited the first the full-length sequence (Jan. 10, 2020 in GenBank). SARS CoV-2 maintains a relatively distant ~80% nucleotide identity to the original SARS epidemic viruses. Shi showed that SARS-CoV-2 had 96.2% overall genome sequence (nt) identity to bat RaTG13 (Wu, F., 2020. *Nature* 579, 265-269), a betacoronavirus, collected from horse-shoe bat, *Rhinolophus affinis* upon a cave expedition by Shi at the Yunnan province, China (Zhou, P., 2020. *Nature* 579, 270-273). The S protein accounts for the host range. The subregion S1 contains the receptor-binding domain (RBD) for huACE2. Notably, Guan reported that receptor-binding domain (RBD) of pangolin-CoV of the Guandong Province, China, exhibits 97.4% amino acid identity to that of human SARS CoV-2 (although ~92.4% in nt identity to CoV-2) (Lam, T. T.-Y., 2020. *Nature* 583, 282-285), including identity of all five key amino acid contact residues to ACE2 as later shown the identical five amino acids in CoV-2 RBD all contact importantly to huACE2 cocrystal (Yan, R., 2020. *Science* 367, 1444).

The structural and genetic observations indicate that a niche ecology of genetic exchange among natural reservoirs of bats, and pangolins (or masked palm civets) in the Wuhan's exotic animal food market, substantiating zoonotic to human transmission. This transmission is also supported by two early clinical observations in that (i) the high proportion of earlier patents admitted in Wuhan hospitals (before Jan. 1, 2020) with history of market visits, tapered to human-to-human transmission exclusively afterwards (Li, Q., 2020. NEJM 382, 1199-1207); and in that (ii) 14 of the 41 patients (34%) has no contact with this marketplace (Huang, C., 2020. Lancet 395, 497-506). Thus, the clinical pattern suggests an alternative behavior contact with the intermediate hosts (pet companionship; lab environment and the patient zero) raising the possibility relating to accidental source of contamination with RaTG13 stock in the Wuhan's P4 laboratory. Therefore, modifying cultural behavior in the country indigenous with the intermediate hosts is central to future emergence and infectious disease control.

Epidemiology plays a central role to trace the origins and the modalities of the pandemic spread of the Covid-19 infectious disease. Epidemiological prevalence seroconversion data of Santa Clara County indicate up to 5.7% (2.58-5.7%), 85-fold more cases than current voluntary testing based on clinical urgency. Therefore, an effective vaccine, is in a dire need to break the transmission chain.

Recognition of the ACE2 receptor by the spike(S) membrane glycoprotein of SARS-CoV-2 is a major ligand for virus binding to host cells (Wrapp, D., 2020. *Science* 367, 1260), infectivity, initiation of cytokine storm pathogenesis, and its mutations and adaptation to the various host range. S is a trimeric assembled protein, consisting of a central helical stalk, made of three interacting S2 portion, diverging at the surface using the S1 portion. Each S1 component consists of two large domains, the N-terminal domain (NTD) and receptor-binding domain (RBD), which contains highly immunogenic B cell epitopes. In virus membranes, Spike protein can exist in open and close form, regulating by the NTD, and the open form is accessible to ACE2 binding from cryoEM studies on the S of SARS-CoV.

Of the two RBDs per trimer that are not engaged with the receptor, either both are closed or one of the RBDs remains closed and one is in the open conformation. Trimers can bind two to three ACE2 receptors bound. ACE2 binding affects the bound RBD by a torqued forced, rigid-body rotation ~5.5 Å away from the trimeric center, along with affected the NTD shift as well, and the rest two NTDs of all three S1 components move by ~1.5-3.0 Å. Binding of more than one ACE2 remains the same altered configuration. Thus, the monomers are separated, make less contact with each other in the receptor-bound state. The stoichiometry is two RBD binding to three ACE receptors and leaving one RBD idling in the close conformation. Thus, one embodiment of the invention is to render vaccine induced-antibodies that lock the RBD open or close in a fixed state that do not permit the RBD binding to receptors, or do not permit rigid body torque force transmission and separation from the neighboring monomer for re-anchoring at the S2 moiety. ACE2-stabilised S1 opening therefore leads to opening up of S2 structure, exposing the S1' and S1-S2 furin or proteolytic enzyme site, and the unleashing further conformation opening up of the fusion peptide for host cell fusion. Therefore, the embodiment of the invention is to have vaccine-elicited antibodies, anticipating the appearance of the aforementioned three sequences and arrest the viral infectivity due to torque force/rigid body induced conformational change.

Moreover, the torque also affects helix-loop-helix approximately, 980-990 within the HR1 region in CoV-1 studies: at the end of the S2 domain in that the torque creates 50×65 Å$^2$ open cavity around the trimer axis that is for solvent exposed HR1, serving as additional target site for the vaccine-elicited antibodies in one embodiment of this invention. Noticeably, the embodiment of the invention focuses on the early and late stage of RBD phenomenology, namely, first neutralizing the open conformation of the monomer to prevent the ACE2 binding as a prerequisite; and second, focusing on maturation producing B cell epitopes, ignoring the cleaved or left over RBD-ACE since these are vestiges or left-over on the cell membrane without any protective significance. The left-over, or hanging the S trimers permit this RBD in a more open ACE2-binding conformation of no more infectious disease significance, or passively, these vestiges can absorb neutralizing antibodies as a sink. In the process, the interaction of the closed form of S1 with a segment of the S2 chain that precedes the putative fusion peptide region is lost in the open form. Thus, the embodiment of the invention is to provide strong T cell help such as that from the herd immunity memory response to diphtheria or tetanus or viral measles CD4 helper T cells or Covid-19 viral CD4 helper T cells by using Covid-19 B cell epitopes integrated to a library of helper peptides. Successive trimeric RBD opening and ACE2 binding leads to a fully open and ACE2-bound form where the trimeric S1 ring remains bound to the core S2 trimer by limited contacts through the intermediate subdomains of S1. This structural and physiological arrangement leaves the top of the S2 helices fully exposed.

In recognition of the thermodynamic rule of folding as categorically governed by the primary amino acid sequence, the removal of the RBD due to cleavage, lead to the reconfiguration of the rest of the S2 polypeptide according to the remaining sequences, which are free from the torque force due to the RBD binding to the ACE2 receptors. The rest of the sequences can be under the constraint of the non-binding two free RBD or with one free and one bound RBD, which is yet to be cleaved and released. In the embodiment of the invention of using a series of protein scaffold such as beta-strands of lipocalin, fibronectin, ankyrin repeat, CDR regions of human VH3 and camelid VHH, equivalent to the "beta strand-loop-beta strand" motif of conventional immunoglobulins or CDR regions of an antibody light chain or heavy chain scaffolding, and N-, C-terminals of thermostable GFP for the primary furin site and fusion site sequences in the reformation of the natural folding of furin or fusion peptides similar to the devoid of RBD (de-RBDed) S2 using said protein scaffolds.

Another embodiment of the invention is to use the "alpha helix-loop-alpha helix" motif of ankyrin repeat (AR) motif as yet another protein scaffold for alpha helices B cell epitopes, and beta-hairpin loop or a large or long B cell loop epitope. The AR is a modular, protein-protein interaction motif in nature, by compiling a given AR protein containing multiple repeats, being monomeric, of high thermostability. The ankyrin scaffold is organized in a unit of five, consisting of 5' and 3' capped and central three ankyrin will be synthesized, and the library will be replaced with amino acids in random in the three alpha helical regions and at three the beta turns, The consensus amino acid sequence contains all information required to define the ankyrin repeat fold for engineering B cell epitopes of Covid-19, Covid-n. One main embodiment is the 33-residue sequence motif into a helix-loop-helix structure with a beta hairpin/loop region projecting outward from the helices at a 90° angle. The repeats stack together to form a concave L-shaped structure with the inserted B cell epitope accessible as a concave recognizable structure by antibodies as receptor or pharmacological receptor. Moreover, the beta-hairpin loop or a longer 7.1 loop can also contain a B cell epitope or a pharmacophore. Thus, the AR scaffold is a bifunctional representation of B cell epitopic conformations of secondary a helical structures and loop structure. Another versatility of the AR is for scaffolding coiled coils distorting away from the alpha helix or 3-10 helix.

Additionally, the ankyrin scaffold is also adapted into the eukaryotic ribosome display system, and the prokaryotic transcription/translation sequences, replaced with the eukaryotic enabling sequences. This system will be compared among protein scaffolds by the ribosome display (RD). We will test whether anti-ANK antibodies are elicited by random aptamers on ANK vs VHH scaffolded constructs, and antibodies to human VHIII family of immunoglobulin. Humanization of non-human immunoglobulins if employed such as VHH, will be conducted to eliminate immunogenicity. It is prudent to establish an efficacious RD technology platform, which is also safe for discovery of IgE drug or others.

Herein we further illustrate the principle of the loop scaffolding by two adjacent alpha-helices. The beta hairpin/loop region and the short alpha helices comprising the concave face have been previously characterized as the recognition surface. Positions classified as non-conserved and semiconserved of different type are mainly present on the recognition surface, whereas the opposite face shows mostly semiconserved positions of the same type. The embodiment of the invention is to replace the loop and short alpha helices with the B cell epitopes, or insert B cell epitopes into the loop or extend the short alpha helices as protruding concave B cell epitope so that AR then exhibits the highest variability to accommodate a diverse group of potential B cell epitopes or pharmacophore. Because the resilience of AR backbone and the foreign AR equivalent (from 20 to 40) will be replacing the constituent repeat for B cell epitopic or pharmacophore display. Thus, the consensus sequence carries the necessary structural integrity in the presence of a foreign alpha-helix, which can be subject to molecular evolution and protein display for more effective B cell epitopes and pharmacophore as a blueprint for reshaping CoV-2 and CoV-n protein engineering or to create novel biological functions.

Embodying B Cell Epitopic Vaccines of CoV-2, CoV-N

1. Foundation Paradigm

The precision vaccine to target viral host range and infectivity is based on the foundation work of Harrison/

Farzan/Li who established huACE2 as the receptor; and later elucidated RBD/ACE2 cocrystal for SARS CoV-1, and offered the molecular biology pathways leading to a clinical infection (Li, W., 2003. *Nature* 426, 450-454). Similarly, this strategy is rapidly established for SARS Cov-2 infection in human ACE2+ cells (Wrapp, D., 2020. *Science* 367, 1260). Coronavirus S glycoprotein exists as a metastable prefusion homotrimer, comprising two functional subunits, S1 and S2. S protein exhibits the most diversity among coronaviruses, accounting for its wide host range (Li, F., 2013. *Antiviral Res* 100, 246-254). Thus, its threefold infection strategy unfolds, culminating in a productive infection:

(i) S1 Binding to ACE2 receptor: RBD or its core RBM or RBE (Receptor Binding B cell Epitope, 438-506 aa) (SEQ ID NO: 11 to SEQ ID NO: 17, SEQ ID NO: 1215, SEQ ID NO: 1215 to SEQ ID NO: 1219) in S1/2 (SEQ ID NO: 52, SEQ ID NO: 53, SEQ ID NO:1252, SEQ ID NO: 1221 to SEQ ID NO: 1223) exhibits extensive contact with ACE2 receptor oriented, by the N-terminus domain, NTD (aa 1-332 aa) (SEQ ID NO: 2 to SEQ ID NO: 10, SEQ ID NO: 1214) (Wrapp, D., 2020. *Science* 367, 1260).

(ii) S2 cleavage SEQ ID NO: 1252 and global conformational change: Receptor binding triggers proteolytic processing by the host surface enzymes, promoting a global (tectonic) conformational change to permit exposure of proteolytic furin sites (Wrapp, D., 2020. *Science* 367, 1260);

(iii) Fusion: the remaining trimeric S2 subunit (SEQ ID NO: 1221 to SEQ ID NO: 1223) arranging around a central triple-helical bundle to juxtapose the fusion peptide (trimeric) to the host membrane lipid bilayer, culminating in the delivery of the viral genome into the host cells (Wrapp, D., 2020. *Science* 367, 1260). Notably, the three-fold sophisticate strategy adopted by SARS CoV-2 reveals its natural prowess as well as its triple Achilles' heels subject to protective immune attack. Herein we will make three firewall vaccines in the proposed NIH-NOSI application. (i) Firewall $1^{st}$ The first neutralizing antibody firewall blocks, competes or dissociates viral S trimer to the ACE2 receptor; (ii) Firewall $2^{nd}$ the second neutralizing antibody firewall blocks furin cleavage sites to prevent S trimer maturation; (iii) Firewall $3^{rd}$ the third neutralizing antibody firewall blocks and dissociates fusion peptide docking onto the lipid bilayer or micelles. Next, we will describe the technology platforms to build the protective shell via the three aforementioned firewall vaccines.

2. Vaccine Platform: The Technology Platform to Construct the Three Successive Layers of Firewall Vaccines The protein folding is dictated by primary sequence and the secondary structure of beta strands or beta-sheet, and the most thermostable beta barrel thereof, accommodating the loop structures, which assume conformations as an antigenic site, a pharmacophore, or enzymatic sites. The scaffold protein is defined as a candidate protein with such beta strands that can constrain a given loop of protein, or a beta sheet that can accommodate multiple loops in adjacent orientations. Beta strands of protein scaffold are colored yellow bar, and the loop sequences are left blank, while the alpha helical sequences are colored. The lipocalins are a family of proteins which transport small hydrophobic molecules. They share limited regions of sequence homology and a common tertiary structure architecture. This is an eight stranded antiparallel highly thermostable beta barrel. GFP (SEQ ID NO: 1257, SEQ ID NO: 1262) consists of a stable beta barrel consisting of 8 anti-parallel beta strands that can accommodate the loop structure wherein. Fibronectin exhibits six beta strands in a barrel. Immunoglobulin heavy and light chain consist of six beta strands in a barrel. The complementarity-determining region (CDR) are typical loop region scaffolded by the two beta-strands of camelid VHH and human VH3. The invention embodies the replacement of the native loop sequences of immunoglobulin CDRs with loop sequences of CoV-2. These scaffold proteins are embodied to exhibit and conformationally constrained antigenic B cell epitopes of CoV-2, CoV-1 and CoV-n variants, defined as a CoV-2 mutant, or a next generation of CoV-2 with distinct which can be a recombinant with zoonotic origins, as warranted by general consumption of exotic food in China, e.g., civets, bats, pangolins.

Protein scaffolds, and Immunoglobulin heavy or light chain in humans or rodents as a constraining molecular clamp (chaperone), or a single heavy chain VHH antibody that is highly soluble due to the deletion of two hydrophobic residues in the hinge region mediating light chain pairing (Ewert, S., 2002. *Biochem* 41, 3628-3636). Human heavy chains, VH3 (SEQ ID NO: 1259, SEQ ID NO: 1264) and camelid heavy chains in particular CDR2 and CDR3 can accommodate longer, between 12 to 33 or more amino acids: the fact hypervariable regions can accommodate diverse amino acid sequences at will, are two-fold important in the embodiment of the invention (i) stably scaffolded within evolutionarily conserved thermostable framework regions as a highly thermostable β-barrel, acting as molecular scaffolds or chaperones; thus likewise (ii) the sequence space within the CDR1-CDR3 antibody binding loops can be replaced by antigenic B cell epitopes, or by conformation-delineated sequences acting as receptor agonists/antagonists, depending on the context of application.

The molecularly clamped, substituted CDR2 and/or CDR3 heavy or light chain, as antigenized constructs, can stabilize native configurations of the replaced foreign antigenic loop sequence to its native conformation on the parent protein. In this invention, the above three-firewall protective B cell epitopes will be clamped and constrained in the CDRs of heavy or light chain proven technology platform.

Furthermore, the embodiment of the invention expands the diversity of the constrained enclosed CoV-2 loop sequences via mutations and molecular evolution. the molecular clamped antigenized vaccine B cell epitopes constrained by the secondary structures, beta-strands and alpha-helices can in turn be displayed along with its mRNA on ribosomes, e.g., forming an Antigen/Ribosome/mRNA (ARM) ternary complexes, captured by huACE2 receptor-coated solid phase. Therefore phenotype-genotype linked selection can be subjected to molecular Darwinian evolution. And antigens can therefore be readily re-shaped for better fit antigens for eliciting neutralizing antibodies. The embodiment of the three firewall vaccines (including the Cov-2 S (SEQ ID NO: 1243), NC/C (SEQ ID NO: 1251), M (SEQ ID NO: 1246), E (SEQ ID NO: 1245) compositions; and ORF-translated products (SEQ ID NO: 1228 to SEQ ID NO: 1251), and all the truncated engineered proteins indicated by FIG. 9-10 including SEQ ID NO: 1228 to SEQ ID NO: 1251 on the aforementioned said protein scaffolds, responding to the Covid-19 epidemic/pandemic challenge, and emerging mutants and continually evolving CoV-19, Covid-20, 21 or CoV-n. The embodiment of the invention covers all the mutant strain sequences, generated in the molecular evolution, Darwinian selection platform of the said protein display in the invention. The efficacies of the three firewall neutralizing antibodies to block or abrogate infection of huACE2+BHK-21 or HEK293 by CoV-2 S pseudotype virus as well as protection of pseudotype infection in huACE2 Tg mice.

Safety Margin: Need for a Precision SARS CoV-2, CoV-n Vaccine to Avoid the Lethal Cytokine Storm An important advantage of the precision vaccine is its avoidance of an inappropriate immune enhancement or viral antigen-induced cytokine storm. The two most immunogenic components conducted in SARS CoV-1 research, are attributed to S protein, and next to nucleocapsid (NC) protein, followed by M, E, and replicase and NSPs processed from the replicase/transcriptase complex. Acute respiratory distress syndrome (ARDS) in both CoV-1 and CoV-2 infected patients is the cause of death due to viral antigen specific CD4 and CD8-mediated cytokine storm (Mehta, P., 2020. *Lancet* 395, 1033-1034). Inactivated or attenuated CoV-2 carries the antigenic universe for CD4 and CD8 T-cell epitopes; the complete S protein as vaccines carries the immunodominant CD4 helper T cell epitopes (Grifoni, A., 2020. *Cell Host Microbe* 27, 671-680.e672). Herein the three firewall CoV-2 precision vaccines made solely from critical and minimal protective B cell epitopes, can hit the three Achilles' heels for attachment, maturation and fusion of S protein life cycle without causing immune enhancement and cytokine storm detrimental to the host, henceforth increases vaccine safety margin (Chen, S.-S., 2020. USPTO 62/985,792; Chen, S.-S., 2020. USPTO Priority date: Feb. 11, 2020, 62/972,847).

CoV-n Vaccines: Selecting the Emerging CoV-2 and CoV-n Variants or Mutants:

Two concerns of viral adaption are in the continuum:
  (i) Emerging zoonosis: The five highly variable amino acid residues in RBE contacting ACE2, spanning among palm civets, bats, pangolins, and humans, exhibit a positive dN/dS trend for positive selection (Gralinski, L. E., 2020. *Viruses* 12, 13). Zoonotic migration of the fittest to humans poses a continual threat without human behavior modification.
  (ii) Emerging new CoV-n or 'seasonal flu' evading herd immunity. The next waves of viral mutants are likely to re-emerge facing a sterile anti-RBD herd immunity for example as the most current FDA-approved vaccines are directed against a single protein or DNA sequence of a single viral strain to the SARS CoV-2 genomes of the year 2019 database. Cov-2 spike protein mutants such as B.1.526, E484K, S477N, within the region of RBD can be predicted by in vitro RD. Via ribosome display, we can the select molecular Darwinian antigenic variants of the entire S protein that bind ACE2 receptors under the three-firewall neutralizing antibody we made for the first generation of CoV-2 or herd immunity (Chen, S.-S., 2014. U.S. Pat. No. 8,865,179; Chen, S.-S., 2015. U.S. Pat. No. 9,187,553; Taussig, M., 2003. U.S. Pat. No. 6,620,587 B1).

In summary, the precision vaccines using said protein scaffolds raise three firewall neutralizing antibodies to abrogate productive CoV-2 pseudotype infection in human ACE2 cells and ACE2+Tg mice. The platform technology integrated with molecular evolution permits selection of S variants of emerging newer CoV-2, which can be used as future vaccines.

Embodying CTL Vaccine

Any conception of cytotoxic T lymphocytes (CTL) to protect from a viral infected disease is based the observation of CTL in recognizing a processed viral protein constituent, restricted to major histocompatibility complex (MHC) I in killing virus infected cells. This original observation sheds the first light on the importance of processed protein constituents and its presentation by MHC I. The two critical pieces information is that nonameric cytotoxic peptides is generated in the ER via an unfold protein response or ER stress. The second piece information stems from the purification and sequencing of the nonameric peptides eluted platform the MHC I protein (Falk et al., 1991. Nature. 351, 290-6). In summary, this includes the totality of the prior knowledge across different species that CTL recognize viral protein nonameric to decameric peptides according to the MHC I polymorphisms.

The embodiment of the invention is to compute nonameric peptide CoV-2 human 10 MHC I supertypes. The MHC I supertypes are: HLA-A01.01; HLA-A02.01; HLA-A03.01 (HLA-A11.01); HLA-A24.02; HLA-A26.01; HLA-B07.02; HLA-B08.01; HLA-B40.01; HLA-B58.01; HLA-B15.01 (Sidney, 2008. BMC Immunology. 9:1-15) Any high affinity supertype binding peptides from such as the spike protein or nucleocapsid protein and ORF1a of Cov-2 should yield the protective CTL vaccine epitopes that are used as CTL vaccines, and exclusively non-mutated and mutated sequences to severe acute respiratory syndrome (SARS) as listed in TABLE 1 to TABLE 11 according to the CoV-2 translation frame: ORF1a, ORF-1ab, leader protein (SEQ ID: 1228), nsp-2 (SEQ ID: 1229), nsp-3 (SEQ ID: 1230), nsp-4 (SEQ ID: 1231), 3C-like proteinase (SEQ ID: 1232), nsp-5 (SEQ ID: 1232), nsp-6 (SEQ ID: 1233), nsp-7 (SEQ ID: 1234), nsp-8 (SEQ ID: 1235), nsp-9 (SEQ ID: 1236), nsp-10 (SEQ ID: 1237), RNA-dependent RNA polymerase (SEQ ID: 1238. Table 1: SEQ ID NO: 396 to SEQ ID NO: 571, helicase (SEQ ID: 1239, Table2: SEQ ID NO: 572 to SEQ ID NO: 699), 3→5' exonuclease (SEQ ID: 1240, Table 3: SEQ ID NO: 700 to SEQ ID NO: 803), endoRNAse (SEQ ID: 1241, Table 4: SEQ ID NO: 804 to SEQ ID NO: 882), 2-O' ribose methyltransferase (SEQ ID: 1242. Table 5: SEQ ID NO: 883 to SEQ ID NO: 953), Surface Glycoprotein (S) (SEQ ID: 1243: SEQ ID NO: 60 to SEQ ID NO: 236), ORF-3a (SEQ ID: 1244, Table 8: SEQ ID NO: 1045 to SEQ ID NO: 1112), E (SEQ ID: 1245. Table 7: SEQ ID NO: 1015 to SEQ ID NO: 1044), M (SEQ ID: 1246. Table 6: SEQ ID NO: 954 to SEQ ID NO: 1014), ORF-6 (SEQ ID: 1247. Table 9: SEQ ID NO: 1113 to SEQ ID NO: 1125), N/NC (SEQ ID NO: 1251: SEQ ID NO: 237 to SEQ ID NO: 280), ORF-7a (SEQ ID: 1248. Table 10: SEQ ID NO: 1126 to SEQ ID NO: 1135), ORF-7b (SEQ ID: 1249), ORF-8 (SEQ ID: 1250, Table 11: SEQ ID NO: 1136 to SEQ ID NO: 1174), nucleocapsid (NC) (SEQ ID: 1251).

The embodiment of the invention will permit a use of a single or double or up to 12 such epitopes. The multiple epitopes can be arrayed in a linear head to tail format in a multimeric peptide assembly or a polypeptide produced as recombinant. Alternatively, the peptide in single or multimers can be inserted into the β-β loop structures or replacing the loop structures of the aforementioned protein scaffolds (SEQ ID NO: 1255 to SEQ ID NO: 1264), including CDR1/2/3 substitution or replacement of camelid VHH (SEQ ID NO: 41255, SEQ ID NO: 1260). Because the loop of a protein scaffolded by exposed toward the surface and characterized by its hydrophilicity, and accessible to ER stress-mediated processing and degradation and assembly with the MHCI binding pocket. Therefore, the embodiment of the invention is to prolong the half-life of the peptide, or a contiguous peptide multimers or a polypeptide with contiguous peptides. In another embodiment of DNA/RNA immunization, the single peptide or contiguous peptide can be cloned into a eukaryotic expression vector that transcribed and translated in the modality of DNA/RNA immunization.

Antigenic variation due to molecular shift are frequent with the host range such as affinity of attachment increase or deviation away of attachment due to neutralization or protecting antibodies. CTL determinants are cryptic to immune evolutionary pressure, for the following reasons:
  (i) Especially the multiple nonameric epitopes constellated upon a given MHCI haplotype or supertypes; thus, a mutation of a given nonamer does not affect the CTL protection to other nonamer of the given protein of interest.
  (ii) The polymorphisms of a particular haplotype or supertype permit multiple different heterozygote combinations with respect to the diverse nonamers, and the redundancy or heterozygosity of the nonamer-presenting MHCI permit a robust defense repertoire. (iii) Even there is a mutation within the nonameric (+1/−1) sequences, the escape mutants have to be at the second and seven amino acid positions since these two are the anchor binding sites for the MHCI; and amino acids in non-anchored position will not affect the capacity of CTL induction. Therefore, the embodiment of the invention will ensure the CTL protection using the combination of nonameric or octameric or decameric peptides to defend against the CoV-2 or CoV-n infections and mutants.

Example One

Embodying Cov-2 B Cell Epitopic Sequences Illustrated

Hypervariable and conserved regions of surface or spike protein: The CoV-2 S exhibits 17 receptor binding amino acids (5 hypervariable+6 conserved+6 invariant amino acids in the RBE region of RBD) over ~80 amino acid in one contiguous sequence contacting ACE2 receptor over 1750 $A^2$ area (Lan, J., 2020. Nature 581, 215-220). The embodiment of the invention is to claim the five hypervariable amino acids offering flexibility of change into any of the 20 amino acids selectable by RD or any kind of protein display platform to increase the mutant S binding to ACE2; and the six amino acids can suffer a conserved amino acid substitution for increasing binding affinity to ACE2. The embodiment of the invention includes mutants showing any or a combination of mutation of spike protein to gain advantage to high affinity binding to ACE2.

Therefore, the RBE will be used for replacement in CDR1 to CDR3 of camelid VHHCoV-2 (SEQ ID NO: 1215 to SEQ ID NO: 1220; SEQ ID NO: 11 to SEQ ID NO: 17; SEQ ID NO: 37 to SEQ ID NO: 42) as a precision vaccine. CDRs as a molecular clamp also for Covid-19: (i) defining precision B cell vaccine epitopes, of the S protein, and RBE (RBD) of CoV-2; (ii) bifunctional T cell costimulation can be delivered using GFP helping the S B cell epitopes. Using the entire S protein as vaccine (1250 amino acids) may cause unfavorable immune enhancement, currently a major focus of several key vaccine projects [DNA vaccine (Inovio), RNA vaccine (Moderna), CoV-2 S pseudotype flu (J&J), S protein on vaccinia virus (Oxford U), and recombinant S protein).
NTD Region within the Spike Protein:

Moreover, three additional sites on the NTD regions (SEQ ID NO: 1 to SEQ ID NO: 10; SEQ ID NO: 1214) are considered. A vaccine neutralizing and blocking the entry of 2019_nCoV via human ACE2, constrained by VHH and optimized by mRNA and ribosome display coupled to molecular evolution The patent invention claims a vaccine representing a combination of four antigenic sites of 2019_nCoV onto a protein constraining scaffold.

Four prominent antigenic sites are:
  Site 1: TNGTKR 71-79 (SEQ ID NO: 293) of the spike protein of 2019_nCoV
  Site 2: HKNNKS 145-150 (SEQ ID NO: 294)
  Site 3: RSYLTPGDSSSG 245-256 (SEQ ID NO: 295)
  Site 4: QTNSPRRA 676-684 (flanking RBD) (SEQ ID NO: 296)

The patent invention uses the camelid nanobody as a scaffold to constrain or encompass said four sites (site1, site 2, site 3 and site 4) of the spike protein of CoV-2, 2019_new coronavirus that segregate and assemble together in a folding strategy on a protein scaffold as a vaccine. Said vaccine elicits neutralizing antibodies to destabilize the viral monomeric around/or the trimeric spike protein in order to block the contact of the amino acid region or the protein domain(s) of the spike protein of the CoV-2 to the angiotensin converting enzyme 2 (ACE2) as entry into susceptible lungs, kidney tissues and hearts.

The four dis-contiguous sites, from regions distinct from the alpha-helix or 3-10 helix fusion domain, are chosen for inserting into, arranging in between, or replacing the native sequences of CDR of immunoglobulin or substitute native loop sequences of other protein scaffolds. Said platform can be optimized by mRNA and ribosome display, coupled to molecular evolution via solid phase ACE2. The four sites of the spike protein of CoV-2, 2019_nCoV in natural history, serve as anchors for the stabilizing the beta-pleated sheet and loops of the contact regions to the ACE2 receptor. The four sites of the spike protein of CoV-2, 2019_nCoV, in this patent invention hence assembled substituting the native loop sequences of the aforementioned protein scaffolds, are claimed the prophylactic and/or therapeutic vaccine for eliciting neutralizing and/or blocking antibodies that inhibit entry of CoV-2, 2019_nCoV via contacting ACE2 of human susceptible lung and kidney tissues and hearts.

Example Two

Embodying Molecular Darwinian Evolution of Fitness Antigen-Ribosome/mRNA (ARM) Display Platform The precision vaccines can be further re-shaped for fitness as a more efficacious vaccine, using the inhouse antigen ribosome/mRNA display (RD) platform (Chen, S.-S., 2014. USPTO 8,865,179; Chen, S.-S., 2015. U.S. Pat. No. 9,187,553). The evolving ARM Platform (for antigens/antagonists) by various protein scaffolds, including said protein scaffolds (FIG. 1) was established and patented in the laboratory of the small concern. FIG. 2 shows the ARM platform integrated with the Darwinian molecular evolution (DME) and DNA shuffling for selecting a high-affinity final vaccine candidate.
  (i) The inserted CoV-2 loop sequences SEQ ID NO: 1215 to SEQ ID NO: 1220; SEQ ID NO: 11 to SEQ ID NO: 17; SEQ ID NO: 37 to SEQ ID NO: 42) in said protein scaffolds can be enabled for transcription initiation with the T7 promoter, translation with the Kozak sequence that scans rRNA binding site of the eukaryotic 40S ribosomes, wherein the termination codon protein scaffold stuffer region (using GFP or using Cκ) was deleted so that the transcribed-translated antigen-ribosome-mRNA (ARM) ternary complex was not released from the P site of the ribosomes (e.g., stalled on eukaryotic ribosomes as a ternary ARM complex) (Chen, S.-S., 2014. U.S. Pat. No. 8,865,179; Chen, S.-S., 2015. U.S. Pat. No. 9,187,553).

(ii) Next, this bulky ARM is selectable and captured by huACE2 receptor, chemically coupled to beads or coated on a 96-well plate.

(iii) Selectable mRNA can be dissociated from the 96-well plate and mutations can be introduced by base analogues and error-prone RT-PCR (Chen, S.-S., 2014. U.S. Pat. No. 8,865,179; Chen, S.-S., 2015. U.S. Pat. No. 9,187,553). After 3-5 reiterative rounds of selection, the clonal DNA can be prepared and undergo DNA shuffling recombination/inbreeding to generate a high-affinity product upon Darwinian competition. The ARM finalists and mRNA throughputs selected will be tested as the ultimate API or precision vaccines for cell-based assay and animal protection.

Example Three

Embodying the Precision Vaccines of S Protein of Covid-19 Using the Molecular Clamps In the example: we focus on insertion of the RBD domain SEQ ID NO: 1215 to SEQ ID NO: 1220; SEQ ID NO: 11 to SEQ ID NO: 17; SEQ ID NO: 37 to SEQ ID NO: 42), which contact ACE2 into camelid CDR constructs as blocking or neutralizing antigenic epitopes using a linker sequence co-synthesized along with GFP as additional constrainer and also serve to activate CD4 helper T cells to generate an anti-RBD antibody response. In IgE and FceRI receptors system, we pioneer IgE B cell epitopic vaccine discovery using on X-ray of ligand/receptor cocrystal, and most antigenic loops are delineated by the secondary b-strand flanking structure, which coincide with the tertiary structure by X-ray. This methodology based on empirical data (other than biocomputing) has yielded productive means to define minimal B cell epitopes, including IgE receptor-binding loops of IgE as universal allergy vaccines in raising neutralizing antibodies. Recently, high resolution X ray of CoV-2 S protein is finally available, as elucidated by Veesler in FIG. 3 and FIG. 4. X ray cocrystal using CTD1 (containing RBD)/ACE2 receptor was also reported by this group (Walls, A. C., 2020. Cell 181, 281-292.e286), as well as a high resolution CoV-2 RBD/ACE2 cocrystal by Wang (Lan, J., 2020. Nature 581, 215-220) in FIG. 3 showing tertiary structure here. These pivotal studies provide critical structural based information herein for designing molecular clamped precision three-firewall vaccines. Importantly, there are five key receptor binding amino acid residues (the hypervariable tract among humans and intermediate hosts), and 12 conserved amino acid residues with eight identical residues, embracing the ACE2 over an overall total area of 1,750 A2 (Yan, R., 2020. Science 367, 1444; Lan, J., 2020. Nature 581, 215-220), encompassing 17 H bond and one salt bridge: Tyr (Y), 479, 489,495, 505 with receptor hydroxyl group; among 12 amino acids shared with CoV-1, 6 identical sequences, 6 conserved, and five distinct different residues (Lan, J., 2020. Nature 581, 215-220).

S-ACE2 induced twist can cause exposure and furin cleavage site on S protomer/homotrimer. The precision vaccine against RBD will be tested to not only block the initial attachment, but also tested for dissociation of S from huACE2. Importantly, dissociation will bring a 'cure' since stage 2 and 3 enzyme catalysis and membrane fusion are summarily blocked. All the sequence information is described by Veesler and Wang in their X ray crystal/cocrystals, as illustrated in the secondary structure enables an initial roadmap for B cell epitope discovery. The precision candidates are indicated in the flexible loops (hydrophilic, open accessible), flanked by the beta strands, or by alpha helix, or alpha-beta., As an example, Table 1 showed putative B cell epitopes of the loops flanked by the beta stands (RBE/RBD and NTD sequences), and B cell epitopes are over the entire spike protein, not limited to the example sequences, moreover, can include any sequences of the secondary structure α-helix, 3-10 helix, and beta strand itself for substituting the CDR loop(s). Table 2 (furin sites and fusion peptides), delineated by the secondary and tertiary structures of FIG. 4 (Veesler, pdb deposit: 6VXX). Table 1 also showed the replacement of immunoglobulin CDR1 CDR2 and CDR3 with the RBE.

The embodiment of the invention: Coronavirus Co-V2 or Covid_19, CoV-1, initiate human infection by the attachment of coronavirus spike protein (S protein) to the angiotensin converting enzyme II (ACE2) receptors in the lung, kidneys and hearts. We invent vaccines using sequences of the entire S protein SEQ ID NO: 43 to SEQ ID NO: 51; SEQ ID NO: 281 to SEQ ID NO: 292; SEQ ID NO: 297 to SEQ ID NO: 309): NTD (SEQ ID NO: 1 to SEQ ID NO: 10; SEQ ID NO: 1214), RBD (RBM) SEQ ID NO: 1215 to SEQ ID NO: 1220; SEQ ID NO: 11 to SEQ ID NO: 17; SEQ ID NO: 37 to SEQ ID NO: 42), NTD partner, furin cleavage domain SEQ ID NO: 18 to SEQ ID NO: 36), HRN-HRC for fusion domain, and TM for transmembrane anchorage, as well as translated proteins of ORF1a, ORF-1ab, leader protein, nsp-2, nsp-3, nsp-4, 3C-like proteinase, nsp-5, nsp-6, nsp-7, nsp-8, nsp-9, nsp-10, RNA-dependent RNA polymerase, helicase, 3→5' exonuclease, endoRNAse, 2-O' ribose methyltransferase, ORF-3a, E, M, ORF-6, N, ORF-7a, ORF-7b, ORF-8, nucleocapsid (NC) the envelope protein (E). Protective B cell vaccine epitopes will be discovered around the loop regions of the entire S protein as a paradigm and aforementioned proteins scaffolded by the beta-strands or beta-sheet or alpha-helices, including also the N- and C-terminal loops as antigenic sites. Moreover, vaccines are made against envelope protein and rdrp to perturb viral life cycle. Vaccine against the variable regions such as RBD can be catered to the infectious endemic or pandemic strains. Vaccine against the universal protective epitopes such as non-variant amino acids on S as well as canonical nonvariant sequences on rdrp and envelope proteins are universal vaccines. This patent invention also embodies the B cell epitopes from the nonstructural proteins.

Herein, the vaccine platform extended to CoV-1, and CoV-n, the evolving variants as the close relatives and kindreds to B.1.526, E484K, S477N. The constraining scaffold will include lipocalin, protein A, green fluorescent protein (GFP), fibronectin, immunoglobulin, super beta strand of FG of human IgE, shark antibodies, and VHH of the species of the Camelidae, including camels and llamas.

Three Layers of Protective Fire Work

Wuhan's strain (WUHAN/WVIO4), including and not limited to all the variable isolates from China and worldwide, amino acid sequences that can be accommodated into the CDRs of the immunoglobulin heavy chains.

1. The First Firewall

Anti-RBE/RBD Neutralizing Antibodies. Furthermore, cryo-EM structures show that the RBD of a protomer exists in two states, the up or open state capable binding to the receptor, while the down or close position is cryptic, waiting for its kinetic moment opening up to bind to receptor next (Wrapp, D., 2020. *Science* 367, 1260). Like a spinning wheel, with three sharp spikes there be in two states present in homotrimer. Noteworthily, an X ray study using the complete untruncated huACE2, chaperoned as a dimer by amino acid transporters (BoAT1) in the membrane that have the potential to form multiple cross-linking networks with multiple homotrimers (Lam, T. T.-Y., 2020. *Nature* 583, 282-285). Since each RBD fragment binds to truncated huACE2 (most done in this expedient way) in the Biacore assay scores at a high affinity of 4.5 nM (Wrapp, D., 2020, *Science* 367, 1260), it is likely homotrimeric to dimeric synergistic binding may approach picomolar affinity posing challenging situations for vaccine makers.

The advantage of the precision first firewall vaccine in Table 1A-1B rendering RBE/RBD an Achilles' heel, over the current vaccine ventures (whole S-mRNA, -DNA, -recombinant, and whole S pseudotype) is:
  (i) Molecular clamp can capture the lowest free energy configuration and render immunogenic either the open or the close state depending on the replacement of the different demarcated RBE shown in FIGS. 5 and 6, into the CDR1, CDR2 and CDR3, using camelid VHH prototype (SEQ ID NO: 1215 to SEQ ID NO: 1220; SEQ ID NO: 11 to SEQ ID NO: 17; SEQ ID NO: 37 to SEQ ID NO: 42).
  (ii) Molecular clamping using demarcated precision peptide subregions, like the clamped IgE vaccine, is highly efficient to elicit antibodies causing dissociation of the huACE2-bound CoV-2 S, despite at high affinity. Therefore, we will assay the dissociation of biotinylated RBE/RBD and S protein from huACE2 receptors on the solid phase.
  (iii) Type-specific vs. broadly neutralizing or cross-reactive antibodies: Despite its immunogenicity, we anticipate that the molecularly clamped RBE vaccine including the hypervariable receptor-binding amino acids as a precision antigen, may be CoV-2 type-specific (i.e., RBE between CoV-1 and CoV-2 shares only 33% homology) (Lan, J., 2020. *Nature* 581, 215-220) but not for neutralizing an emerging variant as a seasonal 'flu'. Nevertheless, molecular clamped precision vaccine using RBD outside the RBE regions, exhibits greater conservation (77% homology) (Lan, J., 2020. *Nature* 581, 215-220), therefore precision vaccine, constructed accordingly offers an opportunity as a broad-spectrum vaccine.

Indeed, comparative X-ray of cocrystal of CoV-1 RBD vs CoV-2 RBD with huACE2 receptors, lends support for a highly homologous contour of the overall RBD region: six out of 17 receptor contact residues of RBD are identical, and the other six exhibit conserved amino acid change, while the α-carbon chain tracing the two respective receptor-bound RBD contour shows impressive side by side overlap (Lan, J., 2020. *Nature* 581, 215-220). This observation lends credence that a precision vaccine targeting the evolutionarily conserved configuration of RBD can then be broadly neutralizing (BN) or cross-reactive for both SARS CoV-1 and CoV-2, which will be tested by ELISAs: S protein, RBE/RBD capture by ACE2 receptor-coated plates were established for evaluating the titers of first firewall antibodies, and biological neutralizing activities will be ascertained by neutralizing infection of CoV-2 S pseudotype in huACE2+ cells.

2. The Second Firewall

Type-specific and Universal vaccines aim at blocking the furin cleavage sites (SEQ ID NO: 18 to SEQ ID NO: 36; SEQ ID NO: 1221 to SEQ ID NO: 1223; SEQ ID NO: 1252 to SEQ ID NO: 1254) to prevent cleavage of S1-S2, posing S'2 cut as well as the S'2 site, cut at S'2 for S2 maturation, poising for the critical later membrane fusion event by fusion peptides. S'2 site being cryptic and evolutionarily conserved is exempt from immune surveillance, which is exposed only following global conformational change after S1 binding to ACE2 (Wrapp, D., 2020. *Science* 367, 1260; Song, W., 2018. *PLOS path* 14, e1007236). Noticeably, whole S protein-based vaccines typically miss this important vaccine component due to their crypticity. Therefore, these epitopes molecularly clamped in VHH, are ideal candidates as universal vaccines to tackle the two more Achilles' heels once exposed.

(i) Anti-Furin Site-Specific Neutralizing Antibodies: Furin (a proprotein convertase, PC) enzymatic site exposure plays a critical role for generating S2 fragment for completing the stage 2 infectious cycle post RBD binding; noteworthily, NTD the adjacent N-terminal I domain (1 aa-333 aa) is also dramatically altered in conformation following the binding event of S/ACE2 (Song, W., 2018. PLOS path 14, e1007236), raising the importance of the 'accessory NTD vaccine' synergizing with the three firewall vaccines, attenuating S2 cleavage. (ii) Antibody against the global conformational change of S1 in cooperativity with S2, essential for priming (opening up) the first furin site at S1-S2 junction (TNSPRAR/SA, SEQ ID NO: 1272), which then boosts further conformational change in opening up the S2' site (SKPSKR/SF, SEQ ID NO: 1273) for cleavage by furin or serine protease (TMPRSS, SEQ ID NO: 1274), or cathepsin B/L (Hoffmann, M., 2020. Cell 181, 271-280) at the plasma membrane junction of host cells.

Therefore, anti-S1-S2 vaccines are prepared using: QTNSPPRARSVASQSIIAY/TMSLG (SEQ ID NO: 1252) 676-700 furin cleavage site S1-S2; or anti-S2' vaccine: PSKPSKR/SFIEDLLFNKVTLADAGFIK (SEQ ID NO: 1221) 810-828 S'2 furin cleavage site (Coutard, B., 2020. *Antiviral Res* 176, 104742) will be prepared into CDR2 or CDR3 domains in singles or a pair onto the camelid VHH.

ELISAs: S1-S2 and S'2 with C-terminal His tag are captured by plated coated with anti-His, and anti-second and firewall antibodies are assayed via binding to the S1-S2 and S'2 fragments respectively, whereby the neutralizing activities tested by neutralizing CoV-2 S pseudotype infection in huACE2+ cells. Noticeably, S1-S2 cleavage site unique in CoV-2 provides enhanced infection capability (an additional virulence factor) as compared to CoV-1, due its 'priming' then opening up S'2 being universal to realize productive infection. These furin sites can only be attached with precision vaccines but the entire S injection as vaccine lacking exposure of these critical antigenic determinants. We anticipate that S1-S2 precision vaccine is unique for CoV-2 protection, while anti-S' precision vaccine (commonly shared among CoV-2 and CoV-1 or -n) will be employed for broader spectrum CoV-2 protection or for CoV-n as the Universal Vaccine. And a combined bivalent second firewall vaccine offers a stronger protection for the pandemic SARS CoV-2.

3. The Third Firewall

Universal vaccine is directed at blocking the conserved fusion peptide sequence, when CoV-2 escapes or leaks through the first and the second line of defense firewall. Anti-Fusion Peptide Neutralizing Antibodies: Should CoV-2 break through the second firewall, the mature homotrimers form the extended α-helix to present the triple bullets of fusion peptide, juxtaposing the membrane for fusion and genome entry. Hence, the exposed fusion presents yet another Achilles' heel, which the precision anti fusion peptide vaccine can instantly pull apart the injecting virion from the host cells: in particular, devoid now of S1, CoV-2 is nearly 'dangling 'in thin air' with no more attachment to ACE2 (Harrison, S. C., 2008. *Nature Struc Mol Bio* 15, 690-698). Precision vaccine against the fusion peptide: YKTPPIKDFGGFNFSQILPDPSKPSKR (SEQ ID NO: 1254) (a-a) 770-778 (Wrapp, D., 2020. *Science* 367, 1260) replaced into the CDR2 or CDR3 of camelid VHH (FIG. 6), is intended for the third firewall specific neutralizing antibodies to block or dissociate the mature S2 from host cell membrane as a universal vaccine. ELISAs His-tag fusion peptides are captured by anti-His on 96 wells, and added with anti-third firewall antibodies, detected by HRP-anti-IgA vs. IgG, wherein neutralizing evaluated by abrogating CoV-2 S pseudotype infection in huACE2+ cells.

4. The Fourth Firewall

Similarly, the vaccine is directed against CoV-2 membrane antigen, envelope antigen and nucleocapsid and rdrp to neutralize viral infectivity. CTL inhibition of viral replication and eliminate the CoV-2 infected foci and reservoir. This firewall is particularly effective against mutant virus.

Impact of Vaccination: Mucosal IgA, systemic IgG and CTL induction, and protection of CoV-2 S pseudotype infection: The RBD is PCR-amplified fused to GFP, used as a positive control. Immunogenicity of the above precision vaccine constructs will be tested in BALB/c and B6 mice via SC and IM immunization for circulating IgG as well as peroral and intranasal (IN) immunization with cholera toxin (CT) for IgA production, in particular, IgA in bronchoalveolar fluid (BALF) will be evaluated for neutralizing IgA abrogating binding of S protein to the receptors by ELISA and blocking CoV-2 S viral pseudotype infection, which requires the entire S protein for initial attachment RBD/S1, priming of S1-S2 and boosting S'2 cleavage and the insertion of the boosted fusion peptides, wherein the three life cycles are subjected to the attack of each respective precision vaccines or a combination thereof.

Further Considerations (i) Glycan Shield: The landmark discovery of ACE2 receptor for CoV-1 by Harrison, Farzan and Li (Li, F., 2005. *Science* 309, 1864) and later elucidation of X ray cocrystal of RBD and ACE2 (2.5 $A^2$), entirely verified also in CoV-2 cocrystal (Lan, J., 2020. *Nature* 581, 215-220) provides a gateway for B cell vaccine discovery for coronavirus. The conserved feature of CoV-1 and CoV-2 S/ACE2 interaction indicate that vaccine designed using the conserved RBE clamped in B cell epitopes enveloping the ACE2 receptor, may be applicable across coronavirus variants. However, the above major vaccine RBD paradigm, wherein most investigators concentrate the effort, does not take into account the 18 N- and 4 O-glycan shields, which can mask the target B cell epitopes in S1 as well as S2.

(ii) Synergism for $1^{st}$ Firewall by NTD1 (CTD1): Since the RBE/RBD conformation is influenced by the NTD domain of S1 (Song, W., 2018. *PLOS path* 14, e1007236), which is a 330-amino acid domain prior to RBD (sugar-binding in MERS) (Li, F., 2015. J Virol 89, 1954-1964). Therefore, we will test whether anti-NTD may alter a covert an up (open) position for ACE2 binding into a down (close) position incapable of receptor binding, which can also play a role in dissociating the initial RBD binding to human ACE2, subsequently negatively influence the opening up or priming of the furin site at S1-S2 junction. NTD exhibits an overall 50% homology between CoV-1 and CoV-2, however there are two tracts delineated by b-strands, exhibiting 90% homology as a choice for making precision broadly neutralizing vaccines.

The embodiment of the vaccine using GFP as help: GFP offers a strong CD4 T cell help for antibody response; and its extreme thermostability (Tm~100° C.) indirectly enhances the camelid chaperone capacity as a molecular clamp (Chen, S.-S., 2014. U.S. Pat. No. 8,865,179). Although GFP is approved for clinical imaging, it is not conventionally thought as carrier protein for helper T cells. hence, the camelid VHH displaying vaccine B cell epitopes can be conjugated to tetanus toxoid or diphtheria toxoid or measles peptides (SEQ ID NO: 1265 to SEQ ID NO: 1270) to elicit long-term memory helper T cells, safely taking advantage of the herd immunity.

Vaccine Purification (GLP)

Recombinant human ACE2 is purchased. Complete S gene will be prepared by gene synthesis, and prepared in full and in truncation for immune specificities. Primer sets designed and executed for PCR cloning for preparing the S1 (SEQ ID NO: 309), truncated S1 (removing NTD): RBD/RBE (SEQ ID NO: 43 to SEQ ID NO: 51; SEQ ID NO: 281 to SEQ ID NO: 292; SEQ ID NO: 297 to SEQ ID NO: 308) at N-, or C-terminus of protein scaffold, as well as binding epitopes of RBD/RBE (SEQ ID NO: 11 to SEQ ID NO: 17; SEQ ID NO: 37 to SEQ ID NO: 42; SEQ ID NO: 1215 to SEQ ID NO: 1220); NTD (SEQ ID NO: 1 to SEQ ID NO:10; SEQ ID NO: 1214); furin primed S2 (cleaved by S1-S2 site) and furin-boosted S2' (cleaved at S2' site) (SEQ ID NO: 18 to SEQ ID NO: 36; SEQ ID NO: 1221 to SEQ ID NO: 1223; SEQ ID NO: 1252 to SEQ ID NO: 1254) placed into β-β loops of the protein scaffolds, and wherein the constructs are produced in periplasmic space purification of ST2 signal peptide engineered into pET11b. The proteins or polypeptides are properly tagged. The CoV-2 S protein epitopes from the N- as well as C-terminal S1/S2 are cloned into β-β loops of protein scaffolds (SEQ ID NO: 1255 to SEQ ID NO: 1264) including the CDR1, CDR2 and CDR3 of VHH (SEQ ID NO: 1255, SEQ ID NO: 1260) in concatenated expression with GFP (SEQ ID NO: 1257, SEQ ID NO: 1262) on the C-terminus fusion, the destination of the IgV/VHH, is re-routed to cytosol, subject to expedient straightforward purification, sequenced ascertained by MS/MS.

The Advantage of the Embodiment of the Invention of the Above Molecular Defined B Cell and T Cell Epitopes in Contrast to Full Length S Protein as Vaccines a. Cytokine Storm, Immune Deviation or Tolerance Inappropriately prepared CoV-2 vaccine can lead to immune complexes (directed against harmful B-cell epitopes)-mediated T cell activation, viral CD4 T-cell epitope activation, resulting in immune dysregulation and cytokine storm, which is the cause of death of Covid-19 or SARS-Cov-2. In SARS CoV-1, nucleocapsid was found to induce a large repertoire of CD4 and CD8 epitopes contributing to CTL defense, and paradoxically also CD4-CD8 T-cell mediated cytokine storm and death (Janice Oh, H.-L., 2012. Emg Microbes Infect 1, e23-e23). Therefore, it is of critical importance to appreciate the intricate web of the B-cell epitopes of the typically highly complex S protein (1,255 amino acids), in a recent biocomputing analysis stated that ~80% repertoire of Covid-19 B cell epitopes as well as abundant CD4 helper T cell epitopes are on the S protein (Grifoni, A., 2020. *Cell Host Microbe* 27, 671-680).

The cytokine storm can be inhibited with suppressive RNA vaccines accommodating the above B and T cell epitopes. Several whole S protein vaccines in contrast to that of the precision firewall approach, are currently in progress, including the mRNA vaccine, DNA vaccine, recombinant vaccines and the S pseudotype adenoviral vaccine (J&J) in the phase 1 trial sponsored by CEPI/Gates Foundation and NIH. The precision vaccines lack viral CD4/CD8 T cell epitope, since GFP carrier-specific helper T cells contribute to activation of B cells specific for molecular clamped B cell epitopes.

b. Ribosome mRNA Display (RD) to Further Optimize Four Firewall Vaccines

The thermodynamic law dictates the RBE peptide folding scaffolded by the molecular clamps assumes the lowest free energy state, which is accounted for by the lowest enthalpy with one degree of freedom for a fixed configuration for the native B cell epitope. Thus, the underlying thermodynamic force govern one unique folding of the peptide sequences given in the context of highly thermostable molecular chaperone providing the super-β flanking strands (Chen, S.-S., 2014. U.S. Pat. No. 8,865,179; Chen, S.-S., 2015. U.S. Pat. No. 9,187,553).

c. Re-Shaped Conformation for a Better Fit

As shown in the Preliminary results, we have in place a proprietary ribosome display technology, which can positively select conformation of the mutated molecular clamped RBE via error prone PCR for a best fit conformation with high affinity to huACE2 receptors. Therefore, mutated Antigenic RBE B cell epitopes-mRNA-Ribosome (ARM) ternary complexes, exhibiting a better fit to the receptors can be selected onto the Dynabeads covalently coupled with lower threshold of huACE2 or in the presence of excess first generation of RBE-immunoglobulin heavy chain for competitive selection, streamlined for potency antigenicity and immunogenicity.

Example Four

Embodying Precision Vaccines that Predict and Protect Against Emerging Covid-19 Variants Using Ribosome Display and Darwinian Molecular Evolution (i) Sequence data L vs S type among 103 strains showed two signature SNP at ORF1ab and ORF8 related to replicase and ER stress ATF6 (Tang, X., 2020. Nat Sci Rev 7:1012-1023). A new observation showed that a number of stains exhibit SNP at the S protein, alarmingly varying even with one amino acid missense SNP at the spike protein causes conspicuous pathogenicity. Thus, given cumulatively (December 2019 to April 2020, GISAID) 3,123 viral genomes known to date, pertinent information and insight can be continually accumulated. Therefore, we hypothesize that critical and cumulative adaptive changes at the S1-ACE2 interface, S1-S2, and S2 crucial sites of mutants facing herd immunity has the likelihood of breakthrough in renewed endemic, epidemic or pandemic proportion as a 'season's flu. Alternatively, the source strains can continue unabated via cultural culinary habits and history repeated. Herein we proposed a safe method to predict new strains by ribosome display platform using the entire S protein/ACE2 forced Darwinian evolution applying selective pressure using herd immunity as well as three firewalls of neutralizing antibodies.

(ii) Host range adaptation-lesson learned There have been impressive comparative data (including 4× ray cocrystals) of the RBE binding sites of different hosts, bats, humans, palm civets, pangolins having different adaptive binding motifs to the respective host ACE2. Moreover, the overall binding motif between CoV-1 and CoV-2 S protein is highly conserved around ACE2 contour region beside the intimate contact amino acid five (CoV-2/Cov-1: L455/Y442; F486/L472; Q493/N479; N501/T487, K417/V404; hence conveying the prowess of plastic adaptive binding extraordinaire) (Lan, J., 2020. Nature 581, 215-220). The evolution force behind this molecular fact can be interpreted as follows, despite the variability at the key contact, the evolutionarily conserved 14 'shared' amino acids, amongst eight identical invariable amino acids, and the rest of six conserved amino acid changes (can still make conserved amino acid changes to meet the free energy change of five hypervariable amino acids), can constrain the five highly variable amino acids into spatial arrangement such that the any evolutive combination of the 19 amino acids of S, which contact the 20 amino acids of huACE2, is at the lowest free energy state.

As a result, one anticipates that the versatility of the rule of 17:12 (6+6): the invariant 6 amino acids accompanied by six 'semi-variable conservative' 6, along with the five hypervariable amino acids can derive a sizable SARS CoV-2 variants, and impressive repertoire of CoV-n ready for continual selection upon human ACE2 selection: (i) purposefully to evade existing neutralizing antibody-based herd immunity; (ii) purposefully in an intermediate host to maximize zoonotic ecological, niche expansion. The proposed Aim 2 focus on selecting the S breakthrough mutants, and the vaccines that can be preempted thereof.

A SARS-CoV-2 variant carrying the Spike protein amino acid change D614G has become the most prevalent form in the global pandemic. Dynamic tracking of variant frequencies revealed a recurrent pattern of G614 increase at multiple geographic levels: national, regional, and municipal. The shift occurred even in local epidemics where the original D614 form was well established prior to introduction of the G614 variant. The consistency of this pattern was highly statistically significant, suggesting that the G614 variant may have a fitness advantage. The G614 variant grows to a higher titer as pseudotyped virions. In infected individuals, G614 is associated with lower RT-PCR cycle thresholds, suggestive of higher upper respiratory tract viral loads, but not with increased disease severity. These findings indicate changes important for a mechanistic understanding of the virus and support continuing surveillance of spike mutations to aid with development of immunological interventions (Korber et al., 2020, Cell 182, 812-827).

Reiterative Rounds of Darwinian Selection in the Presence of Selective Pressure

The natural selection must be based on the intact whole S genes, e.g., the prefusion S ectodomain aa 1-1208 (GenBank MN908947), or complete or partially truncated RBE/RBD domains (SEQ ID NO: 43 to SEQ ID NO: 51; SEQ ID NO: 281 to SEQ ID NO: 292; SEQ ID NO: 297 to SEQ ID NO: 309) piggyback on the stuff protein (deleted termination codon for ribosome attachment, forming ternary complexes) for re-iterative rounds of Darwinian selection (two US patents awarded the platform). The binding of the RBE (RBM)/RBD of the S protein (in contrast to using RBD or subunits) is influenced by NTD and S2 domain reflecting the natural binding/selection, for huACE2 receptor on the solid phase. The scenario is that re-emergence of the new CoV-2 strain or CoV-n in the presence of herd immunity to be accompanied expediently via mutating the RBE sufficiently in the total 18 amino acid residues, and since NTD (within CTD1) and S2 contribute to post-binding event, which need be included in order to bypass or evade the herd immunity.

This can be accomplished in three steps using ribosome display integrated with molecular evolution:
  (i) First, selecting high affinity S-mRNA-ribosome ternary complexes (SMR) binding to the solid phase ACE2 in the presence of increasing amounts of competing ligands: S protein (non-mutated), RBD fragment, or the RBE clamped in the VHH constructs. Via RT-PCT, mRNA carried these selective mutations can be obtained as a mutated gene, which can in turn be subjected to re-iterative rounds of mutations.
  (ii) Second, by selecting high affinity SMR in plates coated with diminished levels of ACE2.
  (iii) Third, and importantly, selection of SMR is performed in the presence of neutralizing antibodies (Aim 1) or convalescent sera showing sterile herd immunity. Fourth, it is inexplicable for origin of the four identical HIV sequences inserted around NTD: three identical stretches of gp120 sequences at N-terminus of NTD, and one identical Gag sequences post RBD. Selection of SMR will be performed in the presence of anti-HIV sequence antibody, which may affect orientation of open vs. close RBD, and the folding of S2, which diminish an overall RBD binding to huACE2. The escape mutants of these HIV sequences may exhibit synergy in ACE2 binding due to conformational changes at the NTD and S2 region due to negative selection by anti-HIV antibodies.

The above selection can be accomplished using the mutant library: Mutation is randomly introduced into the S protein by using error-prone, low fidelity Taq PCR under $Mg^{2+}/Mn^{2+}$ stress (0.1 U/µl in the presence of high $Mg^{2+}$ at 7 mM and $Mn^{2+}$ at 0.5 mM), or further aided by 6-oxo-guanidine (0.2-1 mM nucleotide), mutations will be introduced into RBE/RBD, and the supportive NTD and S2 region equally distributed and the four receptor binding IgE moieties of the DE-FG-VHHs or other construct candidates. Several types of mutant libraries with mutation percentages ranging from 0.5% to 5% will be pooled. Selection of the better fit in reiterative Darwinian rounds of selection will be carried out by the capture of the ternary complexes to ACE2 receptor solid phase under negative selection pressure in the presence of (i) RBE/RBD ligands, (ii) diminishing levels of receptor on solid phase resulting in more efficient high affinity binders to gain super-infectivity, alternatively in the presence of firewall specific neutralizing antibodies against RBD, or the convalescent sera, resulting in mutants overcoming the herd immunity.

The affinity of binding (Kd) to ACE2 will be determined using plasmon resonance by Biacore in the laboratory. To further improve receptor-binding affinity, DNA shuffle, routinely performed in the laboratory will be used to mimic genetic recombination and reassortment after viral mutation and selection, using Darwinian molecular evolution (Stemmer, W. P., 1995. Science 270, 1510; Stemmer, W. P., 1994. Nature 370, 389-391). High binding DNA from the above higher binder S candidates will be digested with DNase I and 100 bp fragments will be purified, shuffled/recombined, amplified with high fidelity pfu PCR, and assembled using terminal primer-based PCR reactions (Chen, S.-S., 2014. U.S. Pat. No. 8,865,179). Hundreds of shuffled library-transformed colonies in pET11b will be selected screening for final candidates exhibiting high-affinity binding to ACE2 coated 96 well plates. The pertinent mutated sequences for RBE/RBE, NTD, furin site sequences, will be ascertained, ready for molecular clamping in camelid preemptive for emerging viral escape mutants.

Further Considerations a. Advantage

X-ray cocrystals typically use RBD or CTD1 fragment and truncated ACE2 domain. In contrast, we employ the complete S protein and ACE2 protein in the modality of 'natural selection'; the complete protein ligand/receptor set therefore takes advantage of a full fledge conformational changes, wherein the mechanical torque force (generated post-binding of multivalent trimer/rigid receptor dimers) propagates onto the covalent S2, exposing the furin sites at S1-S2, and S', mimicking a natural selection for viral host interactions. Selection of RBD variant retaining S2, e.g, use the complete S gene in our display setting simulates the state of binding under natural infection circumstances prior to cleavage.

b. Disadvantage

One vs. three and dangling/noncleaved S2 However, the ARM complexes consisting of a ternary complex exhibiting only one protomer, not the natural homotrimer, which impose a higher avidity toward the natural dimeric huACE2 (Yan, R., 2020. Science 367, 1444); moreover, dimeric ACE2 receptor coating can be improved by using full length ACEs chaperoned by amino acid transporter as the coating reagent. Nevertheless, the weakness of the chemical display is not endowed the biological, proteolytic cleavage of S2 by host enzymes: furin, serine protease, cathepsin B/D at plasma membrane post the tectonic conformational S2-altered conformational landscape.

Example Five

Embodying Precision Vaccines Against Covid-19 Pseudotype in huACE2+ Cells as Well as Human ACE2+ Tg Animals Neutralizing antibodies elicited by the precision vaccine should abrogate infectivity of SARS CoV-2 in ACE2+ cells or Tg animal expressing huACE2. Viral pseudotypes using the rVSV delta G was widely investigated for complementing influenza, rabies, Ebola, Dengue, MERS, as well as SARS CoV-1 for inhibition of vial entry by pseudotype-specific neutralizing antibodies. The rVSV delta G retaining only 16 amino acids (the stem) 5' to the transmembrane domain of G protein gene is competent for viral budding, wherein the stem is fused to GFP for monitoring infectivity. Herein we construct CoV-2 S rVSV delta G two component systems for infecting ACE2+ cell lines, and Tg. And we will evaluate whether neutralizing antibodies elicited by the precision firewall vaccines can abort/abrogate CoV-2 pseudotype infection in huACE2+ cells in vitro, as well as in huACE2 Tg animals (one round) in vivo. These two criteria will serve as the in vitro and in vivo clinical correlates of vaccine efficacies, respectively. Thus, 1. Viral Pseudotype and ACE2+ Cell Cultures We will clone CoV-2 S protein truncated of 19 amino acids (S delta 19) on the C-terminus into CMV-pCAGGS-G. CoV-2 S gene modified delta 19 will be cloned into pCAGGS vector with CMV promoter, with optimized Kozak sequences. huACE2+ BHK-21 or HEK 293 transfected with truncated S will then be super-infected with the high titer viral stock of rVSV delta G_G* (rVSV genome with GFP cloned in MCS, deleting G protein ectodomain, and phenotypically transiently complemented with G protein (for entry into packaging cell only without being part of the pseudotype) (a generous gift from Dr. MA Whitt). Therefore, we will expediently produce the CoV-2 pseudotype using the two-component system, e.g., CoV-2 S delta 19 pseudotype packaged in rVSV delta G_G* in the transfected HEK 293 cells at the BSL-2 levels. Next, we will then evaluate whether the three firewall neutralizing antibodies abrogate the infectivity of CoV-2 S pseudotype in susceptible huACE2+ BHK-21 or HeLa cell, and TCID50 and cytopathic effect will be examined by microscopy, and percentage of infected cells by GFP based immunofluorescence using Nikon laser-based epifluorescence, and by FACS analysis. We anticipate that the hyper-immune sera from type 1 precision anti-RBE/RBD vaccine(s) will diminish the above criteria up to 90%; and we anticipate up to 70% inhibition by neutralizing antibodies to second and third firewall. IgG in the serum (IM, subcut.) vs. IgA in the BALF (IN) by ELISA will be correlated to neutralizing titers using CoV-2 S pseudotype infection. Since viral entry relies on three successive pivotal events: ACE2 attachment, furin cleavage and fusion attachment, we anticipate pseudotype infection in the presence of all three firewall antibodies, can reach 95~99% according to GFP fluorescence and TCID50.

Furthermore, pulse-chase metabolic labeling analysis will be conducted to monitor (the one round of) diminished viral replication (pseudotype being a defective particle, capable of only one round of replication) to corroborate viral neutralization by GFP and cytopathic effect, cells will be pulsed with S35 methionine, and de novo viral protein synthesis and replication in infected cells will be monitored, analyzed on denatured and native PAGE gel using cell lysates: native gel will reveal S homotrimer; moreover, CoV-2 S protein will be immunoprecipitated with anti-S prepared in the laboratory. By preventing entry, we anticipate that triple firewall antibodies will conspicuously also attenuate all the metabolically synthesized rVSV proteins.

Moreover, for large supplies, the rVSV (ΔG-P/M-MCS2-2.6) and packing vectors have been obtained from the Kerafast lab, and helper plasmids for P, L, M, N, and G with T7, and T7 constitutive cell lines. CMV-pCAGGS-CoV2 S delta 19 vector along long with helper plasmids will be transfected into HEK293 with CMV-pCAGGS-G, providing G* protein in trans and rVSV delta G culminating in the efficient assembly of the CoV-2 S pseudotype plaques, repeatedly handpicked for high titers, concentrated by centrifugation (~109 per ml) for the following animal experiments.

2. Animal Model

Neutralization of CoV-2 S Pseudotype in the Lung of huACE2 Tg Mice

Human ACE2 transgenic animals B6.Cg-Tg (K18-S2) 2Prlmn/J (Jackson lab) will be purchased for in vivo protection of rodent lung tissue with huACE2 transgene. Each group of three will be vaccinated with the respective layer of precision firewall vaccine or in four different combination ($1^{st}+2^{nd}$; $1^{st}+3^{rd}$; $2^{nd}+3^{rd}$; and $1^{st}+2^{nd}+3^{rd}$) vs VHH control three times via the IN for mucosal IgA pulmonary protection, and the SC or IM route for the IgG comparative purpose. Routes of vaccination is the pillar for the success of vaccines because the route is sentineled by the resident classical dendritic cells, subsequent chemokine-mediated migration of cDCs and resident and migratory CD4 helper and Treg to different compartments of lymphoid tissues, in particular the mucosal pulmonary tissues for Covid-19 protection. And 107 particle CoV-2 pseudotype will be introduced IN vs. IM/SC to normal vs. huACE2 Tg mice.

Cov-2 B Cell Vaccines Offering Protection

One week later, mice will be sacrificed, and single cell suspension of lung cells will be examined for GFP by fluorescent microscopy, FACS analysis according to viral encoded GFP marker and biomarker for lung cell types: epithelial, endothelial, CD45+ lymphocytes, type I and II alveolar epithelial cells, alveolar macrophages. Individual serum and BALF will be collected for different firewall-specific IgG and IgA antibodies. Residual surviving or the compromised viral pseudotype viral particles in the BALF fluid in vaccinated vs control mice will be assayed for reinfection in huACE2+ BHK-21 and Hela cells. The accelerated degradation of the infectivity of viral particles in vaccinated animals will be attributed to the neutralizing titers elicited by the above vaccination strategy with different precision vaccines, and with respect to the protective ratios of monomeric IgA vs IgG vs mixed IgA and IgG (in the serum), as well as the ratios of monomeric IgA vs secretory dimeric IgA in BALF. "The first pass" of pseudotype in animal protection in vaccinated vs. normal is therefore ascertained. Due to the affordability of normal mice, the role of antibody isotypes, and different routes-offered protection and mucosal immunity, can be comprehensively conducted. The comparison will provide relevant insight of the molecular clamped precision vaccines in this embodiment of invention over the entire S protein vaccines using DNA, RNA (RNA-1273, Moderna), recombinant proteins, or CoV-2 pseudotype (J&J) via IM.

High titers and memory: Precision vaccines building the shell of three firewalls that elicit high titers neutralizing antibodies may offer sterile immunity to Covid-19. Therefore, optimizing protective mucosal IgA in high titers as well as recalling memory IgA or IgG are important to be validated in this Aim.

CoV-2 and CoV-n CTL vaccines (nonameric epitope +1/−1) offering protection: Furthermore, the cell-mediated mucosal and systemic immunity non-mutated or mutated sequences according to the CoV-2 translation frame: ORF1a, ORF-1ab, leader protein (SEQ ID: 1228), nsp-2 (SEQ ID: 1229), nsp-3 (SEQ ID: 1230), nsp-4 (SEQ ID: 1231), 3C-like proteinase (SEQ ID: 1232), nsp-5 (SEQ ID: 1232), nsp-6 (SEQ ID: 1233), nsp-7 (SEQ ID: 1234), nsp-8 (SEQ ID: 1235), nsp-9 (SEQ ID: 1236), nsp-10 (SEQ ID: 1237), RNA-dependent RNA polymerase (SEQ ID: 1238. Table 1: SEQ ID NO: 396 to SEQ ID NO: 571, helicase (SEQ ID: 1239, Table2: SEQ ID NO: 572 to SEQ ID NO: 699), 3→5' exonuclease (SEQ ID: 1240, Table 3: SEQ ID NO: 700 to SEQ ID NO: 803), endoRNAse (SEQ ID: 1241, Table 4: SEQ ID NO: 804 to SEQ ID NO: 882), 2-O' ribose methyltransferase (SEQ ID: 1242. Table 5: SEQ ID NO: 883 to SEQ ID NO: 953), Surface Glycoprotein (S) (SEQ ID: 1243: SEQ ID NO: 60 to SEQ ID NO: 236), ORF-3a (SEQ ID: 1244, Table 8: SEQ ID NO: 1045 to SEQ ID NO: 1112), E (SEQ ID: 1245. Table 7: SEQ ID NO: 1015 to SEQ ID NO: 1044), M (SEQ ID: 1246. Table 6: SEQ ID NO: 954 to SEQ ID NO: 1014), ORF-6 (SEQ ID: 1247. Table 9: SEQ ID NO: 1113 to SEQ ID NO: 1125), N/NC (SEQ ID NO: 1251: SEQ ID NO: 237 to SEQ ID NO: 280), ORF-7a (SEQ ID: 1248. Table 10: SEQ ID NO: 1126 to SEQ ID NO: 1135), ORF-7b (SEQ ID: 1249), ORF-8 (SEQ ID: 1250, Table 11: SEQ ID NO: 1136 to SEQ ID NO: 1174), nucleocapsid (NC) (SEQ ID: 1251).

The CTL Nonameric Epitopes of the open reading frame proteins are enlisted in Table 1 to Table 11 as follows,

TABLE 1

RDRP

| Allele | Sequence ID No. | Sequence Start | Annotation | Length | Sequence | Score | Percentile_rank |
|---|---|---|---|---|---|---|---|
| HLA-A*01:01 | 396 | 450 | RDRP A1.01_450 | 9 | ISDYDYYRY | 0.987873 | 0.01 |
| HLA-A*01:01 | 397 | 738 | RDRP A1.01_738 | 9 | DTDFVNEFY | 0.987646 | 0.01 |
| HLA-A*01:01 | 398 | 907 | RDRP A1.01_907 | 9 | LTNDNTSRY | 0.973398 | 0.01 |
| HLA-A*01:01 | 399 | 475 | RDRP A1.01_475 | 9 | VVDKYFDCY | 0.93711 | 0.02 |
| HLA-A*01:01 | 400 | 681 | RDRP A1.01_681 | 9 | SSGDATTAY | 0.855722 | 0.05 |
| HLA-A*01:01 | 401 | 895 | RDRP A1.01_895 | 9 | LTGHMLDMY | 0.666481 | 0.1 |
| HLA-A*01:01 | 402 | 869 | RDRP A1.01_869 | 9 | LTKHPNQEY | 0.648646 | 0.11 |
| HLA-A*01:01 | 403 | 366 | RDRP A1.01_366 | 9 | LSFKELLVY | 0.62167 | 0.13 |
| HLA-A*01:01 | 404 | 758 | RDRP A1.01_758 | 9 | LSDDAVVCF | 0.574853 | 0.15 |
| HLA-A*01:01 | 405 | 877 | RDRP A1.01_877 | 9 | YADVFHLYL | 0.452167 | 0.23 |
| HLA-A*01:01 | 406 | 209 | RDRP A1.01_209 | 9 | NQDLNGNWY | 0.448436 | 0.23 |
| HLA-A*01:01 | 407 | 606 | RDRP A1.01_606 | 9 | YSDVENPHL | 0.443161 | 0.23 |
| HLA-A*01:01 | 408 | 27 | RDRP A1.01_27 | 9 | STDVVYRAF | 0.44026 | 0.24 |
| HLA-A*01:01 | 409 | 471 | RDRP A1.01_471 | 9 | FVVEVVDKY | 0.431406 | 0.24 |
| HLA-A*01:01 | 410 | 538 | RDRP A1.01_538 | 9 | TITQMNLKY | 0.388855 | 0.28 |
| HLA-A*01:01 | 411 | 859 | RDRP A1.01_859 | 9 | FVSLAIDAY | 0.361526 | 0.3 |
| HLA-A*01:01 | 412 | 448 | RDRP A1.01_448 | 9 | AAISDYDYY | 0.35683 | 0.3 |
| HLA-A*01:01 | 413 | 281 | RDRP A1.01_281 | 9 | KLFDRYFKY | 0.336405 | 0.32 |
| HLA-A*02:01 | 414 | 123 | RDRP A2.01_123 | 9 | TMADLVYAL | 0.933263 | 0.03 |
| HLA-A*02:01 | 415 | 854 | RDRP A2.01_854 | 9 | LMIERFVSL | 0.906906 | 0.03 |
| HLA-A*02:01 | 416 | 334 | RDRP A2.01_334 | 9 | FVDGVPFVV | 0.902701 | 0.03 |
| HLA-A*02:01 | 417 | 64 | RDRP A2.01_64 | 9 | NLIDSYFVV | 0.822701 | 0.07 |
| HLA-A*02:01 | 418 | 239 | RDRP A2.01_239 | 9 | SLLMPILTL | 0.793618 | 0.08 |
| HLA-A*02:01 | 419 | 741 | RDRP A2.01_741 | 9 | FVNEFYAYL | 0.760859 | 0.1 |
| HLA-A*02:01 | 420 | 899 | RDRP A2.01_899 | 9 | MLDMYSVML | 0.701191 | 0.13 |
| HLA-A*02:01 | 421 | 654 | RDRP A2.01_654 | 9 | RLANECAQV | 0.659383 | 0.15 |
| HLA-A*02:01 | 422 | 467 | RDRP A2.01_467 | 9 | RQLLFVVEV | 0.65728 | 0.16 |
| HLA-A*02:01 | 423 | 88 | RDRP A2.01_88 | 9 | NLLKDCPAV | 0.553623 | 0.23 |
| HLA-A*02:01 | 424 | 240 | RDRP A2.01_240 | 9 | LLMPILTLT | 0.514208 | 0.26 |
| HLA-A*02:01 | 425 | 667 | RDRP A2.01_667 | 9 | VMCGGSLYV | 0.482022 | 0.27 |
| HLA-A*02:01 | 426 | 821 | RDRP A2.01_821 | 9 | KQGDDYVYL | 0.449688 | 0.32 |
| HLA-A*02:01 | 427 | 122 | RDRP A2.01_122 | 9 | YTMADLVYA | 0.448847 | 0.32 |
| HLA-A*02:01 | 428 | 647 | RDRP A2.01_647 | 9 | SLSHRFYRL | 0.438669 | 0.32 |
| HLA-A*02:01 | 429 | 365 | RDRP A2.01_365 | 9 | RLSFKELLV | 0.406213 | 0.35 |
| HLA-A*02:01 | 430 | 923 | RDRP A2.01_923 | 9 | AMYTPHTVL | 0.33343 | 0.48 |
| HLA-A*02:01 | 431 | 397 | RDRP A2.01_397 | 9 | SVAALTNNV | 0.322593 | 0.5 |
| HLA-A*02:01 | 432 | 307 | RDRP A2.01_307 | 9 | ILHCANFNV | 0.311923 | 0.53 |
| HLA-A*02:01 | 433 | 574 | RDRP A2.01_574 | 9 | KLLKSIAAT | 0.298377 | 0.56 |

TABLE 1-continued

RDRP

| Allele | Sequence ID No. | Sequence Start | Annotation | Length | Sequence | Score | Percentile_rank |
|---|---|---|---|---|---|---|---|
| HLA-A*03:01 | 434 | 281 | RDRP_A3.01_281 | 9 | KLFDRYFKY | 0.94431 | 0.02 |
| HLA-A*03:01 | 435 | 324 | RDRP_A3.01_324 | 9 | TSFGPLVRK | 0.940452 | 0.02 |
| HLA-A*03:01 | 436 | 500 | RDRP_A3.01_500 | 9 | KSAGFPFNK | 0.938515 | 0.02 |
| HLA-A*03:01 | 437 | 569 | RDRP_A3.01_569 | 9 | RQFHQKLLK | 0.936158 | 0.02 |
| HLA-A*03:01 | 438 | 513 | RDRP_A3.01_513 | 9 | RLYYDSMSY | 0.933607 | 0.02 |
| HLA-A*03:01 | 439 | 882 | RDRP_A3.01_882 | 9 | HLYLQYIRK | 0.930444 | 0.02 |
| HLA-A*03:01 | 440 | 863 | RDRP_A3.01_863 | 9 | AIDAYPLTK | 0.849649 | 0.05 |
| HLA-A*03:01 | 441 | 409 | RDRP_A3.01_409 | 9 | TVKPGNFNK | 0.830192 | 0.06 |
| HLA-A*03:01 | 442 | 95 | RDRP_A3.01_95 | 9 | AVAKHDFFK | 0.813978 | 0.07 |
| HLA-A*03:01 | 443 | 566 | RDRP_A3.01_566 | 9 | MTNRQFHQK | 0.779259 | 0.1 |
| HLA-A*03:01 | 444 | 173 | RDRP_A3.01_173 | 9 | RVYANLGER | 0.738206 | 0.14 |
| HLA-A*03:01 | 445 | 585 | RDRP_A3.01_585 | 9 | ATVVIGTSK | 0.724568 | 0.14 |
| HLA-A*03:01 | 446 | 113 | RDRP_A3.01_113 | 9 | HISRQRLTK | 0.710757 | 0.15 |
| HLA-A*03:01 | 447 | 775 | RDRP_A3.01_775 | 9 | LVASIKNFK | 0.669788 | 0.19 |
| HLA-A*03:01 | 448 | 33 | RDRP_A3.01_33 | 9 | RAFDIYNDK | 0.50112 | 0.33 |
| HLA-A*03:01 | 449 | 613 | RDRP_A3.01_613 | 9 | HLMGWDYPK | 0.486599 | 0.36 |
| HLA-A*03:01 | 450 | 706 | RDRP_A3.01_706 | 9 | ALLSTDGNK | 0.409837 | 0.47 |
| HLA-A*03:01 | 451 | 141 | RDRP_A3.01_141 | 9 | TLKEILVTY | 0.406267 | 0.47 |
| HLA-A*03:01 | 452 | 543 | RDRP_A3.01_543 | 9 | NLKYAISAK | 0.37021 | 0.53 |
| HLA-A*03:01 | 453 | 890 | RDRP_A3.01_890 | 9 | KLHDELTGH | 0.366656 | 0.53 |
| HLA-A*03:01 | 454 | 632 | RDRP_A3.01_632 | 9 | IMASLVLAR | 0.361638 | 0.54 |
| HLA-A*03:01 | 455 | 65 | RDRP_A3.01_65 | 9 | LIDSYFVVK | 0.336463 | 0.59 |
| HLA-A*24:02 | 456 | 37 | RDRP_A24.02_37 | 9 | IYNDKVAGF | 0.947951 | 0.01 |
| HLA-A*24:02 | 457 | 883 | RDRP_A24.02_883 | 9 | LYLQYIRKL | 0.838016 | 0.04 |
| HLA-A*24:02 | 458 | 688 | RDRP_A24.02_688 | 9 | AYANSVFNI | 0.809659 | 0.06 |
| HLA-A*24:02 | 459 | 69 | RDRP_A24.02_69 | 9 | YFVVKRHTF | 0.807841 | 0.06 |
| HLA-A*24:02 | 460 | 876 | RDRP_A24.02_876 | 9 | EYADVFHLY | 0.790376 | 0.06 |
| HLA-A*24:02 | 461 | 745 | RDRP_A24.02_745 | 9 | FYAYLRKHF | 0.687371 | 0.11 |
| HLA-A*24:02 | 462 | 747 | RDRP_A24.02_747 | 9 | AYLRKHFSM | 0.651172 | 0.13 |
| HLA-A*24:02 | 463 | 520 | RDRP_A24.02_520 | 9 | SYEDQDALF | 0.62922 | 0.13 |
| HLA-A*24:02 | 464 | 594 | RDRP_A24.02_594 | 9 | FYGGWHNML | 0.610031 | 0.14 |
| HLA-A*24:02 | 465 | 593 | RDRP_A24.02_593 | 9 | KFYGGWHNM | 0.606663 | 0.14 |
| HLA-A*24:02 | 466 | 455 | RDRP_A24.02_455 | 9 | YYRYNLPTM | 0.599652 | 0.15 |
| HLA-A*24:02 | 467 | 414 | RDRP_A24.02_414 | 9 | NFNKDFYDF | 0.560985 | 0.16 |
| HLA-A*24:02 | 468 | 786 | RDRP_A24.02_786 | 9 | LYYQNNVFM | 0.542169 | 0.18 |
| HLA-A*24:02 | 469 | 237 | RDRP_A24.02_237 | 9 | YYSLLMPIL | 0.539305 | 0.18 |
| HLA-A*24:02 | 470 | 325 | RDRP_A24.02_325 | 9 | SFGPLVRKI | 0.471972 | 0.21 |

TABLE 1-continued

RDRP

| Allele | Sequence ID No. | Sequence Start | Annotation | Length | Sequence | Score | Percentile_rank |
|---|---|---|---|---|---|---|---|
| HLA-A*24:02 | 471 | 174 | RDRP_A24.02_174 | 9 | VYANLGERV | 0.450562 | 0.22 |
| HLA-A*24:02 | 472 | 830 | RDRP_A24.02_830 | 9 | PYPDPSRIL | 0.445807 | 0.23 |
| HLA-A*24:02 | 473 | 236 | RDRP_A24.02_236 | 9 | SYYSLLMPI | 0.406355 | 0.26 |
| HLA-A*24:02 | 474 | 267 | RDRP_A24.02_267 | 9 | KWDLLKYDF | 0.357142 | 0.29 |
| HLA-A*24:02 | 475 | 272 | RDRP_A24.02_272 | 9 | KYDFTEERL | 0.340771 | 0.31 |
| HLA-A*26:01 | 476 | 471 | RDRP_A26.01_471 | 9 | FVVEVVDKY | 0.974688 | 0.01 |
| HLA-A*26:01 | 477 | 534 | RDRP_A26.01_534 | 9 | NVIPTITQM | 0.958845 | 0.01 |
| HLA-A*26:01 | 478 | 879 | RDRP_A26.01_879 | 9 | DVFHLYLQY | 0.93494 | 0.01 |
| HLA-A*26:01 | 479 | 141 | RDRP_A26.01_141 | 9 | TLKEILVTY | 0.786238 | 0.04 |
| HLA-A*26:01 | 480 | 907 | RDRP_A26.01_907 | 9 | LINDNTSRY | 0.775465 | 0.05 |
| HLA-A*26:01 | 481 | 318 | RDRP_A26.01_318 | 9 | STVFPPTSF | 0.717593 | 0.06 |
| HLA-A*26:01 | 482 | 587 | RDRP_A26.01_587 | 9 | VVIGTSKFY | 0.686358 | 0.06 |
| HLA-A*26:01 | 483 | 586 | RDRP_A26.01_586 | 9 | TVVIGTSKF | 0.685805 | 0.06 |
| HLA-A*26:01 | 484 | 876 | RDRP_A26.01_876 | 9 | EYADVFHLY | 0.648839 | 0.07 |
| HLA-A*26:01 | 485 | 265 | RDRP_A26.01_265 | 9 | YIKWDLLKY | 0.592281 | 0.08 |
| HLA-A*26:01 | 486 | 666 | RDRP_A26.01_666 | 9 | MVMCGGSLY | 0.528754 | 0.1 |
| HLA-A*26:01 | 487 | 340 | RDRP_A26.01_340 | 9 | FVVSTGYHF | 0.528092 | 0.1 |
| HLA-A*26:01 | 488 | 859 | RDRP_A26.01_859 | 9 | FVSLAIDAY | 0.517477 | 0.11 |
| HLA-A*26:01 | 489 | 167 | RDRP_A26.01_167 | 9 | ENPDILRVY | 0.468802 | 0.13 |
| HLA-A*26:01 | 490 | 869 | RDRP_A26.01_869 | 9 | LTKHPNQEY | 0.463446 | 0.13 |
| HLA-A*26:01 | 491 | 126 | RDRP_A26.01_126 | 9 | DLVYALRHF | 0.407151 | 0.17 |
| HLA-A*26:01 | 492 | 762 | RDRP_A26.01_762 | 9 | AVVCFNSTY | 0.379217 | 0.19 |
| HLA-A*26:01 | 493 | 538 | RDRP_A26.01_538 | 9 | TITQMNLKY | 0.372912 | 0.19 |
| HLA-A*26:01 | 494 | 738 | RDRP_A26.01_738 | 9 | DTDFVNEFY | 0.360999 | 0.2 |
| HLA-A*26:01 | 495 | 686 | RDRP_A26.01_686 | 9 | TTAYANSVF | 0.353076 | 0.21 |
| HLA-A*26:01 | 496 | 741 | RDRP_A26.01_741 | 9 | FVNEFYAYL | 0.325335 | 0.22 |
| HLA-A*26:01 | 497 | 358 | RDRP_A26.01_358 | 9 | DVNLHSSRL | 0.307842 | 0.24 |
| HLA-B*07:02 | 498 | 111 | RDRP_B07.02_111 | 9 | VPHISRQRL | 0.97802 | 0.02 |
| HLA-B*07:02 | 499 | 263 | RDRP_B07.02_263 | 9 | KPYIKWDLL | 0.713089 | 0.12 |
| HLA-B*07:02 | 500 | 536 | RDRP_B07.02_536 | 9 | IPTITQMNL | 0.663521 | 0.14 |
| HLA-B*07:02 | 501 | 829 | RDRP_B07.02_829 | 9 | LPYPDPSRI | 0.562533 | 0.2 |
| HLA-B*07:02 | 502 | 321 | RDRP_B07.02_321 | 9 | FPPTSFGPL | 0.535352 | 0.21 |
| HLA-B*07:02 | 503 | 226 | RDRP_B07.02_226 | 9 | TPGSGVPVV | 0.376591 | 0.37 |
| HLA-B*07:02 | 504 | 778 | RDRP_B07.02_778 | 9 | SIKNFKSVL | 0.343102 | 0.42 |
| HLA-B*07:02 | 505 | 887 | RDRP_B07.02_887 | 9 | YIRKLHDEL | 0.34074 | 0.43 |
| HLA-B*07:02 | 506 | 626 | RDRP_B07.02_626 | 9 | MPNMLRIMA | 0.334597 | 0.43 |
| HLA-B*07:02 | 507 | 719 | RDRP_B07.02_719 | 9 | YVRNLQHRL | 0.320658 | 0.45 |
| HLA-B*15:01 | 508 | 141 | RDRP_B15.01_141 | 9 | TLKEILVTY | 0.974655 | 0.01 |

TABLE 1-continued

RDRP

| Allele | Sequence ID No. | Sequence Start | Annotation | Length | Sequence | Score | Percentile_rank |
|---|---|---|---|---|---|---|---|
| HLA-B*15:01 | 509 | 513 | RDRP_B15.01_513 | 9 | RLYYDSMSY | 0.97292 | 0.01 |
| HLA-B*15:01 | 510 | 869 | RDRP_B15.01_869 | 9 | LTKHPNQEY | 0.858889 | 0.03 |
| HLA-B*15:01 | 511 | 785 | RDRP_B15.01_785 | 9 | VLYYQNNVF | 0.836058 | 0.05 |
| HLA-B*15:01 | 512 | 281 | RDRP_B15.01_281 | 9 | KLFDRYFKY | 0.826664 | 0.05 |
| HLA-B*15:01 | 513 | 360 | RDRP_B15.01_360 | 9 | NLHSSRLSF | 0.761224 | 0.09 |
| HLA-B*15:01 | 514 | 265 | RDRP_B15.01_265 | 9 | YIKWDLLKY | 0.757898 | 0.1 |
| HLA-B*15:01 | 515 | 318 | RDRP_B15.01_318 | 9 | STVFPPTSF | 0.735881 | 0.11 |
| HLA-B*15:01 | 516 | 116 | RDRP_B15.01_116 | 9 | RQRLTKYTM | 0.712443 | 0.12 |
| HLA-B*15:01 | 517 | 587 | RDRP_B15.01_587 | 9 | VVIGTSKFY | 0.70216 | 0.13 |
| HLA-B*15:01 | 518 | 923 | RDRP_B15.01_923 | 9 | AMYTPHTVL | 0.694507 | 0.13 |
| HLA-B*15:01 | 519 | 366 | RDRP_B15.01_366 | 9 | LSFKELLVY | 0.692667 | 0.14 |
| HLA-B*15:01 | 520 | 471 | RDRP_B15.01_471 | 9 | FVVEVVDKY | 0.666634 | 0.16 |
| HLA-B*15:01 | 521 | 660 | RDRP_B15.01_660 | 9 | AQVLSEMVM | 0.660662 | 0.17 |
| HLA-B*15:01 | 522 | 279 | RDRP_B15.01_279 | 9 | RLKLFDRYF | 0.629707 | 0.19 |
| HLA-B*15:01 | 523 | 332 | RDRP_B15.01_332 | 9 | KIFVDGVPF | 0.609134 | 0.21 |
| HLA-B*15:01 | 524 | 907 | RDRP_B15.01_907 | 9 | LINDNTSRY | 0.597212 | 0.21 |
| HLA-B*15:01 | 525 | 681 | RDRP_B15.01_681 | 9 | SSGDATTAY | 0.555694 | 0.24 |
| HLA-B*15:01 | 526 | 340 | RDRP_B15.01_340 | 9 | FVVSTGYHF | 0.544647 | 0.25 |
| HLA-B*15:01 | 527 | 30 | RDRP_B15.01_30 | 9 | VVYRAFDIY | 0.533353 | 0.26 |
| HLA-B*15:01 | 528 | 774 | RDRP_B15.01_774 | 9 | GLVASIKNF | 0.529503 | 0.26 |
| HLA-B*15:01 | 529 | 762 | RDRP_B15.01_762 | 9 | AVVCFNSTY | 0.512271 | 0.28 |
| HLA-B*15:01 | 530 | 586 | RDRP_B15.01_586 | 9 | TVVIGTSKF | 0.511355 | 0.29 |
| HLA-B*15:01 | 531 | 114 | RDRP_B15.01_114 | 9 | ISRQRLTKY | 0.505383 | 0.29 |
| HLA-B*15:01 | 532 | 229 | RDRP_B15.01_229 | 9 | SGVPVVDSY | 0.469878 | 0.33 |
| HLA-B*15:01 | 533 | 666 | RDRP_B15.01_666 | 9 | MVMCGGSLY | 0.463589 | 0.34 |
| HLA-B*15:01 | 534 | 859 | RDRP_B15.01_859 | 9 | FVSLAIDAY | 0.44269 | 0.39 |
| HLA-B*15:01 | 535 | 748 | RDRP_B15.01_748 | 9 | YLRKHFSMM | 0.442028 | 0.39 |
| HLA-B*15:01 | 536 | 854 | RDRP_B15.01_854 | 9 | LMIERFVSL | 0.415997 | 0.41 |
| HLA-B*15:01 | 537 | 407 | RDRP_B15.01_407 | 9 | FQTVKPGNF | 0.413296 | 0.42 |
| HLA-B*15:01 | 538 | 534 | RDRP_B15.01_534 | 9 | NVIPTITQM | 0.392871 | 0.44 |
| HLA-B*15:01 | 539 | 847 | RDRP_B15.01_847 | 9 | IVKTDGTLM | 0.37484 | 0.47 |
| HLA-B*15:01 | 540 | 780 | RDRP_B15.01_780 | 9 | KNFKSVLYY | 0.347435 | 0.52 |
| HLA-B*15:01 | 541 | 538 | RDRP_B15.01_538 | 9 | TITQMNLKY | 0.347019 | 0.52 |
| HLA-B*15:01 | 542 | 286 | RDRP_B15.01_286 | 9 | YFKYWDQTY | 0.319992 | 0.59 |
| HLA-B*15:01 | 543 | 818 | RDRP_B15.01_818 | 9 | MLVKQGDDY | 0.315119 | 0.59 |
| HLA-B*15:01 | 544 | 898 | RDRP_B15.01_898 | 9 | HMLDMYSVM | 0.306896 | 0.62 |
| HLA-B*40:01 | 545 | 875 | RDRP_B40.01_875 | 9 | QEYADVFHL | 0.976681 | 0.01 |

TABLE 1-continued

RDRP

| Allele | Sequence ID No. | Sequence Start | Annotation | Length | Sequence | Score | Percentile_rank |
|---|---|---|---|---|---|---|---|
| HLA-B*40:01 | 546 | 82 | RDRP_B40.01_82 | 9 | HEETIYNLL | 0.948908 | 0.04 |
| HLA-B*40:01 | 547 | 810 | RDRP_B40.01_810 | 9 | HEFCSQHTM | 0.927691 | 0.05 |
| HLA-B*40:01 | 548 | 253 | RDRP_B40.01_253 | 9 | AESHVDTDL | 0.90571 | 0.06 |
| HLA-B*40:01 | 549 | 166 | RDRP_B40.01_166 | 9 | VENPDILRV | 0.652113 | 0.18 |
| HLA-B*40:01 | 550 | 57 | RDRP_B40.01_57 | 9 | QEKDEDDNL | 0.623482 | 0.2 |
| HLA-B*40:01 | 551 | 916 | RDRP_B40.01_916 | 9 | WEPEFYEAM | 0.388761 | 0.39 |
| HLA-B*40:01 | 552 | 179 | RDRP_B40.01_179 | 9 | GERVRQALL | 0.365028 | 0.41 |
| HLA-B*58:01 | 553 | 501 | RDRP_B58.01_501 | 9 | SAGFPFNKW | 0.902772 | 0.06 |
| HLA-B*58:01 | 554 | 433 | RDRP_B58.01_433 | 9 | SSVELKHFF | 0.89824 | 0.06 |
| HLA-B*58:01 | 555 | 366 | RDRP_B58.01_366 | 9 | LSFKELLVY | 0.853406 | 0.09 |
| HLA-B*58:01 | 556 | 96 | RDRP_B58.01_96 | 9 | VAKHDFFKF | 0.656886 | 0.21 |
| HLA-B*58:01 | 557 | 624 | RDRP_B58.01_624 | 9 | RAMPNMLRI | 0.631663 | 0.23 |
| HLA-B*58:01 | 558 | 318 | RDRP_B58.01_318 | 9 | STVFPPTSF | 0.630451 | 0.23 |
| HLA-B*58:01 | 559 | 590 | RDRP_B58.01_590 | 9 | GTSKFYGGW | 0.619113 | 0.24 |
| HLA-B*58:01 | 560 | 184 | RDRP_B58.01_184 | 9 | QALLKTVQF | 0.512542 | 0.31 |
| HLA-B*58:01 | 561 | 432 | RDRP_B58.01_432 | 9 | GSSVELKHF | 0.487645 | 0.33 |
| HLA-B*58:01 | 562 | 908 | RDRP_B58.01_908 | 9 | TNDNTSRYW | 0.443616 | 0.38 |
| HLA-B*58:01 | 563 | 758 | RDRP_B58.01_758 | 9 | LSDDAVVCF | 0.431197 | 0.38 |
| HLA-B*58:01 | 564 | 27 | RDRP_B58.01_27 | 9 | STDVVYRAF | 0.417409 | 0.4 |
| HLA-B*58:01 | 565 | 780 | RDRP_B58.01_780 | 9 | KNFKSVLYY | 0.382597 | 0.42 |
| HLA-B*58:01 | 566 | 609 | RDRP_B58.01_609 | 9 | VENPHLMGW | 0.366443 | 0.44 |
| HLA-B*58:01 | 567 | 281 | RDRP_B58.01_281 | 9 | KLFDRYFKY | 0.35087 | 0.47 |
| HLA-B*58:01 | 568 | 907 | RDRP_B58.01_907 | 9 | LINDNTSRY | 0.34387 | 0.48 |
| HLA-B*58:01 | 569 | 869 | RDRP_B58.01_869 | 9 | LTKHPNQEY | 0.341203 | 0.49 |
| HLA-B*58:01 | 570 | 450 | RDRP_B58.01_450 | 9 | ISDYDYYRY | 0.329408 | 0.51 |
| HLA-B*58:01 | 571 | 563 | RDRP_B58.01_563 | 9 | CSTMTNRQF | 0.302352 | 0.55 |

TABLE 2

Helicase

| Allele | Sequence ID No. | Start | Sequence Annotation | Length | Sequence | Score | Percentile_rank |
|---|---|---|---|---|---|---|---|
| HLA-A*01:01 | 572 | 56 | Heli_A1.01_56 | 9 | DVTDVTQLY | 0.673792 | 0.1 |
| HLA-A*01:01 | 573 | 57 | Heli_A1.01_57 | 9 | VTDVTQLYL | 0.669117 | 0.1 |
| HLA-A*01:01 | 574 | 535 | Heli_A1.01_535 | 9 | SSQGSEYDY | 0.659933 | 0.1 |
| HLA-A*01:01 | 575 | 347 | Heli_A1.01_347 | 9 | KVNSTLEQY | 0.456717 | 0.22 |
| HLA-A*01:01 | 576 | 291 | Heli_A1.01_291 | 9 | FAIGLALYY | 0.42898 | 0.25 |
| HLA-A*01:01 | 577 | 238 | Heli_A1.01_238 | 9 | PTLVPQEHY | 0.38219 | 0.29 |
| HLA-A*01:01 | 578 | 316 | Heli_A1.01_316 | 9 | ALCEKALKY | 0.366728 | 0.29 |

TABLE 2-continued

Helicase

| Allele | Sequence ID No. | Start | Sequence Annotation | Length | Sequence | Score | Percentile_rank |
|---|---|---|---|---|---|---|---|
| HLA-A*01:01 | 579 | 533 | Heli A1.01_533 | 9 | VDSSQGSEY | 0.350748 | 0.31 |
| HLA-A*01:01 | 580 | 209 | Heli A1.01_209 | 9 | VVYRGTTTY | 0.337049 | 0.32 |
| HLA-A*01:01 | 581 | 258 | Heli A1.01_258 | 9 | ISDEFSSNV | 0.334115 | 0.32 |
| HLA-A*01:01 | 582 | 141 | Heli A1.01_141 | 9 | TEETFKLSY | 0.286378 | 0.39 |
| HLA-A*01:01 | 583 | 62 | Heli A1.01_62 | 9 | QLYLGGMSY | 0.265626 | 0.43 |
| HLA-A*01:01 | 584 | 190 | Heli A1.01_190 | 9 | NSKVQIGEY | 0.257774 | 0.44 |
| HLA-A*01:01 | 585 | 574 | Heli A1.01_574 | 9 | CIMSDRDLY | 0.192125 | 0.56 |
| HLA-A*01:01 | 586 | 468 | Heli A1.01_468 | 9 | SAQCFKMFY | 0.164928 | 0.64 |
| HLA-A*02:01 | 587 | 239 | Heli A2.01_239 | 9 | TLVPQEHYV | 0.94681 | 0.02 |
| HLA-A*02:01 | 588 | 146 | Heli A2.01_146 | 9 | KLSYGIATV | 0.89166 | 0.03 |
| HLA-A*02:01 | 589 | 157 | Heli A2.01_157 | 9 | VLSDRELHL | 0.834765 | 0.06 |
| HLA-A*02:01 | 590 | 525 | Heli A2.01_525 | 9 | ILGLPTQTV | 0.699124 | 0.13 |
| HLA-A*02:01 | 591 | 218 | Heli A2.01_218 | 9 | KLNVGDYFV | 0.692351 | 0.14 |
| HLA-A*02:01 | 592 | 41 | Heli A2.01_41 | 9 | LVLSVNPYV | 0.641882 | 0.17 |
| HLA-A*02:01 | 593 | 520 | Heli A2.01_520 | 9 | AVASKILGL | 0.445682 | 0.32 |
| HLA-A*02:01 | 594 | 448 | Heli A2.01_448 | 9 | IVDTVSALV | 0.413249 | 0.35 |
| HLA-A*02:01 | 595 | 371 | Heli A2.01_371 | 9 | VVFDEISMA | 0.359348 | 0.43 |
| HLA-A*02:01 | 596 | 296 | Heli A2.01_296 | 9 | ALYYPSARI | 0.320686 | 0.51 |
| HLA-A*02:01 | 597 | 248 | Heli A2.01_248 | 9 | RITGLYPTL | 0.319478 | 0.51 |
| HLA-A*02:01 | 598 | 294 | Heli A2.01_294 | 9 | GLALYYPSA | 0.314282 | 0.52 |
| HLA-A*02:01 | 599 | 403 | Heli A2.01_403 | 9 | AQLPAPRTL | 0.313863 | 0.52 |
| HLA-A*02:01 | 600 | 584 | Heli A2.01_584 | 9 | KLQFTSLEI | 0.28788 | 0.57 |
| HLA-A*02:01 | 601 | 232 | Heli A2.01_232 | 9 | VMPLSAPTL | 0.262038 | 0.62 |
| HLA-A*02:01 | 602 | 6 | Heli A2.01_6 | 9 | VLCNSQTSL | 0.260918 | 0.62 |
| HLA-A*02:01 | 603 | 362 | Heli A2.01_362 | 9 | ALPETTADI | 0.257268 | 0.63 |
| HLA-A*02:01 | 604 | 33 | Heli A2.01_33 | 9 | HVISTSHKL | 0.232777 | 0.7 |
| HLA-A*02:01 | 605 | 258 | Heli A2.01_258 | 9 | ISDEFSSNV | 0.208091 | 0.76 |
| HLA-A*02:01 | 606 | 430 | Heli A2.01_430 | 9 | KTIGPDMFL | 0.185051 | 0.86 |
| HLA-A*02:01 | 607 | 487 | Heli A2.01_487 | 9 | AINRPQIGV | 0.185002 | 0.86 |
| HLA-A*02:01 | 608 | 332 | Heli A2.01_332 | 9 | RIIPARARV | 0.163014 | 0.97 |
| HLA-A*03:01 | 609 | 131 | Heli A3.01_131 | 9 | KLFAAETLK | 0.957259 | 0.01 |
| HLA-A*03:01 | 610 | 209 | Heli A3.01_209 | 9 | VVYRGTTTY | 0.827356 | 0.06 |
| HLA-A*03:01 | 611 | 386 | Heli A3.01_386 | 9 | VVNARLRAK | 0.776827 | 0.11 |
| HLA-A*03:01 | 612 | 321 | Heli A3.01_321 | 9 | ALKYLPIDK | 0.742179 | 0.14 |
| HLA-A*03:01 | 613 | 62 | Heli A3.01_62 | 9 | QLYLGGMSY | 0.676025 | 0.18 |
| HLA-A*03:01 | 614 | 347 | Heli A3.01_347 | 9 | KVNSTLEQY | 0.65183 | 0.2 |
| HLA-A*03:01 | 615 | 500 | Heli A3.01_500 | 9 | LTRNPAWRK | 0.619996 | 0.23 |

TABLE 2-continued

Helicase

| Allele | Sequence ID No. | Start | Sequence Annotation | Length | Sequence | Score | Percentile_rank |
|---|---|---|---|---|---|---|---|
| HLA-A*03:01 | 616 | 316 | Heli A3.01_316 | 9 | ALCEKALKY | 0.589629 | 0.26 |
| HLA-A*03:01 | 617 | 469 | Heli A3.01_469 | 9 | AQCFKMFYK | 0.549939 | 0.29 |
| HLA-A*03:01 | 618 | 280 | Heli A3.01_280 | 9 | LQGPPGTGK | 0.501505 | 0.33 |
| HLA-A*03:01 | 619 | 68 | Heli A3.01_68 | 9 | MSYYCKSHK | 0.484421 | 0.36 |
| HLA-A*03:01 | 620 | 194 | Heli A3.01_194 | 9 | QIGEYTFEK | 0.39373 | 0.49 |
| HLA-A*03:01 | 621 | 390 | Heli A3.01_390 | 9 | RLRAKHYVY | 0.333977 | 0.59 |
| HLA-A*03:01 | 622 | 263 | Heli A3.01_263 | 9 | SSNVANYQK | 0.328995 | 0.6 |
| HLA-A*03:01 | 623 | 454 | Heli A3.01_454 | 9 | ALVYDNKLK | 0.228612 | 0.84 |
| HLA-A*03:01 | 624 | 147 | Heli A3.01_147 | 9 | LSYGIATVR | 0.183323 | 0.99 |
| HLA-A*24:02 | 625 | 397 | Heli A24.02_397 | 9 | VYIGDPAQL | 0.913596 | 0.02 |
| HLA-A*24:02 | 626 | 420 | Heli A24.02_420 | 9 | EYFNSVCRL | 0.465424 | 0.21 |
| HLA-A*24:02 | 627 | 298 | Heli A24.02_298 | 9 | YYPSARIVY | 0.400243 | 0.26 |
| HLA-A*24:02 | 628 | 297 | Heli A24.02_297 | 9 | LYYPSARIV | 0.334529 | 0.32 |
| HLA-A*24:02 | 629 | 232 | Heli A24.02_232 | 9 | VMPLSAPTL | 0.311964 | 0.33 |
| HLA-A*24:02 | 630 | 192 | Heli A24.02_192 | 9 | KVQIGEYTF | 0.301849 | 0.34 |
| HLA-A*24:02 | 631 | 73 | Heli A24.02_73 | 9 | KSHKPPISF | 0.255341 | 0.4 |
| HLA-A*24:02 | 632 | 179 | Heli A24.02_179 | 9 | NYVFTGYRV | 0.209981 | 0.47 |
| HLA-A*24:02 | 633 | 63 | Heli A24.02_63 | 9 | LYLGGMSYY | 0.191939 | 0.52 |
| HLA-A*24:02 | 634 | 498 | Heli A24.02_498 | 9 | EFLTRNPAW | 0.177523 | 0.55 |
| HLA-A*24:02 | 635 | 224 | Heli A24.02_224 | 9 | YFVLTSHTV | 0.161541 | 0.6 |
| HLA-A*26:01 | 636 | 56 | Heli A26.01_56 | 9 | DVTDVTQLY | 0.981717 | 0.01 |
| HLA-A*26:01 | 637 | 447 | Heli A26.01_447 | 9 | EIVDTVSAL | 0.866408 | 0.03 |
| HLA-A*26:01 | 638 | 365 | Heli A26.01_365 | 9 | ETTADIVVF | 0.69931 | 0.06 |
| HLA-A*26:01 | 639 | 209 | Heli A26.01_209 | 9 | VVYRGTTTY | 0.665769 | 0.06 |
| HLA-A*26:01 | 640 | 291 | Heli A26.01_291 | 9 | FAIGLALYY | 0.65294 | 0.07 |
| HLA-A*26:01 | 641 | 33 | Heli A26.01_33 | 9 | HVISTSHKL | 0.577552 | 0.09 |
| HLA-A*26:01 | 642 | 261 | Heli A26.01_261 | 9 | EFSSNVANY | 0.365121 | 0.2 |
| HLA-A*26:01 | 643 | 62 | Heli A26.01_62 | 9 | QLYLGGMSY | 0.348444 | 0.21 |
| HLA-A*26:01 | 644 | 347 | Heli A26.01_347 | 9 | KVNSTLEQY | 0.276517 | 0.27 |
| HLA-A*26:01 | 645 | 190 | Heli A26.01_190 | 9 | NSKVQIGEY | 0.274137 | 0.27 |
| HLA-A*26:01 | 646 | 143 | Heli A26.01_143 | 9 | ETFKLSYGI | 0.180406 | 0.41 |
| HLA-A*26:01 | 647 | 269 | Heli A26.01_269 | 9 | YQKVGMQKY | 0.163497 | 0.45 |
| HLA-A*26:01 | 648 | 290 | Heli A26.01_290 | 9 | HFAIGLALY | 0.160078 | 0.46 |
| HLA-B*07:02 | 649 | 592 | Heli B7.02_592 | 9 | IPRRNVATL | 0.991193 | 0.01 |
| HLA-B*07:02 | 650 | 513 | Heli B7.02_513 | 9 | SPYNSQNAV | 0.884275 | 0.05 |
| HLA-B*07:02 | 651 | 503 | Heli B7.02_503 | 9 | NPAWRKAVF | 0.856265 | 0.06 |
| HLA-B*07:02 | 652 | 334 | Heli B7.02_334 | 9 | IPARARVEC | 0.550566 | 0.21 |
| HLA-B*07:02 | 653 | 173 | Heli B7.02_173 | 9 | RPPLNRNYV | 0.548195 | 0.21 |

TABLE 2-continued

Helicase

| Allele | Sequence ID No. | Start | Sequence Annotation | Length | Sequence | Score | Percentile_rank |
|---|---|---|---|---|---|---|---|
| HLA-B*07:02 | 654 | 241 | Heli_B7.02_241 | 9 | VPQEHYVRI | 0.503526 | 0.24 |
| HLA-B*07:02 | 655 | 233 | Heli_B7.02_233 | 9 | MPLSAPTLV | 0.384993 | 0.35 |
| HLA-B*07:02 | 656 | 405 | Heli_B7.02_405 | 9 | LPAPRTLLT | 0.340578 | 0.43 |
| HLA-B*07:02 | 657 | 168 | Heli_B7.02_168 | 9 | EVGKPRPPL | 0.249123 | 0.57 |
| HLA-B*07:02 | 658 | 73 | Heli_B7.02_73 | 9 | KSHKPPISF | 0.2024 | 0.67 |
| HLA-B*07:02 | 659 | 325 | Heli_B7.02_325 | 9 | LPIDKCSRI | 0.200774 | 0.68 |
| HLA-B*07:02 | 660 | 407 | Heli_B7.02_407 | 9 | APRTLLTKG | 0.160167 | 0.82 |
| HLA-B*15:01 | 661 | 269 | Heli_B15.01_269 | 9 | YQKVGMQKY | 0.977243 | 0.01 |
| HLA-B*15:01 | 662 | 209 | Heli_B15.01_209 | 9 | VVYRGTTTY | 0.975234 | 0.01 |
| HLA-B*15:01 | 663 | 62 | Heli_B15.01_62 | 9 | QLYLGGMSY | 0.958133 | 0.01 |
| HLA-B*15:01 | 664 | 347 | Heli_B15.01_347 | 9 | KVNSTLEQY | 0.888728 | 0.03 |
| HLA-B*15:01 | 665 | 137 | Heli_B15.01_137 | 9 | TLKATEETF | 0.87839 | 0.03 |
| HLA-B*15:01 | 666 | 390 | Heli_B15.01_390 | 9 | RLRAKHYVY | 0.791589 | 0.08 |
| HLA-B*15:01 | 667 | 73 | Heli_B15.01_73 | 9 | KSHKPPISF | 0.769419 | 0.08 |
| HLA-B*15:01 | 668 | 403 | Heli_B15.01_403 | 9 | AQLPAPRTL | 0.767849 | 0.09 |
| HLA-B*15:01 | 669 | 40 | Heli_B15.01_40 | 9 | KLVLSVNPY | 0.722868 | 0.12 |
| HLA-B*15:01 | 670 | 316 | Heli_B15.01_316 | 9 | ALCEKALKY | 0.708448 | 0.13 |
| HLA-B*15:01 | 671 | 491 | Heli_B15.01_491 | 9 | PQIGVVREF | 0.447628 | 0.38 |
| HLA-B*15:01 | 672 | 291 | Heli_B15.01_291 | 9 | FAIGLALYY | 0.384168 | 0.44 |
| HLA-B*15:01 | 673 | 192 | Heli_B15.01_192 | 9 | KVQIGEYTF | 0.320994 | 0.59 |
| HLA-B*15:01 | 674 | 190 | Heli_B15.01_190 | 9 | NSKVQIGEY | 0.261432 | 0.74 |
| HLA-B*15:01 | 675 | 428 | Heli_B15.01_428 | 9 | LMKTIGPDM | 0.248093 | 0.77 |
| HLA-B*15:01 | 676 | 517 | Heli_B15.01_517 | 9 | SQNAVASKI | 0.207199 | 0.91 |
| HLA-B*15:01 | 677 | 225 | Heli_B15.01_225 | 9 | FVLTSHTVM | 0.202742 | 0.94 |
| HLA-B*15:01 | 678 | 33 | Heli_B15.01_33 | 9 | HVISTSHKL | 0.190861 | 0.98 |
| HLA-B*15:01 | 679 | 507 | Heli_B15.01_507 | 9 | RKAVFISPY | 0.179546 | 1.1 |
| HLA-B*40:01 | 680 | 155 | Heli_B40.01_155 | 9 | REVLSDREL | 0.952984 | 0.03 |
| HLA-B*40:01 | 681 | 161 | Heli_B40.01_161 | 9 | RELHLSWEV | 0.756562 | 0.13 |
| HLA-B*40:01 | 682 | 403 | Heli_B40.01_403 | 9 | AQLPAPRTL | 0.490454 | 0.28 |
| HLA-B*40:01 | 683 | 446 | Heli_B40.01_446 | 9 | AEIVDTVSA | 0.278573 | 0.49 |
| HLA-B*40:01 | 684 | 417 | Heli_B40.01_417 | 9 | LEPEYFNSV | 0.23923 | 0.56 |
| HLA-B*40:01 | 685 | 539 | Heli_B40.01_539 | 9 | SEYDYVIFT | 0.167767 | 0.72 |
| HLA-B*58:01 | 686 | 73 | Heli_B58.01_73 | 9 | KSHKPPISF | 0.972889 | 0.02 |
| HLA-B*58:01 | 687 | 467 | Heli_B58.01_467 | 9 | KSAQCFKMF | 0.67623 | 0.2 |
| HLA-B*58:01 | 688 | 347 | Heli_B58.01_347 | 9 | KVNSTLEQY | 0.629461 | 0.23 |
| HLA-B*58:01 | 689 | 192 | Heli_B58.01_192 | 9 | KVQIGEYTF | 0.628101 | 0.23 |
| HLA-B*58:01 | 690 | 430 | Heli_B58.01_430 | 9 | KTIGPDMFL | 0.560184 | 0.28 |

TABLE 2-continued

Helicase

| Allele | Sequence ID No. | Start | Sequence Annotation | Length | Sequence | Score | Percentile rank |
|---|---|---|---|---|---|---|---|
| HLA-B*58:01 | 691 | 139 | Heli_B58.01_139 | 9 | KATEETFKL | 0.505766 | 0.32 |
| HLA-B*58:01 | 692 | 209 | Heli_B58.01_209 | 9 | VVYRGTTTY | 0.495186 | 0.32 |
| HLA-B*58:01 | 693 | 291 | Heli_B58.01_291 | 9 | FAIGLALYY | 0.409308 | 0.4 |
| HLA-B*58:01 | 694 | 57 | Heli_B58.01_57 | 9 | VTDVTQLYL | 0.318403 | 0.53 |
| HLA-B*58:01 | 695 | 159 | Heli_B58.01_159 | 9 | SDRELHLSW | 0.274911 | 0.58 |
| HLA-B*58:01 | 696 | 35 | Heli_B58.01_35 | 9 | ISTSHKLVL | 0.267303 | 0.62 |
| HLA-B*58:01 | 697 | 349 | Heli_B58.01_349 | 9 | NSTLEQYVF | 0.267298 | 0.62 |
| HLA-B*58:01 | 698 | 365 | Heli_B58.01_365 | 9 | ETTADIVVF | 0.172291 | 0.87 |
| HLA-B*58:01 | 699 | 414 | Heli_B58.01_414 | 9 | KGTLEPEYF | 0.169262 | 0.88 |

TABLE 3

Exonuclease

| Allele | Sequence ID No. | Start | Sequence Annotation | Length | Sequence | Score | Rank |
|---|---|---|---|---|---|---|---|
| HLA-A*01:01 | 700 | 343 | ExNuc_A1.01_343 | 9 | QADVEWKFY | 0.845088 | 0.05 |
| HLA-A*01:01 | 701 | 362 | ExNuc_A1.01_362 | 9 | KIEELFYSY | 0.580712 | 0.15 |
| HLA-A*01:01 | 702 | 252 | ExNuc_A1.01_252 | 9 | NLQSNHDLY | 0.565641 | 0.16 |
| HLA-A*01:01 | 703 | 447 | ExNuc_A1.01_447 | 9 | YSDSPCESH | 0.529832 | 0.18 |
| HLA-A*01:01 | 704 | 229 | ExNuc_A1.01_229 | 9 | HSIGFDYVY | 0.411767 | 0.26 |
| HLA-A*01:01 | 705 | 322 | ExNuc_A1.01_322 | 9 | LADKFPVLH | 0.392505 | 0.28 |
| HLA-A*01:01 | 706 | 377 | ExNuc_A1.01_377 | 9 | FTDGVCLFW | 0.345315 | 0.31 |
| HLA-A*01:01 | 707 | 509 | ExNuc_A1.01_509 | 9 | WVYKQFDTY | 0.228543 | 0.5 |
| HLA-A*01:01 | 708 | 373 | ExNuc_A1.01_373 | 9 | HSDKFTDGV | 0.214528 | 0.51 |
| HLA-A*01:01 | 709 | 241 | ExNuc_A1.01_241 | 9 | MIDVQQWGF | 0.212108 | 0.51 |
| HLA-A*01:01 | 710 | 438 | ExNuc_A1.01_438 | 9 | NLKQLPFFY | 0.204092 | 0.54 |
| HLA-A*01:01 | 711 | 503 | ExNuc_A1.01_503 | 9 | SAGFSLWVY | 0.203487 | 0.54 |
| HLA-A*02:01 | 712 | 321 | ExNuc_A2.01_321 | 9 | LLADKFPVL | 0.936725 | 0.03 |
| HLA-A*02:01 | 713 | 176 | ExNuc_A2.01_176 | 9 | NLSDRVVFV | 0.931365 | 0.03 |
| HLA-A*02:01 | 714 | 184 | ExNuc_A2.01_184 | 9 | VLWAHGFEL | 0.920969 | 0.03 |
| HLA-A*02:01 | 715 | 494 | ExNuc_A2.01_494 | 9 | YLDAYNMMI | 0.909759 | 0.03 |
| HLA-A*02:01 | 716 | 169 | ExNuc_A2.01_169 | 9 | MLSDTLKNL | 0.760198 | 0.1 |
| HLA-A*02:01 | 717 | 320 | ExNuc_A2.01_320 | 9 | ALLADKFPV | 0.73306 | 0.11 |
| HLA-A*02:01 | 718 | 518 | ExNuc_A2.01_518 | 9 | NLWNTFTRL | 0.700692 | 0.13 |
| HLA-A*02:01 | 719 | 6 | ExNuc_A2.01_6 | 9 | GLFKDCSKV | 0.583242 | 0.21 |
| HLA-A*02:01 | 720 | 500 | ExNuc_A2.01_500 | 9 | MMISAGFSL | 0.447826 | 0.32 |
| HLA-A*02:01 | 721 | 107 | ExNuc_A2.01_107 | 9 | LQLGFSTGV | 0.431342 | 0.33 |
| HLA-A*02:01 | 722 | 21 | ExNuc_A2.01_21 | 9 | TQAPTHLSV | 0.428025 | 0.33 |
| HLA-A*02:01 | 723 | 156 | ExNuc_A2.01_156 | 9 | GLPWNVVRI | 0.2757 | 0.59 |

TABLE 3-continued

Exonuclease

| Allele | Sequence ID No. | Start | Sequence Annotation | Length | Sequence | Score | Rank |
|---|---|---|---|---|---|---|---|
| HLA-A*02:01 | 724 | 37 | ExNuc A2.01_37 | 9 | GLCVDIPGI | 0.249963 | 0.64 |
| HLA-A*02:01 | 725 | 492 | ExNuc A2.01_492 | 9 | RLYLDAYNM | 0.223591 | 0.72 |
| HLA-A*03:01 | 726 | 53 | ExNuc A3.01_53 | 9 | RLISMMGFK | 0.880959 | 0.04 |
| HLA-A*03:01 | 727 | 328 | ExNuc A3.01_328 | 9 | VLHDIGNPK | 0.784051 | 0.1 |
| HLA-A*03:01 | 728 | 56 | ExNuc A3.01_56 | 9 | SMMGFKMNY | 0.704771 | 0.15 |
| HLA-A*03:01 | 729 | 61 | ExNuc A3.01_61 | 9 | KMNYQVNGY | 0.513948 | 0.32 |
| HLA-A*03:01 | 730 | 504 | ExNuc A3.01_504 | 9 | AGFSLWVYK | 0.450184 | 0.41 |
| HLA-A*03:01 | 731 | 368 | ExNuc A3.01_368 | 9 | YSYATHSDK | 0.395871 | 0.49 |
| HLA-A*03:01 | 732 | 281 | ExNuc A3.01_281 | 9 | AVHECFVKR | 0.331708 | 0.59 |
| HLA-A*03:01 | 733 | 26 | ExNuc A3.01_26 | 9 | HLSVDTKFK | 0.321534 | 0.61 |
| HLA-A*03:01 | 734 | 39 | ExNuc A3.01_39 | 9 | CVDIPGIPK | 0.303197 | 0.65 |
| HLA-A*03:01 | 735 | 188 | ExNuc A3.01_188 | 9 | HGFELTSMK | 0.232477 | 0.84 |
| HLA-A*03:01 | 736 | 270 | ExNuc A3.01_270 | 9 | ASCDAIMTR | 0.215693 | 0.88 |
| HLA-A*03:01 | 737 | 192 | ExNuc A3.01_192 | 9 | LTSMKYFVK | 0.201816 | 0.92 |
| HLA-A*24:02 | 738 | 369 | ExNuc A24.02_369 | 9 | SYATHSDKF | 0.87261 | 0.04 |
| HLA-A*24:02 | 739 | 223 | ExNuc A24.02_223 | 9 | TYACWHHSI | 0.6881 | 0.11 |
| HLA-A*24:02 | 740 | 493 | ExNuc A24.02_493 | 9 | LYLDAYNMM | 0.66176 | 0.12 |
| HLA-A*24:02 | 741 | 376 | ExNuc A24.02_376 | 9 | KFTDGVCLF | 0.607745 | 0.14 |
| HLA-A*24:02 | 742 | 153 | ExNuc A24.02_153 | 9 | MYKGLPWNV | 0.521798 | 0.18 |
| HLA-A*24:02 | 743 | 182 | ExNuc A24.02_182 | 9 | VFVLWAHGF | 0.520171 | 0.18 |
| HLA-A*24:02 | 744 | 512 | ExNuc A24.02_512 | 9 | KQFDTYNLW | 0.459256 | 0.22 |
| HLA-A*24:02 | 745 | 234 | ExNuc A24.02_234 | 9 | DYVYNPFMI | 0.39123 | 0.26 |
| HLA-A*24:02 | 746 | 239 | ExNuc A24.02_239 | 9 | PFMIDVQQW | 0.358467 | 0.29 |
| HLA-A*24:02 | 747 | 236 | ExNuc A24.02_236 | 9 | VYNPFMIDV | 0.318057 | 0.33 |
| HLA-A*24:02 | 748 | 295 | ExNuc A24.02_295 | 9 | EYPIIGDEL | 0.311669 | 0.33 |
| HLA-A*24:02 | 749 | 359 | ExNuc A24.02_359 | 9 | KAYKIEELF | 0.202243 | 0.49 |
| HLA-A*24:02 | 750 | 50 | ExNuc A24.02_50 | 9 | TYRRLISMM | 0.192555 | 0.52 |
| HLA-A*24:02 | 751 | 423 | ExNuc A24.02_423 | 9 | KHAFHTPAF | 0.191351 | 0.52 |
| HLA-A*24:02 | 752 | 418 | ExNuc A24.02_418 | 9 | SLYVNKHAF | 0.187194 | 0.53 |
| HLA-A*26:01 | 753 | 515 | ExNuc A26.01_515 | 9 | DTYNLWNTF | 0.81449 | 0.04 |
| HLA-A*26:01 | 754 | 509 | ExNuc A26.01_509 | 9 | WVYKQFDIY | 0.625643 | 0.07 |
| HLA-A*26:01 | 755 | 116 | ExNuc A26.01_116 | 9 | NLVAVPTGY | 0.476247 | 0.12 |
| HLA-A*26:01 | 756 | 229 | ExNuc A26.01_229 | 9 | HSIGFDYVY | 0.445885 | 0.14 |
| HLA-A*26:01 | 757 | 49 | ExNuc A26.01_49 | 9 | MTYRRLISM | 0.441044 | 0.14 |
| HLA-A*26:01 | 758 | 65 | ExNuc A26.01_65 | 9 | QVNGYPNMF | 0.393098 | 0.18 |
| HLA-A*26:01 | 759 | 78 | ExNuc A26.01_78 | 9 | EAIRHVRAW | 0.358489 | 0.2 |
| HLA-A*26:01 | 760 | 56 | ExNuc A26.01_56 | 9 | SMMGFKMNY | 0.276548 | 0.27 |

TABLE 3-continued

Exonuclease

| Allele | Sequence ID No. | Start | Sequence Annotation | Length | Sequence | Score | Rank |
|---|---|---|---|---|---|---|---|
| HLA-A*26:01 | 761 | 438 | ExNuc A26.01_438 | 9 | NLKQLPFFY | 0.216819 | 0.34 |
| HLA-B*07:02 | 762 | 19 | ExNuc B07.02_19 | 9 | HPTQAPTHL | 0.944978 | 0.04 |
| HLA-B*07:02 | 763 | 428 | ExNuc B07.02_428 | 9 | TPAFDKSAF | 0.82409 | 0.07 |
| HLA-B*07:02 | 764 | 466 | ExNuc B07.02_466 | 9 | VPLKSATCI | 0.343923 | 0.42 |
| HLA-B*07:02 | 765 | 487 | ExNuc B07.02_487 | 9 | HANEYRLYL | 0.274952 | 0.51 |
| HLA-B*07:02 | 766 | 161 | ExNuc B07.02_161 | 9 | VVRIKIVQM | 0.268223 | 0.53 |
| HLA-B*07:02 | 767 | 411 | ExNuc B07.02_411 | 9 | LPGCDGGSL | 0.265949 | 0.53 |
| HLA-B*15:01 | 768 | 418 | ExNuc B15.01_418 | 9 | SLYVNKHAF | 0.837903 | 0.05 |
| HLA-B*15:01 | 769 | 56 | ExNuc B15.01_56 | 9 | SMMGFKMNY | 0.81477 | 0.06 |
| HLA-B*15:01 | 770 | 61 | ExNuc B15.01_61 | 9 | KMNYQVNGY | 0.771234 | 0.08 |
| HLA-B*15:01 | 771 | 509 | ExNuc B15.01_509 | 9 | WVYKQFDIY | 0.679954 | 0.15 |
| HLA-B*15:01 | 772 | 457 | ExNuc B15.01_457 | 9 | KQVVSDIDY | 0.679003 | 0.15 |
| HLA-B*15:01 | 773 | 353 | ExNuc B15.01_353 | 9 | AQPCSDKAY | 0.636589 | 0.19 |
| HLA-B*15:01 | 774 | 116 | ExNuc B15.01_116 | 9 | NLVAVPTGY | 0.536427 | 0.25 |
| HLA-B*15:01 | 775 | 512 | ExNuc B15.01_512 | 9 | KQFDTYNLW | 0.534301 | 0.26 |
| HLA-B*15:01 | 776 | 362 | ExNuc B15.01_362 | 9 | KIEELFYSY | 0.465824 | 0.33 |
| HLA-B*15:01 | 777 | 438 | ExNuc B15.01_438 | 9 | NLKQLPFFY | 0.462862 | 0.35 |
| HLA-B*15:01 | 778 | 64 | ExNuc B15.01_64 | 9 | YQVNGYPNM | 0.45844 | 0.36 |
| HLA-B*15:01 | 779 | 21 | ExNuc B15.01_21 | 9 | TQAPTHLSV | 0.432814 | 0.4 |
| HLA-B*15:01 | 780 | 229 | ExNuc B15.01_229 | 9 | HSIGFDYVY | 0.416088 | 0.41 |
| HLA-B*15:01 | 781 | 436 | ExNuc B15.01_436 | 9 | FVNLKQLPF | 0.402551 | 0.43 |
| HLA-B*15:01 | 782 | 359 | ExNuc B15.01_359 | 9 | KAYKIEELF | 0.373895 | 0.47 |
| HLA-B*15:01 | 783 | 65 | ExNuc B15.01_65 | 9 | QVNGYPNMF | 0.341338 | 0.54 |
| HLA-B*15:01 | 784 | 500 | ExNuc B15.01_500 | 9 | MMISAGFSL | 0.287737 | 0.67 |
| HLA-B*15:01 | 785 | 321 | ExNuc B15.01_321 | 9 | LLADKFPVL | 0.240636 | 0.8 |
| HLA-B*15:01 | 786 | 161 | ExNuc B15.01_161 | 9 | VVRIKIVQM | 0.229016 | 0.84 |
| HLA-B*15:01 | 787 | 146 | ExNuc B15.01_146 | 9 | FKHLIPLMY | 0.195674 | 0.96 |
| HLA-B*40:01 | 788 | 190 | ExNuc B40.01_190 | 9 | FELTSMKYF | 0.242418 | 0.56 |
| HLA-B*40:01 | 789 | 452 | ExNuc B40.01_452 | 9 | CESHGKQVV | 0.195196 | 0.65 |
| HLA-B*58:01 | 790 | 359 | ExNuc B58.01_359 | 9 | KAYKIEELF | 0.981071 | 0.01 |
| HLA-B*58:01 | 791 | 501 | ExNuc B58.01_501 | 9 | MISAGFSLW | 0.880824 | 0.07 |
| HLA-B*58:01 | 792 | 219 | ExNuc B58.01_219 | 9 | TASDTYACW | 0.877406 | 0.07 |
| HLA-B*58:01 | 793 | 512 | ExNuc B58.01_512 | 9 | KQFDTYNLW | 0.875971 | 0.07 |
| HLA-B*58:01 | 794 | 377 | ExNuc B58.01_377 | 9 | FTDGVCLFW | 0.823576 | 0.1 |
| HLA-B*58:01 | 795 | 318 | ExNuc B58.01_318 | 9 | KAALLADKF | 0.682783 | 0.2 |
| HLA-B*58:01 | 796 | 78 | ExNuc B58.01_78 | 9 | EAIRHVRAW | 0.671935 | 0.21 |
| HLA-B*58:01 | 797 | 229 | ExNuc B58.01_229 | 9 | HSIGFDYVY | 0.67101 | 0.21 |
| HLA-B*58:01 | 798 | 506 | ExNuc B58.01_506 | 9 | FSLWVYKQF | 0.479531 | 0.34 |

TABLE 3-continued

Exonuclease

| Allele | Sequence ID No. | Start | Sequence Annotation | Length | Sequence | Score | Rank |
|---|---|---|---|---|---|---|---|
| HLA-B*58:01 | 799 | 177 | ExNuc_B58.01_177 | 9 | LSDRVVFVL | 0.330223 | 0.51 |
| HLA-B*58:01 | 800 | 340 | ExNuc_B58.01_340 | 9 | CVPQADVEW | 0.295757 | 0.56 |
| HLA-B*58:01 | 801 | 49 | ExNuc_B58.01_49 | 9 | MTYRRLISM | 0.247743 | 0.64 |
| HLA-B*58:01 | 802 | 193 | ExNuc_B58.01_193 | 9 | TSMKYFVKI | 0.219788 | 0.72 |
| HLA-B*58:01 | 803 | 278 | ExNuc_B58.01_278 | 9 | RCLAVHECF | 0.204788 | 0.76 |

TABLE 4

EndoRNAse

| Allele | Sequence ID No. | Start | Sequence Annotation | Length | Sequence | Score | Rank |
|---|---|---|---|---|---|---|---|
| HLA-A*01:01 | 804 | 217 | EndoRNA_A1.01_217 | 9 | AMDEFIERY | 0.957737 | 0.02 |
| HLA-A*01:01 | 805 | 270 | EndoRNA_A1.01_270 | 9 | PMDSTVKNY | 0.565302 | 0.16 |
| HLA-A*01:01 | 806 | 185 | EndoRNA_A1.01_185 | 9 | VVQQLPETY | 0.455162 | 0.22 |
| HLA-A*01:01 | 807 | 126 | EndoRNA_A1.01_126 | 9 | RVDGQVDLF | 0.403582 | 0.27 |
| HLA-A*01:01 | 808 | 80 | EndoRNA_A1.01_80 | 9 | AANTVIWDY | 0.340249 | 0.32 |
| HLA-A*01:01 | 809 | 324 | EndoRNA_A1.01_324 | 9 | YTEISFMLW | 0.313596 | 0.35 |
| HLA-A*01:01 | 810 | 24 | EndoRNA_A1.01_24 | 9 | VSIINNTVY | 0.278296 | 0.41 |
| HLA-A*01:01 | 811 | 170 | EndoRNA_A1.01_170 | 9 | EAVKTQFNY | 0.229558 | 0.49 |
| HLA-A*01:01 | 812 | 321 | EndoRNA_A1.01_321 | 9 | TIDYTEISF | 0.205817 | 0.53 |
| HLA-A*01:01 | 813 | 171 | EndoRNA_A1.01_171 | 9 | AVKTQFNYY | 0.193908 | 0.55 |
| HLA-A*02:01 | 814 | 297 | EndoRNA_A2.01_297 | 9 | LLLDDFVEI | 0.949682 | 0.02 |
| HLA-A*02:01 | 815 | 181 | EndoRNA_A2.01_181 | 9 | KVDGVVQQL | 0.836673 | 0.06 |
| HLA-A*02:01 | 816 | 312 | EndoRNA_A2.01_312 | 9 | SVVSKVVKV | 0.798599 | 0.08 |
| HLA-A*02:01 | 817 | 243 | EndoRNA_A2.01_243 | 9 | SQLGGLHLL | 0.787679 | 0.09 |
| HLA-A*02:01 | 818 | 298 | EndoRNA_A2.01_298 | 9 | LLDDFVEll | 0.677666 | 0.15 |
| HLA-A*02:01 | 819 | 34 | EndoRNA_A2.01_34 | 9 | KVDGVDVEL | 0.580429 | 0.21 |
| HLA-A*02:01 | 820 | 1 | EndoRNA_A2.01_1 | 9 | SLENVAFNV | 0.531107 | 0.24 |
| HLA-A*02:01 | 821 | 30 | EndoRNA_A2.01_30 | 9 | TVYTKVDGV | 0.38397 | 0.39 |
| HLA-A*02:01 | 822 | 41 | EndoRNA_A2.01_41 | 9 | ELFENKTTL | 0.368489 | 0.41 |
| HLA-A*02:01 | 823 | 18 | EndoRNA_A2.01_18 | 9 | QQGEVPVSI | 0.290526 | 0.57 |
| HLA-A*02:01 | 824 | 147 | EndoRNA_A2.01_147 | 9 | SVKGLQPSV | 0.248532 | 0.65 |
| HLA-A*02:01 | 825 | 244 | EndoRNA_A2.01_244 | 9 | QLGGLHLLI | 0.205953 | 0.77 |
| HLA-A*03:01 | 826 | 26 | EndoRNA_A3.01_26 | 9 | IINNTVYTK | 0.854165 | 0.05 |
| HLA-A*03:01 | 827 | 150 | EndoRNA_A3.01_150 | 9 | GLQPSVGPK | 0.821194 | 0.07 |
| HLA-A*03:01 | 828 | 173 | EndoRNA_A3.01_173 | 9 | KTQFNYYKK | 0.658832 | 0.2 |
| HLA-A*03:01 | 829 | 308 | EndoRNA_A3.01_308 | 9 | SQDLSVVSK | 0.411216 | 0.47 |
| HLA-A*03:01 | 830 | 316 | EndoRNA_A3.01_316 | 9 | KVVKVTIDY | 0.386608 | 0.51 |

TABLE 4-continued

EndoRNAse

| Allele | Sequence ID No. | Start | Sequence Annotation | Length | Sequence | Score | Rank |
|---|---|---|---|---|---|---|---|
| HLA-A*03:01 | 831 | 141 | EndoRNA_A3.01_141 | 9 | VLITEGSVK | 0.353311 | 0.55 |
| HLA-A*03:01 | 832 | 4 | EndoRNA_A3.01_4 | 9 | NVAFNVVNK | 0.332838 | 0.59 |
| HLA-A*03:01 | 833 | 171 | EndoRNA_A3.01_171 | 9 | AVKTQFNYY | 0.301184 | 0.66 |
| HLA-A*03:01 | 834 | 62 | EndoRNA_A3.01_62 | 9 | NIKPVPEVK | 0.196395 | 0.94 |
| HLA-A*24:02 | 835 | 224 | EndoRNA_A24.02_224 | 9 | RYKLEGYAF | 0.809296 | 0.06 |
| HLA-A*24:02 | 836 | 192 | EndoRNA_A24.02_192 | 9 | TYFTQSRNL | 0.711481 | 0.09 |
| HLA-A*24:02 | 837 | 257 | EndoRNA_A24.02_257 | 9 | RFKESPFEL | 0.692999 | 0.11 |
| HLA-A*24:02 | 838 | 323 | EndoRNA_A24.02_323 | 9 | DYTEISFML | 0.55007 | 0.17 |
| HLA-A*24:02 | 839 | 195 | EndoRNA_A24.02_195 | 9 | TQSRNLQEF | 0.192654 | 0.52 |
| HLA-A*26:01 | 840 | 170 | EndoRNA_A26.01_170 | 9 | EAVKTQFNY | 0.817141 | 0.04 |
| HLA-A*26:01 | 841 | 171 | EndoRNA_A26.01_171 | 9 | AVKTQFNYY | 0.546803 | 0.1 |
| HLA-A*26:01 | 842 | 47 | EndoRNA_A26.01_47 | 9 | TTLPVNVAF | 0.441299 | 0.14 |
| HLA-A*26:01 | 843 | 312 | EndoRNA_A26.01_312 | 9 | SVVSKVVKV | 0.285044 | 0.26 |
| HLA-A*26:01 | 844 | 41 | EndoRNA_A26.01_41 | 9 | ELFENKTTL | 0.23014 | 0.32 |
| HLA-A*26:01 | 845 | 78 | EndoRNA_A26.01_78 | 9 | DIAANTVIW | 0.2014 | 0.38 |
| HLA-A*26:01 | 846 | 217 | EndoRNA_A26.01_217 | 9 | AMDEFIERY | 0.192512 | 0.39 |
| HLA-A*26:01 | 847 | 185 | EndoRNA_A26.01_185 | 9 | VVQQLPETY | 0.190377 | 0.39 |
| HLA-B*07:02 | 848 | 64 | EndoRNA_A07.02_64 | 9 | KPVPEVKIL | 0.87903 | 0.05 |
| HLA-B*07:02 | 849 | 154 | EndoRNA_A07.02_154 | 9 | SVGPKQASL | 0.468325 | 0.27 |
| HLA-B*07:02 | 850 | 49 | EndoRNA_A07.02_49 | 9 | LPVNVAFEL | 0.449505 | 0.29 |
| HLA-B*07:02 | 851 | 152 | EndoRNA_A07.02_152 | 9 | QPSVGPKQA | 0.195335 | 0.69 |
| HLA-B*15:01 | 852 | 195 | EndoRNA_A15.01_195 | 9 | TQSRNLQEF | 0.846768 | 0.04 |
| HLA-B*15:01 | 853 | 185 | EndoRNA_A15.01_185 | 9 | VVQQLPETY | 0.832035 | 0.05 |
| HLA-B*15:01 | 854 | 186 | EndoRNA_A15.01_186 | 9 | VQQLPETYF | 0.831024 | 0.05 |
| HLA-B*15:01 | 855 | 171 | EndoRNA_A15.01_171 | 9 | AVKTQFNYY | 0.785894 | 0.08 |
| HLA-B*15:01 | 856 | 316 | EndoRNA_A15.01_316 | 9 | KVVKVTIDY | 0.7276 | 0.12 |
| HLA-B*15:01 | 857 | 24 | EndoRNA_A15.01_24 | 9 | VSIINNTVY | 0.567129 | 0.23 |
| HLA-B*15:01 | 858 | 217 | EndoRNA_A15.01_217 | 9 | AMDEFIERY | 0.491104 | 0.31 |
| HLA-B*15:01 | 859 | 114 | EndoRNA_A15.01_114 | 9 | TICAPLTVF | 0.478278 | 0.32 |
| HLA-B*15:01 | 860 | 250 | EndoRNA_A15.01_250 | 9 | LLIGLAKRF | 0.467424 | 0.33 |
| HLA-B*15:01 | 861 | 243 | EndoRNA_A15.01_243 | 9 | SQLGGLHLL | 0.446004 | 0.38 |
| HLA-B*15:01 | 862 | 47 | EndoRNA_A15.01_47 | 9 | TTLPVNVAF | 0.41661 | 0.41 |
| HLA-B*40:01 | 863 | 201 | EndoRNA_A40.01_201 | 9 | QEFKPRSQM | 0.899475 | 0.06 |
| HLA-B*40:01 | 864 | 303 | EndoRNA_A40.01_303 | 9 | VEIIKSQDL | 0.768551 | 0.13 |
| HLA-B*40:01 | 865 | 263 | EndoRNA_A40.01_263 | 9 | FELEDFIPM | 0.68244/1 | 0.16 |
| HLA-B*40:01 | 866 | 219 | EndoRNA_A40.01_219 | 9 | DEFIERYKL | 0.436831 | 0.32 |
| HLA-B*40:01 | 867 | 243 | EndoRNA_A40.01_243 | 9 | SQLGGLHLL | 0.410667 | 0.36 |
| HLA-B*40:01 | 868 | 43 | EndoRNA_A40.01_43 | 9 | FENKTTLPV | 0.355108 | 0.42 |

TABLE 4-continued

EndoRNAse

| Allele | Sequence ID No. | Start | Sequence Annotation | Length | Sequence | Score | Rank |
|---|---|---|---|---|---|---|---|
| HLA-B*40:01 | 869 | 2 | EndoRNA A40.01_2 | 9 | LENVAFNVV | 0.323778 | 0.45 |
| HLA-B*40:01 | 870 | 67 | EndoRNA A40.01_67 | 9 | PEVKILNNL | 0.321118 | 0.46 |
| HLA-B*40:01 | 871 | 55 | EndoRNA A40.01_55 | 9 | FELWAKRNI | 0.24051 | 0.56 |
| HLA-B*58:01 | 872 | 324 | EndoRNA A58.01_324 | 9 | YTEISFMLW | 0.93187 | 0.04 |
| HLA-B*58:01 | 873 | 47 | EndoRNA A58.01_47 | 9 | TTLPVNVAF | 0.878973 | 0.07 |
| HLA-B*58:01 | 874 | 115 | EndoRNA A58.01_115 | 9 | ICAPLTVFF | 0.688753 | 0.2 |
| HLA-B*58:01 | 875 | 24 | EndoRNA A58.01_24 | 9 | VSIINNTVY | 0.474435 | 0.34 |
| HLA-B*58:01 | 876 | 50 | EndoRNA A58.01_50 | 9 | PVNVAFELW | 0.457307 | 0.35 |
| HLA-B*58:01 | 877 | 185 | EndoRNA A58.01_185 | 9 | VVQQLPETY | 0.407242 | 0.4 |
| HLA-B*58:01 | 878 | 316 | EndoRNA A58.01_316 | 9 | KVVKVTIDY | 0.347361 | 0.48 |
| HLA-B*58:01 | 879 | 181 | EndoRNA A58.01_181 | 9 | KVDGVVQQL | 0.305934 | 0.55 |
| HLA-B*58:01 | 880 | 80 | EndoRNA A58.01_80 | 9 | AANTVIWDY | 0.300606 | 0.55 |
| HLA-B*58:01 | 881 | 126 | EndoRNA A58.01_126 | 9 | RVDGQVDLF | 0.266188 | 0.62 |
| HLA-B*58:01 | 882 | 107 | EndoRNA A58.01_107 | 9 | IAKKPTETI | 0.217414 | 0.73 |

TABLE 5

Methyl-Transferase

| Allele | Sequence ID No. | Start | Sequence Annotation | Length | Sequence | Score | Rank |
|---|---|---|---|---|---|---|---|
| HLA-A*01:01 | 883 | 143 | MthlTrns A1.01_143 | 9 | DSKEGFFTY | 0.454043 | 0.22 |
| HLA-A*01:01 | 884 | 55 | MthlTrns A1.01_55 | 9 | NTLTLAVPY | 0.221872 | 0.5 |
| HLA-A*01:01 | 885 | 103 | MthlTrns A1.01_103 | 9 | VSDADSTLI | 0.214979 | 0.51 |
| HLA-A*02:01 | 886 | 53 | MthlTrns A2.01_53 | 9 | YLNTLTLAV | 0.893078 | 0.03 |
| HLA-A*02:01 | 887 | 109 | MthlTrns A2.01_109 | 9 | TLIGDCATV | 0.667919 | 0.15 |
| HLA-A*02:01 | 888 | 265 | MthlTrns A2.01_265 | 9 | QINDMILSL | 0.569069 | 0.22 |
| HLA-A*02:01 | 889 | 87 | MthlTrns A2.01_87 | 9 | WLPTGTLLV | 0.419197 | 0.34 |
| HLA-A*02:01 | 890 | 102 | MthlTrns A2.01_102 | 9 | FVSDADSTL | 0.404239 | 0.36 |
| HLA-A*02:01 | 891 | 169 | MthlTrns A2.01_169 | 9 | KITEHSWNA | 0.348693 | 0.45 |
| HLA-A*02:01 | 892 | 76 | MthlTrns A2.01_76 | 9 | KVAPGTAVL | 0.315817 | 0.52 |
| HLA-A*02:01 | 893 | 210 | MthlTrns A2.01_210 | 9 | YLGKPREQI | 0.29128 | 0.57 |
| HLA-A*02:01 | 894 | 49 | MthlTrns A2.01_49 | 9 | QLCQYLNTL | 0.286361 | 0.57 |
| HLA-A*03:01 | 895 | 8 | MthlTrns A3.01_8 | 9 | GVAMPNLYK | 0.924863 | 0.02 |
| HLA-A*03:01 | 896 | 16 | MthlTrns A3.01_16 | 9 | KMQRMLLEK | 0.887509 | 0.04 |
| HLA-A*03:01 | 897 | 161 | MthlTrns A3.01_161 | 9 | ALGGSVAIK | 0.779901 | 0.1 |
| HLA-A*03:01 | 898 | 173 | MthlTrns A3.01_173 | 9 | HSWNADLYK | 0.471426 | 0.38 |
| HLA-A*03:01 | 899 | 151 | MthlTrns A3.01_151 | 9 | YICGFIQQK | 0.453062 | 0.4 |
| HLA-A*03:01 | 900 | 254 | MthlTrns A3.01_254 | 9 | RGTAVMSLK | 0.333629 | 0.59 |

TABLE 5-continued

Methyl-Transferase

| Allele | Sequence ID No. | Start | Sequence Annotation | Length | Sequence | Score | Rank |
|---|---|---|---|---|---|---|---|
| HLA-A*03:01 | 901 | 165 | MthlTrns A3.01_165 | 9 | SVAIKITEH | 0.209014 | 0.9 |
| HLA-A*24:02 | 902 | 46 | MthlTrns A24.02_46 | 9 | KYTQLCQYL | 0.825165 | 0.05 |
| HLA-A*24:02 | 903 | 62 | MthlTrns A24.02_62 | 9 | PYNMRVIHF | 0.798089 | 0.06 |
| HLA-A*24:02 | 904 | 236 | MthlTrns A24.02_236 | 9 | IQLSSYSLF | 0.543077 | 0.18 |
| HLA-A*24:02 | 905 | 86 | MthlTrns A24.02_86 | 9 | QWLPTGTLL | 0.511035 | 0.19 |
| HLA-A*24:02 | 906 | 130 | MthlTrns A24.02_130 | 9 | MYDPKTKNV | 0.460873 | 0.22 |
| HLA-A*24:02 | 907 | 174 | MthlTrns A24.02_174 | 9 | SWNADLYKL | 0.423192 | 0.24 |
| HLA-A*24:02 | 908 | 222 | MthlTrns A24.02_222 | 9 | VMHANYIFW | 0.318127 | 0.33 |
| HLA-A*24:02 | 909 | 14 | MthlTrns A24.02_14 | 9 | LYKMQRMLL | 0.266761 | 0.38 |
| HLA-A*24:02 | 910 | 221 | MthlTrns A24.02_221 | 9 | YVMHANYIF | 0.25404 | 0.4 |
| HLA-A*24:02 | 911 | 220 | MthlTrns A24.02_220 | 9 | GYVMHANYI | 0.209373 | 0.47 |
| HLA-A*24:02 | 912 | 181 | MthlTrns A24.02_181 | 9 | KLMGHFAWW | 0.153946 | 0.64 |
| HLA-A*26:01 | 913 | 143 | MthlTrns A26.01_143 | 9 | DSKEGFFTY | 0.845441 | 0.03 |
| HLA-A*26:01 | 914 | 202 | MthlTrns A26.01_202 | 9 | EAFLIGCNY | 0.541176 | 0.1 |
| HLA-A*26:01 | 915 | 178 | MthlTrns A26.01_178 | 9 | DLYKLMGHF | 0.444497 | 0.14 |
| HLA-A*26:01 | 916 | 55 | MthlTrns A26.01_55 | 9 | NTLTLAVPY | 0.229069 | 0.32 |
| HLA-A*26:01 | 917 | 39 | MthlTrns A26.01_39 | 9 | GIMMNVAKY | 0.220047 | 0.34 |
| HLA-A*26:01 | 918 | 221 | MthlTrns A26.01_221 | 9 | YVMHANYIF | 0.16875 | 0.44 |
| HLA-A*26:01 | 919 | 265 | MthlTrns A26.01_265 | 9 | QINDMILSL | 0.16064 | 0.46 |
| HLA-A*26:01 | 920 | 3 | MthlTrns A26.01_3 | 9 | QAWQPGVAM | 0.158924 | 0.47 |
| HLA-B*07:02 | 921 | 76 | MthlTrns B07.02_76 | 9 | KVAPGTAVL | 0.64873 | 0.15 |
| HLA-B07:02 | 922 | 36 | MthlTrns B07.02_36 | 9 | LPKGIMMNV | 0.485039 | 0.25 |
| HLA-B*07:02 | 923 | 249 | MthlTrns B07.02_249 | 9 | FPLKLRGTA | 0.459763 | 0.29 |
| HLA-B*07:02 | 924 | 6 | MthlTrns B07.02_6 | 9 | QPGVAMPNL | 0.432742 | 0.31 |
| HLA-B*07:02 | 925 | 3 | MthlTrns B07.02_3 | 9 | QAWQPGVAM | 0.401898 | 0.34 |
| HLA-B*07:02 | 926 | 213 | MthlTrns B07.02_213 | 9 | KPREQIDGY | 0.322174 | 0.44 |
| HLA-B*15:01 | 927 | 236 | MthlTrns B15.01_236 | 9 | IQLSSYSLF | 0.79202 | 0.08 |
| HLA-B*15:01 | 928 | 85 | MthlTrns B15.01_85 | 9 | RQWLPTGTL | 0.59587 | 0.21 |
| HLA-B*15:01 | 929 | 39 | MthlTrns B15.01_39 | 9 | GIMMNVAKY | 0.487521 | 0.31 |
| HLA-B*15:01 | 930 | 76 | MthlTrns B15.01_76 | 9 | KVAPGTAVL | 0.478756 | 0.32 |
| HLA-B*15:01 | 931 | 51 | MthlTrns B15.01_51 | 9 | CQYLNTLTL | 0.342603 | 0.54 |
| HLA-B*15:01 | 932 | 221 | MthlTrns B15.01_221 | 9 | YVMHANYIF | 0.307316 | 0.62 |
| HLA-B*15:01 | 933 | 143 | MthlTrns B15.01_143 | 9 | DSKEGFFTY | 0.241386 | 0.8 |
| HLA-B*15:01 | 934 | 45 | MthlTrns B15.01_45 | 9 | AKYTQLCQY | 0.237921 | 0.8 |
| HLA-B*15:01 | 935 | 3 | MthlTrns B15.01_3 | 9 | QAWQPGVAM | 0.207896 | 0.91 |
| HLA-B*15:01 | 936 | 167 | MthlTrns B15.01_167 | 9 | AIKITEHSW | 0.16209 | 1.2 |
| HLA-B*40:01 | 937 | 215 | MthlTrns B40.01_215 | 9 | REQIDGYVM | 0.880693 | 0.07 |
| HLA-B*40:01 | 938 | 140 | MthlTrns B40.01_140 | 9 | KENDSKEGF | 0.753159 | 0.13 |

TABLE 5-continued

Methyl-Transferase

| Allele | Sequence ID No. | Start | Sequence Annotation | Length | Sequence | Score | Rank |
|---|---|---|---|---|---|---|---|
| HLA-B*40:01 | 939 | 171 | MthlTrns_B40.01_171 | 9 | TEHSWNADL | 0.752718 | 0.13 |
| HLA-B*40:01 | 940 | 262 | MthlTrns_B40.01_262 | 9 | KEGQINDMI | 0.41942 | 0.35 |
| HLA-B*40:01 | 941 | 85 | MthlTrns_B40.01_85 | 9 | RQWLPTGTL | 0.332816 | 0.45 |
| HLA-B*58:01 | 942 | 115 | MthlTrns_B58.01_115 | 9 | ATVHTANKW | 0.968816 | 0.02 |
| HLA-B*58:01 | 943 | 167 | MthlTrns_B58.01_167 | 9 | AIKITEHSW | 0.695131 | 0.19 |
| HLA-B*58:01 | 944 | 181 | MthlTrns_B58.01_181 | 9 | KLMGHFAWW | 0.641824 | 0.22 |
| HLA-B*58:01 | 945 | 241 | MthlTrns_B58.01_241 | 9 | YSLFDMSKF | 0.631228 | 0.23 |
| HLA-B*58:01 | 946 | 222 | MthlTrns_B58.01_222 | 9 | VMHANYIFW | 0.581609 | 0.27 |
| HLA-B*58:01 | 947 | 9 | MthlTrns_B58.01_9 | 9 | VAMPNLYKM | 0.543539 | 0.29 |
| HLA-B*58:01 | 948 | 57 | MthlTrns_B58.01_57 | 9 | LTLAVPYNM | 0.448643 | 0.37 |
| HLA-B*58:01 | 949 | 79 | MthlTrns_B58.01_79 | 9 | PGTAVLRQW | 0.325426 | 0.52 |
| HLA-B*58:01 | 950 | 221 | MthlTrns_B58.01_221 | 9 | YVMHANYIF | 0.237627 | 0.68 |
| HLA-B*58:01 | 951 | 198 | MthlTrns_B58.01_198 | 9 | ASSSEAFLI | 0.232174 | 0.69 |
| HLA-B*58:01 | 952 | 34 | MthlTrns_B58.01_34 | 9 | ATLPKGIMM | 0.210574 | 0.75 |
| HLA-B*58:01 | 953 | 76 | MthlTrns_B58.01_76 | 9 | KVAPGTAVL | 0.170736 | 0.87 |

TABLE 6

Membrane

| Allele | Sequence ID No. | Start | Sequence Annotation | Length | Sequence | Score | Rank |
|---|---|---|---|---|---|---|---|
| HLA-A*01:01 | 954 | 171 | Mem_A1.01_171 | 9 | ATSRTLSYY | 0.903381 | 0.03 |
| HLA-A*01:01 | 955 | 39 | Mem_A1.01_39 | 9 | YANRNRFLY | 0.69359 | 0.1 |
| HLA-A*01:01 | 956 | 188 | Mem_A1.01_188 | 9 | AGDSGFAAY | 0.664115 | 0.1 |
| HLA-A*01:01 | 957 | 213 | Mem_A1.01_213 | 9 | SSDNIALLV | 0.59507 | 0.14 |
| HLA-A*01:01 | 958 | 170 | Mem_A1.01_170 | 9 | VATSRTLSY | 0.591769 | 0.14 |
| HLA-A*02:01 | 959 | 15 | Mem_A2.01_15 | 9 | KLLEQWNLV | 0.892896 | 0.03 |
| HLA-A*02:01 | 960 | 65 | Mem_A2.01_65 | 9 | FVLAAVYRI | 0.460313 | 0.29 |
| HLA-A*02:01 | 961 | 108 | Mem_A2.01_108 | 9 | SMWSFNPET | 0.447798 | 0.32 |
| HLA-A*02:01 | 962 | 89 | Mem_A2.01_89 | 9 | GLMWLSYFI | 0.432387 | 0.33 |
| HLA-A*02:01 | 963 | 56 | Mem_A2.01_56 | 9 | LLWPVTLAC | 0.256837 | 0.63 |
| HLA-A*02:01 | 964 | 55 | Mem_A2.01_55 | 9 | WLLWPVTLA | 0.177647 | 0.89 |
| HLA-A*02:01 | 965 | 101 | Mem_A2.01_101 | 9 | RLFARTRSM | 0.173774 | 0.91 |
| HLA-A*03:01 | 966 | 150 | Mem_A3.01_150 | 9 | RIAGHHLGR | 0.795487 | 0.09 |
| HLA-A*03:01 | 967 | 171 | Mem_A3.01_171 | 9 | ATSRTLSYY | 0.410177 | 0.47 |
| HLA-A*03:01 | 968 | 172 | Mem_A3.01_172 | 9 | TSRTLSYYK | 0.319722 | 0.62 |
| HLA-A*03:01 | 969 | 6 | Mem_A3.01_6 | 9 | GTITVEELK | 0.240085 | 0.82 |
| HLA-A*03:01 | 970 | 93 | Mem_A3.01_93 | 9 | LSYFIASFR | 0.235381 | 0.83 |

TABLE 6-continued

Membrane

| Allele | Sequence ID No. | Start | Sequence Annotation | Length | Sequence | Score | Rank |
|---|---|---|---|---|---|---|---|
| HLA-A*03:01 | 971 | 138 | Mem A3.01_138 | 9 | LVIGAVILR | 0.201656 | 0.93 |
| HLA-A*24:02 | 972 | 95 | Mem A24.02_95 | 9 | YFIASFRLF | 0.913594 | 0.02 |
| HLA-A*24:02 | 973 | 94 | Mem A24.02_94 | 9 | SYFIASFRL | 0.83484 | 0.05 |
| HLA-A*24:02 | 974 | 46 | Mem A24.02_46 | 9 | LYIIKLIFL | 0.685153 | 0.11 |
| HLA-A*24:02 | 975 | 198 | Mem A24.02_198 | 9 | RYRIGNYKL | 0.670153 | 0.12 |
| HLA-A*24:02 | 976 | 54 | Mem A24.02_54 | 9 | LWLLWPVTL | 0.522979 | 0.18 |
| HLA-A*24:02 | 977 | 57 | Mem A24.02_57 | 9 | LWPVTLACF | 0.472421 | 0.21 |
| HLA-A*24:02 | 978 | 111 | Mem A24.02_111 | 9 | SFNPETNIL | 0.364757 | 0.28 |
| HLA-A*24:02 | 979 | 38 | Mem A24.02_38 | 9 | AYANRNRFL | 0.364322 | 0.28 |
| HLA-A*24:02 | 980 | 102 | Mem A24.02_102 | 9 | LFARTRSMW | 0.264358 | 0.39 |
| HLA-A*24:02 | 981 | 44 | Mem A24.02_44 | 9 | RFLYIIKLI | 0.237445 | 0.42 |
| HLA-A*26:01 | 982 | 171 | Mem A26.01_171 | 9 | ATSRTLSYY | 0.465163 | 0.13 |
| HLA-A*26:01 | 983 | 170 | Mem A26.01_170 | 9 | VATSRTLSY | 0.253246 | 0.29 |
| HLA-A*26:01 | 984 | 196 | Mem A26.01_196 | 9 | YSRYRIGNY | 0.22437 | 0.33 |
| HLA-A*26:01 | 985 | 39 | Mem A26.01_39 | 9 | YANRNRFLY | 0.172251 | 0.43 |
| HLA-A*26:01 | 986 | 37 | Mem A26.01_37 | 9 | FAYANRNRF | 0.167471 | 0.44 |
| HLA-B*07:02 | 987 | 164 | Mem B7.02_164 | 9 | LPKEITVAT | 0.452806 | 0.29 |
| HLA-B*07:02 | 988 | 148 | Mem B7.02_148 | 9 | HLRIAGHHL | 0.369452 | 0.37 |
| HLA-B*07:02 | 989 | 101 | Mem B7.02_101 | 9 | RLFARTRSM | 0.33272 | 0.43 |
| HLA-B*15:01 | 990 | 101 | Mem B15.01_101 | 9 | RLFARTRSM | 0.715954 | 0.12 |
| HLA-B*15:01 | 991 | 170 | Mem B15.01_170 | 9 | VATSRTLSY | 0.649814 | 0.18 |
| HLA-B*15:01 | 992 | 171 | Mem B15.01_171 | 9 | ATSRTLSYY | 0.454935 | 0.36 |
| HLA-B*15:01 | 993 | 37 | Mem B15.01_37 | 9 | FAYANRNRF | 0.373977 | 0.47 |
| HLA-B*15:01 | 994 | 191 | Mem B15.01_191 | 9 | SGFAAYSRY | 0.344812 | 0.53 |
| HLA-B*15:01 | 995 | 39 | Mem B15.01_39 | 9 | YANRNRFLY | 0.292655 | 0.65 |
| HLA-B*15:01 | 996 | 196 | Mem B15.01_196 | 9 | YSRYRIGNY | 0.285031 | 0.68 |
| HLA-B*15:01 | 997 | 148 | Mem B15.01_148 | 9 | HLRIAGHHL | 0.279509 | 0.68 |
| HLA-B*15:01 | 998 | 18 | Mem B15.01_18 | 9 | EQWNLVIGF | 0.244266 | 0.78 |
| HLA-B*15:01 | 999 | 45 | Mem B15.01_45 | 9 | FLYIIKLIF | 0.20731 | 0.91 |
| HLA-B*40:01 | 1000 | 136 | Mem B40_01_136 | 9 | SELVIGAVI | 0.729021 | 0.14 |
| HLA-B*58:01 | 1001 | 84 | Mem B58.01_84 | 9 | MACLVGLMW | 0.913908 | 0.06 |
| HLA-B*58:01 | 1002 | 67 | Mem B58.01_67 | 9 | LAAVYRINW | 0.87252 | 0.08 |
| HLA-B*58:01 | 1003 | 47 | Mem B58.01_47 | 9 | YIIKLIFLW | 0.737525 | 0.15 |
| HLA-B*58:01 | 1004 | 39 | Mem B58.01_39 | 9 | YANRNRFLY | 0.532269 | 0.29 |
| HLA-B*58:01 | 1005 | 171 | Mem B58.01_171 | 9 | ATSRTLSYY | 0.512223 | 0.31 |
| HLA-B*58:01 | 1006 | 23 | Mem B58.01_23 | 9 | VIGFLFLTW | 0.459109 | 0.35 |
| HLA-B*58:01 | 1007 | 12 | Mem B58.01_12 | 9 | ELKKLLEQW | 0.447047 | 0.37 |
| HLA-B*58:01 | 1008 | 50 | Mem B58.01_50 | 9 | KLIFLWLLW | 0.402934 | 0.41 |

TABLE 6-continued

Membrane

| Allele | Sequence ID No. | Start | Sequence Annotation | Length | Sequence | Score | Rank |
|---|---|---|---|---|---|---|---|
| HLA-B*58:01 | 1009 | 170 | Mem B58.01_170 | 9 | VATSRTLSY | 0.388936 | 0.42 |
| HLA-B*58:01 | 1010 | 168 | Mem B58.01_168 | 9 | ITVATSRTL | 0.308282 | 0.54 |
| HLA-B*58:01 | 1011 | 102 | Mem B58.01_102 | 9 | LFARTRSMW | 0.265216 | 0.62 |
| HLA-B*58:01 | 1012 | 37 | Mem B58.01_37 | 9 | FAYANRNRF | 0.225301 | 0.71 |
| HLA-B*58:01 | 1013 | 29 | Mem B58.01_29 | 9 | LTWICLLQF | 0.196817 | 0.79 |
| HLA-B*58:01 | 1014 | 8 | Mem B58.01_8 | 9 | ITVEELKKL | 0.181947 | 0.83 |

TABLE 7

Envelope

| Allele | Sequence ID No. | Start | Sequence Annotation | Length | Sequence | Score | Rank |
|---|---|---|---|---|---|---|---|
| HLA-A*01:01 | 1015 | 49 | Evlp A1.01_49 | 9 | VSLVKPSFY | 0.462205 | 0.21 |
| HLA-A*01:01 | 1016 | 34 | Evlp A1.01_34 | 9 | LTALRLCAY | 0.395652 | 0.27 |
| HLA-A*01:01 | 1017 | 51 | Evlp A1.01_51 | 9 | LVKPSFYVY | 0.150715 | 0.68 |
| HLA-A*02:01 | 1018 | 50 | Evlp A2.01_50 | 9 | SLVKPSFYV | 0.846768 | 0.06 |
| HLA-A*02:01 | 1019 | 57 | Evlp A2.01_57 | 9 | YVYSRVKNL | 0.49818 | 0.26 |
| HLA-A*02:01 | 1020 | 20 | Evlp A2.01_20 | 9 | FLAFVVFLL | 0.482968 | 0.27 |
| HLA-A*02:01 | 1021 | 13 | Evlp A2.01_13 | 9 | IVNSVLLFL | 0.358211 | 0.43 |
| HLA-A*02:01 | 1022 | 11 | Evlp A2.01_11 | 9 | TLIVNSVLL | 0.319511 | 0.51 |
| HLA-A*02:01 | 1023 | 4 | Evlp A2.01_4 | 9 | FVSEETGTL | 0.299489 | 0.55 |
| HLA-A*02:01 | 1024 | 26 | Evlp A2.01_26 | 9 | FLLVTLAIL | 0.284749 | 0.58 |
| HLA-A*02:01 | 1025 | 16 | Evlp A2.01_16 | 9 | SVLLFLAFV | 0.207941 | 0.76 |
| HLA-A*03:01 | 1026 | 61 | Evlp A3.01_61 | 9 | RVKNLNSSR | 0.496778 | 0.34 |
| HLA-A*03:01 | 1027 | 45 | Evlp A3.01_45 | 9 | NIVNVSLVK | 0.234744 | 0.83 |
| HLA-A*26:01 | 1028 | 51 | Evlp A26.01_51 | 9 | LVKPSFYVY | 0.462542 | 0.13 |
| HLA-A*26:01 | 1029 | 57 | Evlp A26.01_57 | 9 | YVYSRVKNL | 0.290721 | 0.26 |
| HLA-A*26:01 | 1030 | 48 | Evlp A26.01_48 | 9 | NVSLVKPSF | 0.265747 | 0.27 |
| HLA-A*26:01 | 1031 | 4 | Evlp A26.01_4 | 9 | FVSEETGTL | 0.190459 | 0.39 |
| HLA-A*26:01 | 1032 | 34 | Evlp A26.01_34 | 9 | LTALRLCAY | 0.188337 | 0.4 |
| HLA-A*26:01 | 1033 | 12 | Evlp A26.01_12 | 9 | LIVNSVLLF | 0.171493 | 0.43 |
| HLA-B*07:02 | 1034 | 57 | Evlp B07.02_57 | 9 | YVYSRVKNL | 0.154246 | 0.83 |
| HLA-B*15:01 | 1035 | 51 | Evlp B15.01_51 | 9 | LVKPSFYVY | 0.890774 | 0.03 |
| HLA-B*15:01 | 1036 | 12 | Evlp B15.01_12 | 9 | LIVNSVLLF | 0.427014 | 0.41 |
| HLA-B*15:01 | 1037 | 18 | Evlp B15.01_18 | 9 | LLFLAFVVF | 0.271964 | 0.7 |
| HLA-B*15:01 | 1038 | 34 | Evlp B15.01_34 | 9 | LTALRLCAY | 0.259594 | 0.74 |
| HLA-B*15:01 | 1039 | 49 | Evlp B15.01_49 | 9 | VSLVKPSFY | 0.231883 | 0.83 |
| HLA-B*40:01 | 1040 | 6 | Evlp B40.01_6 | 9 | SEETGTLIV | 0.553646 | 0.24 |

TABLE 7-continued

Envelope

| Allele | Sequence ID No. | Start | Sequence Annotation | Length | Sequence | Score | Rank |
|---|---|---|---|---|---|---|---|
| HLA-B*58:01 | 1041 | 49 | Evlp B58.01_49 | 9 | VSLVKPSFY | 0.498101 | 0.32 |
| HLA-B*58:01 | 1042 | 51 | Evlp B58.01_51 | 9 | LVKPSFYVY | 0.274628 | 0.59 |
| HLA-B*58:01 | 1043 | 12 | Evlp B58.01_12 | 9 | LIVNSVLLF | 0.18442 | 0.82 |
| HLA-B*58:01 | 1044 | 29 | Evlp B58.01_29 | 9 | VTLAILTAL | 0.175332 | 0.86 |

TABLE 8

ORF-3A

| Allele | Sequence ID No. | Start | Sequence Annotation | Length | Sequence | Score | Rank |
|---|---|---|---|---|---|---|---|
| HLA-A*01:01 | 1045 | 207 | ORF3a A1.01_207 | 9 | FTSDYYQLY | 0.980978 | 0.01 |
| HLA-A*01:01 | 1046 | 204 | ORF3a A1.01_204 | 9 | HSYFTSDYY | 0.789539 | 0.07 |
| HLA-A*01:01 | 1047 | 176 | ORF3a A1.01_176 | 9 | TSPISEHDY | 0.409915 | 0.26 |
| HLA-A*01:01 | 1048 | 220 | ORF3a A1.01_220 | 9 | STDTGVEHV | 0.348237 | 0.31 |
| HLA-A*01:01 | 1049 | 101 | ORF3a A1.01_101 | 9 | LEAPFLYLY | 0.214665 | 0.51 |
| HLA-A*01:01 | 1050 | 146 | ORF3a A1.01_146 | 9 | FLCWHTNCY | 0.20996 | 0.52 |
| HLA-A*02:01 | 1051 | 139 | ORF3a A2.01_139 | 9 | LLYDANYFL | 0.961842 | 0.02 |
| HLA-A*02:01 | 1052 | 72 | ORF3a A2.01_72 | 9 | ALSKGVHFV | 0.953159 | 0.02 |
| HLA-A*02:01 | 1053 | 89 | ORF3a A2.01_89 | 9 | TVYSHLLLV | 0.839324 | 0.06 |
| HLA-A*02:01 | 1054 | 107 | ORF3a A2.01_107 | 9 | YLYALVYFL | 0.826661 | 0.06 |
| HLA-A*02:01 | 1055 | 236 | ORF3a A2.01_236 | 9 | IVDEPEEHV | 0.636237 | 0.17 |
| HLA-A*02:01 | 1056 | 110 | ORF3a A2.01_110 | 9 | ALVYFLQSI | 0.573805 | 0.21 |
| HLA-A*02:01 | 1057 | 51 | ORF3a A2.01_51 | 9 | ALLAVFQSA | 0.558561 | 0.23 |
| HLA-A*02:01 | 1058 | 100 | ORF3a A2.01_100 | 9 | GLEAPFLYL | 0.430573 | 0.33 |
| HLA-A*02:01 | 1059 | 82 | ORF3a A2.01_82 | 9 | NLLLLFVTV | 0.354378 | 0.44 |
| HLA-A*02:01 | 1060 | 33 | ORF3a A2.01_33 | 9 | ATIPIQASL | 0.32159 | 0.51 |
| HLA-A*02:01 | 1061 | 87 | ORF3a A2.01_87 | 9 | FVTVYSHLL | 0.274081 | 0.6 |
| HLA-A*02:01 | 1062 | 45 | ORF3a A2.01_45 | 9 | WLIVGVALL | 0.263005 | 0.62 |
| HLA-A*02:01 | 1063 | 247 | ORF3a A2.01_247 | 9 | HTIDGSSGV | 0.205907 | 0.77 |
| HLA-A*02:01 | 1064 | 220 | ORF3a A2.01_220 | 9 | STDTGVEHV | 0.180098 | 0.88 |
| HLA-A*03:01 | 1065 | 58 | ORF3a A3.01_58 | 9 | SASKIITLK | 0.830102 | 0.06 |
| HLA-A*03:01 | 1066 | 59 | ORF3a A3.01_59 | 9 | ASKIITLKK | 0.784036 | 0.1 |
| HLA-A*03:01 | 1067 | 8 | ORF3a A3.01_8 | 9 | FTIGTVTLK | 0.654487 | 0.2 |
| HLA-A*03:01 | 1068 | 227 | ORF3a A3.01_227 | 9 | HVTFFIYNK | 0.444929 | 0.41 |
| HLA-A*03:01 | 1069 | 184 | ORF3a A3.01_184 | 9 | YQIGGYTEK | 0.257177 | 0.76 |
| HLA-A*03:01 | 1070 | 13 | ORF3a A3.01_13 | 9 | VTLKQGEIK | 0.182774 | 0.99 |
| HLA-A*24:02 | 1071 | 112 | ORF3a A24.02_112 | 9 | VYFLQSINF | 0.969883 | 0.01 |
| HLA-A*24:02 | 1072 | 211 | ORF3a A24.02_211 | 9 | YYQLYSTQL | 0.862532 | 0.04 |
| HLA-A*24:02 | 1073 | 106 | ORF3a A24.02_106 | 9 | LYLYALVYF | 0.772667 | 0.06 |

TABLE 8-continued

ORF-3A

| Allele | Sequence ID No. | Start | Sequence Annotation | Length | Sequence | Score | Rank |
|---|---|---|---|---|---|---|---|
| HLA-A*24:02 | 1074 | 159 | ORF3a A24.02_159 | 9 | PYNSVTSSI | 0.669199 | 0.12 |
| HLA-A*24:02 | 1075 | 206 | ORF3a A24.02_206 | 9 | YFTSDYYQL | 0.598801 | 0.15 |
| HLA-A*24:02 | 1076 | 7 | ORF3a A24.02_7 | 9 | IFTIGTVTL | 0.46568 | 0.21 |
| HLA-A*24:02 | 1077 | 86 | ORF3a A24.02_86 | 9 | LFVTVYSHL | 0.271524 | 0.38 |
| HLA-A*24:02 | 1078 | 37 | ORF3a A24.02_37 | 9 | IQASLPFGW | 0.203184 | 0.48 |
| HLA-A*24:02 | 1079 | 119 | ORF3a A24.02_119 | 9 | NFVRIIMRL | 0.180996 | 0.54 |
| HLA-A*24:02 | 1080 | 55 | ORF3a A24.02_55 | 9 | VFQSASKII | 0.179447 | 0.54 |
| HLA-A*26:01 | 1081 | 207 | ORF3a A26.01_207 | 9 | FTSDYYQLY | 0.92003 | 0.02 |
| HLA-A*26:01 | 1082 | 247 | ORF3a A26.01_247 | 9 | HTIDGSSGV | 0.441513 | 0.14 |
| HLA-A*26:01 | 1083 | 33 | ORF3a A26.01_33 | 9 | ATIPIQASL | 0.386256 | 0.18 |
| HLA-A*26:01 | 1084 | 204 | ORF3a A26.01_204 | 9 | HSYFTSDYY | 0.355037 | 0.21 |
| HLA-A*26:01 | 1085 | 89 | ORF3a A26.01_89 | 9 | TVYSHLLLV | 0.217806 | 0.34 |
| HLA-B*07:02 | 1086 | 35 | ORF3a B07.02_35 | 9 | IPIQASLPF | 0.765631 | 0.1 |
| HLA-B*07:02 | 1087 | 103 | ORF3a B07.02_103 | 9 | APFLYLYAL | 0.646458 | 0.15 |
| HLA-B*07:02 | 1088 | 33 | ORF3a B07.02_33 | 9 | ATIPIQASL | 0.179015 | 0.74 |
| HLA-B*15:01 | 1089 | 207 | ORF3a B15.01_207 | 9 | FTSDYYQLY | 0.436442 | 0.4 |
| HLA-B*15:01 | 1090 | 204 | ORF3a B15.01_204 | 9 | HSYFTSDYY | 0.396492 | 0.43 |
| HLA-B*15:01 | 1091 | 105 | ORF3a B15.01_105 | 9 | FLYLYALVY | 0.351637 | 0.51 |
| HLA-B*15:01 | 1092 | 71 | ORF3a B15.01_71 | 9 | LALSKGVHF | 0.329022 | 0.56 |
| HLA-B*15:01 | 1093 | 146 | ORF3a B15.01_146 | 9 | FLCWHTNCY | 0.324971 | 0.58 |
| HLA-B*15:01 | 1094 | 33 | ORF3a B15.01_33 | 9 | ATIPIQASL | 0.236974 | 0.81 |
| HLA-B*15:01 | 1095 | 83 | ORF3a B15.01_83 | 9 | LLLLFVTVY | 0.217874 | 0.87 |
| HLA-B*40:01 | 1096 | 241 | ORF3a B40.01_241 | 9 | EEHVQIHTI | 0.56881 | 0.22 |
| HLA-B*40:01 | 1097 | 193 | ORF3a B40.01_193 | 9 | WESGVKDCV | 0.189099 | 0.66 |
| HLA-B*58:01 | 1098 | 61 | ORF3a B58.01_61 | 9 | KIITLKKRW | 0.792637 | 0.12 |
| HLA-B*58:01 | 1099 | 37 | ORF3a B58.01_37 | 9 | IQASLPFGW | 0.770898 | 0.14 |
| HLA-B*58:01 | 1100 | 39 | ORF3a B58.01_39 | 9 | ASLPFGWLI | 0.600839 | 0.25 |
| HLA-B*58:01 | 1101 | 185 | ORF3a B58.01_185 | 9 | QIGGYTEKW | 0.594673 | 0.25 |
| HLA-B*58:01 | 1102 | 33 | ORF3a B58.01_33 | 9 | ATIPIQASL | 0.593727 | 0.26 |
| HLA-B*58:01 | 1103 | 71 | ORF3a B58.01_71 | 9 | LALSKGVHF | 0.526496 | 0.3 |
| HLA-B*58:01 | 1104 | 207 | ORF3a B58.01_207 | 9 | FTSDYYQLY | 0.50603 | 0.32 |
| HLA-B*58:01 | 1105 | 63 | ORF3a B58.01_63 | 9 | ITLKKRWQL | 0.388217 | 0.42 |
| HLA-B*58:01 | 1106 | 57 | ORF3a B58.01_57 | 9 | QSASKIITL | 0.385737 | 0.42 |
| HLA-B*58:01 | 1107 | 120 | ORF3a B58.01_120 | 9 | FVRIIMRLW | 0.362631 | 0.45 |
| HLA-B*58:01 | 1108 | 123 | ORF3a B58.01_123 | 9 | IIMRLWLCW | 0.362597 | 0.45 |
| HLA-B*58:01 | 1109 | 204 | ORF3a B58.01_204 | 9 | HSYFTSDYY | 0.35909 | 0.45 |
| HLA-B*58:01 | 1110 | 99 | ORF3a B58.01_99 | 9 | AGLEAPFLY | 0.302287 | 0.55 |

TABLE 8-continued

ORF-3A

| Allele | Sequence ID No. | Start | Sequence Annotation | Length | Sequence | Score | Rank |
|---|---|---|---|---|---|---|---|
| HLA-B*58:01 | 1111 | 88 | ORF3a_B58.01_88 | 9 | VTVYSHLLL | 0.206627 | 0.76 |
| HLA-B*58:01 | 1112 | 79 | ORF3a_B58.01_79 | 9 | FVCNLLLLF | 0.194224 | 0.79 |

TABLE 9

ORF-6

| Allele | Sequence ID No. | Start | Sequence Annotation | Length | Sequence | Score | Rank |
|---|---|---|---|---|---|---|---|
| HLA-A*01:01 | 1113 | 23 | ORF6_A1.01_23 | 9 | KVSIWNLDY | 0.175977 | 0.61 |
| HLA-A*02:01 | 1114 | 3 | ORF6_A2.01_3 | 9 | HLVDFQVTI | 0.910832 | 0.03 |
| HLA-A*02:01 | 1115 | 28 | ORF6_A2.01_28 | 9 | NLDYIINLI | 0.366871 | 0.41 |
| HLA-A*02:01 | 1116 | 10 | ORF6_A2.01_10 | 9 | TIAEILLII | 0.252135 | 0.64 |
| HLA-A*02:01 | 1117 | 16 | ORF6_A2.01_16 | 9 | LIIMRTFKV | 0.204711 | 0.77 |
| HLA-A*03:01 | 1118 | 15 | ORF6_A3.01_15 | 9 | LLIIMRTFK | 0.435841 | 0.43 |
| HLA-A*03:01 | 1119 | 34 | ORF6_A3.01_34 | 9 | NLIIKNLSK | 0.378646 | 0.53 |
| HLA-A*03:01 | 1120 | 23 | ORF6_A3.01_23 | 9 | KVSIWNLDY | 0.237379 | 0.82 |
| HLA-A*24:02 | 1121 | 21 | ORF6_A24.02_21 | 9 | TFKVSIWNL | 0.422545 | 0.25 |
| HLA-B*07:02 | 1122 | 36 | ORF6_B07.01_36 | 9 | IIKNLSKSL | 0.241687 | 0.59 |
| HLA-B*15:01 | 1123 | 50 | ORF6_B15.01_50 | 9 | SQLDEEQPM | 0.368542 | 0.48 |
| HLA-B*15:01 | 1124 | 23 | ORF6_B15.01_23 | 9 | KVSIWNLDY | 0.189586 | 0.99 |
| HLA-B*58:01 | 1125 | 9 | ORF6_B58.01_9 | 9 | VTIAEILLI | 0.45441 | 0.36 |

TABLE 10

ORF-7

| Allele | Sequence ID No. | Start | Sequence Annotation | Length | Sequence | Score | Rank |
|---|---|---|---|---|---|---|---|
| HLA-A*02:01 | 1126 | 13 | ORF7_A2.01_13 | 9 | FLAFLLFLV | 0.391043 | 0.38 |
| HLA-A*02:01 | 1127 | 26 | ORF7_A2.01_26 | 9 | IIFWFSLEL | 0.311542 | 0.53 |
| HLA-A*02:01 | 1128 | 10 | ORF7_A2.01_10 | 9 | YLCFLAFLL | 0.238134 | 0.67 |
| HLA-A*02:01 | 1129 | 3 | ORF7_A2.01_3 | 9 | ELSLIDFYL | 0.173084 | 0.91 |
| HLA-A*02:01 | 1130 | 17 | ORF7_A2.01_17 | 9 | LLFLVLIML | 0.114475 | 1.3 |
| HLA-A*24:02 | 1131 | 5 | ORF7_A24.02_5 | 9 | SLIDFYLCF | 0.162262 | 0.6 |
| HLA-A*24:02 | 1132 | 9 | ORF7_A24.02_9 | 9 | FYLCFLAFL | 0.098668 | 0.86 |
| HLA-A*26:01 | 1133 | 5 | ORF7_A26.01_5 | 9 | SLIDFYLCF | 0.158145 | 0.47 |
| HLA-B*15:01 | 1134 | 5 | ORF7_B15.01_5 | 9 | SLIDFYLCF | 0.494646 | 0.31 |
| HLA-B*58:01 | 1135 | 21 | ORF7_B58.01_21 | 9 | VLIMLIIFW | 0.30633 | 0.54 |

TABLE 11

ORF-8

| Allele | Sequence ID No. | Start | Sequence Annotation | Length | Sequence | Score | Rank |
|---|---|---|---|---|---|---|---|
| HLA-A*01:01 | 1136 | 23 | ORF8_A1.01_23 | 9 | QSCTQHQPY | 0.336403 | 0.32 |
| HLA-A*01:01 | 1137 | 65 | ORF8_A1.01_65 | 9 | AGSKSPIQY | 0.187336 | 0.57 |
| HLA-A*01:01 | 1138 | 102 | ORF8_A1.01_102 | 9 | SFYEDFLEY | 0.168125 | 0.62 |
| HLA-A*01:01 | 1139 | 32 | ORF8_A1.01_32 | 9 | VVDDPCPIH | 0.147161 | 0.69 |
| HLA-A*01:01 | 1140 | 33 | ORF8_A1.01_33 | 9 | VDDPCPIHF | 0.07727 | 1.2 |
| HLA-A*01:01 | 1141 | 96 | ORF8_A1.01_96 | 9 | SLVVRCSFY | 0.073703 | 1.2 |
| HLA-A*02:01 | 1142 | 107 | ORF8_A2.01_107 | 9 | FLEYHDVRV | 0.675619 | 0.15 |
| HLA-A*02:01 | 1143 | 93 | ORF8_A2.01_93 | 9 | KLGSLVVRC | 0.277075 | 0.59 |
| HLA-A*02:01 | 1144 | 31 | ORF8_A2.01_31 | 9 | YVVDDPCPI | 0.197175 | 0.8 |
| HLA-A*02:01 | 1145 | 6 | ORF8_A2.01_6 | 9 | FLGIITTVA | 0.182085 | 0.88 |
| HLA-A*02:01 | 1146 | 5 | ORF8_A2.01_5 | 9 | VFLGIITTV | 0.161779 | 0.97 |
| HLA-A*02:01 | 1147 | 72 | ORF8_A2.01_72 | 9 | QYIDINYTV | 0.075501 | 1.6 |
| HLA-A*03:01 | 1148 | 102 | ORF8_A3.01_102 | 9 | SFYEDFLEY | 0.16552 | 1.1 |
| HLA-A*24:02 | 1149 | 72 | ORF8_A24.02_72 | 9 | QYIDINYTV | 0.871876 | 0.04 |
| HLA-A*24:02 | 1150 | 109 | ORF8_A24.02_109 | 9 | EYHDVRVVL | 0.515969 | 0.19 |
| HLA-A*24:02 | 1151 | 41 | ORF8_A24.02_41 | 9 | FYSKWYIRV | 0.421822 | 0.25 |
| HLA-A*24:02 | 1152 | 77 | ORF8_A24.02_77 | 9 | NYTVSCLPF | 0.324175 | 0.32 |
| HLA-A*24:02 | 1153 | 102 | ORF8_A24.02_102 | 9 | SFYEDFLEY | 0.222279 | 0.45 |
| HLA-A*24:02 | 1154 | 5 | ORF8_A24.02_5 | 9 | VFLGIITIV | 0.190632 | 0.53 |
| HLA-A*26:01 | 1155 | 102 | ORF8_A26.01_102 | 9 | SFYEDFLEY | 0.318827 | 0.23 |
| HLA-A*26:01 | 1156 | 8 | ORF8_A26.01_8 | 9 | GIITTVAAF | 0.192488 | 0.39 |
| HLA-A*26:01 | 1157 | 75 | ORF8_A26.01_75 | 9 | DINYTVSCL | 0.083624 | 0.81 |
| HLA-A*26:01 | 1158 | 34 | ORF8_A26.01_34 | 9 | DDPCPIHFY | 0.071197 | 0.92 |
| HLA-B*07:02 | 1159 | 91 | ORF8_B07.02_91 | 9 | EPKLGSLVV | 0.422674 | 0.32 |
| HLA-B*15:01 | 1160 | 8 | ORF8_B15.01_8 | 9 | GIITIVAAF | 0.702601 | 0.13 |
| HLA-B*15:01 | 1161 | 102 | ORF8_B15.01_102 | 9 | SFYEDFLEY | 0.47413 | 0.33 |
| HLA-B*15:01 | 1162 | 65 | ORF8_B15.01_65 | 9 | AGSKSPIQY | 0.386821 | 0.44 |
| HLA-B*15:01 | 1163 | 96 | ORF8_B15.01_96 | 9 | SLVVRCSFY | 0.260667 | 0.74 |
| HLA-B*15:01 | 1164 | 23 | ORF8_B15.01_23 | 9 | QSCTQHQPY | 0.143528 | 1.3 |
| HLA-B*15:01 | 1165 | 89 | ORF8_B15.01_89 | 9 | CQEPKLGSL | 0.101927 | 1.6 |
| HLA-B*40:01 | 1166 | 108 | ORF8_B40.01_108 | 9 | LEYHDVRVV | 0.478756 | 0.29 |
| HLA-B*40:01 | 1167 | 90 | ORF8_B40.01_90 | 9 | QEPKLGSLV | 0.346977 | 0.44 |
| HLA-B*40:01 | 1168 | 52 | ORF8_B40.01_52 | 9 | RKSAPLIEL | 0.070944 | 1.2 |
| HLA-B*58:01 | 1169 | 53 | ORF8_B58.01_53 | 9 | KSAPLIELC | 0.331298 | 0.5 |
| HLA-B*58:01 | 1170 | 95 | ORF8_B58.01_95 | 9 | GSLVVRCSF | 0.245213 | 0.65 |
| HLA-B*58:01 | 1171 | 65 | ORF8_B58.01_65 | 9 | AGSKSPIQY | 0.215598 | 0.73 |
| HLA-B*58:01 | 1172 | 37 | ORF8_B58.01_37 | 9 | CPIHFYSKW | 0.165769 | 0.89 |

TABLE 11-continued

ORF-8

| Allele | Sequence ID No. | Start | Sequence Annotation | Length | Sequence | Score | Rank |
|---|---|---|---|---|---|---|---|
| HLA-B*58:01 | 1173 | 66 | ORF8_B58.01_66 | 9 | GSKSPIQYI | 0.137132 | 1.1 |
| HLA-B*58:01 | 1174 | 23 | ORF8_B58.01_23 | 9 | QSCTQHQPY | 0.097082 | 1.3 |

The delivery is via four forms
(i) Peptide in liposomes and ionizable liposomes: vaccine peptides plus promiscuous helper peptides in said liposomes.
(ii) Peptide in protein scaffolds as DNA vaccines in said liposomes: vaccine peptides are inserted into the loop regions constrained by a pair of beta strands, a pair of alpha helices or a mixed of beta strand and alpha helix of the said protein scaffolds, and additional helper peptides sequences cloned in the scaffolded regions, or at the N- or C-terminus. Recombinant DNA can be used for DNA immunization.
(iii) Peptide in protein scaffolds as RNA vaccines in said liposomes: the constructs can be arranged in the following three manners for generating RNA as RNA vaccines. In modality one: candidate genes including but not limited to such as substituted vaccine peptides/scaffold, are followed the Mary Kozak translation sequence; GM-CSF, which can be substituted with another effector or suppressive cytokine or combinations of cytokines as CTL adjuvant is one example only including but not limited to microbial or viral protection and prevention of cytokine storms; and two different UTR are included followed by optimal length of poly(A), and cloned into a conventional vector. In second motif, one of the UTR is moved prior to the candidate peptide vaccine. In the third motif, multiple CoV-2 CTL vaccine peptides or other protective epitopes are in tandem and interspersed with promiscuous helper peptides (SEQ ID NO: 1265 to SEQ ID NO: 1270) for CD4 helper T cell induction.
(iv) Bifunctionality: B cell epitopes or using truncated CoV-2 proteins, for example different portions or functional segmental domains of the S protein, inserted either in replaced loop regions scaffolded by the adjacent constraining secondary structures, attached to the N- or C-terminus of the protein scaffolds in aforementioned (i) to (iii). Noticeably, RNA vaccines-encoded proteins are produced in the cytosol, functionally assembled in 3-D conformation to elicit B cell and T cell responses. Furthermore, the RNA vaccines synthesized in the cytosol via released from endosomes, or into ER and Golgi can be degraded into peptide fragments and are utilized in the MHC pathways to be presented for induction of CoV-2 CTL or for helper T cells. Thus, the RNA vaccine embodied in the invention will yield immunogenic and/or suppressive tolerogenic RNA vaccines with/o cytokine help (GM-CSF) (SEQ ID NO: 1175 vs. SEQ ID NO: 1177) or with/o helper peptides (SEQ ID NO: 1180, SEQ ID NO: 1265 to SEQ ID NO: 1270) in not only B cell epitopic protective antibody responses but also T cells protective responses, resulting in protection from microbial infection and cytokine storms from the inserted B cell and T cell epitopes in the loop regions of the protein scaffolds.

Example Six

Embodying Three Designs for Cov-2 RNA Vaccines: First and Second Design Motifs Offer Both B Cell Epitopic as Well as CTL Nonameric (+1/−1), which are Processed Via the ER Stress Pathways.

The three prototype vaccines (SEQ ID: 1175; SEQ ID: 1177; SEQ ID: 1179) for accommodating the larger protein and peptide fragments are listed below; and the three filled-in examples (complete) with the candidate genes are chosen from the human IgE-mediated allergy therapeutic and tolerogenic sequences to mitigate cytokine storm are listed in the Sequence Files as SEQ ID: 1176; SEQ ID: 1178; SEQ ID: 1180. A CoV-2 vaccine candidate gene can be placed into the position in one of the three motifs.

```
First Motif:
Candidate gene-GMCSF-mRNA I Vaccine:
Kpn I-Kozak-candidate genes-linker=GMCSF-UTR-UTR-Poly(A)-Spa I-Xba I
CTGGTACCGCCACCATGATCGATCGATCGA
GTGGCGGCGGAGGATCCatgtggctgcagaatttacttttcctgggcatt
gtggtctacagcctctcagcacccacccgctcacccatcactgtcacccg
gccttggaagcatgtagaggccatcaaagaagccctgaacctcctggatg
acatgctgtcacgttgaatgaagaggtagaagtcgtctctaacgagttc
tccttcaagaagctaacatgtgtgcagacccgcctgaagatattcgagca
gggtctacggggcaatttcaccaaactcaagggcgccttgaacatgacag
ccagctactaccagacatactgcccccaactccggaaacggactgtgaa
acacaagttaccacctatgcggatttcatagacagccttaaaacctttct
gactgatatcccctttgaatgcaaaaaaccaggccaaaaaTAAagctcgc
tttcttgctgtccaatttctattaaaggttcctttgttccctaagtccaa
ctactaaactgggggatattatgaagggccttgagcatctggattctgcc
taataaaaaacattttattttcattgcagctcgctttcttgctgtccaatt
tctattaaaggttcctttgttccctaagtccaactactaaactgggggat
attatgaagggccttgagcatctggattctgcctaataaaaaacatttat
tttcattgcaaaaaaaaaaaaaaaaaaaaaaaaaaaaaaaGcatatgactA
aaaaaaaaaaaaaaaaaaaaaaaaaaaaaaaaaaaaaaaaaaaaaaaaa
aaaaaaaaaaaaaaaaaaaGAAGAGCTCTAGATG (SEQ ID: 1175)
```

-continued

```
Second Motif
Candidate gene-mRNA Vaccine II
Kpn I-5UTR-Candidate gene(s)3UTR-Poly(A)-SpaI-Xba I
CTGGTACC
TCTCAACACAACATATACAAAACAAACGAATCTCAAGCAATCAAGCATTC
TACTTCTATTGCAGCAATTTAAATCATTTCTTTTAAAGCAAAAGCAATTT
TCTGAAAATTTTCACCATTTACGAACGATAGCCandidate
genesCTGGTACTGCATGCACGCAATGCTAGC
TGCCCCTTTCCCGTCCTGGGTACCCCGAGTCTCCCCCGACCTCGGGTCCC
AGGTATGCTCCCACCTCCACCTGCCCCACTCACCACCTCTGCTAGTTCCA
GACACCTCCCA TABLE 12-continued Mutant Covid-19 RNA Frames

| Sequence ID No. | Sequence Annotation | Length | Sequence |
| --- | --- | --- | --- |
| 1176 | M TABLE 12-continued Mutant Covid-19 RNA Frames

| Sequence ID No. | Sequence Annotation | Length | Sequence |
|---|---|---|---|
| | | | CCCCTTTGAATGCA <213> ORGANISM: CoV-2
<220> FEATURE:
<223> OTHER INFORMATION: NTD 2

<400> SEQUENCE: 2

His Ala Ile His Val Ser Gly Thr Asn Gly Thr Lys Arg Phe Asp Asn
1               5                   10                  15

Pro

<210> SEQ ID NO 3
<211> LENGTH: 6
<212> TYPE: PRT
<213> ORGANISM: CoV-2
<220> FEATURE:
<223> OTHER INFORMATION: NTD 3

<400> SEQUENCE: 3

Lys Ser Asn Ile Ile Arg
1               5

<210> SEQ ID NO 4
<211> LENGTH: 9
<212> TYPE: PRT
<213> ORGANISM: CoV-2
<220> FEATURE:
<223> OTHER INFORMATION: NTD 4

<400> SEQUENCE: 4

Thr Thr Leu Asp Ser Lys Thr Gln Ser
1               5

<210> SEQ ID NO 5
<211> LENGTH: 39
<212> TYPE: PRT
<213> ORGANISM: CoV-2
<220> FEATURE:
<223> OTHER INFORMATION: NTD 5

<400> SEQUENCE: 5

Val Cys Glu Phe Gln Phe Cys Asn Asp Pro Phe Leu Gly Val Tyr Tyr
1               5                   10                  15

His Lys Asn Asn Lys Ser Trp Met Glu Ser Glu Phe Arg Val Tyr Ser
                20                  25                  30

Ser Ala Asn Asn Cys Thr Phe
        35

<210> SEQ ID NO 6
<211> LENGTH: 16
<212> TYPE: PRT
<213> ORGANISM: CoV-2
<220> FEATURE:
<223> OTHER INFORMATION: NTD 6

<400> SEQUENCE: 6

Ser Gln Pro Phe Leu Met Asp Leu Glu Gly Lys Gln Gly Asn Phe Lys
1               5                   10                  15

<210> SEQ ID NO 7
<211> LENGTH: 13
<212> TYPE: PRT
<213> ORGANISM: CoV-2
<220> FEATURE:
<223> OTHER INFORMATION: NTD 7

<400> SEQUENCE: 7

-continued

```
Ile Asn Leu Val Arg Asp Leu Pro Gln Gly Phe Ser Ala
1               5                   10

<210> SEQ ID NO 8
<211> LENGTH: 6
<212> TYPE: PRT
<213> ORGANISM: CoV-2
<220> FEATURE:
<223> OTHER INFORMATION: NTD 8

<400> SEQUENCE: 8

Ile Gly Ile Asn Ile Thr
1               5

<210> SEQ ID NO 9
<211> LENGTH: 23
<212> TYPE: PRT
<213> ORGANISM: CoV-2
<220> FEATURE:
<223> OTHER INFORMATION: NTD 9

<400> SEQUENCE: 9

Leu Ala Leu His Arg Ser Tyr Leu Thr Pro Gly Asp Ser Ser Ser Gly
1               5                   10                  15

Trp Thr Ala Gly Ala Ala Ala
            20

<210> SEQ ID NO 10
<211> LENGTH: 20
<212> TYPE: PRT
<213> ORGANISM: CoV-2
<220> FEATURE:
<223> OTHER INFORMATION: NTD 10

<400> SEQUENCE: 10

Cys Ala Leu Asp Pro Leu Ser Glu Thr Lys Cys Thr Leu Lys Ser Phe
1               5                   10                  15

Thr Val Glu Lys
            20

<210> SEQ ID NO 11
<211> LENGTH: 25
<212> TYPE: PRT
<213> ORGANISM: CoV-2
<220> FEATURE:
<223> OTHER INFORMATION: RBD 1

<400> SEQUENCE: 11

Phe Pro Asn Ile Thr Asn Leu Cys Pro Phe Gly Glu Val Phe Asn Ala
1               5                   10                  15

Thr Arg Phe Ala Ser Val Tyr Ala Trp
            20                  25

<210> SEQ ID NO 12
<211> LENGTH: 13
<212> TYPE: PRT
<213> ORGANISM: CoV-2
<220> FEATURE:
<223> OTHER INFORMATION: RBD 2

<400> SEQUENCE: 12

Ala Asp Tyr Ser Val Leu Tyr Asn Ser Ala Ser Phe Ser
1               5                   10

<210> SEQ ID NO 13
```

```
<211> LENGTH: 11
<212> TYPE: PRT
<213> ORGANISM: CoV-2
<220> FEATURE:
<223> OTHER INFORMATION: RBD 3

<400> SEQUENCE: 13

Tyr Gly Val Ser Pro Thr Lys Leu Asn Asp Leu
1               5                   10

<210> SEQ ID NO 14
<211> LENGTH: 27
<212> TYPE: PRT
<213> ORGANISM: CoV-2
<220> FEATURE:
<223> OTHER INFORMATION: RBD 4

<400> SEQUENCE: 14

Gly Asp Glu Val Arg Gln Ile Ala Pro Gly Gln Thr Gly Lys Ile Ala
1               5                   10                  15

Asp Tyr Asn Tyr Lys Leu Pro Asp Asp Phe Thr
            20                  25

<210> SEQ ID NO 15
<211> LENGTH: 14
<212> TYPE: PRT
<213> ORGANISM: CoV-2
<220> FEATURE:
<223> OTHER INFORMATION: RBE 1

<400> SEQUENCE: 15

Ser Asn Asn Leu Asp Ser Lys Val Gly Gly Asn Tyr Asn Tyr
1               5                   10

<210> SEQ ID NO 16
<211> LENGTH: 37
<212> TYPE: PRT
<213> ORGANISM: CoV-2
<220> FEATURE:
<223> OTHER INFORMATION: RBE 2

<400> SEQUENCE: 16

Leu Phe Arg Lys Ser Asn Leu Lys Pro Phe Glu Arg Asp Ile Ser Thr
1               5                   10                  15

Glu Ile Tyr Gln Ala Gly Ser Thr Pro Cys Asn Gly Val Glu Gly Phe
            20                  25                  30

Asn Cys Tyr Phe Pro
        35

<210> SEQ ID NO 17
<211> LENGTH: 12
<212> TYPE: PRT
<213> ORGANISM: CoV-2
<220> FEATURE:
<223> OTHER INFORMATION: RBE 3

<400> SEQUENCE: 17

Tyr Gly Phe Gln Pro Thr Asn Gly Val Gly Tyr Gln
1               5                   10

<210> SEQ ID NO 18
<211> LENGTH: 7
<212> TYPE: PRT
<213> ORGANISM: CoV-2
<220> FEATURE:
<223> OTHER INFORMATION: S2 1
```

<400> SEQUENCE: 18

Leu Leu His Ala Pro Ala Thr
1               5

<210> SEQ ID NO 19
<211> LENGTH: 12
<212> TYPE: PRT
<213> ORGANISM: CoV-2
<220> FEATURE:
<223> OTHER INFORMATION: S2 2

<400> SEQUENCE: 19

Gly Pro Lys Lys Ser Thr Asn Leu Val Lys Asn Lys
1               5                   10

<210> SEQ ID NO 20
<211> LENGTH: 10
<212> TYPE: PRT
<213> ORGANISM: CoV-2
<220> FEATURE:
<223> OTHER INFORMATION: S2 3

<400> SEQUENCE: 20

Ser Asn Lys Lys Phe Leu Pro Phe Gln Gln
1               5                   10

<210> SEQ ID NO 21
<211> LENGTH: 6
<212> TYPE: PRT
<213> ORGANISM: CoV-2
<220> FEATURE:
<223> OTHER INFORMATION: S2 4

<400> SEQUENCE: 21

Asp Pro Gln Thr Leu Glu
1               5

<210> SEQ ID NO 22
<211> LENGTH: 9
<212> TYPE: PRT
<213> ORGANISM: CoV-2
<220> FEATURE:
<223> OTHER INFORMATION: S2 5

<400> SEQUENCE: 22

Pro Gly Thr Asn Thr Ser Asn Glu Val
1               5

<210> SEQ ID NO 23
<211> LENGTH: 28
<212> TYPE: PRT
<213> ORGANISM: CoV-2
<220> FEATURE:
<223> OTHER INFORMATION: S2 6

<400> SEQUENCE: 23

Asp Val Asn Cys Thr Glu Val Pro Val Ala Ile His Ala Asp Gln Leu
1               5                   10                  15

Thr Pro Thr Trp Arg Val Tyr Ser Thr Gly Ser Asn
            20                  25

<210> SEQ ID NO 24
<211> LENGTH: 8
<212> TYPE: PRT
<213> ORGANISM: CoV-2

```
<220> FEATURE:
<223> OTHER INFORMATION: S2 7

<400> SEQUENCE: 24

Val Asn Asn Ser Tyr Glu Cys Asp
1               5

<210> SEQ ID NO 25
<211> LENGTH: 15
<212> TYPE: PRT
<213> ORGANISM: CoV-2
<220> FEATURE:
<223> OTHER INFORMATION: Furin S1-S2 1

<400> SEQUENCE: 25

Thr Gln Thr Asn Ser Pro Ser Gly Ala Gly Ser Val Ala Ser Gln
1               5                   10                  15

<210> SEQ ID NO 26
<211> LENGTH: 8
<212> TYPE: PRT
<213> ORGANISM: CoV-2
<220> FEATURE:
<223> OTHER INFORMATION: Furin S1-S2 2

<400> SEQUENCE: 26

Asn Ser Val Ala Tyr Ser Asn Asn
1               5

<210> SEQ ID NO 27
<211> LENGTH: 10
<212> TYPE: PRT
<213> ORGANISM: CoV-2
<220> FEATURE:
<223> OTHER INFORMATION: S2 8

<400> SEQUENCE: 27

Asp Cys Thr Met Tyr Ile Cys Gly Asp Ser
1               5                   10

<210> SEQ ID NO 28
<211> LENGTH: 28
<212> TYPE: PRT
<213> ORGANISM: CoV-2
<220> FEATURE:
<223> OTHER INFORMATION: CoV-2 Fusion Peptide

<400> SEQUENCE: 28

Tyr Lys Thr Pro Pro Ile Lys Asp Phe Gly Gly Phe Asn Phe Ser Gln
1               5                   10                  15

Ile Leu Pro Asp Pro Ser Lys Pro Ser Lys Arg Ser
            20                  25

<210> SEQ ID NO 29
<211> LENGTH: 5
<212> TYPE: PRT
<213> ORGANISM: CoV-2
<220> FEATURE:
<223> OTHER INFORMATION: S2 9

<400> SEQUENCE: 29

Pro Pro Leu Leu Thr
1               5

<210> SEQ ID NO 30
<211> LENGTH: 8
```

```
<212> TYPE: PRT
<213> ORGANISM: CoV-2
<220> FEATURE:
<223> OTHER INFORMATION: S2 10

<400> SEQUENCE: 30

Gly Ala Ala Leu Gln Ile Pro Phe
1               5

<210> SEQ ID NO 31
<211> LENGTH: 12
<212> TYPE: PRT
<213> ORGANISM: CoV-2
<220> FEATURE:
<223> OTHER INFORMATION: S2 11

<400> SEQUENCE: 31

Gly Ile Gly Val Thr Gln Asn Val Leu Tyr Glu Asn
1               5                   10

<210> SEQ ID NO 32
<211> LENGTH: 9
<212> TYPE: PRT
<213> ORGANISM: CoV-2
<220> FEATURE:
<223> OTHER INFORMATION: S2 12

<400> SEQUENCE: 32

Ser Asn Phe Gly Ala Ile Ser Ser Val
1               5

<210> SEQ ID NO 33
<211> LENGTH: 14
<212> TYPE: PRT
<213> ORGANISM: CoV-2
<220> FEATURE:
<223> OTHER INFORMATION: S2 13

<400> SEQUENCE: 33

Val Leu Gly Gln Ser Lys Arg Val Asp Phe Cys Gly Lys Gly
1               5                   10

<210> SEQ ID NO 34
<211> LENGTH: 7
<212> TYPE: PRT
<213> ORGANISM: CoV-2
<220> FEATURE:
<223> OTHER INFORMATION: S2 14

<400> SEQUENCE: 34

Gln Arg Asn Phe Tyr Glu Pro
1               5

<210> SEQ ID NO 35
<211> LENGTH: 7
<212> TYPE: PRT
<213> ORGANISM: CoV-2
<220> FEATURE:
<223> OTHER INFORMATION: S2 15

<400> SEQUENCE: 35

Cys Asp Val Val Ile Gly Ile
1               5

<210> SEQ ID NO 36
<211> LENGTH: 6
<212> TYPE: PRT
```

-continued

```
<213> ORGANISM: CoV-2
<220> FEATURE:
<223> OTHER INFORMATION: S2 16

<400> SEQUENCE: 36

Asn Thr Val Tyr Asp Pro
1               5

<210> SEQ ID NO 37
<211> LENGTH: 35
<212> TYPE: PRT
<213> ORGANISM: CoV-2
<220> FEATURE:
<223> OTHER INFORMATION: RBE 4

<400> SEQUENCE: 37

Phe Asn Lys Val Thr Leu Ala Asp Ala Gly Phe Ile Lys Gln Tyr Gly
1               5                   10                  15

Asp Cys Leu Gly Asp Ile Ala Ala Arg Asp Leu Ile Cys Ala Gln Lys
            20                  25                  30

Phe Asn Gly
        35

<210> SEQ ID NO 38
<211> LENGTH: 27
<212> TYPE: PRT
<213> ORGANISM: CoV-2
<220> FEATURE:
<223> OTHER INFORMATION: RBE 5

<400> SEQUENCE: 38

Tyr Gln Thr Gln Thr Asn Ser Pro Arg Arg Ala Arg Ser Val Ala Ser
1               5                   10                  15

Gln Ser Ile Ile Ala Tyr Thr Met Ser Leu Gly
            20                  25

<210> SEQ ID NO 39
<211> LENGTH: 8
<212> TYPE: PRT
<213> ORGANISM: CoV-2
<220> FEATURE:
<223> OTHER INFORMATION: RBE 6

<400> SEQUENCE: 39

Ser Pro Arg Arg Ala Arg Ser Val
1               5

<210> SEQ ID NO 40
<211> LENGTH: 18
<212> TYPE: PRT
<213> ORGANISM: CoV-2
<220> FEATURE:
<223> OTHER INFORMATION: RBE 7

<400> SEQUENCE: 40

Ser Phe Ile Glu Asp Leu Leu Phe Asn Lys Val Thr Leu Ala Asp Ala
1               5                   10                  15

Gly Phe

<210> SEQ ID NO 41
<211> LENGTH: 27
<212> TYPE: PRT
<213> ORGANISM: CoV-2
<220> FEATURE:
<223> OTHER INFORMATION: RBE 8
```

<400> SEQUENCE: 41

Pro Ser Lys Pro Ser Lys Arg Ser Phe Ile Glu Asp Leu Leu Phe Asn
1               5                   10                  15

Lys Val Thr Leu Ala Asp Ala Gly Phe Ile Lys
                20                  25

<210> SEQ ID NO 42
<211> LENGTH: 46
<212> TYPE: PRT
<213> ORGANISM: CoV-2
<220> FEATURE:
<223> OTHER INFORMATION: RBE 9

<400> SEQUENCE: 42

Gln Met Asp Ser Leu Lys Pro Glu Asp Thr Ala Val Tyr Tyr Cys Ala
1               5                   10                  15

Ala Gly Val Glu Gly Phe Asn Cys Tyr Phe Pro Leu Gln Ser Tyr Gly
                20                  25                  30

Phe Gln Pro Thr Asn Gly Val Gly Tyr Gln Pro Tyr Arg Val
            35                  40                  45

<210> SEQ ID NO 43
<211> LENGTH: 160
<212> TYPE: PRT
<213> ORGANISM: CoV-2
<220> FEATURE:
<223> OTHER INFORMATION: RBE 10

<400> SEQUENCE: 43

Gly Gln Val Gln Leu Val Glu Ser Gly Gly Gly Ser Val Gln Ala Gly
1               5                   10                  15

Gly Ser Leu Arg Leu Ser Cys Ala Ala Ser Gly Tyr Thr Phe Ser Ser
                20                  25                  30

Tyr Pro Met Gly Trp Tyr Arg Gln Ala Pro Gly Lys Glu Cys Glu Leu
            35                  40                  45

Val Ser Phe Arg Lys Ser Asn Leu Lys Pro Phe Glu Arg Asp Ile Ser
50                  55                  60

Thr Glu Ile Tyr Gln Ala Gly Ser Thr Pro Cys Asn Ala Asn Tyr Ala
65                  70                  75                  80

Gly Ser Val Lys Gly Arg Phe Thr Ile Ser Arg Asp Asn Ala Lys Asn
                85                  90                  95

Thr Ala Tyr Leu Gln Met Asp Ser Leu Lys Pro Glu Asp Thr Ala Val
            100                 105                 110

Tyr Tyr Cys Ala Ala Gly Val Glu Gly Phe Asn Cys Tyr Phe Pro Leu
        115                 120                 125

Gln Ser Tyr Gly Phe Gln Pro Thr Asn Gly Val Gly Tyr Gln Pro Tyr
    130                 135                 140

Arg Val Trp Gly Gln Gly Thr Gln Val Thr Val Ser Ser Gly Gly Gly
145                 150                 155                 160

<210> SEQ ID NO 44
<211> LENGTH: 133
<212> TYPE: PRT
<213> ORGANISM: CoV-2
<220> FEATURE:
<223> OTHER INFORMATION: RBE 11

<400> SEQUENCE: 44

Gly Gln Val Gln Leu Val Glu Ser Gly Gly Gly Ser Val Gln Ala Gly

```
                1               5                   10                  15
          Gly Ser Leu Arg Leu Ser Cys Ala Ala Ser Gly Tyr Thr Phe Ser Ser
                        20                  25                  30

Tyr Pro Met Gly Trp Tyr Arg Gln Ala Pro Gly Lys Glu Cys Glu Leu
                        35                  40                  45

Val Ser Ser Pro Arg Arg Ala Arg Ser Val Asp Gly Ser Ala Asn Tyr
                        50                  55                  60

Ala Gly Ser Val Lys Gly Arg Phe Thr Ile Ser Arg Asp Asn Ala Lys
          65                  70                  75                  80

Asn Thr Ala Tyr Leu Gln Met Asp Ser Leu Lys Pro Glu Asp Thr Ala
                        85                  90                  95

Val Tyr Tyr Cys Ala Ala Ser Phe Ile Glu Asp Leu Leu Phe Asn Lys
                        100                 105                 110

Val Thr Leu Ala Asp Ala Gly Phe Trp Gly Gln Gly Thr Gln Val Thr
                        115                 120                 125

Val Ser Ser Gly Gly
                        130

<210> SEQ ID NO 45
<211> LENGTH: 145
<212> TYPE: PRT
<213> ORGANISM: CoV-2
<220> FEATURE:
<223> OTHER INFORMATION: RBE 12

<400> SEQUENCE: 45

-continued

Gly Ser Leu Arg Leu Ser Cys Ala Ala Ser Gly Tyr Thr Phe Ser Ser
            20                  25                  30

Tyr Pro Met Gly Trp Tyr Arg Gln Ala Pro Gly Lys Glu Cys Glu Leu
        35                  40                  45

Val Ser Ile Tyr Lys Thr Pro Pro Ile Lys Asp Phe Gly Gly Phe Asn
 50                  55                  60

Phe Ser Gln Ile Leu Ala Asn Tyr Ala Gly Ser Val Lys Gly Arg Phe
65                  70                  75                  80

Thr Ile Ser Arg Asp Asn Ala Lys Asn Thr Ala Tyr Leu Gln Met Asp
                85                  90                  95

Ser Leu Lys Pro Glu Asp Thr Ala Val Tyr Tyr Cys Ala Ala Gly Pro
            100                 105                 110

Gly Ser Gly Lys Leu Val Val Ala Gly Arg Thr Cys Tyr Gly Pro Asn
        115                 120                 125

Tyr Trp Gly Gln Gly Thr Gln Val Thr Val Ser Ser Gly Gly
    130                 135                 140

<210> SEQ ID NO 47
<211> LENGTH: 130
<212> TYPE: PRT
<213> ORGANISM: CoV-2
<220> FEATURE:
<223> OTHER INFORMATION: RBE 14

<400> SEQUENCE: 47

Gly Gln Val Gln Leu Val Glu Ser Gly Gly Gly Ser Val Gln Ala Gly
1               5                   10                  15

Gly Ser Leu Arg Leu Ser Cys Ala Ala Ser Gly Tyr Thr Phe Ser Ser
            20                  25                  30

Tyr Pro Met Gly Trp Tyr Arg Gln Ala Pro Gly Lys Glu Cys Glu Leu
        35                  40                  45

Val Ser Arg Ile Phe Ser Asp Gly Ser Ala Asn Tyr Ala Gly Ser Val
 50                  55                  60

Lys Gly Arg Phe Thr Ile Ser Arg Asp Asn Ala Lys Asn Thr Ala Tyr
65                  70                  75                  80

Leu Gln Met Asp Ser Leu Lys Pro Glu Asp Thr Ala Val Tyr Tyr Cys
                85                  90                  95

Ala Ala Ile Tyr Lys Thr Pro Pro Ile Lys Asp Phe Gly Gly Phe Asn
            100                 105                 110

Phe Ser Gln Ile Leu Trp Gly Gln Gly Thr Gln Val Thr Val Ser Ser
        115                 120                 125

Gly Gly
    130

<210> SEQ ID NO 48
<211> LENGTH: 138
<212> TYPE: PRT
<213> ORGANISM: CoV-2
<220> FEATURE:
<223> OTHER INFORMATION: RBE 15

<400> SEQUENCE: 48

Gly Gln Val Gln Leu Val Glu Ser Gly Gly Gly Ser Val Gln Ala Gly
1               5                   10                  15

Gly Ser Leu Arg Leu Ser Cys Ala Ala Ser Gly Tyr Thr Phe Ser Ser
            20                  25                  30

Tyr Pro Met Gly Trp Tyr Arg Gln Ala Pro Gly Lys Glu Cys Glu Leu
        35                  40                  45

Val Ser Arg Ile Phe Ser Asp Gly Ser Ala Asn Tyr Ala Gly Ser Val
     50                  55                  60

Lys Gly Arg Phe Thr Ile Ser Arg Asp Asn Ala Lys Asn Thr Ala Tyr
 65                  70                  75                  80

Leu Gln Met Asp Ser Leu Lys Pro Glu Asp Thr Ala Val Tyr Tyr Cys
                 85                  90                  95

Ala Ala Tyr Gln Thr Gln Thr Asn Ser Pro Arg Arg Ala Arg Ser Val
                100                 105                 110

Ala Ser Gln Ser Ile Ile Ala Tyr Thr Met Ser Leu Gly Trp Gly Gln
            115                 120                 125

Gly Thr Gln Val Thr Val Ser Ser Gly Gly
        130                 135

<210> SEQ ID NO 49
<211> LENGTH: 130
<212> TYPE: PRT
<213> ORGANISM: CoV-2
<220> FEATURE:
<223> OTHER INFORMATION: RBE 16

<400> SEQUENCE: 49

Gly Gln Val Gln Leu Val Glu Ser Gly Gly Gly Ser Val Gln Ala Gly
 1               5                  10                  15

Gly Ser Leu Arg Leu Ser Cys Ala Ala Ser Gly Tyr Thr Phe Ser Ser
                 20                  25                  30

Tyr Pro Met Gly Trp Tyr Arg Gln Ala Pro Gly Lys Glu Cys Glu Leu
             35                  40                  45

Val Ser Arg Ile Phe Ser Asp Gly Ser Ala Asn Tyr Ala Gly Ser Val
     50                  55                  60

Lys Gly Arg Phe Thr Ile Ser Arg Asp Asn Ala Lys Asn Thr Ala Tyr
 65                  70                  75                  80

Leu Gln Met Asp Ser Leu Lys Pro Glu Asp Thr Ala Val Tyr Tyr Cys
                 85                  90                  95

Ala Ala Asn Ser Asn Asn Leu Asp Ser Lys Val Gly Gly Asn Tyr Asn
                100                 105                 110

Tyr Leu Tyr Arg Leu Trp Gly Gln Gly Thr Gln Val Thr Val Ser Ser
            115                 120                 125

Gly Gly
130

<210> SEQ ID NO 50
<211> LENGTH: 142
<212> TYPE: PRT
<213> ORGANISM: CoV-2
<220> FEATURE:
<223> OTHER INFORMATION: RBE 17

<400> SEQUENCE: 50

Gly Gln Val Gln Leu Val Glu Ser Gly Gly Gly Ser Val Gln Ala Gly
 1               5                  10                  15

Gly Ser Leu Arg Leu Ser Cys Ala Ala Ser Gly Tyr Thr Phe Ser Ser
                 20                  25                  30

Tyr Pro Met Gly Trp Tyr Arg Gln Ala Pro Gly Lys Glu Cys Glu Leu
             35                  40                  45

Val Ser Asn Ser Asn Asn Leu Asp Ser Lys Val Gly Gly Asn Tyr Asn
     50                  55                  60

Tyr Leu Tyr Arg Leu Ala Asn Tyr Ala Gly Ser Val Lys Gly Arg Phe 65             70              75              80
Thr Ile Ser Arg Asp Asn Ala Lys Asn Thr Ala Tyr Leu Gln Met Asp
                85              90              95

Ser Leu Lys Pro Glu Asp Thr Ala Val Tyr Tyr Cys Ala Ala Gly Pro
            100             105             110

Gly Ser Gly Lys Leu Val Val Ala Gly Arg Thr Cys Tyr Gly Pro Asn
            115             120             125

Tyr Trp Gly Gln Gly Thr Gln Val Thr Val Ser Ser Gly Gly
        130             135             140

<210> SEQ ID NO 51
<211> LENGTH: 299
<212> TYPE: PRT
<213> ORGANISM: CoV-2
<220> FEATURE:
<223> OTHER INFORMATION: RBE 18

<400> SEQUENCE: 51

Cys Pro Asn Ile Thr Asn Leu Cys Pro Phe Gly Glu Val Phe Asn Ala
1               5               10              15

Thr Arg Phe Ala Ser Val Tyr Ala Trp Asn Arg Lys Arg Ile Ser Asn
            20              25              30

Cys Val Ala Asp Tyr Ser Val Leu Tyr Asn Ser Ala Ser Phe Ser Thr
        35              40              45

Phe Lys Cys Tyr Gly Val Ser Pro Thr Lys Leu Asn Asp Leu Cys Phe
    50              55              60

Thr Asn Val Tyr Ala Asp Ser Phe Val Ile Arg Gly Asp Glu Val Arg
65              70              75              80

Gln Ile Ala Pro Gly Gln Thr Gly Lys Ile Ala Asp Tyr Asn Tyr Lys
                85              90              95

Leu Pro Asp Asp Phe Thr Gly Cys Val Ile Ala Trp Asn Ser Asn Asn
            100             105             110

Leu Asp Ser Lys Val Gly Gly Asn Tyr Asn Tyr Leu Tyr Arg Leu Phe
        115             120             125

Arg Lys Ser Asn Leu Lys Pro Phe Glu Arg Asp Ile Ser Thr Glu Ile
130             135             140

Tyr Gln Ala Gly Ser Thr Pro Cys Asn Gly Val Glu Gly Phe Asn Cys
145             150             155             160

Tyr Phe Pro Leu Gln Ser Tyr Gly Phe Gln Pro Thr Asn Gly Val Gly
                165             170             175

Tyr Gln Pro Tyr Arg Val Val Val Leu Ser Phe Glu Leu Leu His Ala
            180             185             190

Pro Met Gly Lys Gly Glu Glu Leu Phe Thr Gly Val Val Pro Ile Leu
        195             200             205

Val Glu Leu Asp Gly Asp Val Asn Gly His Lys Phe Ser Val Ser Gly
    210             215             220

Glu Gly Glu Gly Asp Ala Thr Tyr Gly Lys Leu Thr Leu Lys Phe Ile
225             230             235             240

Cys Thr Thr Gly Lys Leu Pro Val Pro Trp Pro Thr Leu Val Thr Thr
                245             250             255

Phe Ser Tyr Gly Val Gln Cys Phe Ser Arg Tyr Pro Asp His Met Lys
            260             265             270

Arg His Asp Phe Phe Lys Ser Ala Met Pro Glu Gly Tyr Val Gln Glu
        275             280             285

Arg Thr Ile Ser Phe Lys Asp Asp Gly Asn Tyr
    290             295

```
                      295
        290

<210> SEQ ID NO 52
<211> LENGTH: 23
<212> TYPE: PRT
<213> ORGANISM: CoV-1
<220> FEATURE:
<223> OTHER INFORMATION: CoV-1 S1-S2

<400> SEQUENCE: 52

Tyr His Thr Val Ser Leu Leu Leu Arg Ser Thr Gln Lys Ser Ile Val
1               5                   10                  15

Ala Tyr Thr Met Ser Leu Gly
            20

<210> SEQ ID NO 53
<211> LENGTH: 27
<212> TYPE: PRT
<213> ORGANISM: CoV-1
<220> FEATURE:
<223> OTHER INFORMATION: CoV-1 Furin S2'

<400> SEQUENCE: 53

Pro Leu Lys Pro Thr Lys Arg Ser Phe Ile Glu Asp Leu Leu Phe Asn
1               5                   10                  15

Lys Val Thr Leu Ala Asp Ala Gly Phe Met Lys
            20                  25

<210> SEQ ID NO 54
<211> LENGTH: 27
<212> TYPE: PRT
<213> ORGANISM: CoV-1
<220> FEATURE:
<223> OTHER INFORMATION: CoV-1 RBE 1

<400> SEQUENCE: 54

Tyr Leu Arg Asn Gly Lys Leu Arg Pro Phe Glu Arg Asp Ile Ser Asn
1               5                   10                  15

Val Pro Phe Ser Pro Asp Gly Lys Pro Cys Thr
            20                  25

<210> SEQ ID NO 55
<211> LENGTH: 52
<212> TYPE: PRT
<213> ORGANISM: CoV-1
<220> FEATURE:
<223> OTHER INFORMATION: CoV-1 RBE 2

<400> SEQUENCE: 55

Tyr Leu Arg Asn Gly Lys Leu Arg Pro Phe Glu Arg Asp Ile Ser Asn
1               5                   10                  15

Val Pro Phe Ser Pro Asp Gly Lys Pro Cys Thr Pro Pro Ala Leu Asn
            20                  25                  30

Cys Tyr Trp Pro Leu Asn Asp Tyr Gly Phe Tyr Thr Thr Thr Gly Ile
        35                  40                  45

Gly Tyr Gln Pro
    50

<210> SEQ ID NO 56
<211> LENGTH: 24
<212> TYPE: PRT
<213> ORGANISM: CoV-1
<220> FEATURE:
<223> OTHER INFORMATION: CoV-1 RBE 3
```

-continued

```
<400> SEQUENCE: 56

Pro Pro Ala Leu Asn Cys Tyr Trp Pro Leu Asn Asp Tyr Gly Phe Tyr
1               5                   10                  15

Thr Thr Thr Gly Ile Tyr Gln Pro
            20

<210> SEQ ID NO 57
<211> LENGTH: 16
<212> TYPE: PRT
<213> ORGANISM: CoV-1
<220

```
<223> OTHER INFORMATION: S A1.01_604

<400> SEQUENCE: 61

Thr Ser Asn Gln Val Ala Val Leu Tyr
1               5

<210> SEQ ID NO 62
<211> LENGTH: 9
<212> TYPE: PRT
<213> ORGANISM: CoV-2
<220> FEATURE:
<223> OTHER INFORMATION: S A1.01_258

<400> SEQUENCE: 62

Trp Thr Ala Gly Ala Ala Ala Tyr Tyr
1               5

<210> SEQ ID NO 63
<211> LENGTH: 9
<212> TYPE: PRT
<213> ORGANISM: CoV-2
<220> FEATURE:
<223> OTHER INFORMATION: S A1.01_196

<400> SEQUENCE: 63

Asn Ile Asp Gly Tyr Phe Lys Ile Tyr
1               5

<210> SEQ ID NO 64
<211> LENGTH: 9
<212> TYPE: PRT
<213> ORGANISM: CoV-2
<220> FEATURE:
<223> OTHER INFORMATION: S A1.01_733

<400> SEQUENCE: 64

Lys Thr Ser Val Asp Cys Thr Met Tyr
1               5

<210> SEQ ID NO 65
<211> LENGTH: 9
<212> TYPE: PRT
<213> ORGANISM: CoV-2
<220> FEATURE:
<223> OTHER INFORMATION: S A1.01_361

<400> SEQUENCE: 65

Cys Val Ala Asp Tyr Ser Val Leu Tyr
1               5

<210> SEQ ID NO 66
<211> LENGTH: 9
<212> TYPE: PRT
<213> ORGANISM: CoV-2
<220> FEATURE:
<223> OTHER INFORMATION: S A1.01_652

<400> SEQUENCE: 66

Gly Ala Glu His Val Asn Asn Ser Tyr
1               5

<210> SEQ ID NO 67
<211> LENGTH: 9
<212> TYPE: PRT
<213> ORGANISM: CoV-2
<220> FEATURE:
<223> OTHER INFORMATION: S A1.01_30
```

<400> SEQUENCE: 67

Asn Ser Phe Thr Arg Gly Val Tyr Tyr
1               5

<210> SEQ ID NO 68
<211> LENGTH: 9
<212> TYPE: PRT
<213> ORGANISM: CoV-2
<220> FEATURE:
<223> OTHER INFORMATION: S A1.01_162

<400> SEQUENCE: 68

Ser Ala Asn Asn Cys Thr Phe Glu Tyr
1               5

<210> SEQ ID NO 69
<211> LENGTH: 9
<212> TYPE: PRT
<213> ORGANISM: CoV-2
<220> FEATURE:
<223> OTHER INFORMATION: S A1.01_1039

<400> SEQUENCE: 69

Arg Val Asp Phe Cys Gly Lys Gly Tyr
1               5

<210> SEQ ID NO 70
<211> LENGTH: 9
<212> TYPE: PRT
<213> ORGANISM: CoV-2
<220> FEATURE:
<223> OTHER INFORMATION: S A1.01_152

<400> SEQUENCE: 70

Trp Met Glu Ser Glu Phe Arg Val Tyr
1               5

<210> SEQ ID NO 71
<211> LENGTH: 9
<212> TYPE: PRT
<213> ORGANISM: CoV-2
<220> FEATURE:
<223> OTHER INFORMATION: S A1.01_687

<400> SEQUENCE: 71

Val Ala Ser Gln Ser Ile Ile Ala Tyr
1               5

<210> SEQ ID NO 72
<211> LENGTH: 9
<212> TYPE: PRT
<213> ORGANISM: CoV-2
<220> FEATURE:
<223> OTHER INFORMATION: S A1.01_136

<400> SEQUENCE: 72

Cys Asn Asp Pro Phe Leu Gly Val Tyr
1               5

<210> SEQ ID NO 73
<211> LENGTH: 9
<212> TYPE: PRT
<213> ORGANISM: CoV-2
<220> FEATURE:
<223> OTHER INFORMATION: S A1.01_748

```
<400> SEQUENCE: 73

Glu Cys Ser Asn Leu Leu Leu Gln Tyr
1               5

<210> SEQ ID NO 74
<211> LENGTH: 9
<212> TYPE: PRT
<213> ORGANISM: CoV-2
<220> FEATURE:
<223> OTHER INFORMATION: S A2.01_269

<400> SEQUENCE: 74

Tyr Leu Gln Pro Arg Thr Phe Leu Leu
1               5

<210> SEQ ID NO 75
<211> LENGTH: 9
<212> TYPE: PRT
<213> ORGANISM: CoV-2
<220> FEATURE:
<223> OTHER INFORMATION: S A2.01_976

<400> SEQUENCE: 75

Val Leu Asn Asp Ile Leu Ser Arg Leu
1               5

<210> SEQ ID NO 76
<211> LENGTH: 9
<212> TYPE: PRT
<213> ORGANISM: CoV-2
<220> FEATURE:
<223> OTHER INFORMATION: S A2.01_109

<400> SEQUENCE: 76

Thr Leu Asp Ser Lys Thr Gln Ser Leu
1               5

<210> SEQ ID NO 77
<211> LENGTH: 9
<212> TYPE: PRT
<213> ORGANISM: CoV-2
<220> FEATURE:
<223> OTHER INFORMATION: S A2.01_417

<400> SEQUENCE: 77

Lys Ile Ala Asp Tyr Asn Tyr Lys Leu
1               5

<210> SEQ ID NO 78
<211> LENGTH: 9
<212> TYPE: PRT
<213> ORGANISM: CoV-2
<220> FEATURE:
<223> OTHER INFORMATION: S A2.01_983

<400> SEQUENCE: 78

Arg Leu Asp Lys Val Glu Ala Glu Val
1               5

<210> SEQ ID NO 79
<211> LENGTH: 9
<212> TYPE: PRT
<213> ORGANISM: CoV-2
<220> FEATURE:
<223> OTHER INFORMATION: S A2.01_1000

<400> SEQUENCE: 79
```

```
Arg Leu Gln Ser Leu Gln Thr Tyr Val
1               5

<210> SEQ ID NO 80
<211> LENGTH: 9
<212> TYPE: PRT
<213> ORGANISM: CoV-2
<220> FEATURE:
<223> OTHER INFORMATION: S A2.01_821

<400> SEQUENCE: 80

Leu Leu Phe Asn Lys Val Thr Leu Ala
1               5

<210> SEQ ID NO 81
<211> LENGTH: 9
<212> TYPE: PRT
<213> ORGANISM: CoV-2
<220> FEATURE:
<223> OTHER INFORMATION: S A2.01_1048

<400> SEQUENCE: 81

His Leu Met Ser Phe Pro Gln Ser Ala
1               5

<210> SEQ ID NO 82
<211> LENGTH: 9
<212> TYPE: PRT
<213> ORGANISM: CoV-2
<220> FEATURE:
<223> OTHER INFORMATION: S A2.01_1060

<400> SEQUENCE: 82

Val Val Phe Leu His Val Thr Tyr Val
1               5

<210> SEQ ID NO 83
<211> LENGTH: 9
<212> TYPE: PRT
<213> ORGANISM: CoV-2
<220> FEATURE:
<223> OTHER INFORMATION: S A2.01_1220

<400> SEQUENCE: 83

Phe Ile Ala Gly Leu Ile Ala Ile Val
1               5

<210> SEQ ID NO 84
<211> LENGTH: 9
<212> TYPE: PRT
<213> ORGANISM: CoV-2
<220> FEATURE:
<223> OTHER INFORMATION: S A2.01_1185

<400> SEQUENCE: 84

Arg Leu Asn Glu Val Ala Lys Asn Leu
1               5

<210> SEQ ID NO 85
<211> LENGTH: 9
<212> TYPE: PRT
<213> ORGANISM: CoV-2
<220> FEATURE:
<223> OTHER INFORMATION: S A2.01_1192

<400> SEQUENCE: 85
```

Asn Leu Asn Glu Ser Leu Ile Asp Leu
1               5

<210> SEQ ID NO 86
<211> LENGTH: 9
<212> TYPE: PRT
<213> ORGANISM: CoV-2
<220> FEATURE:
<223> OTHER INFORMATION: S A2.01_958

<400> SEQUENCE: 86

Ala Leu Asn Thr Leu Val Lys Gln Leu
1               5

<210> SEQ ID NO 87
<211> LENGTH: 9
<212> TYPE: PRT
<213> ORGANISM: CoV-2
<220> FEATURE:
<223> OTHER INFORMATION: S A2.01_857

<400> SEQUENCE: 87

Gly Leu Thr Val Leu Pro Pro Leu Leu
1               5

<210> SEQ ID NO 88
<211> LENGTH: 9
<212> TYPE: PRT
<213> ORGANISM: CoV-2
<220> FEATURE:
<223> OTHER INFORMATION: S A2.01_691

<400> SEQUENCE: 88

Ser Ile Ile Ala Tyr Thr Met Ser Leu
1               5

<210> SEQ ID NO 89
<211> LENGTH: 9
<212> TYPE: PRT
<213> ORGANISM: CoV-2
<220> FEATURE:
<223> OTHER INFORMATION: S A2.01_915

<400> SEQUENCE: 89

Val Leu Tyr Glu Asn Gln Lys Leu Ile
1               5

<210> SEQ ID NO 90
<211> LENGTH: 9
<212> TYPE: PRT
<213> ORGANISM: CoV-2
<220> FEATURE:
<223> OTHER INFORMATION: S A2.01_718

<400> SEQUENCE: 90

Phe Thr Ile Ser Val Thr Thr Glu Ile
1               5

<210> SEQ ID NO 91
<211> LENGTH: 9
<212> TYPE: PRT
<213> ORGANISM: CoV-2
<220> FEATURE:
<223> OTHER INFORMATION: S A3.01_454

<400> SEQUENCE: 91

Arg Leu Phe Arg Lys Ser Asn Leu Lys

```
1               5
```

<210> SEQ ID NO 92
<211> LENGTH: 9
<212> TYPE: PRT
<213> ORGANISM: CoV-2
<220> FEATURE:
<223> OTHER INFORMATION: S A3.01_787

<400> SEQUENCE: 92

```
Gln Ile Tyr Lys Thr Pro Pro Ile Lys
1               5
```

<210> SEQ ID NO 93
<211> LENGTH: 9
<212> TYPE: PRT
<213> ORGANISM: CoV-2
<220> FEATURE:
<223> OTHER INFORMATION: S A3.01_1065

<400> SEQUENCE: 93

```
Val Thr Tyr Val Pro Ala Gln Glu Lys
1               5
```

<210> SEQ ID NO 94
<211> LENGTH: 9
<212> TYPE: PRT
<213> ORGANISM: CoV-2
<220> FEATURE:
<223> OTHER INFORMATION: S A3.01_89

<400> SEQUENCE: 94

```
Gly Val Tyr Phe Ala Ser Thr Glu Lys
1               5
```

<210> SEQ ID NO 95
<211> LENGTH: 9
<212> TYPE: PRT
<213> ORGANISM: CoV-2
<220> FEATURE:
<223> OTHER INFORMATION: S A3.01_302

<400> SEQUENCE: 95

```
Thr Leu Lys Ser Phe Thr Val Glu Lys
1               5
```

<210> SEQ ID NO 96
<211> LENGTH: 9
<212> TYPE: PRT
<213> ORGANISM: CoV-2
<220> FEATURE:
<223> OTHER INFORMATION: S A3.01_142

<400> SEQUENCE: 96

```
Gly Val Tyr Tyr His Lys Asn Asn Lys
1               5
```

<210> SEQ ID NO 97
<211> LENGTH: 9
<212> TYPE: PRT
<213> ORGANISM: CoV-2
<220> FEATURE:
<223> OTHER INFORMATION: S A3.01_41

<400> SEQUENCE: 97

```
Lys Val Phe Arg Ser Ser Val Leu His
1               5
```

```
<210> SEQ ID NO 98
<211> LENGTH: 9
<212> TYPE: PRT
<213> ORGANISM: CoV-2
<220> FEATURE:
<223> OTHER INFORMATION: S A3.01_409

<400> SEQUENCE: 98

Gln Ile Ala Pro Gly Gln Thr Gly Lys
1               5

<210> SEQ ID NO 99
<211> LENGTH: 9
<212> TYPE: PRT
<213> ORGANISM: CoV-2
<220> FEATURE:
<223> OTHER INFORMATION: S A3.01_1020

<400> SEQUENCE: 99

Ala Ser Ala Asn Leu Ala Ala Thr Lys
1               5

<210> SEQ ID NO 100
<211> LENGTH: 9
<212> TYPE: PRT
<213> ORGANISM: CoV-2
<220> FEATURE:
<223> OTHER INFORMATION: S A3.01_349

<400> SEQUENCE: 100

Ser Val Tyr Ala Trp Asn Arg Lys Arg
1               5

<210> SEQ ID NO 101
<211> LENGTH: 9
<212> TYPE: PRT
<213> ORGANISM: CoV-2
<220> FEATURE:
<223> OTHER INFORMATION: S A3.01_378

<400> SEQUENCE: 101

Lys Cys Tyr Gly Val Ser Pro Thr Lys
1               5

<210> SEQ ID NO 102
<211> LENGTH: 9
<212> TYPE: PRT
<213> ORGANISM: CoV-2
<220> FEATURE:
<223> OTHER INFORMATION: S A3.01_529

<400> SEQUENCE: 102

Lys Ser Thr Asn Leu Val Lys Asn Lys
1               5

<210> SEQ ID NO 103
<211> LENGTH: 9
<212> TYPE: PRT
<213> ORGANISM: CoV-2
<220> FEATURE:
<223> OTHER INFORMATION: S A3.01_827

<400> SEQUENCE: 103

Thr Leu Ala Asp Ala Gly Phe Ile Lys
1               5
```

```
<210> SEQ ID NO 104
<211> LENGTH: 9
<212> TYPE: PRT
<213> ORGANISM: CoV-2
<220> FEATURE:
<223> OTHER INFORMATION: S A3.01_311

<400> SEQUENCE: 104

Gly Ile Tyr Gln Thr Ser Asn Phe Arg
1               5

<210> SEQ ID NO 105
<211> LENGTH: 9
<212> TYPE: PRT
<213> ORGANISM: CoV-2
<220> FEATURE:
<223> OTHER INFORMATION: S A3.01_292

<400> SEQUENCE: 105

Ala Leu Asp Pro Leu Ser Glu Thr Lys
1               5

<210> SEQ ID NO 106
<211> LENGTH: 9
<212> TYPE: PRT
<213> ORGANISM: CoV-2
<220> FEATURE:
<223> OTHER INFORMATION: S A3.01_1264

<400> SEQUENCE: 106

Val Leu Lys Gly Val Lys Leu His Tyr
1               5

<210> SEQ ID NO 107
<211> LENGTH: 9
<212> TYPE: PRT
<213> ORGANISM: CoV-2
<220> FEATURE:
<223> OTHER INFORMATION: S A3.01_725

<400> SEQUENCE: 107

Glu Ile Leu Pro Val Ser Met Thr Lys
1               5

<210> SEQ ID NO 108
<211> LENGTH: 9
<212> TYPE: PRT
<213> ORGANISM: CoV-2
<220> FEATURE:
<223> OTHER INFORMATION: S A3.01_1099

<400> SEQUENCE: 108

Gly Thr His Trp Phe Val Thr Gln Arg
1               5

<210> SEQ ID NO 109
<211> LENGTH: 9
<212> TYPE: PRT
<213> ORGANISM: CoV-2
<220> FEATURE:
<223> OTHER INFORMATION: S A24.02_1208

<400> SEQUENCE: 109

Gln Tyr Ile Lys Trp Pro Trp Tyr Ile
1               5
```

```
<210> SEQ ID NO 110
<211> LENGTH: 9
<212> TYPE: PRT
<213> ORGANISM: CoV-2
<220> FEATURE:
<223> OTHER INFORMATION: S A24.02_635

<400> SEQUENCE: 110

Val Tyr Ser Thr Gly Ser Asn Val Phe
1               5

<210> SEQ ID NO 111
<211> LENGTH: 9
<212> TYPE: PRT
<213> ORGANISM: CoV-2
<220> FEATURE:
<223> OTHER INFORMATION: S A24.02_448

<400> SEQUENCE: 111

Asn Tyr Asn Tyr Leu Tyr Arg Leu Phe
1               5

<210> SEQ ID NO 112
<211> LENGTH: 9
<212> TYPE: PRT
<213> ORGANISM: CoV-2
<220> FEATURE:
<223> OTHER INFORMATION: S A24.02_1137

<400> SEQUENCE: 112

Val Tyr Asp Pro Leu Gln Pro Glu Leu
1               5

<210> SEQ ID NO 113
<211> LENGTH: 9
<212> TYPE: PRT
<213> ORGANISM: CoV-2
<220> FEATURE:
<223> OTHER INFORMATION: S A24.02_144

<400> SEQUENCE: 113

Tyr Tyr His Lys Asn Asn Lys Ser Trp
1               5

<210> SEQ ID NO 114
<211> LENGTH: 9
<212> TYPE: PRT
<213> ORGANISM: CoV-2
<220> FEATURE:
<223> OTHER INFORMATION: S A24.02_489

<400> SEQUENCE: 114

Tyr Phe Pro Leu Gln Ser Tyr Gly Phe
1               5

<210> SEQ ID NO 115
<211> LENGTH: 9
<212> TYPE: PRT
<213> ORGANISM: CoV-2
<220> FEATURE:
<223> OTHER INFORMATION: S A24.02_507

<400> SEQUENCE: 115

Pro Tyr Arg Val Val Val Leu Ser Phe
1               5

<210> SEQ ID NO 116
```

```
<211> LENGTH: 9
<212> TYPE: PRT
<213> ORGANISM: CoV-2
<220> FEATURE:
<223> OTHER INFORMATION: S A24.02_1094

<400> SEQUENCE: 116

Val Phe Val Ser Asn Gly Thr His Trp
1               5

<210> SEQ ID NO 117
<211> LENGTH: 9
<212> TYPE: PRT
<213> ORGANISM: CoV-2
<220> FEATURE:
<223> OTHER INFORMATION: S A24.02_169

<400> SEQUENCE: 117

Glu Tyr Val Ser Gln Pro Phe Leu Met
1               5

<210> SEQ ID NO 118
<211> LENGTH: 9
<212> TYPE: PRT
<213> ORGANISM: CoV-2
<220> FEATURE:
<223> OTHER INFORMATION: S A24.02_1101

<400> SEQUENCE: 118

His Trp Phe Val Thr Gln Arg Asn Phe
1               5

<210> SEQ ID NO 119
<211> LENGTH: 9
<212> TYPE: PRT
<213> ORGANISM: CoV-2
<220> FEATURE:
<223> OTHER INFORMATION: S A24.02_78

<400> SEQUENCE: 119

Arg Phe Asp Asn Pro Val Leu Pro Phe
1               5

<210> SEQ ID NO 120
<211> LENGTH: 9
<212> TYPE: PRT
<213> ORGANISM: CoV-2
<220> FEATURE:
<223> OTHER INFORMATION: S A24.02_312

<400> SEQUENCE: 120

Ile Tyr Gln Thr Ser Asn Phe Arg Val
1               5

<210> SEQ ID NO 121
<211> LENGTH: 9
<212> TYPE: PRT
<213> ORGANISM: CoV-2
<220> FEATURE:
<223> OTHER INFORMATION: S A24.02_755

<400> SEQUENCE: 121

Gln Tyr Gly Ser Phe Cys Thr Gln Leu
1               5

<210> SEQ ID NO 122
<211> LENGTH: 9
```

```
<212> TYPE: PRT
<213> ORGANISM: CoV-2
<220> FEATURE:
<223> OTHER INFORMATION: S A24.02_193

<400> SEQUENCE: 122

Val Phe Lys Asn Ile Asp Gly Tyr Phe
1               5

<210> SEQ ID NO 123
<211> LENGTH: 9
<212> TYPE: PRT
<213> ORGANISM: CoV-2
<220> FEATURE:
<223> OTHER INFORMATION: S A24.02_268

<400> SEQUENCE: 123

Gly Tyr Leu Gln Pro Arg Thr Phe Leu
1               5

<210> SEQ ID NO 124
<211> LENGTH: 9
<212> TYPE: PRT
<213> ORGANISM: CoV-2
<220> FEATURE:
<223> OTHER INFORMATION: S A24.02_379

<400> SEQUENCE: 124

Cys Tyr Gly Val Ser Pro Thr Lys Leu
1               5

<210> SEQ ID NO 125
<211> LENGTH: 9
<212> TYPE: PRT
<213> ORGANISM: CoV-2
<220> FEATURE:
<223> OTHER INFORMATION: S A24.02_57

<400> SEQUENCE: 125

Pro Phe Phe Ser Asn Val Thr Trp Phe
1               5

<210> SEQ ID NO 126
<211> LENGTH: 9
<212> TYPE: PRT
<213> ORGANISM: CoV-2
<220> FEATURE:
<223> OTHER INFORMATION: S A26.01_192

<400> SEQUENCE: 126

Phe Val Phe Lys Asn Ile Asp Gly Tyr
1               5

<210> SEQ ID NO 127
<211> LENGTH: 9
<212> TYPE: PRT
<213> ORGANISM: CoV-2
<220> FEATURE:
<223> OTHER INFORMATION: S A26.01_361

<400> SEQUENCE: 127

Cys Val Ala Asp Tyr Ser Val Leu Tyr
1               5

<210> SEQ ID NO 128
<211> LENGTH: 9
<212> TYPE: PRT
```

```
<213> ORGANISM: CoV-2
<220> FEATURE:
<223> OTHER INFORMATION: S A26.01_258

<400> SEQUENCE: 128

Trp Thr Ala Gly Ala Ala Ala Tyr Tyr
1               5

<210> SEQ ID NO 129
<211> LENGTH: 9
<212> TYPE: PRT
<213> ORGANISM: CoV-2
<220> FEATURE:
<223> OTHER INFORMATION: S A26.01_298

<400> SEQUENCE: 129

Glu Thr Lys Cys Thr Leu Lys Ser Phe
1               5

<210> SEQ ID NO 130
<211> LENGTH: 9
<212> TYPE: PRT
<213> ORGANISM: CoV-2
<220> FEATURE:
<223> OTHER INFORMATION: S A26.01_865

<400> SEQUENCE: 130

Leu Thr Asp Glu Met Ile Ala Gln Tyr
1               5

<210> SEQ ID NO 131
<211> LENGTH: 9
<212> TYPE: PRT
<213> ORGANISM: CoV-2
<220> FEATURE:
<223> OTHER INFORMATION: S A26.01_780

<400> SEQUENCE: 131

Glu Val Phe Ala Gln Val Lys Gln Ile
1               5

<210> SEQ ID NO 132
<211> LENGTH: 9
<212> TYPE: PRT
<213> ORGANISM: CoV-2
<220> FEATURE:
<223> OTHER INFORMATION: S A26.01_30

<400> SEQUENCE: 132

Asn Ser Phe Thr Arg Gly Val Tyr Tyr
1               5

<210> SEQ ID NO 133
<211> LENGTH: 9
<212> TYPE: PRT
<213> ORGANISM: CoV-2
<220> FEATURE:
<223> OTHER INFORMATION: S A26.01_1095

<400> SEQUENCE: 133

Phe Val Ser Asn Gly Thr His Trp Phe
1               5

<210> SEQ ID NO 134
<211> LENGTH: 9
<212> TYPE: PRT
<213> ORGANISM: CoV-2
```

```
<220> FEATURE:
<223> OTHER INFORMATION: S A26.01_604

<400> SEQUENCE: 134

Thr Ser Asn Gln Val Ala Val Leu Tyr
1               5

<210> SEQ ID NO 135
<211> LENGTH: 9
<212> TYPE: PRT
<213> ORGANISM: CoV-2
<220> FEATURE:
<223> OTHER INFORMATION: S A26.01_748

<400> SEQUENCE: 135

Glu Cys Ser Asn Leu Leu Leu Gln Tyr
1               5

<210> SEQ ID NO 136
<211> LENGTH: 9
<212> TYPE: PRT
<213> ORGANISM: CoV-2
<220> FEATURE:
<223> OTHER INFORMATION: S A26.01_718

<400> SEQUENCE: 136

Phe Thr Ile Ser Val Thr Thr Glu Ile
1               5

<210> SEQ ID NO 137
<211> LENGTH: 9
<212> TYPE: PRT
<213> ORGANISM: CoV-2
<220> FEATURE:
<223> OTHER INFORMATION: S A26.01_687

<400> SEQUENCE: 137

Val Ala Ser Gln Ser Ile Ile Ala Tyr
1               5

<210> SEQ ID NO 138
<211> LENGTH: 9
<212> TYPE: PRT
<213> ORGANISM: CoV-2
<220> FEATURE:
<223> OTHER INFORMATION: S A26.01_710

<400> SEQUENCE: 138

Asn Ser Ile Ala Ile Pro Thr Asn Phe
1               5

<210> SEQ ID NO 139
<211> LENGTH: 9
<212> TYPE: PRT
<213> ORGANISM: CoV-2
<220> FEATURE:
<223> OTHER INFORMATION: S A26.01_554

<400> SEQUENCE: 139

Glu Ser Asn Lys Lys Phe Leu Pro Phe
1               5

<210> SEQ ID NO 140
<211> LENGTH: 9
<212> TYPE: PRT
<213> ORGANISM: CoV-2
<220> FEATURE:
```

```
<223> OTHER INFORMATION: S A26.01_1054

<400> SEQUENCE: 140

Gln Ser Ala Pro His Gly Val Val Phe
1               5

<210> SEQ ID NO 141
<211> LENGTH: 9
<212> TYPE: PRT
<213> ORGANISM: CoV-2
<220> FEATURE:
<223> OTHER INFORMATION: S A26.01_487

<400> SEQUENCE: 141

Asn Cys Tyr Phe Pro Leu Gln Ser Tyr
1               5

<210> SEQ ID NO 142
<211> LENGTH: 9
<212> TYPE: PRT
<213> ORGANISM: CoV-2
<220> FEATURE:
<223> OTHER INFORMATION: S A26.01_366

<400> SEQUENCE: 142

Ser Val Leu Tyr Asn Ser Ala Ser Phe
1               5

<210> SEQ ID NO 143
<211> LENGTH: 9
<212> TYPE: PRT
<213> ORGANISM: CoV-2
<220> FEATURE:
<223> OTHER INFORMATION: S A26.01_125

<400> SEQUENCE: 143

Asn Val Val Ile Lys Val Cys Glu Phe
1               5

<210> SEQ ID NO 144
<211> LENGTH: 9
<212> TYPE: PRT
<213> ORGANISM: CoV-2
<220> FEATURE:
<223> OTHER INFORMATION: S A26.01_50

<400> SEQUENCE: 144

Ser Thr Gln Asp Leu Phe Leu Pro Phe
1               5

<210> SEQ ID NO 145
<211> LENGTH: 9
<212> TYPE: PRT
<213> ORGANISM: CoV-2
<220> FEATURE:
<223> OTHER INFORMATION: S B7.02_680

<400> SEQUENCE: 145

Ser Pro Arg Arg Ala Arg Ser Val Ala
1               5

<210> SEQ ID NO 146
<211> LENGTH: 9
<212> TYPE: PRT
<213> ORGANISM: CoV-2
<220> FEATURE:
<223> OTHER INFORMATION: S B7.02_526
```

```
<400> SEQUENCE: 146

Gly Pro Lys Lys Ser Thr Asn Leu Val
1               5

<210> SEQ ID NO 147
<211> LENGTH: 9
<212> TYPE: PRT
<213> ORGANISM: CoV-2
<220> FEATURE:
<223> OTHER INFORMATION: S B7.02_208

<400> SEQUENCE: 147

Thr Pro Ile Asn Leu Val Arg Asp Leu
1               5

<210> SEQ ID NO 148
<211> LENGTH: 9
<212> TYPE: PRT
<213> ORGANISM: CoV-2
<220> FEATURE:
<223> OTHER INFORMATION: S B7.02_1262

<400> SEQUENCE: 148

Glu Pro Val Leu Lys Gly Val Lys Leu
1               5

<210> SEQ ID NO 149
<211> LENGTH: 9
<212> TYPE: PRT
<213> ORGANISM: CoV-2
<220> FEATURE:
<223> OTHER INFORMATION: S B7.02_321

<400> SEQUENCE: 149

Gln Pro Thr Glu Ser Ile Val Arg Phe
1               5

<210> SEQ ID NO 150
<211> LENGTH: 9
<212> TYPE: PRT
<213> ORGANISM: CoV-2
<220> FEATURE:
<223> OTHER INFORMATION: S B7.02_1052

<400> SEQUENCE: 150

Phe Pro Gln Ser Ala Pro His Gly Val
1               5

<210> SEQ ID NO 151
<211> LENGTH: 9
<212> TYPE: PRT
<213> ORGANISM: CoV-2
<220> FEATURE:
<223> OTHER INFORMATION: S B7.02_714

<400> SEQUENCE: 151

Ile Pro Thr Asn Phe Thr Ile Ser Val
1               5

<210> SEQ ID NO 152
<211> LENGTH: 9
<212> TYPE: PRT
<213> ORGANISM: CoV-2
<220> FEATURE:
<223> OTHER INFORMATION: S B7.02_24
```

```
<400> SEQUENCE: 152

Leu Pro Pro Ala Tyr Thr Asn Ser Phe
1               5

<210> SEQ ID NO 153
<211> LENGTH: 9
<212> TYPE: PRT
<213> ORGANISM: CoV-2
<220> FEATURE:
<223> OTHER INFORMATION: S B8.01_269

<400> SEQUENCE: 153

Tyr Leu Gln Pro Arg Thr Phe Leu Leu
1               5

<210> SEQ ID NO 154
<211> LENGTH: 9
<212> TYPE: PRT
<213> ORGANISM: CoV-2
<220> FEATURE:
<223> OTHER INFORMATION: S B8.01_109

<400> SEQUENCE: 154

Thr Leu Asp Ser Lys Thr Gln Ser Leu
1               5

<210> SEQ ID NO 155
<211> LENGTH: 9
<212> TYPE: PRT
<213> ORGANISM: CoV-2
<220> FEATURE:
<223> OTHER INFORMATION: S B8.01_233

<400> SEQUENCE: 155

Ile Asn Ile Thr Arg Phe Gln Thr Leu
1               5

<210> SEQ ID NO 156
<211> LENGTH: 9
<212> TYPE: PRT
<213> ORGANISM: CoV-2
<220> FEATURE:
<223> OTHER INFORMATION: S B8.01_1262

<400> SEQUENCE: 156

Glu Pro Val Leu Lys Gly Val Lys Leu
1               5

<210> SEQ ID NO 157
<211> LENGTH: 9
<212> TYPE: PRT
<213> ORGANISM: CoV-2
<220> FEATURE:
<223> OTHER INFORMATION: S B8.01_505

<400> SEQUENCE: 157

Tyr Gln Pro Tyr Arg Val Val Val Leu
1               5

<210> SEQ ID NO 158
<211> LENGTH: 9
<212> TYPE: PRT
<213> ORGANISM: CoV-2
<220> FEATURE:
<223> OTHER INFORMATION: S B8.01_996

<400> SEQUENCE: 158
```

```
Leu Ile Thr Gly Arg Leu Gln Ser Leu
1               5

<210> SEQ ID NO 159
<211> LENGTH: 9
<212> TYPE: PRT
<213> ORGANISM: CoV-2
<220> FEATURE:
<223> OTHER INFORMATION: S B8.01_820

<400> SEQUENCE: 159

Asp Leu Leu Phe Asn Lys Val Thr Leu
1               5

<210> SEQ ID NO 160
<211> LENGTH: 9
<212> TYPE: PRT
<213> ORGANISM: CoV-2
<220> FEATURE:
<223> OTHER INFORMATION: S B8.01_1137

<400> SEQUENCE: 160

Val Tyr Asp Pro Leu Gln Pro Glu Leu
1               5

<210> SEQ ID NO 161
<211> LENGTH: 9
<212> TYPE: PRT
<213> ORGANISM: CoV-2
<220> FEATURE:
<223> OTHER INFORMATION: S B8.01_342

<400> SEQUENCE: 161

Phe Asn Ala Thr Arg Phe Ala Ser Val
1               5

<210> SEQ ID NO 162
<211> LENGTH: 9
<212> TYPE: PRT
<213> ORGANISM: CoV-2
<220> FEATURE:
<223> OTHER INFORMATION: S B8.01_241

<400> SEQUENCE: 162

Leu Leu Ala Leu His Arg Ser Tyr Leu
1               5

<210> SEQ ID NO 163
<211> LENGTH: 9
<212> TYPE: PRT
<213> ORGANISM: CoV-2
<220> FEATURE:
<223> OTHER INFORMATION: S B8.01_533

<400> SEQUENCE: 163

Leu Val Lys Asn Lys Cys Val Asn Phe
1               5

<210> SEQ ID NO 164
<211> LENGTH: 9
<212> TYPE: PRT
<213> ORGANISM: CoV-2
<220> FEATURE:
<223> OTHER INFORMATION: S B8.01_453

<400> SEQUENCE: 164
```

-continued

```
Tyr Arg Leu Phe Arg Lys Ser Asn Leu
1               5

<210> SEQ ID NO 165
<211> LENGTH: 9
<212> TYPE: PRT
<213> ORGANISM: CoV-2
<220> FEATURE:
<223> OTHER INFORMATION: S B8.01_40

<400> SEQUENCE: 165

Asp Lys Val Phe Arg Ser Ser Val Leu
1               5

<210> SEQ ID NO 166
<211> LENGTH: 9
<212> TYPE: PRT
<213> ORGANISM: CoV-2
<220> FEATURE:
<223> OTHER INFORMATION: S B8.01_554

<400> SEQUENCE: 166

Glu Ser Asn Lys Lys Phe Leu Pro Phe
1               5

<210> SEQ ID NO 167
<211> LENGTH: 9
<212> TYPE: PRT
<213> ORGANISM: CoV-2
<220> FEATURE:
<223> OTHER INFORMATION: S B8.01_833

<400> SEQUENCE: 167

Phe Ile Lys Gln Tyr Gly Asp Cys Leu
1               5

<210> SEQ ID NO 168
<211> LENGTH: 9
<212> TYPE: PRT
<213> ORGANISM: CoV-2
<220> FEATURE:
<223> OTHER INFORMATION: S B8.01_691

<400> SEQUENCE: 168

Ser Ile Ile Ala Tyr Thr Met Ser Leu
1               5

<210> SEQ ID NO 169
<211> LENGTH: 9
<212> TYPE: PRT
<213> ORGANISM: CoV-2
<220> FEATURE:
<223> OTHER INFORMATION: S B8.01_202

<400> SEQUENCE: 169

Lys Ile Tyr Ser Lys His Thr Pro Ile
1               5

<210> SEQ ID NO 170
<211> LENGTH: 9
<212> TYPE: PRT
<213> ORGANISM: CoV-2
<220> FEATURE:
<223> OTHER INFORMATION: S B8.01_869

<400> SEQUENCE: 170

Met Ile Ala Gln Tyr Thr Ser Ala Leu
```

```
-continued
1               5
```

```
<210> SEQ ID NO 171
<211> LENGTH: 9
<212> TYPE: PRT
<213> ORGANISM: CoV-2
<220> FEATURE:
<223> OTHER INFORMATION: S B27.05_999

<400> SEQUENCE: 171

Gly Arg Leu Gln Ser Leu Gln Thr Tyr
1               5

<210> SEQ ID NO 172
<211> LENGTH: 9
<212> TYPE: PRT
<213> ORGANISM: CoV-2
<220> FEATURE:
<223> OTHER INFORMATION: S B27.05_236

<400> SEQUENCE: 172

Thr Arg Phe Gln Thr Leu Leu Ala Leu
1               5

<210> SEQ ID NO 173
<211> LENGTH: 9
<212> TYPE: PRT
<213> ORGANISM: CoV-2
<220> FEATURE:
<223> OTHER INFORMATION: S B27.05_327

<400> SEQUENCE: 173

Val Arg Phe Pro Asn Ile Thr Asn Leu
1               5

<210> SEQ ID NO 174
<211> LENGTH: 9
<212> TYPE: PRT
<213> ORGANISM: CoV-2
<220> FEATURE:
<223> OTHER INFORMATION: S B27.05_20

<400> SEQUENCE: 174

Thr Arg Thr Gln Leu Pro Pro Ala Tyr
1               5

<210> SEQ ID NO 175
<211> LENGTH: 9
<212> TYPE: PRT
<213> ORGANISM: CoV-2
<220> FEATURE:
<223> OTHER INFORMATION: S B27.05_345

<400> SEQUENCE: 175

Thr Arg Phe Ala Ser Val Tyr Ala Trp
1               5

<210> SEQ ID NO 176
<211> LENGTH: 9
<212> TYPE: PRT
<213> ORGANISM: CoV-2
<220> FEATURE:
<223> OTHER INFORMATION: S B27.05_814

<400> SEQUENCE: 176

Lys Arg Ser Phe Ile Glu Asp Leu Leu
1               5
```

<210> SEQ ID NO 177
<211> LENGTH: 9
<212> TYPE: PRT
<213> ORGANISM: CoV-2
<220> FEATURE:
<223> OTHER INFORMATION: S B27.05_453

<400> SEQUENCE: 177

Tyr Arg Leu Phe Arg Lys Ser Asn Leu
1               5

<210> SEQ ID NO 178
<211> LENGTH: 9
<212> TYPE: PRT
<213> ORGANISM: CoV-2
<220> FEATURE:
<223> OTHER INFORMATION: S B27.05_318

<400> SEQUENCE: 178

Phe Arg Val Gln Pro Thr Glu Ser Ile
1               5

<210> SEQ ID NO 179
<211> LENGTH: 9
<212> TYPE: PRT
<213> ORGANISM: CoV-2
<220> FEATURE:
<223> OTHER INFORMATION: S B27.05_557

<400> SEQUENCE: 179

Lys Lys Phe Leu Pro Phe Gln Gln Phe
1               5

<210> SEQ ID NO 180
<211> LENGTH: 9
<212> TYPE: PRT
<213> ORGANISM: CoV-2
<220> FEATURE:
<223> OTHER INFORMATION: S B27.05_77

<400> SEQUENCE: 180

Lys Arg Phe Asp Asn Pro Val Leu Pro
1               5

<210> SEQ ID NO 181
<211> LENGTH: 9
<212> TYPE: PRT
<213> ORGANISM: CoV-2
<220> FEATURE:
<223> OTHER INFORMATION: S B27.05_576

<400> SEQUENCE: 181

Val Arg Asp Pro Gln Thr Leu Glu Ile
1               5

<210> SEQ ID NO 182
<211> LENGTH: 9
<212> TYPE: PRT
<213> ORGANISM: CoV-2
<220> FEATURE:
<223> OTHER INFORMATION: S B39.01_236

<400> SEQUENCE: 182

Thr Arg Phe Gln Thr Leu Leu Ala Leu
1               5

<210> SEQ ID NO 183
<211> LENGTH: 9
<212> TYPE: PRT
<213> ORGANISM: CoV-2
<220> FEATURE:
<223> OTHER INFORMATION: S B39.01_1158

<400> SEQUENCE: 183

Asn His Thr Ser Pro Asp Val Asp Leu
1               5

<210> SEQ ID NO 184
<211> LENGTH: 9
<212> TYPE: PRT
<213> ORGANISM: CoV-2
<220> FEATURE:
<223> OTHER INFORMATION: S B39.01_318

<400> SEQUENCE: 184

Phe Arg Val Gln Pro Thr Glu Ser Ile
1               5

<210> SEQ ID NO 185
<211> LENGTH: 9
<212> TYPE: PRT
<213> ORGANISM: CoV-2
<220> FEATURE:
<223> OTHER INFORMATION: S B39.01_764

<400> SEQUENCE: 185

Asn Arg Ala Leu Thr Gly Ile Ala Val
1               5

<210> SEQ ID NO 186
<211> LENGTH: 9
<212> TYPE: PRT
<213> ORGANISM: CoV-2
<220> FEATURE:
<223> OTHER INFORMATION: S B39.01_576

<400> SEQUENCE: 186

Val Arg Asp Pro Gln Thr Leu Glu Ile
1               5

<210> SEQ ID NO 187
<211> LENGTH: 9
<212> TYPE: PRT
<213> ORGANISM: CoV-2
<220> FEATURE:
<223> OTHER INFORMATION: S B39.01_327

<400> SEQUENCE: 187

Val Arg Phe Pro Asn Ile Thr Asn Leu
1               5

<210> SEQ ID NO 188
<211> LENGTH: 9
<212> TYPE: PRT
<213> ORGANISM: CoV-2
<220> FEATURE:
<223> OTHER INFORMATION: S B39.01_853

<400> SEQUENCE: 188

Gln Lys Phe Asn Gly Leu Thr Val Leu
1               5

```
<210> SEQ ID NO 189
<211> LENGTH: 9
<212> TYPE: PRT
<213> ORGANISM: CoV-2
<220> FEATURE:
<223> OTHER INFORMATION: S B39.01_48

<400> SEQUENCE: 189

Leu His Ser Thr Gln Asp Leu Phe Leu
1               5

<210> SEQ ID NO 190
<211> LENGTH: 9
<212> TYPE: PRT
<213> ORGANISM: CoV-2
<220> FEATURE:
<223> OTHER INFORMATION: S B39.01_1137

<400> SEQUENCE: 190

Val Tyr Asp Pro Leu Gln Pro Glu Leu
1               5

<210> SEQ ID NO 191
<211> LENGTH: 9
<212> TYPE: PRT
<213> ORGANISM: CoV-2
<220> FEATURE:
<223> OTHER INFORMATION: S B39.01_1087

<400> SEQUENCE: 191

Ala His Phe Pro Arg Glu Gly Val Phe
1               5

<210> SEQ ID NO 192
<211> LENGTH: 9
<212> TYPE: PRT
<213> ORGANISM: CoV-2
<220> FEATURE:
<223> OTHER INFORMATION: S B39.01_773

<400> SEQUENCE: 192

Glu Gln Asp Lys Asn Thr Gln Glu Val
1               5

<210> SEQ ID NO 193
<211> LENGTH: 9
<212> TYPE: PRT
<213> ORGANISM: CoV-2
<220> FEATURE:
<223> OTHER INFORMATION: S B39.01_109

<400> SEQUENCE: 193

Thr Leu Asp Ser Lys Thr Gln Ser Leu
1               5

<210> SEQ ID NO 194
<211> LENGTH: 9
<212> TYPE: PRT
<213> ORGANISM: CoV-2
<220> FEATURE:
<223> OTHER INFORMATION: S B39.01_505

<400> SEQUENCE: 194

Tyr Gln Pro Tyr Arg Val Val Val Leu
1               5

<210> SEQ ID NO 195
```

```
<211> LENGTH: 9
<212> TYPE: PRT
<213> ORGANISM: CoV-2
<220> FEATURE:
<223> OTHER INFORMATION: S B39.01_689

<400> SEQUENCE: 195

Ser Gln Ser Ile Ile Ala Tyr Thr Met
1               5

<210> SEQ ID NO 196
<211> LENGTH: 9
<212> TYPE: PRT
<213> ORGANISM: CoV-2
<220> FEATURE:
<223> OTHER INFORMATION: S B39.01_654

<400> SEQUENCE: 196

Glu His Val Asn Asn Ser Tyr Glu Cys
1               5

<210> SEQ ID NO 197
<211> LENGTH: 9
<212> TYPE: PRT
<213> ORGANISM: CoV-2
<220> FEATURE:
<223> OTHER INFORMATION: S B39.01_1004

<400> SEQUENCE: 197

Leu Gln Thr Tyr Val Thr Gln Gln Leu
1               5

<210> SEQ ID NO 198
<211> LENGTH: 9
<212> TYPE: PRT
<213> ORGANISM: CoV-2
<220> FEATURE:
<223> OTHER INFORMATION: S B39.01_1257

<400> SEQUENCE: 198

Asp Glu Asp Asp Ser Glu Pro Val Leu
1               5

<210> SEQ ID NO 199
<211> LENGTH: 9
<212> TYPE: PRT
<213> ORGANISM: CoV-2
<220> FEATURE:
<223> OTHER INFORMATION: S B40.01_1016

<400> SEQUENCE: 199

Ala Glu Ile Arg Ala Ser Ala Asn Leu
1               5

<210> SEQ ID NO 200
<211> LENGTH: 9
<212> TYPE: PRT
<213> ORGANISM: CoV-2
<220> FEATURE:
<223> OTHER INFORMATION: S B40.01_168

<400> SEQUENCE: 200

Phe Glu Tyr Val Ser Gln Pro Phe Leu
1               5

<210> SEQ ID NO 201
<211> LENGTH: 9
```

```
<212> TYPE: PRT
<213> ORGANISM: CoV-2
<220> FEATURE:
<223> OTHER INFORMATION: S B40.01_464

<400> SEQUENCE: 201

Phe Glu Arg Asp Ile Ser Thr Glu Ile
1               5

<210> SEQ ID NO 202
<211> LENGTH: 9
<212> TYPE: PRT
<213> ORGANISM: CoV-2
<220> FEATURE:
<223> OTHER INFORMATION: S B40.01_1181

<400> SEQUENCE: 202

Lys Glu Ile Asp Arg Leu Asn Glu Val
1               5

<210> SEQ ID NO 203
<211> LENGTH: 9
<212> TYPE: PRT
<213> ORGANISM: CoV-2
<220> FEATURE:
<223> OTHER INFORMATION: S B40.01_989

<400> SEQUENCE: 203

Ala Glu Val Gln Ile Asp Arg Leu Ile
1               5

<210> SEQ ID NO 204
<211> LENGTH: 9
<212> TYPE: PRT
<213> ORGANISM: CoV-2
<220> FEATURE:
<223> OTHER INFORMATION: S B40.01_339

<400> SEQUENCE: 204

Gly Glu Val Phe Asn Ala Thr Arg Phe
1               5

<210> SEQ ID NO 205
<211> LENGTH: 9
<212> TYPE: PRT
<213> ORGANISM: CoV-2
<220> FEATURE:
<223> OTHER INFORMATION: S B40.01_1257

<400> SEQUENCE: 205

Asp Glu Asp Asp Ser Glu Pro Val Leu
1               5

<210> SEQ ID NO 206
<211> LENGTH: 9
<212> TYPE: PRT
<213> ORGANISM: CoV-2
<220> FEATURE:
<223> OTHER INFORMATION: S B58.01_625

<400> SEQUENCE: 206

His Ala Asp Gln Leu Thr Pro Thr Trp
1               5

<210> SEQ ID NO 207
<211> LENGTH: 9
<212> TYPE: PRT
```

```
<213> ORGANISM: CoV-2
<220> FEATURE:
<223> OTHER INFORMATION: S B58.01_815

<400> SEQUENCE: 207

Arg Ser Phe Ile Glu Asp Leu Leu Phe
1               5

<210> SEQ ID NO 208
<211> LENGTH: 9
<212> TYPE: PRT
<213> ORGANISM: CoV-2
<220> FEATURE:
<223> OTHER INFORMATION: S B58.01_878

<400> SEQUENCE: 208

Leu Ala Gly Thr Ile Thr Ser Gly Trp
1               5

<210> SEQ ID NO 209
<211> LENGTH: 9
<212> TYPE: PRT
<213> ORGANISM: CoV-2
<220> FEATURE:
<223> OTHER INFORMATION: S B58.01_1054

<400> SEQUENCE: 209

Gln Ser Ala Pro His Gly Val Val Phe
1               5

<210> SEQ ID NO 210
<211> LENGTH: 9
<212> TYPE: PRT
<213> ORGANISM: CoV-2
<220> FEATURE:
<223> OTHER INFORMATION: S B58.01_880

<400> SEQUENCE: 210

Gly Thr Ile Thr Ser Gly Trp Thr Phe
1               5

<210> SEQ ID NO 211
<211> LENGTH: 9
<212> TYPE: PRT
<213> ORGANISM: CoV-2
<220> FEATURE:
<223> OTHER INFORMATION: S B58.01_604

<400> SEQUENCE: 211

Thr Ser Asn Gln Val Ala Val Leu Tyr
1               5

<210> SEQ ID NO 212
<211> LENGTH: 9
<212> TYPE: PRT
<213> ORGANISM: CoV-2
<220> FEATURE:
<223> OTHER INFORMATION: S B58.01_712

<400> SEQUENCE: 212

Ile Ala Ile Pro Thr Asn Phe Thr Ile
1               5

<210> SEQ ID NO 213
<211> LENGTH: 9
<212> TYPE: PRT
<213> ORGANISM: CoV-2
```

```
<220> FEATURE:
<223> OTHER INFORMATION: S B58.01_710

<400> SEQUENCE: 213

Asn Ser Ile Ala Ile Pro Thr Asn Phe
1               5

<210> SEQ ID NO 214
<211> LENGTH: 9
<212> TYPE: PRT
<213> ORGANISM: CoV-2
<220> FEATURE:
<223> OTHER INFORMATION: S B58.01_898

<400> SEQUENCE: 214

Phe Ala Met Gln Met Ala Tyr Arg Phe
1               5

<210> SEQ ID NO 215
<211> LENGTH: 9
<212> TYPE: PRT
<213> ORGANISM: CoV-2
<220> FEATURE:
<223> OTHER INFORMATION: S B58.01_160

<400> SEQUENCE: 215

Tyr Ser Ser Ala Asn Asn Cys Thr Phe
1               5

<210> SEQ ID NO 216
<211> LENGTH: 9
<212> TYPE: PRT
<213> ORGANISM: CoV-2
<220> FEATURE:
<223> OTHER INFORMATION: S B58.01_56

<400> SEQUENCE: 216

Leu Pro Phe Phe Ser Asn Val Thr Trp
1               5

<210> SEQ ID NO 217
<211> LENGTH: 9
<212> TYPE: PRT
<213> ORGANISM: CoV-2
<220> FEATURE:
<223> OTHER INFORMATION: S B58.01_687

<400> SEQUENCE: 217

Val Ala Ser Gln Ser Ile Ile Ala Tyr
1               5

<210> SEQ ID NO 218
<211> LENGTH: 9
<212> TYPE: PRT
<213> ORGANISM: CoV-2
<220> FEATURE:
<223> OTHER INFORMATION: S B15.01_1264

<400> SEQUENCE: 218

Val Leu Lys Gly Val Lys Leu His Tyr
1               5

<210> SEQ ID NO 219
<211> LENGTH: 9
<212> TYPE: PRT
<213> ORGANISM: CoV-2
<220> FEATURE:
```

<223> OTHER INFORMATION: S B15.01_919

<400> SEQUENCE: 219

Asn Gln Lys Leu Ile Ala Asn Gln Phe
1               5

<210> SEQ ID NO 220
<211> LENGTH: 9
<212> TYPE: PRT
<213> ORGANISM: CoV-2
<220> FEATURE:
<223> OTHER INFORMATION: S B15.01_413

<400> SEQUENCE: 220

Gly Gln Thr Gly Lys Ile Ala Asp Tyr
1               5

<210> SEQ ID NO 221
<211> LENGTH: 9
<212> TYPE: PRT
<213> ORGANISM: CoV-2
<220> FEATURE:
<223> OTHER INFORMATION: S B15.01_962

<400> SEQUENCE: 221

Leu Val Lys Gln Leu Ser Ser Asn Phe
1               5

<210> SEQ ID NO 222
<211> LENGTH: 9
<212> TYPE: PRT
<213> ORGANISM: CoV-2
<220> FEATURE:
<223> OTHER INFORMATION: S B15.01_1054

<400> SEQUENCE: 222

Gln Ser Ala Pro His Gly Val Val Phe
1               5

<210> SEQ ID NO 223
<211> LENGTH: 9
<212> TYPE: PRT
<213> ORGANISM: CoV-2
<220> FEATURE:
<223> OTHER INFORMATION: S B15.01_687

<400> SEQUENCE: 223

Val Ala Ser Gln Ser Ile Ile Ala Tyr
1               5

<210> SEQ ID NO 224
<211> LENGTH: 9
<212> TYPE: PRT
<213> ORGANISM: CoV-2
<220> FEATURE:
<223> OTHER INFORMATION: S B15.01_894

<400> SEQUENCE: 224

Leu Gln Ile Pro Phe Ala Met Gln Met
1               5

<210> SEQ ID NO 225
<211> LENGTH: 9
<212> TYPE: PRT
<213> ORGANISM: CoV-2
<220> FEATURE:
<223> OTHER INFORMATION: S B15.01_628

```
<400> SEQUENCE: 225

Gln Leu Thr Pro Thr Trp Arg Val Tyr
1               5

<210> SEQ ID NO 226
<211> LENGTH: 9
<212> TYPE: PRT
<213> ORGANISM: CoV-2
<220> FEATURE:
<223> OTHER INFORMATION: S B15.01_240

<400> SEQUENCE: 226

Thr Leu Leu Ala Leu His Arg Ser Tyr
1               5

<210> SEQ ID NO 227
<211> LENGTH: 9
<212> TYPE: PRT
<213> ORGANISM: CoV-2
<220> FEATURE:
<223> OTHER INFORMATION: S B15.01_497

<400> SEQUENCE: 227

Phe Gln Pro Thr Asn Gly Val Gly Tyr
1               5

<210> SEQ ID NO 228
<211> LENGTH: 9
<212> TYPE: PRT
<213> ORGANISM: CoV-2
<220> FEATURE:
<223> OTHER INFORMATION: S B15.01_212

<400> SEQUENCE: 228

Leu Val Arg Asp Leu Pro Leu Gly Phe
1               5

<210> SEQ ID NO 229
<211> LENGTH: 9
<212> TYPE: PRT
<213> ORGANISM: CoV-2
<220> FEATURE:
<223> OTHER INFORMATION: S B15.01_47

<400> SEQUENCE: 229

Val Leu His Ser Thr Gln Asp Leu Phe
1               5

<210> SEQ ID NO 230
<211> LENGTH: 9
<212> TYPE: PRT
<213> ORGANISM: CoV-2
<220> FEATURE:
<223> OTHER INFORMATION: S B15.01_35

<400> SEQUENCE: 230

Gly Val Tyr Tyr Pro Asp Lys Val Phe
1               5

<210> SEQ ID NO 231
<211> LENGTH: 9
<212> TYPE: PRT
<213> ORGANISM: CoV-2
<220> FEATURE:
<223> OTHER INFORMATION: S B15.01_372
```

```
<400> SEQUENCE: 231

Ala Ser Phe Ser Thr Phe Lys Cys Tyr
1               5

<210> SEQ ID NO 232
<211> LENGTH: 9
<212> TYPE: PRT
<213> ORGANISM: CoV-2
<220> FEATURE:
<223> OTHER INFORMATION: S B15.01_1059

<400> SEQUENCE: 232

Gly Val Val Phe Leu His Val Thr Tyr
1               5

<210> SEQ ID NO 233
<211> LENGTH: 9
<212> TYPE: PRT
<213> ORGANISM: CoV-2
<220> FEATURE:
<223> OTHER INFORMATION: S B15.01_689

<400> SEQUENCE: 233

Ser Gln Ser Ile Ile Ala Tyr Thr Met
1               5

<210> SEQ ID NO 234
<211> LENGTH: 9
<212> TYPE: PRT
<213> ORGANISM: CoV-2
<220> FEATURE:
<223> OTHER INFORMATION: S B15.01_192

<400> SEQUENCE: 234

Phe Val Phe Lys Asn Ile Asp Gly Tyr
1               5

<210> SEQ ID NO 235
<211> LENGTH: 9
<212> TYPE: PRT
<213> ORGANISM: CoV-2
<220> FEATURE:
<223> OTHER INFORMATION: S B15.01_1113

<400> SEQUENCE: 235

Gln Ile Ile Thr Thr Asp Asn Thr Phe
1               5

<210> SEQ ID NO 236
<211> LENGTH: 9
<212> TYPE: PRT
<213> ORGANISM: CoV-2
<220> FEATURE:
<223> OTHER INFORMATION: S B15.01_152

<400> SEQUENCE: 236

Trp Met Glu Ser Glu Phe Arg Val Tyr
1               5

<210> SEQ ID NO 237
<211> LENGTH: 9
<212> TYPE: PRT
<213> ORGANISM: CoV-2
<220> FEATURE:
<223> OTHER INFORMATION: NC A2.01_222

<400> SEQUENCE: 237
```

-continued

```
Leu Leu Leu Asp Arg Leu Asn Gln Leu
1               5

<210> SEQ ID NO 238
<211> LENGTH: 9
<212> TYPE: PRT
<213> ORGANISM: CoV-2
<220> FEATURE:
<223> OTHER INFORMATION: NC A2.01_338

<400> SEQUENCE: 238

Lys Leu Asp Asp Lys Asp Pro Asn Phe
1               5

<210> SEQ ID NO 239
<211> LENGTH: 9
<212> TYPE: PRT
<213> ORGANISM: CoV-2
<220> FEATURE:
<223> OTHER INFORMATION: NC A1.01_79

<400> SEQUENCE: 239

Ser Pro Asp Asp Gln Ile Gly Tyr Tyr
1               5

<210> SEQ ID NO 240
<211> LENGTH: 9
<212> TYPE: PRT
<213> ORGANISM: CoV-2
<220> FEATURE:
<223> OTHER INFORMATION: NC A1.01_78

<400> SEQUENCE: 240

Ser Ser Pro Asp Asp Gln Ile Gly Tyr
1               5

<210> SEQ ID NO 241
<211> LENGTH: 9
<212> TYPE: PRT
<213> ORGANISM: CoV-2
<220> FEATURE:
<223> OTHER INFORMATION: NC A1.01_352

<400> SEQUENCE: 241

Leu Leu Asn Lys His Ile Asp Ala Tyr
1               5

<210> SEQ ID NO 242
<211> LENGTH: 9
<212> TYPE: PRT
<213> ORGANISM: CoV-2
<220> FEATURE:
<223> OTHER INFORMATION: NC A1.01_104

<400> SEQUENCE: 242

Leu Ser Pro Arg Trp Tyr Phe Tyr Tyr
1               5

<210> SEQ ID NO 243
<211> LENGTH: 9
<212> TYPE: PRT
<213> ORGANISM: CoV-2
<220> FEATURE:
<223> OTHER INFORMATION: NC A1.01_164

<400> SEQUENCE: 243
```

Gly Thr Thr Leu Pro Lys Gly Phe Tyr
1               5

<210> SEQ ID NO 244
<211> LENGTH: 9
<212> TYPE: PRT
<213> ORGANISM: CoV-2
<220> FEATURE:
<223> OTHER INFORMATION: NC A1.01_103

<400> SEQUENCE: 244

Asp Leu Ser Pro Arg Trp Tyr Phe Tyr
1               5

<210> SEQ ID NO 245
<211> LENGTH: 9
<212> TYPE: PRT
<213> ORGANISM: CoV-2
<220> FEATURE:
<223> OTHER INFORMATION: NC A3.01_361

<400> SEQUENCE: 245

Lys Thr Phe Pro Pro Thr Glu Pro Lys
1               5

<210> SEQ ID NO 246
<211> LENGTH: 9
<212> TYPE: PRT
<213> ORGANISM: CoV-2
<220> FEATURE:
<223> OTHER INFORMATION: NC A3.01_249

<400> SEQUENCE: 246

Lys Ser Ala Ala Glu Ala Ser Lys Lys
1               5

<210> SEQ ID NO 247
<211> LENGTH: 9
<212> TYPE: PRT
<213> ORGANISM: CoV-2
<220> FEATURE:
<223> OTHER INFORMATION: NC A3.01_379

<400> SEQUENCE: 247

Thr Gln Ala Leu Pro Gln Arg Gln Lys
1               5

<210> SEQ ID NO 248
<211> LENGTH: 9
<212> TYPE: PRT
<213> ORGANISM: CoV-2
<220> FEATURE:
<223> OTHER INFORMATION: NC A24.02_306

<400> SEQUENCE: 248

Gln Phe Ala Pro Ser Ala Ser Ala Phe
1               5

<210> SEQ ID NO 249
<211> LENGTH: 9
<212> TYPE: PRT
<213> ORGANISM: CoV-2
<220> FEATURE:
<223> OTHER INFORMATION: NC A24.02_299

<400> SEQUENCE: 249

Lys His Trp Pro Gln Ile Ala Gln Phe

```
1               5

<210> SEQ ID NO 250
<211> LENGTH: 9
<212> TYPE: PRT
<213> ORGANISM: CoV-2
<220> FEATURE:
<223> OTHER INFORMATION: NC A24.02_355

<400> SEQUENCE: 250

Lys His Ile Asp Ala Tyr Lys Thr Phe
1               5

<210> SEQ ID NO 251
<211> LENGTH: 9
<212> TYPE: PRT
<213> ORGANISM: CoV-2
<220> FEATURE:
<223> OTHER INFORMATION: NC A24.02_86

<400> SEQUENCE: 251

Tyr Tyr Arg Arg Ala Thr Arg Arg Ile
1               5

<210> SEQ ID NO 252
<211> LENGTH: 9
<212> TYPE: PRT
<213> ORGANISM: CoV-2
<220> FEATURE:
<223> OTHER INFORMATION: NC A24.02_345

<400> SEQUENCE: 252

Asn Phe Lys Asp Gln Val Ile Leu Leu
1               5

<210> SEQ ID NO 253
<211> LENGTH: 9
<212> TYPE: PRT
<213> ORGANISM: CoV-2
<220> FEATURE:
<223> OTHER INFORMATION: NC A26.01_103

<400> SEQUENCE: 253

Asp Leu Ser Pro Arg Trp Tyr Phe Tyr
1               5

<210> SEQ ID NO 254
<211> LENGTH: 9
<212> TYPE: PRT
<213> ORGANISM: CoV-2
<220> FEATURE:
<223> OTHER INFORMATION: NC A26.01_290

<400> SEQUENCE: 254

Glu Leu Ile Arg Gln Gly Thr Asp Tyr
1               5

<210> SEQ ID NO 255
<211> LENGTH: 9
<212> TYPE: PRT
<213> ORGANISM: CoV-2
<220> FEATURE:
<223> OTHER INFORMATION: NC A26.01_48

<400> SEQUENCE: 255

Asn Thr Ala Ser Trp Phe Thr Ala Leu
1               5
```

<210> SEQ ID NO 256
<211> LENGTH: 9
<212> TYPE: PRT
<213> ORGANISM: CoV-2
<220> FEATURE:
<223> OTHER INFORMATION: NC A26.01_78

<400> SEQUENCE: 256

Ser Ser Pro Asp Asp Gln Ile Gly Tyr
1               5

<210> SEQ ID NO 257
<211> LENGTH: 9
<212> TYPE: PRT
<213> ORGANISM: CoV-2
<220> FEATURE:
<223> OTHER INFORMATION: NC A26.01_323

<400> SEQUENCE: 257

Glu Val Thr Pro Ser Gly Thr Trp Leu
1               5

<210> SEQ ID NO 258
<211> LENGTH: 9
<212> TYPE: PRT
<213> ORGANISM: CoV-2
<220> FEATURE:
<223> OTHER INFORMATION: NC B7.02_66

<400> SEQUENCE: 258

Phe Pro Arg Gly Gln Gly Val Pro Ile
1               5

<210> SEQ ID NO 259
<211> LENGTH: 9
<212> TYPE: PRT
<213> ORGANISM: CoV-2
<220> FEATURE:
<223> OTHER INFORMATION: NC B7.02_257

<400> SEQUENCE: 259

Lys Pro Arg Gln Lys Arg Thr Ala Thr
1               5

<210> SEQ ID NO 260
<211> LENGTH: 9
<212> TYPE: PRT
<213> ORGANISM: CoV-2
<220> FEATURE:
<223> OTHER INFORMATION: NC B7.02_105

<400> SEQUENCE: 260

Ser Pro Arg Trp Tyr Phe Tyr Tyr Leu
1               5

<210> SEQ ID NO 261
<211> LENGTH: 9
<212> TYPE: PRT
<213> ORGANISM: CoV-2
<220> FEATURE:
<223> OTHER INFORMATION: NC B8.01_222

<400> SEQUENCE: 261

Leu Leu Leu Asp Arg Leu Asn Gln Leu
1               5

<210> SEQ ID NO 262
<211> LENGTH: 9
<212> TYPE: PRT
<213> ORGANISM: CoV-2
<220> FEATURE:
<223> OTHER INFORMATION: NC B8.01_386

<400> SEQUENCE: 262

Gln Lys Lys Gln Gln Thr Val Thr Leu
1               5

<210> SEQ ID NO 263
<211> LENGTH: 9
<212> TYPE: PRT
<213> ORGANISM: CoV-2
<220> FEATURE:
<223> OTHER INFORMATION: NC B8.01_105

<400> SEQUENCE: 263

Ser Pro Arg Trp Tyr Phe Tyr Tyr Leu
1               5

<210> SEQ ID NO 264
<211> LENGTH: 9
<212> TYPE: PRT
<213> ORGANISM: CoV-2
<220> FEATURE:
<223> OTHER INFORMATION: NC B8.01_403

<400> SEQUENCE: 264

Phe Ser Lys Gln Leu Gln Gln Ser Met
1               5

<210> SEQ ID NO 265
<211> LENGTH: 9
<212> TYPE: PRT
<213> ORGANISM: CoV-2
<220> FEATURE:
<223> OTHER INFORMATION: NC B8.01_345

<400> SEQUENCE: 265

Asn Phe Lys Asp Gln Val Ile Leu Leu
1               5

<210> SEQ ID NO 266
<211> LENGTH: 9
<212> TYPE: PRT
<213> ORGANISM: CoV-2
<220> FEATURE:
<223> OTHER INFORMATION: NC B27.05_9

<400> SEQUENCE: 266

Gln Arg Asn Ala Pro Arg Ile Thr Phe
1               5

<210> SEQ ID NO 267
<211> LENGTH: 9
<212> TYPE: PRT
<213> ORGANISM: CoV-2
<220> FEATURE:
<223> OTHER INFORMATION: NC B27.05_92

<400> SEQUENCE: 267

Arg Arg Ile Arg Gly Gly Asp Gly Lys
1               5

```
<210> SEQ ID NO 268
<211> LENGTH: 9
<212> TYPE: PRT
<213> ORGANISM: CoV-2
<220> FEATURE:
<223> OTHER INFORMATION: NC B39.01_159

<400> SEQUENCE: 268

Leu Gln Leu Pro Gln Gly Thr Thr Leu
1               5

<210> SEQ ID NO 269
<211> LENGTH: 9
<212> TYPE: PRT
<213> ORGANISM: CoV-2
<220> FEATURE:
<223> OTHER INFORMATION: NC B39.01_299

<400> SEQUENCE: 269

Lys His Trp Pro Gln Ile Ala Gln Phe
1               5

<210> SEQ ID NO 270
<211> LENGTH: 9
<212> TYPE: PRT
<213> ORGANISM: CoV-2
<220> FEATURE:
<223> OTHER INFORMATION: NC B39.01_374

<400> SEQUENCE: 270

Lys Lys Ala Asp Glu Thr Gln Ala Leu
1               5

<210> SEQ ID NO 271
<211> LENGTH: 9
<212> TYPE: PRT
<213> ORGANISM: CoV-2
<220> FEATURE:
<223> OTHER INFORMATION: NC B39.01_355

<400> SEQUENCE: 271

Lys His Ile Asp Ala Tyr Lys Thr Phe
1               5

<210> SEQ ID NO 272
<211> LENGTH: 9
<212> TYPE: PRT
<213> ORGANISM: CoV-2
<220> FEATURE:
<223> OTHER INFORMATION: NC B39.01_9

<400> SEQUENCE: 272

Gln Arg Asn Ala Pro Arg Ile Thr Phe
1               5

<210> SEQ ID NO 273
<211> LENGTH: 9
<212> TYPE: PRT
<213> ORGANISM: CoV-2
<220> FEATURE:
<223> OTHER INFORMATION: NC B39.01_386

<400> SEQUENCE: 273

Gln Lys Lys Gln Gln Thr Val Thr Leu
1               5

<210> SEQ ID NO 274
```

-continued

```
<211> LENGTH: 9
<212> TYPE: PRT
<213> ORGANISM: CoV-2
<220> FEATURE:
<223> OTHER INFORMATION: NC B39.01_148

<400> SEQUENCE: 274

Thr Arg Asn Pro Ala Asn Asn Ala Ala
1               5

<210> SEQ ID NO 275
<211> LENGTH: 9
<212> TYPE: PRT
<213> ORGANISM: CoV-2
<220> FEATURE:
<223> OTHER INFORMATION: NC B58.01_124

<400> SEQUENCE: 275

Gly Ala Asn Lys Asp Gly Ile Ile Trp
1               5

<210> SEQ ID NO 276
<211> LENGTH: 9
<212> TYPE: PRT
<213> ORGANISM: CoV-2
<220> FEATURE:
<223> OTHER INFORMATION: NC B58.01_266

<400> SEQUENCE: 276

Lys Ala Tyr Asn Val Thr Gln Ala Phe
1               5

<210> SEQ ID NO 277
<211> LENGTH: 9
<212> TYPE: PRT
<213> ORGANISM: CoV-2
<220> FEATURE:
<223> OTHER INFORMATION: NC B58.01_100

<400> SEQUENCE: 277

Lys Met Lys Asp Leu Ser Pro Arg Trp
1               5

<210> SEQ ID NO 278
<211> LENGTH: 9
<212> TYPE: PRT
<213> ORGANISM: CoV-2
<220> FEATURE:
<223> OTHER INFORMATION: NC B15.01_266

<400> SEQUENCE: 278

Lys Ala Tyr Asn Val Thr Gln Ala Phe
1               5

<210> SEQ ID NO 279
<211> LENGTH: 9
<212> TYPE: PRT
<213> ORGANISM: CoV-2
<220> FEATURE:
<223> OTHER INFORMATION: NC B15.01_352

<400> SEQUENCE: 279

Leu Leu Asn Lys His Ile Asp Ala Tyr
1               5

<210> SEQ ID NO 280
<211> LENGTH: 9
```

```
<212> TYPE: PRT
<213> ORGANISM: CoV-2
<220> FEATURE:
<223> OTHER INFORMATION: NC B15.01_159

<400> SEQUENCE: 280

Leu Gln Leu Pro Gln Gly Thr Thr Leu
1               5

<210> SEQ ID NO 281
<211> LENGTH: 69
<212> TYPE: PRT
<213> ORGANISM: CoV-2
<220> FEATURE:
<223> OTHER INFORMATION: RBE 1-3 Complete

<400> SEQUENCE: 281

Lys Val Gly Gly Asn Tyr Asn Tyr Leu Tyr Arg Leu Phe Arg Lys Ser
1               5                   10                  15

Asn Leu Lys Pro Phe Glu Arg Asp Ile Ser Thr Glu Ile Tyr Gln Ala
                20                  25                  30

Gly Ser Thr Pro Cys Asn Gly Val Glu Gly Phe Asn Cys Tyr Phe Pro
            35                  40                  45

Leu Gln Ser Tyr Gly Phe Gln Pro Thr Asn Gly Val Gly Tyr Gln Pro
        50                  55                  60

Tyr Arg Val Val Val
65

<210> SEQ ID NO 282
<211> LENGTH: 223
<212> TYPE: PRT
<213> ORGANISM: CoV-2
<220> FEATURE:
<223> OTHER INFORMATION: RBD Complete

<400> SEQUENCE: 282

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
                20                  25                  30

Tyr Ala Trp Asn Arg Lys Arg Ile Ser Asn Cys Val Ala Asp Tyr Ser
            35                  40                  45

Val Leu Tyr Asn Ser Ala Ser Phe Ser Thr Phe Lys Cys Tyr Gly Val
        50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
```

```
                180             185                 190
Val Val Leu Ser Phe Glu Leu Leu His Ala Pro Ala Thr Val Cys Gly
            195                 200             205

Pro Lys Lys Ser Thr Asn Leu Val Lys Asn Lys Cys Val Asn Phe
        210                 215             220

<210> SEQ ID NO 283
<211> LENGTH: 133
<212> TYPE: PRT
<213> ORGANISM: Camelid
<220> FEATURE:
<223> OTHER INFORMATION: RBE - Mu 1,2,3 Original

<400> SEQUENCE: 283

Asp Val Gln Leu Gln Ala Ser Gly Gly Gly Ser Val Gln Ala Gly Gly
1               5                   10                  15

Ser Leu Arg Leu Ser Cys Ala Ala Ser Gly Tyr Thr Ile Gly Pro Tyr
            20                  25                  30

Cys Met Gly Trp Phe Arg Gln Ala Pro Gly Lys Glu Arg Glu Gly Val
        35                  40                  45

Ala Ala Ile Asn Met Gly Gly Gly Ile Thr Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Leu Met Asn Ser Leu Glu Pro Glu Asp Thr Ala Ile Tyr Tyr Cys
                85                  90                  95

Ala Ala Asp Ser Thr Ile Tyr Ala Ser Tyr Tyr Glu Cys Gly His Gly
            100                 105                 110

Leu Ser Thr Gly Gly Tyr Gly Tyr Asp Ser Trp Gly Gln Gly Thr Gln
        115                 120                 125

Val Thr Val Ser Ser
    130

<210> SEQ ID NO 284
<211> LENGTH: 399
<212> TYPE: DNA
<213> ORGANISM: Camelid
<220> FEATURE:
<223> OTHER INFORMATION: RBE - Mu 1,2,3 Original (DNA)

<400> SEQUENCE: 284
gatgtgcagc tgcaggcgag cggcggcggc agcgtgcagg cgggcggcag cctgcgcctg     60
agctgcgcgg cgagcggcta ccattggc ccgtattgca tgggctggtt tcgccaggcg    120
ccgggcaaag aacgcgaagg cgtggcggcg attaacatgg cggcggcat tacctattat    180 gcggatagcg tgaaaggccg ctttaccatt agccaggata cgcgaaaaa caccgtgtat    240 ctgctgatga acagcctgga accggaagat accgcgattt attattgcgc ggcggatagc    300
accatttatg cgagctatta tgaatgcggc catggcctga gcaccggcgg ctatggctat    360
gatagctggg gccagggcac ccaggtgacc gtgagcagc                           399

<210> SEQ ID NO 285
<211> LENGTH: 157
<212> TYPE: PRT
<213> ORGANISM: Camelid CoV-2
<220> FEATURE:
<223> OTHER INFORMATION: RBE - Mu 1,2,3 Replaced

<400> SEQUENCE: 285
```

Asp Val Gln Leu Gln Ala Ser Gly Gly Gly Ser Val Gln Ala Gly Gly
1               5                   10                  15

Ser Leu Arg Leu Ser Cys Ala Ala Ser Gly Tyr Thr Ile Gly Lys Val
            20                  25                  30

Gly Gly Asn Tyr Asn Tyr Leu Tyr Arg Leu Phe Arg Lys Ser Asn Leu
            35                  40                  45

Lys Pro Trp Phe Arg Gln Ala Pro Gly Lys Glu Arg Glu Gly Val Ala
50                  55                  60

Phe Glu Arg Asp Ile Ser Thr Glu Ile Tyr Gln Ala Gly Ser Thr Pro
65                  70                  75                  80

Cys Asn Gly Val Arg Phe Thr Ile Ser Gln Asp Asn Ala Lys Asn Thr
                85                  90                  95

Val Tyr Leu Leu Met Asn Ser Leu Glu Pro Glu Asp Thr Ala Ile Tyr
                100                 105                 110

Tyr Cys Ala Ala Glu Gly Phe Asn Cys Tyr Phe Pro Leu Gln Ser Tyr
                115                 120                 125

Gly Phe Gln Pro Thr Asn Gly Val Gly Tyr Gln Pro Tyr Arg Val Val
                130                 135                 140

Val Leu Trp Gly Gln Gly Thr Gln Val Thr Val Ser Ser
145                 150                 155

<210> SEQ ID NO 286
<211> LENGTH: 416
<212> TYPE: PRT
<213> ORGANISM: CoV-2
<220> FEATURE:
<223> OTHER INFORMATION: RBE - Mu 1,2,3 Full Construct

<400> SEQUENCE: 286

Asp Val Gln Leu Gln Ala Ser Gly Gly Gly Ser Val Gln Ala Gly Gly
1               5                   10

```
Ala Thr Tyr Gly Lys Leu Thr Leu Lys Phe Ile Cys Thr Thr Gly Lys
    210                 215                 220

Leu Pro Val Pro Trp Pro Thr Leu Val Thr Thr Phe Ser Tyr Gly Val
225                 230                 235                 240

Gln Cys Phe Ser Arg Tyr Pro Asp His Met Lys Arg His Asp Phe Phe
                245                 250                 255

Lys Ser Ala Met Pro Glu Gly Tyr Val Gln Glu Arg Thr Ile Ser Phe
            260                 265                 270

Lys Asp Asp Gly Asn Tyr Lys Thr Arg Ala Glu Val Lys Phe Glu Gly
        275                 280                 285

Asp Thr Leu Val Asn Arg Ile Glu Leu Lys Gly Ile Asp Phe Lys Glu
    290                 295                 300

Asp Gly Asn Ile Leu Gly His Lys Leu Glu Tyr Asn Tyr Asn Ser His
305                 310                 315                 320

Asn Val Tyr Ile Thr Ala Asp Lys Gln Lys Asn Gly Ile Lys Val Asn
                325                 330                 335

Phe Lys Ile Arg His Asn Ile Glu Asp Gly Ser Val Gln Leu Ala Asp
            340                 345                 350

His Tyr Gln Gln Asn Thr Pro Ile Gly Asp Gly Pro Val Leu Leu Pro
        355                 360                 365

Asp Asn His Tyr Leu Ser Thr Gln Ser Ala Leu Ser Lys Asp Pro Asn
    370                 375                 380

Glu Lys Arg Asp His Met Val Leu Leu Glu Phe Val Thr Ala Ala Gly
385                 390                 395                 400

Ile Thr His Gly Met Asp Glu Leu Tyr Lys His His His His His His
                405                 410                 415

<210> SEQ ID NO 287
<211> LENGTH: 121
<212> TYPE: PRT
<213> ORGANISM: CoV-2
<220> FEATURE:
<223> OTHER INFORMATION: RBE - Du 1,2,3 Original cAb-HuL6

<400> SEQUENCE: 287

Gln Val Gln Leu Val Glu Ser Gly Gly Gly Ser Val Gln Ala Gly Gly
1               5                   10                  15

Ser Leu Arg Leu Ser Cys Ser Ala Ser Gly Tyr Thr Tyr Ile Ser Gly
            20                  25                  30

Trp Phe Arg Gln Ala Pro Gly Lys Glu Arg Glu Gly Val Ala Ala Ile
        35                  40                  45

Arg Ser Ser Asp Gly Thr Thr Tyr Tyr Ala Asp Ser Val Lys Gly Arg
    50                  55                  60

Phe Thr Ile Ser Gln Asp Asn Ala Lys Asn Thr Val Tyr Leu Gln Met
65                  70                  75                  80

Asn Ser Leu Lys Pro Glu Asp Thr Ala Met Tyr Tyr Cys Ala Ala Thr
                85                  90                  95

Glu Val Ala Gly Trp Pro Leu Asp Ile Gly Ile Tyr Asp Tyr Trp Gly
            100                 105                 110

Gln Gly Thr Gln Val Thr Val Ser Ser
        115                 120

<210> SEQ ID NO 288
<211> LENGTH: 152
<212> TYPE: PRT
<213> ORGANISM: CoV-2
<220> FEATURE:
```

<223> OTHER INFORMATION: RBE - Du 1,2,3 Replaced

<400> SEQUENCE: 288

```
Gln Val Gln Leu Val Glu Ser Gly Gly Gly Ser Val Gln Ala Gly Gly
1               5                   10                  15

Ser Leu Arg Leu Ser Cys Ser Ala Ser Lys Val Gly Gly Asn Tyr Asn
            20                  25                  30

Tyr Leu Tyr Arg Leu Phe Arg Lys Ser Asn Leu Lys Pro Trp Phe Arg
        35                  40                  45

Gln Ala Pro Gly Lys Glu Arg Glu Gly Val Ala Phe Glu Arg Asp Ile
    50                  55                  60

Ser Thr Glu Ile Tyr Gln Ala Gly Ser Thr Pro Cys Asn Gly Val Arg
65                  70                  75                  80

Phe Thr Ile Ser Gln Asp Asn Ala Lys Asn Thr Val Tyr Leu Gln Met
                85                  90                  95

Asn Ser Leu Lys Pro Glu Asp Thr Ala Met Tyr Tyr Cys Ala Ala Glu
            100                 105                 110

Gly Phe Asn Cys Tyr Phe Pro Leu Gln Ser Tyr Gly Phe Gln Pro Thr
        115                 120                 125

Asn Gly Val Gly Tyr Gln Pro Tyr Arg Val Val Leu Trp Gly Gln
    130                 135                 140

Gly Thr Gln Val Thr Val Ser Ser
145                 150
```

<210> SEQ ID NO 289
<211> LENGTH: 411
<212> TYPE: PRT
<213> ORGANISM: CoV-2
<220> FEATURE:
<223> OTHER INFORMATION: RBE - Du 1,2,3 Full Construct

<400> SEQUENCE: 289

```
Gln Val Gln Leu Val Glu Ser Gly Gly Gly Ser Val Gln Ala Gly Gly
1               5                   10                  15

Ser Leu Arg Leu Ser Cys Ser Ala Ser Lys Val Gly Gly Asn Tyr Asn
            20                  25                  30

Tyr Leu Tyr Arg Leu Phe Arg Lys Ser Asn Leu Lys Pro Trp Phe Arg
        35                  40                  45

Gln Ala Pro Gly Lys Glu Arg Glu Gly Val Ala Phe Glu Arg Asp Ile
    50                  55                  60

Ser Thr Glu Ile Tyr Gln Ala Gly Ser Thr Pro Cys Asn Gly Val Arg
65                  70                  75                  80

Phe Thr Ile Ser Gln Asp Asn Ala Lys Asn Thr Val Tyr Leu Gln Met
                85                  90                  95

Asn Ser Leu Lys Pro Glu Asp Thr Ala Met Tyr Tyr Cys Ala Ala Glu
            100                 105                 110

Gly Phe Asn Cys Tyr Phe Pro Leu Gln Ser Tyr Gly Phe Gln Pro Thr
        115                 120                 125

Asn Gly Val Gly Tyr Gln Pro Tyr Arg Val Val Leu Trp Gly Gln
    130                 135                 140

Gly Thr Gln Val Thr Val Ser Ser Gly Gly Gly Ser Gly Gly
145                 150                 155                 160

Gly Ser Gly Gly Gly Ser Met Gly Lys Gly Glu Glu Leu Phe Thr
            165                 170                 175

Gly Val Val Pro Ile Leu Val Glu Leu Asp Gly Asp Val Asn Gly His
        180                 185                 190
```

Lys Phe Ser Val Ser Gly Glu Gly Glu Gly Asp Ala Thr Tyr Gly Lys
            195                 200                 205

Leu Thr Leu Lys Phe Ile Cys Thr Thr Gly Lys Leu Pro Val Pro Trp
210                 215                 220

Pro Thr Leu Val Thr Thr Phe Ser Tyr Gly Val Gln Cys Phe Ser Arg
225                 230                 235                 240

Tyr Pro Asp His Met Lys Arg His Asp Phe Phe Lys Ser Ala Met Pro
            245                 250                 255

Glu Gly Tyr Val Gln Glu Arg Thr Ile Ser Phe Lys Asp Asp Gly Asn
            260                 265                 270

Tyr Lys Thr Arg Ala Glu Val Lys Phe Glu Gly Asp Thr Leu Val Asn
            275                 280                 285

Arg Ile Glu Leu Lys Gly Ile Asp Phe Lys Glu Asp Gly Asn Ile Leu
290                 295                 300

Gly His Lys Leu Glu Tyr Asn Tyr Asn Ser His Asn Val Tyr Ile Thr
305                 310                 315                 320

Ala Asp Lys Gln Lys Asn Gly Ile Lys Val Asn Phe Lys Ile Arg His
            325                 330                 335

Asn Ile Glu Asp Gly Ser Val Gln Leu Ala Asp His Tyr Gln Gln Asn
            340                 345                 350

Thr Pro Ile Gly Asp Gly Pro Val Leu Leu Pro Asp Asn His Tyr Leu
            355                 360                 365

Ser Thr Gln Ser Ala Leu Ser Lys Asp Pro Asn Glu Lys Arg Asp His
            370                 375                 380

Met Val Leu Leu Glu Phe Val Thr Ala Ala Gly Ile Thr His Gly Met
385                 390                 395                 400

Asp Glu Leu Tyr Lys His His His His His His
            405                 410

<210> SEQ ID NO 290
<211> LENGTH: 127
<212> TYPE: PRT
<213> ORGANISM: CoV-2
<220> FEATURE:
<223> OTHER INFORMATION: RBE - Vi 1,2,3 Original (cAb 2: AMYL-B7)

<400> SEQUENCE: 290

Gln Val Gln Leu Val Glu Ser Gly Gly Gly Ser Val Gln Ala Gly Gly
1               5                   10                  15

Ser Leu Arg Leu Ser Cys Ala Ala Ser Gly Tyr Thr Phe Ser Ser Tyr
            20                  25                  30

Pro Met Gly Trp Tyr Arg Gln Ala Pro Gly Lys Glu Cys Glu Leu Val
        35                  40                  45

Ser Arg Ile Phe Ser Asp Gly Ser Ala Asn Tyr Ala Gly Ser Val Lys
    50                  55                  60

Gly Arg Phe Thr Ile Ser Arg Asp Asn Ala Lys Asn Thr Ala Tyr Leu
65                  70                  75                  80

Gln Met Asp Ser Leu Lys Pro Glu Asp Thr Ala Val Tyr Tyr Cys Ala
            85                  90                  95

Ala Gly Pro Gly Ser Gly Lys Leu Val Val Ala Gly Arg Thr Cys Tyr
            100                 105                 110

Gly Pro Asn Tyr Trp Gly Gln Gly Thr Gln Val Thr Val Ser Ser
        115                 120                 125

<210> SEQ ID NO 291

```
<211> LENGTH: 162
<212> TYPE: PRT
<213> ORGANISM: CoV-2
<220> FEATURE:
<223> OTHER INFORMATION: RBE - Vi 1,2,3 Replaced (Camelid?CoV-2)

<400> SEQUENCE: 291
```

Gln Val Gln Leu Val Glu Ser Gly Gly Gly Ser Val Gln Ala Gly Gly
1               5                   10                  15

Ser Leu Arg Leu Ser Cys Ala Ala Ser Gly Lys Val Gly Gly Asn Tyr
            20                  25                  30

Asn Tyr Leu Tyr Arg Leu Phe Arg Lys Ser Asn Leu Lys Pro Trp Tyr
        35                  40                  45

Arg Gln Ala Pro Gly Lys Glu Cys Glu Leu Val Ser Phe Glu Arg Asp
    50                  55                  60

Ile Ser Thr Glu Ile Tyr Gln Ala Gly Ser Thr Pro Cys Asn Gly Val
65                  70                  75                  80

Ala Asn Tyr Ala Gly Ser Val Lys Gly Arg Phe Thr Ile Ser Arg Asp
                85                  90                  95

Asn Ala Lys Asn Thr Ala Tyr Leu Gln Met Asp Ser Leu Lys Pro Glu
            100                 105                 110

Asp Thr Ala Val Tyr Tyr Cys Ala Ala Glu Gly Phe Asn Cys Tyr Phe
        115                 120                 125

Pro Leu Gln Ser Tyr Gly Phe Gln Pro Thr Asn Gly Val Gly Tyr Gln
    130                 135                 140

Pro Tyr Arg Val Val Val Leu Trp Gly Gln Gly Thr Gln Val Thr Val
145                 150                 155                 160

Ser Ser

```
<210> SEQ ID NO 292
<211> LENGTH: 421
<212> TYPE: PRT
<213> ORGANISM: CoV-2
<220> FEATURE:
<223> OTHER INFORMATION: RBE - Vi 1,2,3 Full Construct Camelid?CoV-2

<400> SEQUENCE: 292
```

Gln Val Gln Leu Val Glu Ser Gly Gly Gly Ser Val Gln Ala Gly Gly
1               5                   10                  15

Ser Leu Arg Leu Ser Cys Ala Ala Ser Gly Lys Val Gly Gly Asn Tyr
            20                  25                  30

Asn Tyr Leu Tyr Arg Leu Phe Arg Lys Ser Asn Leu Lys Pro Trp Tyr
        35                  40                  45

Arg Gln Ala Pro Gly Lys Glu Cys Glu Leu Val Ser Phe Glu Arg Asp
    50                  55                  60

Ile Ser Thr Glu Ile Tyr Gln Ala Gly Ser Thr Pro Cys Asn Gly Val
65                  70                  75                  80

Ala Asn Tyr Ala Gly Ser Val Lys Gly Arg Phe Thr Ile Ser Arg Asp
                85                  90                  95

Asn Ala Lys Asn Thr Ala Tyr Leu Gln Met Asp Ser Leu Lys Pro Glu
            100                 105                 110

Asp Thr Ala Val Tyr Tyr Cys Ala Ala Glu Gly Phe Asn Cys Tyr Phe
        115                 120                 125

Pro Leu Gln Ser Tyr Gly Phe Gln Pro Thr Asn Gly Val Gly Tyr Gln
    130                 135                 140

Pro Tyr Arg Val Val Val Leu Trp Gly Gln Gly Thr Gln Val Thr Val
145                 150                 155                 160

Ser Ser Gly Gly Gly Ser Gly Gly Gly Ser Gly Gly Gly
            165                 170                 175

Ser Met Gly Lys Gly Glu Glu Leu Phe Thr Gly Val Val Pro Ile Leu
            180                 185                 190

Val Glu Leu Asp Gly Asp Val Asn Gly His Lys Phe Ser Val Ser Gly
            195                 200                 205

Glu Gly Glu Gly Asp Ala Thr Tyr Gly Lys Leu Thr Leu Lys Phe Ile
            210                 215                 220

Cys Thr Thr Gly Lys Leu Pro Val Pro Trp Pro Thr Leu Val Thr Thr
225                 230                 235                 240

Phe Ser Tyr Gly Val Gln Cys Phe Ser Arg Tyr Pro Asp His Met Lys
            245                 250                 255

Arg His Asp Phe Phe Lys Ser Ala Met Pro Glu Gly Tyr Val Gln Glu
            260                 265                 270

Arg Thr Ile Ser Phe Lys Asp Asp Gly Asn Tyr Lys Thr Arg Ala Glu
            275                 280                 285

Val Lys Phe Glu Gly Asp Thr Leu Val Asn Arg Ile Glu Leu Lys Gly
            290                 295                 300

Ile Asp Phe Lys Glu Asp Gly Asn Ile Leu Gly His Lys Leu Glu Tyr
305                 310                 315                 320

Asn Tyr Asn Ser His Asn Val Tyr Ile Thr Ala Asp Lys Gln Lys Asn
            325                 330                 335

Gly Ile Lys Val Asn Phe Lys Ile Arg His Asn Ile Glu Asp Gly Ser
            340                 345                 350

Val Gln Leu Ala Asp His Tyr Gln Gln Asn Thr Pro Ile Gly Asp Gly
            355                 360                 365

Pro Val Leu Leu Pro Asp Asn His Tyr Leu Ser Thr Gln Ser Ala Leu
            370                 375                 380

Ser Lys Asp Pro Asn Glu Lys Arg Asp His Met Val Leu Leu Glu Phe
385                 390                 395                 400

Val Thr Ala Ala Gly Ile Thr His Gly Met Asp Glu Leu Tyr Lys His
            405                 410                 415

His His His His
        420

<210> SEQ ID NO 293
<211> LENGTH: 6
<212> TYPE: PRT
<213> ORGANISM: CoV-2
<220> FEATURE:
<223> OTHER INFORMATION: 71-79

<400> SEQUENCE: 293

Thr Asn Gly Thr Lys Arg
1               5

<210> SEQ ID NO 294
<211> LENGTH: 6
<212> TYPE: PRT
<213> ORGANISM: CoV-2
<220> FEATURE:
<223> OTHER INFORMATION: 145-150

<400> SEQUENCE: 294

His Lys Asn Asn Lys Ser
1               5

```
<210> SEQ ID NO 295
<211> LENGTH: 12
<212> TYPE: PRT
<213> ORGANISM: CoV-2
<220> F

```
Arg Thr Ile Ser Phe Lys Asp Gly Asn Tyr Lys Thr Arg Ala Glu
                245                 250                 255

Val Lys Phe Glu Gly Asp Thr Leu Val Asn Arg Ile Glu Leu Lys Gly
            260                 265                 270

Ile Asp Phe Lys Glu Asp Gly Asn Ile Leu Gly His Lys Leu Glu Tyr
            275                 280                 285

Asn Tyr Asn Ser His Asn Val Tyr Ile Thr Ala Asp Lys Gln Lys Asn
            290                 295                 300

Gly Ile Lys Val Asn Phe Lys Ile Arg His Asn Ile Glu Asp Gly Ser
305                 310                 315                 320

Val Gln Leu Ala Asp His Tyr Gln Gln Asn Thr Pro Ile Gly Asp Gly
                325                 330                 335

Pro Val Leu Leu Pro Asp Asn His Tyr Leu Ser Thr Gln Ser Ala Leu
                340                 345                 350

Ser Lys Asp Pro Asn Glu Lys Arg Asp His Met Val Leu Leu Glu Phe
                355                 360                 365

Val Thr Ala Ala Gly Ile Thr His Gly Met Asp Glu Leu Tyr Lys His
                370                 375                 380

His His His His His His Thr Ala Ala
385                 390

<210> SEQ ID NO 298
<211> LENGTH: 391
<212> TYPE: PRT
<213> ORGANISM: CoV-2
<220> FEATURE:
<223> OTHER INFORMATION: Du - Fu 2,3 - G

<400> SEQUENCE: 298

Met Gln Val Gln Leu Val Glu Ser Gly Gly Gly Ser Val Gln Ala Gly
1               5                   10                  15

Gly Ser Leu Arg Leu Ser Cys Ser Ala Ser Gly Tyr Thr Tyr Ile Ser
                20                  25                  30

Gly Trp Phe Arg Gln Ala Pro Gly Lys Glu Arg Glu Gly Val Ala Ser
                35                  40                  45

Phe Ile Glu Asp Leu Leu Phe Asn Lys Val Thr Leu Ala Asp Ala Gly
            50                  55                  60

Phe Ile Lys Arg Phe Thr Ile Ser Gln Asp Asn Ala Lys Asn Thr Val
65                  70                  75                  80

Tyr Leu Gln Met Asn Ser Leu Lys Pro Glu Asp Thr Ala Met Tyr Tyr
                85                  90                  95

Cys Ala Ala Gln Tyr Gly Asp Cys Leu Gly Asp Ile Ala Ala Arg Asp
                100                 105                 110

Leu Ile Cys Ala Gln Lys Phe Trp Gly Gln Gly Thr Gln Val Thr Val
            115                 120                 125

Ser Ser Gly Gly Gly Ser Gly Gly Gly Ser Gly Gly Gly Ser Met Gly
            130                 135                 140

Lys Gly Glu Glu Leu Phe Thr Gly Val Val Pro Ile Leu Val Glu Leu
145                 150                 155                 160

Asp Gly Asp Val Asn Gly His Lys Phe Ser Val Ser Gly Glu Gly Glu
                165                 170                 175

Gly Asp Ala Thr Tyr Gly Lys Leu Thr Leu Lys Phe Ile Cys Thr Thr
                180                 185                 190

Gly Lys Leu Pro Val Pro Trp Pro Thr Leu Val Thr Thr Phe Ser Tyr
            195                 200                 205
```

```
Gly Val Gln Cys Phe Ser Arg Tyr Pro Asp His Met Lys Arg His Asp
        210                 215                 220

Phe Phe Lys Ser Ala Met Pro Glu Gly Tyr Val Gln Glu Arg Thr Ile
225                 230                 235                 240

Ser Phe Lys Asp Asp Gly Asn Tyr Lys Thr Arg Ala Glu Val Lys Phe
                245                 250                 255

Glu Gly Asp Thr Leu Val Asn Arg Ile Glu Leu Lys Gly Ile Asp Phe
                260                 265                 270

Lys Glu Asp Gly Asn Ile Leu Gly His Lys Leu Glu Tyr Asn Tyr Asn
            275                 280                 285

Ser His Asn Val Tyr Ile Thr Ala Asp Lys Gln Lys Asn Gly Ile Lys
        290                 295                 300

Val Asn Phe Lys Ile Arg His Asn Ile Glu Asp Gly Ser Val Gln Leu
305                 310                 315                 320

Ala Asp His Tyr Gln Gln Asn Thr Pro Ile Gly Asp Gly Pro Val Leu
                325                 330                 335

Leu Pro Asp Asn His Tyr Leu Ser Thr Gln Ser Ala Leu Ser Lys Asp
                340                 345                 350

Pro Asn Glu Lys Arg Asp His Met Val Leu Leu Glu Phe Val Thr Ala
            355                 360                 365

Ala Gly Ile Thr His Gly Met Asp Glu Leu Tyr Lys His His His His
        370                 375                 380

His His His His Thr Ala Ala
385                 390

<210> SEQ ID NO 299
<211> LENGTH: 403
<212> TYPE: PRT
<213> ORGANISM: CoV-2
<220> FEATURE:
<223> OTHER INFORMATION: Vi - Fu 2,3 - G

<400> SEQUENCE: 299

Met Gln Val Gln Leu Val Glu Ser Gly Gly Gly Ser Val Gln Ala Gly
1               5                   10                  15

Gly Ser Leu Arg Leu Ser Cys Ala Ala Ser Gly Tyr Thr Phe Ser Ser
            20                  25                  30

Tyr Pro Met Gly Trp Tyr Arg Gln Ala Pro Gly Lys Glu Cys Glu Leu
        35                  40                  45

Val Ser Ser Phe Ile Glu Asp Leu Leu Phe Asn Lys Val Thr Leu Ala
    50                  55                  60

Asp Ala Gly Phe Ile Lys Ala Asn Tyr Ala Gly Ser Val Lys Gly Arg
65                  70                  75                  80

Phe Thr Ile Ser Arg Asp Asn Ala Lys Asn Thr Ala Tyr Leu Gln Met
                85                  90                  95

Asp Ser Leu Lys Pro Glu Asp Thr Ala Val Tyr Tyr Cys Ala Ala Gln
            100                 105                 110

Tyr Gly Asp Cys Leu Gly Asp Ile Ala Ala Arg Asp Leu Ile Cys Ala
        115                 120                 125

Gln Lys Phe Trp Gly Gln Gly Thr Gln Val Thr Val Ser Ser Gly Gly
    130                 135                 140

Gly Ser Gly Gly Gly Ser Gly Gly Ser Met Gly Lys Gly Glu Glu
145                 150                 155                 160

Leu Phe Thr Gly Val Val Pro Ile Leu Val Glu Leu Asp Gly Asp Val
                165                 170                 175
```

Asn Gly His Lys Phe Ser Val Ser Gly Glu Gly Gly Asp Ala Thr
            180                 185                 190

Tyr Gly Lys Leu Thr Leu Lys Phe Ile Cys Thr Thr Gly Lys Leu Pro
            195                 200                 205

Val Pro Trp Pro Thr Leu Val Thr Thr Phe Ser Tyr Gly Val Gln Cys
210                 215                 220

Phe Ser Arg Tyr Pro Asp His Met Lys Arg His Asp Phe Phe Lys Ser
225                 230                 235                 240

Ala Met Pro Glu Gly Tyr Val Gln Glu Arg Thr Ile Ser Phe Lys Asp
                245                 250                 255

Asp Gly Asn Tyr Lys Thr Arg Ala Glu Val Lys Phe Glu Gly Asp Thr
            260                 265                 270

Leu Val Asn Arg Ile Glu Leu Lys Gly Ile Asp Phe Lys Glu Asp Gly
            275                 280                 285

Asn Ile Leu Gly His Lys Leu Glu Tyr Asn Tyr Asn Ser His Asn Val
    290                 295                 300

Tyr Ile Thr Ala Asp Lys Gln Lys Asn Gly Ile Lys Val Asn Phe Lys
305                 310                 315                 320

Ile Arg His Asn Ile Glu Asp Gly Ser Val Gln Leu Ala Asp His Tyr
                325                 330                 335

Gln Gln Asn Thr Pro Ile Gly Asp Gly Pro Val Leu Leu Pro Asp Asn
            340                 345                 350

His Tyr Leu Ser Thr Gln Ser Ala Leu Ser Lys Asp Pro Asn Glu Lys
            355                 360                 365

Arg Asp His Met Val Leu Leu Glu Phe Val Thr Ala Ala Gly Ile Thr
    370                 375                 380

His Gly Met Asp Glu Leu Tyr Lys His His His His His His His His
385                 390                 395                 400

Thr Ala Gly

<210> SEQ ID NO 300
<211> LENGTH: 206
<212> TYPE: PRT
<213> ORGANISM: CoV-2
<220> FEATURE:
<223> OTHER INFORMATION: Mu - Fu 2,3 - MD

<400> SEQUENCE: 300

Met Asp Val Gln

```
Val Thr Val Ser Ser Gly Gly Gly Ser Gly Gly Gly Ser Gly Gly Gly
    130                 135                 140

Ser Ala Tyr Pro Thr Leu Ser Glu Ile Lys Gly Val Ile Val His Arg
145                 150                 155                 160

Leu Glu Gly Val Ser Tyr Asn Ile Thr Gly Thr Asn Pro Val Phe Ala
                165                 170                 175

Gly Ala Asn Tyr Ala Ala Trp Ala Val Asn Val Ala Gln Val Ile Asp
                180                 185                 190

Ser Glu Thr His His His His His His His Thr Ala Ala
                195                 200                 205
```

<210> SEQ ID NO 301
<211> LENGTH: 203
<212> TYPE: PRT
<213> ORGANISM: CoV-2
<220> FEATURE:
<223> OTHER INFORMATION: Du - Fu 2,3 - MD

<400> SEQUENCE: 301

```
Met Gln Val Gln Leu Val Glu Ser Gly Gly Gly Ser Val Gln Ala Gly
1               5                   10                  15

Gly Ser Leu Arg Leu Ser Cys Ser Ala Ser Gly Tyr Thr Tyr Ile Ser
                20                  25                  30

Gly Trp Phe Arg Gln Ala Pro Gly Lys Glu Arg Glu Gly Val Ala Ser
                35                  40                  45

Phe Ile Glu Asp Leu Leu Phe Asn Lys Val Thr Leu Ala Asp Ala Gly
            50                  55                  60

Phe Ile Lys Arg Phe Thr Ile Ser Gln Asp Asn Ala Lys Asn Thr Val
65                  70                  75                  80

Tyr Leu Gln Met Asn Ser Leu Lys Pro Glu Asp Thr Ala Met Tyr Tyr
                85                  90                  95

Cys Ala Ala Gln Tyr Gly Asp Cys Leu Gly Asp Ile Ala Ala Arg Asp
                100                 105                 110

Leu Ile Cys Ala Gln Lys Phe Trp Gly Gln Gly Thr Gln Val Thr Val
                115                 120                 125

Ser Ser Gly Gly Gly Ser Gly Gly Gly Ser Gly Gly Gly Ser Ala Tyr
            130                 135                 140

Pro Thr Leu Ser Glu Ile Lys Gly Val Ile Val His Arg Leu Glu Gly
145                 150                 155                 160

Val Ser Tyr Asn Ile Thr Gly Thr Asn Pro Val Phe Ala Gly Ala Asn
                165                 170                 175

Tyr Ala Ala Trp Ala Val Asn Val Ala Gln Val Ile Asp Ser Glu Thr
                180                 185                 190

His His His His His His His Thr Ala Ala
            195                 200
```

<210> SEQ ID NO 302
<211> LENGTH: 216
<212> TYPE: PRT
<213> ORGANISM: CoV-2
<220> FEATURE:
<223> OTHER INFORMATION: Vi - Fu 2,3- MD

<400> SEQUENCE: 302

```
Met Gln Val Gln Leu Val Glu Ser Gly Gly Gly Ser Val Gln Ala Gly
1               5                   10                  15

Gly Ser Leu Arg Leu Ser Cys Ala Ala Ser Gly Tyr Thr Phe Ser Ser
                20                  25                  30
```

Tyr Pro Met Gly Trp Tyr Arg Gln Ala Pro Gly Lys Glu Cys Glu Leu
                35                  40                  45

Val Ser Ser Phe Ile Glu Asp Leu Leu Phe Asn Lys Val Thr Leu Ala
 50                  55                  60

Asp Ala Gly Phe Ile Lys Ala Asn Tyr Ala Gly Ser Val Lys Gly Arg
 65                  70                  75                  80

Phe Thr Ile Ser Arg Asp Asn Ala Lys Asn Thr Ala Tyr Leu Gln Met
                 85                  90                  95

Asp Ser Leu Lys Pro Glu Asp Thr Ala Val Tyr Tyr Cys Ala Ala Gln
                100                 105                 110

Tyr Gly Asp Cys Leu Gly Asp Ile Ala Ala Arg Asp Leu Ile Cys Ala
                115                 120                 125

Gln Lys Phe Trp Gly Gln Gly Thr Gln Val Thr Val Ser Ser Gly Gly
            130                 135                 140

Gly Ser Gly Gly Gly Ser Gly Gly Ser Ala Tyr Pro Thr Leu Ser
145                 150                 155                 160

Glu Ile Lys Gly Val Ile Val His Arg Leu Glu Gly Val Ser Tyr Asn
                165                 170                 175

Ile Thr Gly Thr Asn Pro Val Phe Ala Gly Ala Asn Tyr Ala Ala Trp
            180                 185                 190

Ala Val Asn Val Ala Gln Val Ile Asp Ser Glu Thr His His His His
            195                 200                 205

His His His His His Thr Ala Ala
            210                 215

<210> SEQ ID NO 303
<211> LENGTH: 347
<212> TYPE: PRT
<213> ORGANISM: CoV-2
<220> FEATURE:
<223> OTHER INFORMATION: RDB - Mu - MD 2,3

<400> SEQUENCE: 303

Met Pro Asn Ile Thr Asn Leu Cys Pro Phe Gly Glu Val Phe Asn Ala
1 5 10 15

Thr Arg Phe Ala Ser Val Tyr Ala Trp Asn Arg Lys Arg Ile Ser Asn
20 25 30

Cys Val Ala Asp Tyr Ser Val Leu Tyr Asn Ser Ala Ser Phe Ser Thr
35 40 45

Phe Lys Cys Tyr Gly Val Ser Pro Thr Lys Leu Asn Asp Leu Cys Phe
50 55 60

Thr Asn Val Tyr Ala Asp Ser Phe Val Ile Arg Gly Asp Glu Val Arg
65 70 75 80

Gln Ile Ala Pro Gly Gln Thr Gly Lys Ile Ala Asp Tyr Asn Tyr Lys
85 90 95

Leu Pro Asp Asp Phe Thr Gly Cys Val Ile Ala Trp Asn Ser Asn Asn
100 105 110

Leu Asp Ser Lys Val Gly Gly Asn Tyr Asn Tyr Leu Tyr Arg Leu Phe
115 120 125

Arg Lys Ser Asn Leu Lys Pro Phe Glu Arg Asp Ile Ser Thr Glu Ile
130 135 140

Tyr Gln Ala Gly Ser Thr Pro Cys Asn Gly Val Glu Gly Phe Asn Cys
145 150 155 160

Tyr Phe Pro Leu Gln Ser Tyr Gly Phe Gln Pro Thr Asn Gly Val Gly
165 170 175

```
Tyr Gln Pro Tyr Arg Val Val Leu Ser Phe Glu Leu Leu His Ala
            180                 185                 190

Pro Gly Gly Gly Ser Gly Gly Gly Ser Gly Gly Gly Ser
        195                 200                 205

Met Asp Val Gln Leu Gln Ala Ser Gly Gly Ser Val Gln Ala Gly
        210                 215                 220

Gly Ser Leu Arg Leu Ser Cys Ala Ala Ser Gly Tyr Thr Ile Gly Pro
225                 230                 235                 240

Tyr Cys Met Gly Trp Phe Arg Gln Ala Pro Gly Lys Glu Arg Glu Gly
                245                 250                 255

Val Ala Leu Ser Glu Ile Lys Gly Val Ile Val His Arg Leu Glu Gly
            260                 265                 270

Val Arg Phe Thr Ile Ser Gln Asp Asn Ala Lys Asn Thr Val Tyr Leu
            275                 280                 285

Leu Met Asn Ser Leu Glu Pro Glu Asp Thr Ala Ile Tyr Tyr Cys Ala
        290                 295                 300

Ala Pro Val Phe Ala Gly Ala Asn Tyr Ala Ala Trp Ala Val Asn Val
305                 310                 315                 320

Ala Gln Val Ile Trp Gly Gln Gly Thr Gln Val Thr Val Ser Ser His
                325                 330                 335

His His His His His His His Thr Ala Ala
            340                 345

<210> SEQ ID NO 304
<211> LENGTH: 403
<212> TYPE: PRT
<213> ORGANISM: CoV-2
<220

```
Pro Gly Gly Gly Gly Ser Gly Gly Gly Ser Gly Gly Gly Ser
        195                 200                 205

Met Asp Val Gln Leu Gln Ala Ser Gly Gly Ser Val Gln Ala Gly
210                 215                 220

Gly Ser Leu Arg Leu Ser Cys Ala Ala Ser Gly Tyr Thr Ile Gly Pro
225                 230                 235                 240

Tyr Cys Met Gly Trp Phe Arg Gln Ala Pro Gly Lys Glu Arg Glu Gly
                245                 250                 255

Val Ala Ala Ile Asn Met Gly Gly Ile Thr Tyr Tyr Ala Asp Ser
            260                 265                 270

Val Lys Gly Arg Phe Thr Ile Ser Gln Asp Asn Ala Lys Asn Thr Val
        275                 280                 285

Tyr Leu Leu Met Asn Ser Leu Glu Pro Glu Asp Thr Ala Ile Tyr Tyr
        290                 295                 300

Cys Ala Ala Asp Ser Thr Ile Tyr Ala Ser Tyr Tyr Glu Cys Gly His
305                 310                 315                 320

Gly Leu Ser Thr Gly Gly Tyr Gly Tyr Asp Ser Trp Gly Gln Gly Thr
                325                 330                 335

Gln Val Thr Val Ser Ser Ala Tyr Pro Thr Leu Ser Glu Ile Lys Gly
            340                 345                 350

Val Ile Val His Arg Leu Glu Gly Val Ser Tyr Asn Ile Thr Gly Thr
        355                 360                 365

Asn Pro Val Phe Ala Gly Ala Asn Tyr Ala Ala Trp Ala Val Asn Val
        370                 375                 380

Ala Gln Val Ile Asp Ser Glu Thr His His His His His His
385                 390                 395                 400

Thr Ala Ala

<210> SEQ ID NO 305
<211> LENGTH: 344
<212> TYPE: PRT
<213> ORGANISM: CoV-2
<220> FEATURE:
<223> OTHER INFORMATION: RBD - Du - M

Tyr Gln Ala Gly Ser Thr Pro Cys Asn Gly Val Glu Gly Phe Asn Cys
145                 150                 155                 160

Tyr Phe Pro Leu Gln Ser Tyr Gly Phe Gln Pro Thr Asn Gly Val Gly
                165                 170                 175

Tyr Gln Pro Tyr Arg Val Val Val Leu Ser Phe Glu Leu Leu His Ala
            180                 185                 190

Pro Gly Gly Gly Ser Gly Gly Gly Ser Gly Gly Gly Gly Ser
            195                 200                 205

Met Gln Val Gln Leu Val Glu Ser Gly Gly Ser Val Gln Ala Gly
    210                 215                 220

Gly Ser Leu Arg Leu Ser Cys Ser Ala Ser Gly Tyr Thr Tyr Ile Ser
225                 230                 235                 240

Gly Trp Phe Arg Gln Ala Pro Gly Lys Glu Arg Glu Gly Val Ala Leu
                245                 250                 255

Ser Glu Ile Lys Gly Val Ile Val His Arg Leu Glu Gly Val Arg Phe
                260                 265                 270

Thr Ile Ser Gln Asp Asn Ala Lys Asn Thr Val Tyr Leu Gln Met Asn
            275                 280                 285

Ser Leu Lys Pro Glu Asp Thr Ala Met Tyr Tyr Cys Ala Ala Pro Val
290                 295                 300

Phe Ala Gly Ala Asn Tyr Ala Ala Trp Ala Val Asn Val Ala Gln Val
305                 310                 315                 320

Ile Trp Gly Gln Gly Thr Gln Val Thr Val Ser Ser His His His
                325                 330                 335

His His His His His Thr Ala Ala
            340

<210> SEQ ID NO 306
<211> LENGTH: 391
<212> TYPE: PRT
<213> ORGANISM: CoV-2
<220> FEATURE:
<223> OTHER INFORMATION: RBD - Du - MD

<400> SEQUENCE: 306

Met Pro Asn Ile Thr Asn Leu Cys Pro Phe Gly Glu Val Phe Asn Ala
1               5                   10                  15

Thr Arg Phe Ala Ser Val Tyr Ala Trp Asn Arg Lys Arg Ile Ser Asn
                20

-continued

```
Tyr Phe Pro Leu Gln Ser Tyr Gly Phe Gln Pro Thr Asn Gly Val Gly
                165                 170                 175

Tyr Gln Pro Tyr Arg Val Val Leu Ser Phe Glu Leu Leu His Ala
            180                 185                 190

Pro Gly Gly Gly Ser Gly Gly Gly Ser Gly Gly Gly Ser
        195                 200                 205

Met Gln Val Gln Leu Val Glu Ser Gly Gly Ser Val Gln Ala Gly
210                 215                 220

Gly Ser Leu Arg Leu Ser Cys Ser Ala Ser Tyr Thr Tyr Ile Ser
225                 230                 235                 240

Gly Trp Phe Arg Gln Ala Pro Gly Lys Glu Arg Glu Gly Val Ala Ala
                245                 250                 255

Ile Arg Ser Ser Asp Gly Thr Thr Tyr Tyr Ala Asp Ser Val Lys Gly
                260                 265                 270

Arg Phe Thr Ile Ser Gln Asp Asn Ala Lys Asn Thr Val Tyr Leu Gln
            275                 280                 285

Met Asn Ser Leu Lys Pro Glu Asp Thr Ala Met Tyr Tyr Cys Ala Ala
            290                 295                 300

Thr Glu Val Ala Gly Trp Pro Leu Asp Ile Gly Ile Tyr Asp Tyr Trp
305                 310                 315                 320

Gly Gln Gly Thr Gln Val Thr Val Ser Ser Ala Tyr Pro Thr Leu Ser
                325                 330                 335

Glu Ile Lys Gly Val Ile Val His Arg Leu Gly Val Ser Tyr Asn
            340                 345                 350

Ile Thr Gly Thr Asn Pro Val Phe Ala Gly Ala Asn Tyr Ala Ala Trp
            355                 360                 365

Ala Val Asn Val Ala Gln Val Ile Asp Ser Glu Thr His His His His
            370                 375                 380

His His His His Thr Ala Ala
385                 390

<210> SEQ ID NO 307
<211> LENGTH: 356
<212> TYPE: PRT
<213> ORGANISM: CoV-2
<220> FEATURE:
<223> OTHER INFORMATION: RBD - Vi - MD 2,3

<400> SEQUENCE: 307

Met Pro Asn Ile Thr Asn Leu Cys Pro Phe Gly Glu Val Phe Asn Ala
1               5                   10                  15

Thr Arg Phe Ala Ser Val Tyr Ala Trp Asn Arg Lys Arg Ile Ser Asn
            20                  25                  30

Cys Val Ala Asp Tyr Ser Val Leu Tyr As

```
Arg Lys Ser Asn Leu Lys Pro Phe Glu Arg Asp Ile Ser Thr Glu Ile
130                 135                 140

Tyr Gln Ala Gly Ser Thr Pro Cys Asn Gly Val Glu Gly Phe Asn Cys
145                 150                 155                 160

Tyr Phe Pro Leu Gln Ser Tyr Gly Phe Gln Pro Thr Asn Gly Val Gly
                165                 170                 175

Tyr Gln Pro Tyr Arg Val Val Val Leu Ser Phe Glu Leu Leu His Ala
            180                 185                 190

Pro Gly Gly Gly Ser Gly Gly Gly Ser Gly Gly Gly Ser
        195                 200                 205

Met Gln Val Gln Leu Val Glu Ser Gly Gly Ser Val Gln Ala Gly
210                 215                 220

Gly Ser Leu Arg Leu Ser Cys Ala Ala Ser Gly Tyr Thr Phe Ser Ser
225                 230                 235                 240

Tyr Pro Met Gly Trp Tyr Arg Gln Ala Pro Gly Lys Glu Cys Glu Leu
                245                 250                 255

Val Ser Leu Ser Glu Ile Lys Gly Val Ile Val His Arg Leu Glu Gly
            260                 265                 270

Val Ala Asn Tyr Ala Gly Ser Val Lys Gly Arg Phe Thr Ile Ser Arg
            275                 280                 285

Asp Asn Ala Lys Asn Thr Ala Tyr Leu Gln Met Asp Ser Leu Lys Pro
290                 295                 300

Glu Asp Thr Ala Val Tyr Tyr Cys Ala Ala Pro Val Phe Ala Gly Ala
305                 310                 315                 320

Asn Tyr Ala Ala Trp Ala Val Asn Val Ala Gln Val Ile Trp Gly Gln
                325                 330                 335

Gly Thr Gln Val Thr Val Ser Ser His His His His His His His
            340                 345                 350

His Thr Ala Ala
        355

<210> SEQ ID NO 308
<211> LENGTH: 396
<212> TYPE: PRT
<213> ORGANISM: CoV-2
<220> FEATURE:
<223> OTHER INFORMATION: RBD - Vi - MD

<400> SEQUENCE: 308

Met Pro Asn Ile Thr Asn Leu Cys Pro Phe Gly Gl

-continued

```
Arg Lys Ser Asn Leu Lys Pro Phe Glu Arg Asp Ile Ser Thr Glu Ile
130                 135                 140

Tyr Gln Ala Gly Ser Thr Pro Cys Asn Gly Val Glu Gly Phe Asn Cys
145                 150                 155                 160

Tyr Phe Pro Leu Gln Ser Tyr Gly Phe Gln Pro Thr Asn Gly Val Gly
                165                 170                 175

Tyr Gln Pro Tyr Arg Val Val Val Leu Ser Phe Glu Leu Leu His Ala
            180                 185                 190

Pro Gly Gly Gly Ser Gly Gly Gly Ser Gly Gly Gly Ser
            195                 200                 205

Gln Val Gln Leu Val Glu Ser Gly Gly Ser Val Gln Ala Gly Gly
210                 215                 220

Ser Leu Arg Leu Ser Cys Ala Ala Ser Gly Tyr Thr Phe Ser Ser Tyr
225                 230                 235                 240

Pro Met Gly Trp Tyr Arg Gln Ala Pro Gly Lys Cys Glu Leu Val
                245                 250                 255

Ser Arg Ile Phe Ser Asp Gly Ser Ala Asn Tyr Ala Gly Ser Val Lys
            260                 265                 270

Gly Arg Phe Thr Ile Ser Arg Asp Asn Ala Lys Asn Thr Ala Tyr Leu
        275                 280                 285

Gln Met Asp Ser Leu Lys Pro Glu Asp Thr Ala Val Tyr Tyr Cys Ala
290                 295                 300

Ala Gly Pro Gly Ser Gly Lys Leu Val Val Ala Gly Arg Thr Cys Tyr
305                 310                 315                 320

Gly Pro Asn Tyr Trp Gly Gln Gly Thr Gln Val Thr Val Ser Ser Ala
                325                 330                 335

Tyr Pro Thr Leu Ser Glu Ile Lys Gly Val Ile Val His Arg Leu Glu
            340                 345                 350

Gly Val Ser Tyr Asn Ile Thr Gly Thr Asn Pro Val Phe Ala Gly Ala
        355                 360                 365

Asn Tyr Ala Ala Trp Ala Val Asn Val Ala Gln Val Ile Asp Ser Glu
370                 375                 380

Thr His His His His His His His Thr Ala Ala
385                 390                 395
```

<210> SEQ ID NO 309
<211> LENGTH: 605
<212> TYPE: PRT
<213> ORGANISM: CoV-2
<220> FEATURE:
<223> OTHER INFORMATION: RBD - OVA

<400> SEQUENCE: 309

```
Met Pro Asn Ile Thr Asn Leu Cys Pro Phe Gly Glu Val Phe Asn Ala
1               5                   10                  15

Thr Arg Phe

-continued

Leu Pro Asp Asp Phe Thr Gly Cys Val Ile Ala Trp Asn Ser Asn Asn
            100                 105                 110

Leu Asp Ser Lys Val Gly Gly Asn Tyr Asn Tyr Leu Tyr Arg Leu Phe
            115                 120                 125

Arg Lys Ser Asn Leu Lys Pro Phe Glu Arg Asp Ile Ser Thr Glu Ile
            130                 135                 140

Tyr Gln Ala Gly Ser Thr Pro Cys Asn Gly Val Glu Gly Phe Asn Cys
145                 150                 155                 160

Tyr Phe Pro Leu Gln Ser Tyr Gly Phe Gln Pro Thr Asn Gly Val Gly
            165                 170                 175

Tyr Gln Pro Tyr Arg Val Val Leu Ser Phe Glu Leu Leu His Ala
            180                 185                 190

Pro Gly Gly Gly Ser Gly Gly Gly Ser Gly Gly Gly Ser
            195                 200                 205

Met Gly Ser Ile Gly Ala Ala Ser Met Glu Phe Cys Phe Asp Val Phe
            210                 215                 220

Lys Glu Leu Lys Val His His Ala Asn Glu Thr Ile Phe Tyr Cys Pro
225                 230                 235                 240

Ile Ala Ile Met Ser Ala Leu Ala Met Val Tyr Leu Gly Ala Lys Asp
            245                 250                 255

Ser Thr Arg Thr Gln Ile Asn Lys Val Val Arg Phe Asp Lys Leu Pro
            260                 265                 270

Gly Phe Gly Asp Ser Ile Glu Ala Gln Cys Gly Thr Ser Val Asn Val
            275                 280                 285

His Ser Ser Leu Arg Asp Ile Leu Asn Gln Ile Thr Lys Pro Asn Asp
290                 295                 300

Val Tyr Ser Phe Ser Leu Ala Ser Arg Leu Tyr Ala Glu Glu Arg Tyr
305                 310                 315                 320

Pro Ile Leu Pro Glu Tyr Leu Gln Cys Val Lys Glu Leu Tyr Arg Gly
            325                 330                 335

Gly Leu Glu Pro Ile Asn Phe Gln Thr Ala Ala Asp Gln Ala Arg Glu
            340                 345                 350

Leu Ile Asn Ser Trp Val Glu Ser Gln Thr Asn Gly Ile Ile Arg Asn
            355                 360                 365

Val Leu Gln Pro Ser Ser Val Asp Ser Gln Thr Ala Met Val Leu Val
            370                 375                 380

Asn Ala Ile Val Phe Lys Gly Leu Trp Glu Lys Ala Phe Lys Asp Glu
385                 390                 395                 400

Asp Thr Gln Ala Met Pro Phe Arg Val Thr Glu Gln Glu Ser Lys Pro
            405                 410                 415

Val Gln Met Met Tyr Gln Ile Gly Leu Phe Arg Val Ala Ser Met Ala
            420                 425                 430

Ser Glu Lys Met Lys Ile Leu Glu Leu Pro Phe Ala Ser Gly Thr Met
            435                 440                 445

Ser Met Leu Val Leu Leu Pro Asp Glu Val Ser Gly Leu Glu Gln Leu
450                 455                 460

Glu Ser Ile Ile Asn Phe Glu Lys Leu Thr Glu Trp Thr Ser Ser Asn
465                 470                 475                 480

Val Met Glu Glu Arg Lys Ile Lys Val Tyr Leu Pro Arg Met Lys Met
            485                 490                 495

Glu Glu Lys Tyr Asn Leu Thr Phe Val Leu Met Ala Met Gly Ile Thr
            500                 505                 510

Asp Val Phe Ser Ser Ser Ala Asn Leu Ser Gly Ile Ser Ser Ala Glu

```
        515                 520                 525

Ser Leu Lys Ile Ser Gln Ala Val His Ala Ala His Ala Glu Ile Asn
    530                 535                 540

Glu Ala Asp Arg Glu Val Val Gly Ser Ala Glu Ala Gly Val Asp Ala
545                 550                 555                 560

Ala Ser Val Ser Glu Glu Phe Arg Ala Asp His Pro Phe Leu Phe Cys
                565                 570                 575

Ile Lys His Ile Ala Thr Asn Ala Val Leu Phe Phe Gly Arg Cys Val
            580                 585                 590

Ser Pro His His His His His His His His Thr Ala Ala
        595                 600                 605

<210> SEQ ID NO 310
<211> LENGTH: 22
<212> TYPE: PRT
<213> ORGANISM: CoV-1
<220> FEATURE:
<223> OTHER INFORMATION: FP1 - CoV-1

<400> SEQUENCE: 310

Ser Phe Ile Glu Asp Leu Leu Phe Asn Lys Val Thr Leu Ala Asp Ala
1               5                   10                  15

Gly Phe Met Lys Gln Tyr
            20

<210> SEQ ID NO 311
<211> LENGTH: 22
<212> TYPE: PRT
<213> ORGANISM: CoV-1
<220> FEATURE:
<223> OTHER INFORMATION: FP1A - CoV-1

<400> SEQUENCE: 311

Ser Phe Ile Glu Asp Ala Ala Ala Asn Lys Val Thr Leu Ala Asp Ala
1               5                   10                  15

Gly Phe Met Lys Gln Tyr
            20

<210> SEQ ID NO 312
<211> LENGTH: 21
<212> TYPE: PRT
<213> ORGANISM: CoV-1
<220> FEATURE:
<223> OTHER INFORMATION: FP2

<400> SEQUENCE: 312

Lys Gln Tyr Gly Glu Cys Leu Gly Asp Ile Asn Ala Arg Asp Leu Ile
1               5                   10                  15

Cys Ala Gln Lys Phe
            20

<210> SEQ ID NO 313
<211> LENGTH: 244
<212> TYPE: PRT
<213> ORGANISM: CoV-2
<220> FEATURE:
<223> OTHER INFORMATION: GFP

<400> SEQUENCE: 313

Met Gly Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
```

```
            20                  25                  30
Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
            130                 135                 140

Tyr Asn Ser His Asn Val Tyr Ile Thr Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
            195                 200                 205

Lys Asp Pro Asn Glu Lys Arg Asp His Met Val Leu Leu Glu Phe Val
            210                 215                 220

Thr Ala Ala Gly Ile Thr His Gly Met Asp Glu Leu Tyr Lys His His
225                 230                 235                 240

His His His His

<210> SEQ ID NO 314
<211> LENGTH: 9
<212> TYPE: PRT
<213> ORGANISM: Cov-2
<220> FEATURE:
<223> OTHER INFORMATION: ORF A1.01_61

<400> SEQUENCE: 314

Tyr Thr Glu Arg Ser Glu Lys Ser Tyr
1               5

<210> SEQ ID NO 315
<211> LENGTH: 9
<212> TYPE: PRT
<213> ORGANISM: Cov-2
<220> FEATURE:
<223> OTHER INFORMATION: ORF A1.01_41

<400> SEQUENCE: 315

Phe Ile Asp Thr Lys Arg Gly Val Tyr
1               5

<210> SEQ ID NO 316
<211> LENGTH: 9
<212> TYPE: PRT
<213> ORGANISM: Cov-2
<220> FEATURE:
<223> OTHER INFORMATION: ORF A1.01_433

<400> SEQUENCE: 316
```

```
Leu Thr Asn Ile Phe Gly Thr Val Tyr
1               5

<210> SEQ ID NO 317
<211> LENGTH: 9
<212> TYPE: PRT
<213> ORGANISM: Cov-2
<220> FEATURE:
<223> OTHER INFORMATION: ORF A1.01_388

<400> SEQUENCE: 317

Thr Ile Leu Asp Gly Ile Ser Gln Tyr
1               5

<210> SEQ ID NO 318
<211> LENGTH: 9
<212> TYPE: PRT
<213> ORGANISM: Cov-2
<220> FEATURE:
<223> OTHER INFORMATION: ORF A1.01_529

<400> SEQUENCE: 318

Phe Val Thr His Ser Lys Gly Leu Tyr
1               5

<210> SEQ ID NO 319
<211> LENGTH: 9
<212> TYPE: PRT
<213> ORGANISM: Cov-2
<220> FEATURE:
<223> OTHER INFORMATION: ORF A2.01_265

<400> SEQUENCE: 319

Gly Leu Asn Asp Asn Leu Leu Glu Ile
1               5

<210> SEQ ID NO 320
<211> LENGTH: 9
<212> TYPE: PRT
<213> ORGANISM: Cov-2
<220> FEATURE:
<223> OTHER INFORMATION: ORF A2.01_420

<400> SEQUENCE: 320

Tyr Ile Thr Gly Gly Val Val Gln Leu
1               5

<210> SEQ ID NO 321
<211> LENGTH: 9
<212> TYPE: PRT
<213> ORGANISM: Cov-2
<220> FEATURE:
<223> OTHER INFORMATION: ORF A2.01_288

<400> SEQUENCE: 321

Lys Leu Asn Glu Glu Ile Ala Ile Ile
1               5

<210> SEQ ID NO 322
<211> LENGTH: 9
<212> TYPE: PRT
<213> ORGANISM: Cov-2
<220> FEATURE:
<223> OTHER INFORMATION: ORF A2.01_500

<400> SEQUENCE: 322

Lys Leu Val Asn Lys Phe Leu Ala Leu
```

```
                              1               5

<210> SEQ ID NO 323
<211> LENGTH: 9
<212> TYPE: PRT
<213> ORGANISM: Cov-2
<220> FEATURE:
<223> OTHER INFORMATION: ORF A2.01_439

<400> SEQUENCE: 323

Thr Val Tyr Glu Lys Leu Lys Pro Val
1               5

<210> SEQ ID NO 324
<211> LENGTH: 9
<212> TYPE: PRT
<213> ORGANISM: Cov-2
<220> FEATURE:
<223> OTHER INFORMATION: ORF A2.01_34

<400> SEQUENCE: 324

Thr Leu Ser Glu Gln Leu Asp Phe Ile
1               5

<210> SEQ ID NO 325
<211> LENGTH: 9
<212> TYPE: PRT
<213> ORGANISM: Cov-2
<220> FEATURE:
<223> OTHER INFORMATION: ORF A2.01_443

<400> SEQUENCE: 325

Lys Leu Lys Pro Val Leu Asp Trp Leu
1               5

<210> SEQ ID NO 326
<211> LENGTH: 9
<212> TYPE: PRT
<213> ORGANISM: Cov-2
<220> FEATURE:
<223> OTHER INFORMATION: ORF A2.01_461

<400> SEQUENCE: 326

Phe Leu Arg Asp Gly Trp Glu Ile Val
1               5

<210> SEQ ID NO 327
<211> LENGTH: 9
<212> TYPE: PRT
<213> ORGANISM: Cov-2
<220> FEATURE:
<223> OTHER INFORMATION: ORF A2.01_522

<400> SEQUENCE: 327

Ala Leu Asn Leu Gly Glu Thr Phe Val
1               5

<210> SEQ ID NO 328
<211> LENGTH: 9
<212> TYPE: PRT
<213> ORGANISM: Cov-2
<220> FEATURE:
<223> OTHER INFORMATION: ORF A2.01_349

<400> SEQUENCE: 328

Ile Leu Ser Pro Leu Tyr Ala Phe Ala
1               5
```

<210> SEQ ID NO 329
<211> LENGTH: 9
<212> TYPE: PRT
<213> ORGANISM: Cov-2
<220> FEATURE:
<223> OTHER INFORMATION: ORF A2.01_399

<400> SEQUENCE: 329

Arg Leu Ile Asp Ala Met Met Phe Thr
1               5

<210> SEQ ID NO 330
<211> LENGTH: 9
<212> TYPE: PRT
<213> ORGANISM: Cov-2
<220> FEATURE:
<223> OTHER INFORMATION: ORF A3.01_102

<400> SEQUENCE: 330

Lys Thr Ile Gln Pro Arg Val Glu Lys
1               5

<210> SEQ ID NO 331
<211> LENGTH: 9
<212> TYPE: PRT
<213> ORGANISM: Cov-2
<220> FEATURE:
<223> OTHER INFORMATION: ORF A3.01_628

<400> SEQUENCE: 331

Val Thr Asn Asn Thr Phe Thr Leu Lys
1               5

<210> SEQ ID NO 332
<211> LENGTH: 9
<212> TYPE: PRT
<213> ORGANISM: Cov-2
<220> FEATURE:
<223> OTHER INFORMATION: ORF A3.01_496

<400> SEQUENCE: 332

Gln Thr Phe Phe Lys Leu Val Asn Lys
1               5

<210> SEQ ID NO 333
<211> LENGTH: 9
<212> TYPE: PRT
<213> ORGANISM: Cov-2
<220> FEATURE:
<223> OTHER INFORMATION: ORF A3.01_549

<400> SEQUENCE: 333

Leu Leu Met Pro Leu Lys Ala Pro Lys
1               5

<210> SEQ ID NO 334
<211> LENGTH: 9
<212> TYPE: PRT
<213> ORGANISM: Cov-2
<220> FEATURE:
<223> OTHER INFORMATION: ORF A3.01_330

<400> SEQUENCE: 334

Lys Val Thr Lys Gly Lys Ala Lys Lys
1               5

<210> SEQ ID NO 335
<211> LENGTH: 9
<212> TYPE: PRT
<213> ORGANISM: Cov-2
<220> FEATURE:
<223> OTHER INFORMATION: ORF A3.01_362

<400> SEQUENCE: 335

Arg Val Val Arg Ser Ile Phe Ser Arg
1               5

<210> SEQ ID NO 336
<211> LENGTH: 9
<212> TYPE: PRT
<213> ORGANISM: Cov-2
<220> FEATURE:
<223> OTHER INFORMATION: ORF A3.01_513

<400> SEQUENCE: 336

Ile Ile Ile Gly Gly Ala Lys Leu Lys
1               5

<210> SEQ ID NO 337
<211> LENGTH: 9
<212> TYPE: PRT
<213> ORGANISM: Cov-2
<220> FEATURE:
<223> OTHER INFORMATION: ORF A3.01_103

<400> SEQUENCE: 337

Thr Ile Gln Pro Arg Val Glu Lys Lys
1               5

<210> SEQ ID NO 338
<211> LENGTH: 9
<212> TYPE: PRT
<213> ORGANISM: Cov-2
<220> FEATURE:
<223> OTHER INFORMATION: ORF A3.01_530

<400> SEQUENCE: 338

Val Thr His Ser Lys Gly Leu Tyr Arg
1               5

<210> SEQ ID NO 339
<211> LENGTH: 9
<212> TYPE: PRT
<213> ORGANISM: Cov-2
<220> FEATURE:
<223> OTHER INFORMATION: ORF A3.01_435

<400> SEQUENCE: 339

Asn Ile Phe Gly Thr Val Tyr Glu Lys
1               5

<210> SEQ ID NO 340
<211> LENGTH: 9
<212> TYPE: PRT
<213> ORGANISM: Cov-2
<220> FEATURE:
<223> OTHER INFORMATION: ORF A3.01_571

<400> SEQUENCE: 340

Val Leu Thr Glu Glu Val Val Leu Lys
1               5

<210> SEQ ID NO 341
<211> LENGTH: 9
<212> TYPE: PRT
<213> ORGANISM: Cov-2
<220> FEATURE:
<223> OTHER INFORMATION: ORF A24.02_497

<400> SEQUENCE: 341

Thr Phe Phe Lys Leu Val Asn Lys Phe
1 5

<210> SEQ ID NO 342
<211> LENGTH: 9
<212> TYPE: PRT
<213> ORGANISM: Cov-2
<220> FEATURE:
<223> OTHER INFORMATION: ORF A24.02_436

<400> SEQUENCE: 342

Ile Phe Gly Thr Val Tyr Glu Lys Leu
1 5

<210> SEQ ID NO 343
<211> LENGTH: 9
<212> TYPE: PRT
<213> ORGANISM: Cov-2
<220> FEATURE:
<223> OTHER INFORMATION: ORF A24.02_440

<400> SEQUENCE: 343

Val Tyr Glu Lys Leu Lys Pro Val Leu
1 5

<210> SEQ ID NO 344
<211> LENGTH: 9
<212> TYPE: PRT
<213> ORGANISM: Cov-2
<220> FEATURE:
<223> OTHER INFORMATION: ORF A24.02_299

<400> SEQUENCE: 344

Ser Phe Ser Ala Ser Thr Ser Ala Phe
1 5

<210> SEQ ID NO 345
<211> LENGTH: 9
<212> TYPE: PRT
<213> ORGANISM: Cov-2
<220> FEATURE:
<223> OTHER INFORMATION: ORF A24.02_85

<400> SEQUENCE: 345

Thr Phe Asn Gly Glu Cys Pro Asn Phe
1 5

<210> SEQ ID NO 346
<211> LENGTH: 9
<212> TYPE: PRT
<213> ORGANISM: Cov-2
<220> FEATURE:
<223> OTHER INFORMATION: ORF A24.02_78

<400> SEQUENCE: 346

Lys Leu Ala Lys Lys Phe Asp Thr Phe
1 5

<210> SEQ ID NO 347

```
<211> LENGTH: 9
<212> TYPE: PRT
<213> ORGANISM: Cov-2
<220> FEATURE:
<223> OTHER INFORMATION: ORF A24.02

```
<212> TYPE: PRT
<213> ORGANISM: Cov-2
<220> FEATURE:
<223> OTHER INFORMATION: ORF A26.01_373

<400> SEQUENCE: 353

Glu Thr Ala Gln Asn Ser Val Arg Val
1               5

<210> SEQ ID NO 354
<211> LENGTH: 9
<212> TYPE: PRT
<213> ORGANISM: Cov-2
<220> FEATURE:
<223> OTHER INFORMATION: ORF A26.01_493

<400> SEQUENCE: 354

Glu Ser Val Gln Thr Phe Phe Lys Leu
1               5

<210> SEQ ID NO 355
<211> LENGTH: 9
<212> TYPE: PRT
<213> ORGANISM: Cov-2
<220> FEATURE:
<223> OTHER INFORMATION: ORF A26.01_348

<400> SEQUENCE: 355

Ser Ile Leu Ser Pro Leu Tyr Ala Phe
1               5

<210> SEQ ID NO 356
<211> LENGTH: 9
<212> TYPE: PRT
<213> ORGANISM: Cov-2
<220> FEATURE:
<223> OTHER INFORMATION: ORF A26.01_2

<400> SEQUENCE: 356

Tyr Thr Arg Tyr Val Asp Asn Asn Phe
1               5

<210> SEQ ID NO 357
<211> LENGTH: 9
<212> TYPE: PRT
<213> ORGANISM: Cov-2
<220> FEATURE:
<223> OTHER INFORMATION: ORF B7.02_105

<400> SEQUENCE: 357

Gln Pro Arg Val Glu Lys Lys Lys Leu
1               5

<210> SEQ ID NO 358
<211> LENGTH: 9
<212> TYPE: PRT
<213> ORGANISM: Cov-2
<220> FEATURE:
<223> OTHER INFORMATION: ORF B7.02_551

<400> SEQUENCE: 358

Met Pro Leu Lys Ala Pro Lys Glu Ile
1               5

<210> SEQ ID NO 359
<211> LENGTH: 9
<212> TYPE: PRT
```

<213> ORGANISM: Cov-2
<220> FEATURE:
<223> OTHER INFORMATION: ORF B8.01_517

<400> SEQUENCE: 359

Gly Ala Lys Leu Lys Ala Leu Asn Leu
1               5

<210> SEQ ID NO 360
<211> LENGTH: 9
<212> TYPE: PRT
<213> ORGANISM: Cov-2
<220> FEATURE:
<223> OTHER INFORMATION: ORF B8.01_500

<400> SEQUENCE: 360

Lys Leu Val Asn Lys Phe Leu Ala Leu
1               5

<210> SEQ ID NO 361
<211> LENGTH: 9
<212> TYPE: PRT
<213> ORGANISM: Cov-2
<220> FEATURE:
<223> OTHER INFORMATION: ORF B8.01_490

<400> SEQUENCE: 361

Glu Ile Lys Glu Ser Val Gln Thr Phe
1               5

<210> SEQ ID NO 362
<211> LENGTH: 9
<212> TYPE: PRT
<213> ORGANISM: Cov-2
<220> FEATURE:
<223> OTHER INFORMATION: ORF B8.01_63

<400> SEQUENCE: 362

Glu Arg Ser Glu Lys Ser Tyr Glu Leu
1               5

<210> SEQ ID NO 363
<211> LENGTH: 9
<212> TYPE: PRT
<213> ORGANISM: Cov-2
<220> FEATURE:
<223> OTHER INFORMATION: ORF B8.01_105

<400> SEQUENCE: 363

Gln Pro Arg Val Glu Lys Lys Lys Leu
1               5

<210> SEQ ID NO 364
<211> LENGTH: 9
<212> TYPE: PRT
<213> ORGANISM: Cov-2
<220> FEATURE:
<223> OTHER INFORMATION: ORF B8.01_439

<400> SEQUENCE: 364

Thr Val Tyr Glu Lys Leu Lys Pro Val
1               5

<210> SEQ ID NO 365
<211> LENGTH: 9
<212> TYPE: PRT
<213> ORGANISM: Cov-2

```
<220> FEATURE:
<223> OTHER INFORMATION: ORF B8.01_345

<400> SEQUENCE: 365

Glu Gln Lys Ser Ile Leu Ser Pro Leu
1               5

<210> SEQ ID NO 366
<211> LENGTH: 9
<212> TYPE: PRT
<213> ORGANISM: Cov-2
<220> FEATURE:
<223> OTHER INFORMATION: ORF B27.05_364

<400> SEQUENCE: 366

Val Arg Ser Ile Phe Ser Arg Thr Leu
1               5

<210> SEQ ID NO 367
<211> LENGTH: 9
<212> TYPE: PRT
<213> ORGANISM: Cov-2
<220> FEATURE:
<223> OTHER INFORMATION: ORF B27.05_543

<400> SEQUENCE: 367

Ser Arg Glu Glu Thr Gly Leu Leu Met
1               5

<210> SEQ ID NO 368
<211> LENGTH: 9
<212> TYPE: PRT
<213> ORGANISM: Cov-2
<220> FEATURE:
<223> OTHER INFORMATION: ORF B27.05_398

<400> SEQUENCE: 368

Leu Arg Leu Ile Asp Ala Met Met Phe
1               5

<210> SEQ ID NO 369
<211> LENGTH: 9
<212> TYPE: PRT
<213> ORGANISM: Cov-2
<220> FEATURE:
<223> OTHER INFORMATION: ORF B27.05_118

<400> SEQUENCE: 369

Gly Arg Ile Arg Ser Val Tyr Pro Val
1               5

<210> SEQ ID NO 370
<211> LENGTH: 9
<212> TYPE: PRT
<213> ORGANISM: Cov-2
<220> FEATURE:
<223> OTHER INFORMATION: ORF B40.01_196

<400> SEQUENCE: 370

Ser Glu Val Gly Pro Glu His Ser Leu
1               5

<210> SEQ ID NO 371
<211> LENGTH: 9
<212> TYPE: PRT
<213> ORGANISM: Cov-2
<220> FEATURE:
```

```
<223> OTHER INFORMATION: ORF B40.01_564

<400> SEQUENCE: 371

Gly Glu Thr Leu Pro Thr Glu Val Leu
1

<400> SEQUENCE: 377

Ser Glu Ala Val Glu Ala Pro Leu Val
1               5

<210> SEQ ID NO 378
<211> LENGTH: 9
<212> TYPE: PRT
<213> ORGANISM: Cov-2
<220> FEATURE:
<223> OTHER INFORMATION: ORF B40.01_545

<400> SEQUENCE: 378

Glu Glu Thr Gly Leu Leu Met Pro Leu
1               5

<210> SEQ ID NO 379
<211> LENGTH: 9
<212> TYPE: PRT
<213> ORGANISM: Cov-2
<220> FEATURE:
<223> OTHER INFORMATION: ORF B40.01_569

<400> SEQUENCE: 379

Thr Glu Val Leu Thr Glu Glu Val Val
1               5

<210> SEQ ID NO 380
<211> LENGTH: 9
<212> TYPE: PRT
<213> ORGANISM: Cov-2
<220> FEATURE:
<223> OTHER INFORMATION: ORF B40.01_52

<400> SEQUENCE: 380

Arg Glu His Glu His Glu Ile Ala Trp
1               5

<210> SEQ ID NO 381
<211> LENGTH: 9
<212> TYPE: PRT
<213> ORGANISM: Cov-2
<220> FEATURE:
<223> OTHER INFORMATION: ORF B40.01_75

<400> SEQUENCE: 381

Phe Glu Ile Lys Leu Ala Lys Lys Phe
1               5

<210> SEQ ID NO 382
<211> LENGTH: 9
<212> TYPE: PRT
<213> ORGANISM: Cov-2
<220> FEATURE:
<223> OTHER INFORMATION: ORF B40.01_161

<400> SEQUENCE: 382

Cys Glu Phe Cys Gly Thr Glu Asn Leu
1               5

<210> SEQ ID NO 383
<211> LENGTH: 9
<212> TYPE: PRT
<213> ORGANISM: Cov-2
<220> FEATURE:
<223> OTHER INFORMATION: ORF B40.01_271

```
<400> SEQUENCE: 383

Leu Glu Ile Leu Gln Lys Glu Lys Val
1               5

<210> SEQ ID NO 384
<211> LENGTH: 9
<212> TYPE: PRT
<213> ORGANISM: Cov-2
<220> FEATURE:
<223> OTHER INFORMATION: ORF B58.01_521

<400> SEQUENCE: 384

Lys Ala Leu Asn Leu Gly Glu Thr Phe
1               5

<210> SEQ ID NO 385
<211> LENGTH: 9
<212> TYPE: PRT
<213> ORGANISM: Cov-2
<220> FEATURE:
<223> OTHER INFORMATION: ORF B58.01_424

<400> SEQUENCE: 385

Gly Val Val Gln Leu Thr Ser Gln Trp
1               5

<210> SEQ ID NO 386
<211> LENGTH: 9
<212> TYPE: PRT
<213> ORGANISM: Cov-2
<220> FEATURE:
<223> OTHER INFORMATION: ORF B58.01_67

<400> SEQUENCE: 386

Lys Ser Tyr Glu Leu Gln Thr Pro Phe
1               5

<210> SEQ ID NO 387
<211> LENGTH: 9
<212> TYPE: PRT
<213> ORGANISM: Cov-2
<220> FEATURE:
<223> OTHER INFORMATION: ORF B15.01_388

<400> SEQUENCE: 387

Thr Ile Leu Asp Gly Ile Ser Gln Tyr
1               5

<210> SEQ ID NO 388
<211> LENGTH: 9
<212> TYPE: PRT
<213> ORGANISM: Cov-2
<220> FEATURE:
<223> OTHER INFORMATION: ORF B15.01_78

<400> SEQUENCE: 388

Lys Leu Ala Lys Lys Phe Asp Thr Phe
1               5

<210> SEQ ID NO 389
<211> LENGTH: 9
<212> TYPE: PRT
<213> ORGANISM: Cov-2
<220> FEATURE:
<223> OTHER INFORMATION: ORF B15.01_382

<400> SEQUENCE: 389
```

Leu Gln Lys Ala Ala Ile Thr Ile Leu
1               5

<210> SEQ ID NO 390
<211> LENGTH: 9
<212> TYPE: PRT
<213> ORGANISM: Cov-2
<220> FEATURE:
<223> OTHER INFORMATION: ORF B15.01_67

<400> SEQUENCE: 390

Lys Ser Tyr Glu Leu Gln Thr Pro Phe
1               5

<210> SEQ ID NO 391
<211> LENGTH: 9
<212> TYPE: PRT
<213> ORGANISM: Cov-2
<220> FEATURE:
<223> OTHER INFORMATION: ORF B15.01_116

<400> SEQUENCE: 391

Phe Met Gly Arg Ile Arg Ser Val Tyr
1               5

<210> SEQ ID NO 392
<211> LENGTH: 9
<212> TYPE: PRT
<213> ORGANISM: Cov-2
<220> FEATURE:
<223> OTHER INFORMATION: ORF B15.01_490

<400> SEQUENCE: 392

Glu Ile Lys Glu Ser Val Gln Thr Phe
1               5

<210> SEQ ID NO 393
<211> LENGTH: 9
<212> TYPE: PRT
<213> ORGANISM: Cov-2
<220> FEATURE:
<223> OTHER INFORMATION: ORF B15.01_433

<400> SEQUENCE: 393

Leu Thr Asn Ile Phe Gly Thr Val Tyr
1               5

<210> SEQ ID NO 394
<211> LENGTH: 9
<212> TYPE: PRT
<213> ORGANISM: Cov-2
<220> FEATURE:
<223> OTHER INFORMATION: ORF B15.01_348

<400> SEQUENCE: 394

Ser Ile Leu Ser Pro Leu Tyr Ala Phe
1               5

<210> SEQ ID NO 395
<211> LENGTH: 9
<212> TYPE: PRT
<213> ORGANISM: Cov-2
<220> FEATURE:
<223> OTHER INFORMATION: ORF B15.01_181

<400> SEQUENCE: 395

```
Pro Gln Asn Ala Val Val Lys Ile Tyr
1               5
```

<210> SEQ ID NO 396
<211> LENGTH: 9
<212> TYPE: PRT
<213> ORGANISM: CoV-2
<220> FEATURE:
<223> OTHER INFORMATION: RDRP A1.01_450

<400> SEQUENCE: 396

```
Ile Ser Asp Tyr Asp Tyr Tyr Arg Tyr
1               5
```

<210> SEQ ID NO 397
<211> LENGTH: 9
<212> TYPE: PRT
<213> ORGANISM: CoV-2
<220> FEATURE:
<223> OTHER INFORMATION: RDRP A1.01_738

<400> SEQUENCE: 397

```
Asp Thr Asp Phe Val Asn Glu Phe Tyr
1               5
```

<210> SEQ ID NO 398
<211> LENGTH: 9
<212> TYPE: PRT
<213> ORGANISM: CoV-2
<220> FEATURE:
<223> OTHER INFORMATION: RDRP A1.01_907

<400> SEQUENCE: 398

```
Leu Thr Asn Asp Asn Thr Ser Arg Tyr
1               5
```

<210> SEQ ID NO 399
<211> LENGTH: 9
<212> TYPE: PRT
<213> ORGANISM: CoV-2
<220> FEATURE:
<223> OTHER INFORMATION: RDRP A1.01_475

<400> SEQUENCE: 399

```
Val Val Asp Lys Tyr Phe Asp Cys Tyr
1               5
```

<210> SEQ ID NO 400
<211> LENGTH: 9
<212> TYPE: PRT
<213> ORGANISM: CoV-2
<220> FEATURE:
<223> OTHER INFORMATION: RDRP A1.01_681

<400> SEQUENCE: 400

```
Ser Ser Gly Asp Ala Thr Thr Ala Tyr
1               5
```

<210> SEQ ID NO 401
<211> LENGTH: 9
<212> TYPE: PRT
<213> ORGANISM: CoV-2
<220> FEATURE:
<223> OTHER INFORMATION: RDRP A1.01_895

<400> SEQUENCE: 401

```
Leu Thr Gly His Met Leu Asp Met Tyr
```

```
1               5

<210> SEQ ID NO 402
<211> LENGTH: 9
<212> TYPE: PRT
<213> ORGANISM: CoV-2
<220> FEATURE:
<223> OTHER INFORMATION: RDRP A1.01_869

<400> SEQUENCE: 402

Leu Thr Lys His Pro Asn Gln Glu Tyr
1               5

<210> SEQ ID NO 403
<211> LENGTH: 9
<212> TYPE: PRT
<213> ORGANISM: CoV-2
<220> FEATURE:
<223> OTHER INFORMATION: RDRP A1.01_366

<400> SEQUENCE: 403

Leu Ser Phe Lys Glu Leu Leu Val Tyr
1               5

<210> SEQ ID NO 404
<211> LENGTH: 9
<212> TYPE: PRT
<213> ORGANISM: CoV-2
<220> FEATURE:
<223> OTHER INFORMATION: RDRP A1.01_758

<400> SEQUENCE: 404

Leu Ser Asp Asp Ala Val Val Cys Phe
1               5

<210> SEQ ID NO 405
<211> LENGTH: 9
<212> TYPE: PRT
<213> ORGANISM: CoV-2
<220> FEATURE:
<223> OTHER INFORMATION: RDRP A1.01_877

<400> SEQUENCE: 405

Tyr Ala Asp Val Phe His Leu Tyr Leu
1               5

<210> SEQ ID NO 406
<211> LENGTH: 9
<212> TYPE: PRT
<213> ORGANISM: CoV-2
<220> FEATURE:
<223> OTHER INFORMATION: RDRP A1.01_209

<400> SEQUENCE: 406

Asn Gln Asp Leu Asn Gly Asn Trp Tyr
1               5

<210> SEQ ID NO 407
<211> LENGTH: 9
<212> TYPE: PRT
<213> ORGANISM: CoV-2
<220> FEATURE:
<223> OTHER INFORMATION: RDRP A1.01_606

<400> SEQUENCE: 407

Tyr Ser Asp Val Glu Asn Pro His Leu
1               5
```

<210> SEQ ID NO 408
<211> LENGTH: 9
<212> TYPE: PRT
<213> ORGANISM: CoV-2
<220> FEATURE:
<223> OTHER INFORMATION: RDRP A1.01_27

<400> SEQUENCE: 408

Ser Thr Asp Val Val Tyr Arg Ala Phe
1               5

<210> SEQ ID NO 409
<211> LENGTH: 9
<212> TYPE: PRT
<213> ORGANISM: CoV-2
<220> FEATURE:
<223> OTHER INFORMATION: RDRP A1.01_471

<400> SEQUENCE: 409

Phe Val Val Glu Val Val Asp Lys Tyr
1               5

<210> SEQ ID NO 410
<211> LENGTH: 9
<212> TYPE: PRT
<213> ORGANISM: CoV-2
<220> FEATURE:
<223> OTHER INFORMATION: RDRP A1.01_538

<400> SEQUENCE: 410

Thr Ile Thr Gln Met Asn Leu Lys Tyr
1               5

<210> SEQ ID NO 411
<211> LENGTH: 9
<212> TYPE: PRT
<213> ORGANISM: CoV-2
<220> FEATURE:
<223> OTHER INFORMATION: RDRP A1.01_859

<400> SEQUENCE: 411

Phe Val Ser Leu Ala Ile Asp Ala Tyr
1               5

<210> SEQ ID NO 412
<211> LENGTH: 9
<212> TYPE: PRT
<213> ORGANISM: CoV-2
<220> FEATURE:
<223> OTHER INFORMATION: RDRP A1.01_448

<400> SEQUENCE: 412

Ala Ala Ile Ser Asp Tyr Asp Tyr Tyr
1               5

<210> SEQ ID NO 413
<211> LENGTH: 9
<212> TYPE: PRT
<213> ORGANISM: CoV-2
<220> FEATURE:
<223> OTHER INFORMATION: RDRP A1.01_281

<400> SEQUENCE: 413

Lys Leu Phe Asp Arg Tyr Phe Lys Tyr
1               5

```
<210> SEQ ID NO 414
<211> LENGTH: 9
<212> TYPE: PRT
<213> ORGANISM: CoV-2
<220> FEATURE:
<223> OTHER INFORMATION: RDRP A2.01_123

<400> SEQUENCE: 414

Thr Met Ala Asp Leu Val Tyr Ala Leu
1               5

<210> SEQ ID NO 415
<211> LENGTH: 9
<212> TYPE: PRT
<213> ORGANISM: CoV-2
<220> FEATURE:
<223> OTHER INFORMATION: RDRP A2.01_854

<400> SEQUENCE: 415

Leu Met Ile Glu Arg Phe Val Ser Leu
1               5

<210> SEQ ID NO 416
<211> LENGTH: 9
<212> TYPE: PRT
<213> ORGANISM: CoV-2
<220> FEATURE:
<223> OTHER INFORMATION: RDRP A2.01_334

<400> SEQUENCE: 416

Phe Val Asp Gly Val Pro Phe Val Val
1               5

<210> SEQ ID NO 417
<211> LENGTH: 9
<212> TYPE: PRT
<213> ORGANISM: CoV-2
<220> FEATURE:
<223> OTHER INFORMATION: RDRP A2.01_64

<400> SEQUENCE: 417

Asn Leu Ile Asp Ser Tyr Phe Val Val
1               5

<210> SEQ ID NO 418
<211> LENGTH: 9
<212> TYPE: PRT
<213> ORGANISM: CoV-2
<220> FEATURE:
<223> OTHER INFORMATION: RDRP A2.01_239

<400> SEQUENCE: 418

Ser Leu Leu Met Pro Ile Leu Thr Leu
1               5

<210> SEQ ID NO 419
<211> LENGTH: 9
<212> TYPE: PRT
<213> ORGANISM: CoV-2
<220> FEATURE:
<223> OTHER INFORMATION: RDRP A2.01_741

<400> SEQUENCE: 419

Phe Val Asn Glu Phe Tyr Ala Tyr Leu
1               5
```

```
<210> SEQ ID NO 420
<211> LENGTH: 9
<212> TYPE: PRT
<213> ORGANISM: CoV-2
<220> FEATURE:
<223> OTHER INFORMATION: RDRP A2.01_899

<400> SEQUENCE: 420

Met Leu Asp Met Tyr Ser Val Met Leu
1               5

<210> SEQ ID NO 421
<211> LENGTH: 9
<212> TYPE: PRT
<213> ORGANISM: CoV-2
<220> FEATURE:
<223> OTHER INFORMATION: RDRP A2.01_654

<400> SEQUENCE: 421

Arg Leu Ala Asn Glu Cys Ala Gln Val
1               5

<210> SEQ ID NO 422
<211> LENGTH: 9
<212> TYPE: PRT
<213> ORGANISM: CoV-2
<220> FEATURE:
<223> OTHER INFORMATION: RDRP A2.01_467

<400> SEQUENCE: 422

Arg Gln Leu Leu Phe Val Val Glu Val
1               5

<210> SEQ ID NO 423
<211> LENGTH: 9
<212> TYPE: PRT
<213> ORGANISM: CoV-2
<220> FEATURE:
<223> OTHER INFORMATION: RDRP A2.01_88

<400> SEQUENCE: 423

Asn Leu Leu Lys Asp Cys Pro Ala Val
1               5

<210> SEQ ID NO 424
<211> LENGTH: 9
<212> TYPE: PRT
<213> ORGANISM: CoV-2
<220> FEATURE:
<223> OTHER INFORMATION: RDRP A2.01_240

<400> SEQUENCE: 424

Leu Leu Met Pro Ile Leu Thr Leu Thr
1               5

<210> SEQ ID NO 425
<211> LENGTH: 9
<212> TYPE: PRT
<213> ORGANISM: CoV-2
<220> FEATURE:
<223> OTHER INFORMATION: RDRP A2.01_667

<400> SEQUENCE: 425

Val Met Cys Gly Gly Ser Leu Tyr Val
1               5

<210> SEQ ID NO 426
```

```
<211> LENGTH: 9
<212> TYPE: PRT
<213> ORGANISM: CoV-2
<220> FEATURE:
<223> OTHER INFORMATION: RDRP A2.01_821

<400> SEQUENCE: 426

Lys Gln Gly Asp Asp Tyr Val Tyr Leu
1               5

<210> SEQ ID NO 427
<211> LENGTH: 9
<212> TYPE: PRT
<213> ORGANISM: CoV-2
<220> FEATURE:
<223> OTHER INFORMATION: RDRP A2.01_122

<400> SEQUENCE: 427

Tyr Thr Met Ala Asp Leu Val Tyr Ala
1               5

<210> SEQ ID NO 428
<211> LENGTH: 9
<212> TYPE: PRT
<213> ORGANISM: CoV-2
<220> FEATURE:
<223> OTHER INFORMATION: RDRP A2.01_647

<400> SEQUENCE: 428

Ser Leu Ser His Arg Phe Tyr Arg Leu
1               5

<210> SEQ ID NO 429
<211> LENGTH: 9
<212> TYPE: PRT
<213> ORGANISM: CoV-2
<220> FEATURE:
<223> OTHER INFORMATION: RDRP A2.01_365

<400> SEQUENCE: 429

Arg Leu Ser Phe Lys Glu Leu Leu Val
1               5

<210> SEQ ID NO 430
<211> LENGTH: 9
<212> TYPE: PRT
<213> ORGANISM: CoV-2
<220> FEATURE:
<223> OTHER INFORMATION: RDRP A2.01_923

<400> SEQUENCE: 430

Ala Met Tyr Thr Pro His Thr Val Leu
1               5

<210> SEQ ID NO 431
<211> LENGTH: 9
<212> TYPE: PRT
<213> ORGANISM: CoV-2
<220> FEATURE:
<223> OTHER INFORMATION: RDRP A2.01_397

<400> SEQUENCE: 431

Ser Val Ala Ala Leu Thr Asn Asn Val
1               5

<210> SEQ ID NO 432
<211> LENGTH: 9
```

```
<212> TYPE: PRT
<213> ORGANISM: CoV-2
<220> FEATURE:
<223> OTHER INFORMATION: RDRP A2.01_307

<400> SEQUENCE: 432

Ile Leu His Cys Ala Asn Phe Asn Val
1               5

<210> SEQ ID NO 433
<211> LENGTH: 9
<212> TYPE: PRT
<213> ORGANISM: CoV-2
<220> FEATURE:
<223> OTHER INFORMATION: RDRP A2.01_574

<400> SEQUENCE: 433

Lys Leu Leu Lys Ser Ile Ala Ala Thr
1               5

<210> SEQ ID NO 434
<211> LENGTH: 9
<212> TYPE: PRT
<213> ORGANISM: CoV-2
<220> FEATURE:
<223> OTHER INFORMATION: RDRP A3.01_281

<400> SEQUENCE: 434

Lys Leu Phe Asp Arg Tyr Phe Lys Tyr
1               5

<210> SEQ ID NO 435
<211> LENGTH: 9
<212> TYPE: PRT
<213> ORGANISM: CoV-2
<220> FEATURE:
<223> OTHER INFORMATION: RDRP A3.01_324

<400> SEQUENCE: 435

Thr Ser Phe Gly Pro Leu Val Arg Lys
1               5

<210> SEQ ID NO 436
<211> LENGTH: 9
<212> TYPE: PRT
<213> ORGANISM: CoV-2
<220> FEATURE:
<223> OTHER INFORMATION: RDRP A3.01_500

<400> SEQUENCE: 436

Lys Ser Ala Gly Phe Pro Phe Asn Lys
1               5

<210> SEQ ID NO 437
<211> LENGTH: 9
<212> TYPE: PRT
<213> ORGANISM: CoV-2
<220> FEATURE:
<223> OTHER INFORMATION: RDRP A3.01_569

<400> SEQUENCE: 437

Arg Gln Phe His Gln Lys Leu Leu Lys
1               5

<210> SEQ ID NO 438
<211> LENGTH: 9
<212> TYPE: PRT
```

```
<213> ORGANISM: CoV-2
<220> FEATURE:
<223> OTHER INFORMATION: RDRP A3.01_513

<400> SEQUENCE: 438

Arg Leu Tyr Tyr Asp Ser Met Ser Tyr
1               5

<210> SEQ ID NO 439
<211> LENGTH: 9
<212> TYPE: PRT
<213> ORGANISM: CoV-2
<220> FEATURE:
<223> OTHER INFORMATION: RDRP A3.01_882

<400> SEQUENCE: 439

His Leu Tyr Leu Gln Tyr Ile Arg Lys
1               5

<210> SEQ ID NO 440
<211> LENGTH: 9
<212> TYPE: PRT
<213> ORGANISM: CoV-2
<220> FEATURE:
<223> OTHER INFORMATION: RDRP A3.01_863

<400> SEQUENCE: 440

Ala Ile Asp Ala Tyr Pro Leu Thr Lys
1               5

<210> SEQ ID NO 441
<211> LENGTH: 9
<212> TYPE: PRT
<213> ORGANISM: CoV-2
<220> FEATURE:
<223> OTHER INFORMATION: RDRP A3.01_409

<400> SEQUENCE: 441

Thr Val Lys Pro Gly Asn Phe Asn Lys
1               5

<210> SEQ ID NO 442
<211> LENGTH: 9
<212> TYPE: PRT
<213> ORGANISM: CoV-2
<220> FEATURE:
<223> OTHER INFORMATION: RDRP A3.01_95

<400> SEQUENCE: 442

Ala Val Ala Lys His Asp Phe Phe Lys
1               5

<210> SEQ ID NO 443
<211> LENGTH: 9
<212> TYPE: PRT
<213> ORGANISM: CoV-2
<220> FEATURE:
<223> OTHER INFORMATION: RDRP A3.01_566

<400> SEQUENCE: 443

Met Thr Asn Arg Gln Phe His Gln Lys
1               5

<210> SEQ ID NO 444
<211> LENGTH: 9
<212> TYPE: PRT
<213> ORGANISM: CoV-2
```

```
<220> FEATURE:
<223> OTHER INFORMATION: RDRP A3.01_173

<400> SEQUENCE: 444

Arg Val Tyr Ala Asn Leu Gly Glu Arg
1               5

<210> SEQ ID NO 445
<211> LENGTH: 9
<212> TYPE: PRT
<213> ORGANISM: CoV-2
<220> FEATURE:
<223> OTHER INFORMATION: RDRP A3.01_585

<400> SEQUENCE: 445

Ala Thr Val Val Ile Gly Thr Ser Lys
1               5

<210> SEQ ID NO 446
<211> LENGTH: 9
<212> TYPE: PRT
<213> ORGANISM: CoV-2
<220> FEATURE:
<223> OTHER INFORMATION: RDRP A3.01_113

<400> SEQUENCE: 446

His Ile Ser Arg Gln Arg Leu Thr Lys
1               5

<210> SEQ ID NO 447
<211> LENGTH: 9
<212> TYPE: PRT
<213> ORGANISM: CoV-2
<220> FEATURE:
<223> OTHER INFORMATION: RDRP A3.01_775

<400> SEQUENCE: 447

Leu Val Ala Ser Ile Lys Asn Phe Lys
1               5

<210> SEQ ID NO 448
<211> LENGTH: 9
<212> TYPE: PRT
<213> ORGANISM: CoV-2
<220> FEATURE:
<223> OTHER INFORMATION: RDRP A3.01_33

<400> SEQUENCE: 448

Arg Ala Phe Asp Ile Tyr Asn Asp Lys
1               5

<210> SEQ ID NO 449
<211> LENGTH: 9
<212> TYPE: PRT
<213> ORGANISM: CoV-2
<220> FEATURE:
<223> OTHER INFORMATION: RDRP A3.01_613

<400> SEQUENCE: 449

His Leu Met Gly Trp Asp Tyr Pro Lys
1               5

<210> SEQ ID NO 450
<211> LENGTH: 9
<212> TYPE: PRT
<213> ORGANISM: CoV-2
<220> FEATURE:
```

-continued

```
<223> OTHER INFORMATION: RDRP A3.01_706

<400> SEQUENCE: 450

Ala Leu Leu Ser Thr Asp Gly Asn Lys
1               5

<210> SEQ ID NO 451
<211> LENGTH: 9
<212> TYPE: PRT
<213> ORGANISM: CoV-2
<220> FEATURE:
<223> OTHER INFORMATION: RDRP A3.01_141

<400> SEQUENCE: 451

Thr Leu Lys Glu Ile Leu Val Thr Tyr
1               5

<210> SEQ ID NO 452
<211> LENGTH: 9
<212> TYPE: PRT
<213> ORGANISM: CoV-2
<220> FEATURE:
<223> OTHER INFORMATION: RDRP A3.01_543

<400> SEQUENCE: 452

Asn Leu Lys Tyr Ala Ile Ser Ala Lys
1               5

<210> SEQ ID NO 453
<211> LENGTH: 9
<212> TYPE: PRT
<213> ORGANISM: CoV-2
<220> FEATURE:
<223> OTHER INFORMATION: RDRP A3.01_890

<400> SEQUENCE: 453

Lys Leu His Asp Glu Leu Thr Gly His
1               5

<210> SEQ ID NO 454
<211> LENGTH: 9
<212> TYPE: PRT
<213> ORGANISM: CoV-2
<220> FEATURE:
<223> OTHER INFORMATION: RDRP A3.01_632

<400> SEQUENCE: 454

Ile Met Ala Ser Leu Val Leu Ala Arg
1               5

<210> SEQ ID NO 455
<211> LENGTH: 9
<212> TYPE: PRT
<213> ORGANISM: CoV-2
<220> FEATURE:
<223> OTHER INFORMATION: RDRP A3.01_65

<400> SEQUENCE: 455

Leu Ile Asp Ser Tyr Phe Val Val Lys
1               5

<210> SEQ ID NO 456
<211> LENGTH: 9
<212> TYPE: PRT
<213> ORGANISM: CoV-2
<220> FEATURE:
<223> OTHER INFORMATION: RDRP A24.02_37
```

```
<400> SEQUENCE: 456

Ile Tyr Asn Asp Lys Val Ala Gly Phe
1               5

<210> SEQ ID NO 457
<211> LENGTH: 9
<212> TYPE: PRT
<213> ORGANISM: CoV-2
<220> FEATURE:
<223> OTHER INFORMATION: RDRP A24.02_883

<400> SEQUENCE: 457

Leu Tyr Leu Gln Tyr Ile Arg Lys Leu
1               5

<210> SEQ ID NO 458
<211> LENGTH: 9
<212> TYPE: PRT
<213> ORGANISM: CoV-2
<220> FEATURE:
<223> OTHER INFORMATION: RDRP A24.02_688

<400> SEQUENCE: 458

Ala Tyr Ala Asn Ser Val Phe Asn Ile
1               5

<210> SEQ ID NO 459
<211> LENGTH: 9
<212> TYPE: PRT
<213> ORGANISM: CoV-2
<220> FEATURE:
<223> OTHER INFORMATION: RDRP A24.02_69

<400> SEQUENCE: 459

Tyr Phe Val Val Lys Arg His Thr Phe
1               5

<210> SEQ ID NO 460
<211> LENGTH: 9
<212> TYPE: PRT
<213> ORGANISM: CoV-2
<220> FEATURE:
<223> OTHER INFORMATION: RDRP A24.02_876

<400> SEQUENCE: 460

Glu Tyr Ala Asp Val Phe His Leu Tyr
1               5

<210> SEQ ID NO 461
<211> LENGTH: 9
<212> TYPE: PRT
<213> ORGANISM: CoV-2
<220> FEATURE:
<223> OTHER INFORMATION: RDRP A24.02_745

<400> SEQUENCE: 461

Phe Tyr Ala Tyr Leu Arg Lys His Phe
1               5

<210> SEQ ID NO 462
<211> LENGTH: 9
<212> TYPE: PRT
<213> ORGANISM: CoV-2
<220> FEATURE:
<223> OTHER INFORMATION: RDRP A24.02_747
```

```
<400> SEQUENCE: 462

Ala Tyr Leu Arg Lys His Phe Ser Met
1               5

<210> SEQ ID NO 463
<211> LENGTH: 9
<212> TYPE: PRT
<213> ORGANISM: CoV-2
<220> FEATURE:
<223> OTHER INFORMATION: RDRP A24.02_520

<400> SEQUENCE: 463

Ser Tyr Glu Asp Gln Asp Ala Leu Phe
1               5

<210> SEQ ID NO 464
<211> LENGTH: 9
<212> TYPE: PRT
<213> ORGANISM: CoV-2
<220> FEATURE:
<223> OTHER INFORMATION: RDRP A24.02_594

<400> SEQUENCE: 464

Phe Tyr Gly Gly Trp His Asn Met Leu
1               5

<210> SEQ ID NO 465
<211> LENGTH: 9
<212> TYPE: PRT
<213> ORGANISM: CoV-2
<220> FEATURE:
<223> OTHER INFORMATION: RDRP A24.02_593

<400> SEQUENCE: 465

Lys Phe Tyr Gly Gly Trp His Asn Met
1               5

<210> SEQ ID NO 466
<211> LENGTH: 9
<212> TYPE: PRT
<213> ORGANISM: CoV-2
<220> FEATURE:
<223> OTHER INFORMATION: RDRP A24.02_455

<400> SEQUENCE: 466

Tyr Tyr Arg Tyr Asn Leu Pro Thr Met
1               5

<210> SEQ ID NO 467
<211> LENGTH: 9
<212> TYPE: PRT
<213> ORGANISM: CoV-2
<220> FEATURE:
<223> OTHER INFORMATION: RDRP A24.02_414

<400> SEQUENCE: 467

Asn Phe Asn Lys Asp Phe Tyr Asp Phe
1               5

<210> SEQ ID NO 468
<211> LENGTH: 9
<212> TYPE: PRT
<213> ORGANISM: CoV-2
<220> FEATURE:
<223> OTHER INFORMATION: RDRP A24.02_786

<400> SEQUENCE: 468
```

Leu Tyr Tyr Gln Asn Asn Val Phe Met
1               5

<210> SEQ ID NO 469
<211> LENGTH: 9
<212> TYPE: PRT
<213> ORGANISM: CoV-2
<220> FEATURE:
<223> OTHER INFORMATION: RDRP A24.02_237

<400> SEQUENCE: 469

Tyr Tyr Ser Leu Leu Met Pro Ile Leu
1               5

<210> SEQ ID NO 470
<211> LENGTH: 9
<212> TYPE: PRT
<213> ORGANISM: CoV-2
<220> FEATURE:
<223> OTHER INFORMATION: RDRP A24.02_325

<400> SEQUENCE: 470

Ser Phe Gly Pro Leu Val Arg Lys Ile
1               5

<210> SEQ ID NO 471
<211> LENGTH: 9
<212> TYPE: PRT
<213> ORGANISM: CoV-2
<220> FEATURE:
<223> OTHER INFORMATION: RDRP A24.02_174

<400> SEQUENCE: 471

Val Tyr Ala Asn Leu Gly Glu Arg Val
1               5

<210> SEQ ID NO 472
<211> LENGTH: 9
<212> TYPE: PRT
<213> ORGANISM: CoV-2
<220> FEATURE:
<223> OTHER INFORMATION: RDRP A24.02_830

<400> SEQUENCE: 472

Pro Tyr Pro Asp Pro Ser Arg Ile Leu
1               5

<210> SEQ ID NO 473
<211> LENGTH: 9
<212> TYPE: PRT
<213> ORGANISM: CoV-2
<220> FEATURE:
<223> OTHER INFORMATION: RDRP A24.02_236

<400> SEQUENCE: 473

Ser Tyr Tyr Ser Leu Leu Met Pro Ile
1               5

<210> SEQ ID NO 474
<211> LENGTH: 9
<212> TYPE: PRT
<213> ORGANISM: CoV-2
<220> FEATURE:
<223> OTHER INFORMATION: RDRP A24.02_267

<400> SEQUENCE: 474

Lys Trp Asp Leu Leu Lys Tyr Asp Phe
1               5

<210> SEQ ID NO 475
<211> LENGTH: 9
<212> TYPE: PRT
<213> ORGANISM: CoV-2
<220> FEATURE:
<223> OTHER INFORMATION: RDRP A24.02_272

<400> SEQUENCE: 475

Lys Tyr Asp Phe Thr Glu Glu Arg Leu
1               5

<210> SEQ ID NO 476
<211> LENGTH: 9
<212> TYPE: PRT
<213> ORGANISM: CoV-2
<220> FEATURE:
<223> OTHER INFORMATION: RDRP A26.01_471

<400> SEQUENCE: 476

Phe Val Val Glu Val Val Asp Lys Tyr
1               5

<210> SEQ ID NO 477
<211> LENGTH: 9
<212> TYPE: PRT
<213> ORGANISM: CoV-2
<220> FEATURE:
<223> OTHER INFORMATION: RDRP A26.01_534

<400> SEQUENCE: 477

Asn Val Ile Pro Thr Ile Thr Gln Met
1               5

<210> SEQ ID NO 478
<211> LENGTH: 9
<212> TYPE: PRT
<213> ORGANISM: CoV-2
<220> FEATURE:
<223> OTHER INFORMATION: RDRP A26.01_879

<400> SEQUENCE: 478

Asp Val Phe His Leu Tyr Leu Gln Tyr
1               5

<210> SEQ ID NO 479
<211> LENGTH: 9
<212> TYPE: PRT
<213> ORGANISM: CoV-2
<220> FEATURE:
<223> OTHER INFORMATION: RDRP A26.01_141

<400> SEQUENCE: 479

Thr Leu Lys Glu Ile Leu Val Thr Tyr
1               5

<210> SEQ ID NO 480
<211> LENGTH: 9
<212> TYPE: PRT
<213> ORGANISM: CoV-2
<220> FEATURE:
<223> OTHER INFORMATION: RDRP A26.01_907

<400> SEQUENCE: 480

Leu Thr Asn Asp Asn Thr Ser Arg Tyr

```
<210> SEQ ID NO 481
<211> LENGTH: 9
<212> TYPE: PRT
<213> ORGANISM: CoV-2
<220> FEATURE:
<223> OTHER INFORMATION: RDRP A26.01_318

<400> SEQUENCE: 481

Ser Thr Val Phe Pro Pro Thr Ser Phe
1               5

<210> SEQ ID NO 482
<211> LENGTH: 9
<212> TYPE: PRT
<213> ORGANISM: CoV-2
<220> FEATURE:
<223> OTHER INFORMATION: RDRP A26.01_587

<400> SEQUENCE: 482

Val Val Ile Gly Thr Ser Lys Phe Tyr
1               5

<210> SEQ ID NO 483
<211> LENGTH: 9
<212> TYPE: PRT
<213> ORGANISM: CoV-2
<220> FEATURE:
<223> OTHER INFORMATION: RDRP A26.01_586

<400> SEQUENCE: 483

Thr Val Val Ile Gly Thr Ser Lys Phe
1               5

<210> SEQ ID NO 484
<211> LENGTH: 9
<212> TYPE: PRT
<213> ORGANISM: CoV-2
<220> FEATURE:
<223> OTHER INFORMATION: RDRP A26.01_876

<400> SEQUENCE: 484

Glu Tyr Ala Asp Val Phe His Leu Tyr
1               5

<210> SEQ ID NO 485
<211> LENGTH: 9
<212> TYPE: PRT
<213> ORGANISM: CoV-2
<220> FEATURE:
<223> OTHER INFORMATION: RDRP A26.01_265

<400> SEQUENCE: 485

Tyr Ile Lys Trp Asp Leu Leu Lys Tyr
1               5

<210> SEQ ID NO 486
<211> LENGTH: 9
<212> TYPE: PRT
<213> ORGANISM: CoV-2
<220> FEATURE:
<223> OTHER INFORMATION: RDRP A26.01_666

<400> SEQUENCE: 486

Met Val Met Cys Gly Gly Ser Leu Tyr
1               5
```

```
<210> SEQ ID NO 487
<211> LENGTH: 9
<212> TYPE: PRT
<213> ORGANISM: CoV-2
<220> FEATURE:
<223> OTHER INFORMATION: RDRP A26.01_340

<400> SEQUENCE: 487

Phe Val Val Ser Thr Gly Tyr His Phe
1               5

<210> SEQ ID NO 488
<211> LENGTH: 9
<212> TYPE: PRT
<213> ORGANISM: CoV-2
<220> FEATURE:
<223> OTHER INFORMATION: RDRP A26.01_859

<400> SEQUENCE: 488

Phe Val Ser Leu Ala Ile Asp Ala Tyr
1               5

<210> SEQ ID NO 489
<211> LENGTH: 9
<212> TYPE: PRT
<213> ORGANISM: CoV-2
<220> FEATURE:
<223> OTHER INFORMATION: RDRP A26.01_167

<400> SEQUENCE: 489

Glu Asn Pro Asp Ile Leu Arg Val Tyr
1               5

<210> SEQ ID NO 490
<211> LENGTH: 9
<212> TYPE: PRT
<213> ORGANISM: CoV-2
<220> FEATURE:
<223> OTHER INFORMATION: RDRP A26.01_869

<400> SEQUENCE: 490

Leu Thr Lys His Pro Asn Gln Glu Tyr
1               5

<210> SEQ ID NO 491
<211> LENGTH: 9
<212> TYPE: PRT
<213> ORGANISM: CoV-2
<220> FEATURE:
<223> OTHER INFORMATION: RDRP A26.01_126

<400> SEQUENCE: 491

Asp Leu Val Tyr Ala Leu Arg His Phe
1               5

<210> SEQ ID NO 492
<211> LENGTH: 9
<212> TYPE: PRT
<213> ORGANISM: CoV-2
<220> FEATURE:
<223> OTHER INFORMATION: RDRP A26.01_762

<400> SEQUENCE: 492

Ala Val Val Cys Phe Asn Ser Thr Tyr
1               5
```

<210> SEQ ID NO 493
<211> LENGTH: 9
<212> TYPE: PRT
<213> ORGANISM: CoV-2
<220> FEATURE:
<223> OTHER INFORMATION: RDRP A26.01_538

<400> SEQUENCE: 493

Thr Ile Thr Gln Met Asn Leu Lys Tyr
1               5

<210> SEQ ID NO 494
<211> LENGTH: 9
<212> TYPE: PRT
<213> ORGANISM: CoV-2
<220> FEATURE:
<223> OTHER INFORMATION: RDRP A26.01_738

<400> SEQUENCE: 494

Asp Thr Asp Phe Val Asn Glu Phe Tyr
1               5

<210> SEQ ID NO 495
<211> LENGTH: 9
<212> TYPE: PRT
<213> ORGANISM: CoV-2
<220> FEATURE:
<223> OTHER INFORMATION: RDRP A26.01_686

<400> SEQUENCE: 495

Thr Thr Ala Tyr Ala Asn Ser Val Phe
1               5

<210> SEQ ID NO 496
<211> LENGTH: 9
<212> TYPE: PRT
<213> ORGANISM: CoV-2
<220> FEATURE:
<223> OTHER INFORMATION: RDRP A26.01_741

<400> SEQUENCE: 496

Phe Val Asn Glu Phe Tyr Ala Tyr Leu
1               5

<210> SEQ ID NO 497
<211> LENGTH: 9
<212> TYPE: PRT
<213> ORGANISM: CoV-2
<220> FEATURE:
<223> OTHER INFORMATION: RDRP A26.01_358

<400> SEQUENCE: 497

Asp Val Asn Leu His Ser Ser Arg Leu
1               5

<210> SEQ ID NO 498
<211> LENGTH: 9
<212> TYPE: PRT
<213> ORGANISM: CoV-2
<220> FEATURE:
<223> OTHER INFORMATION: RDRP B07.02_111

<400> SEQUENCE: 498

Val Pro His Ile Ser Arg Gln Arg Leu
1               5

```
<210> SEQ ID NO 499
<211> LENGTH: 9
<212> TYPE: PRT
<213> ORGANISM: CoV-2
<220> FEATURE:
<223> OTHER INFORMATION: RDRP B07.02_263

<400> SEQUENCE: 499

Lys Pro Tyr Ile Lys Trp Asp Leu Leu
1               5

<210> SEQ ID NO 500
<211> LENGTH: 9
<212> TYPE: PRT
<213> ORGANISM: CoV-2
<220> FEATURE:
<223> OTHER INFORMATION: RDRP B07.02_536

<400> SEQUENCE: 500

Ile Pro Thr Ile Thr Gln Met Asn Leu
1               5

<210> SEQ ID NO 501
<211> LENGTH: 9
<212> TYPE: PRT
<213> ORGANISM: CoV-2
<220> FEATURE:
<223> OTHER INFORMATION: RDRP B07.02_829

<400> SEQUENCE: 501

Leu Pro Tyr Pro Asp Pro Ser Arg Ile
1               5

<210> SEQ ID NO 502
<211> LENGTH: 9
<212> TYPE: PRT
<213> ORGANISM: CoV-2
<220> FEATURE:
<223> OTHER INFORMATION: RDRP B07.02_321

<400> SEQUENCE: 502

Phe Pro Pro Thr Ser Phe Gly Pro Leu
1               5

<210> SEQ ID NO 503
<211> LENGTH: 9
<212> TYPE: PRT
<213> ORGANISM: CoV-2
<220> FEATURE:
<223> OTHER INFORMATION: RDRP B07.02_226

<400> SEQUENCE: 503

Thr Pro Gly Ser Gly Val Pro Val Val
1               5

<210> SEQ ID NO 504
<211> LENGTH: 9
<212> TYPE: PRT
<213> ORGANISM: CoV-2
<220> FEATURE:
<223> OTHER INFORMATION: RDRP B07.02_778

<400> SEQUENCE: 504

Ser Ile Lys Asn Phe Lys Ser Val Leu
1               5

<210> SEQ ID NO 505
```

```
<211> LENGTH: 9
<212> TYPE: PRT
<213> ORGANISM: CoV-2
<220> FEATURE:
<223> OTHER INFORMATION: RDRP B07.02_887

<400> SEQUENCE: 505

Tyr Ile Arg Lys Leu His Asp Glu Leu
1               5

<210> SEQ ID NO 506
<211> LENGTH: 9
<212> TYPE: PRT
<213> ORGANISM: CoV-2
<220> FEATURE:
<223> OTHER INFORMATION: RDRP B07.02_626

<400> SEQUENCE: 506

Met Pro Asn Met Leu Arg Ile Met Ala
1               5

<210> SEQ ID NO 507
<211> LENGTH: 9
<212> TYPE: PRT
<213> ORGANISM: CoV-2
<220> FEATURE:
<223> OTHER INFORMATION: RDRP B07.02_719

<400> SEQUENCE: 507

Tyr Val Arg Asn Leu Gln His Arg Leu
1               5

<210> SEQ ID NO 508
<211> LENGTH: 9
<212> TYPE: PRT
<213> ORGANISM: CoV-2
<220> FEATURE:
<223> OTHER INFORMATION: RDRP B15.01_141

<400> SEQUENCE: 508

Thr Leu Lys Glu Ile Leu Val Thr Tyr
1               5

<210> SEQ ID NO 509
<211> LENGTH: 9
<212> TYPE: PRT
<213> ORGANISM: CoV-2
<220> FEATURE:
<223> OTHER INFORMATION: RDRP B15.01_513

<400> SEQUENCE: 509

Arg Leu Tyr Tyr Asp Ser Met Ser Tyr
1               5

<210> SEQ ID NO 510
<211> LENGTH: 9
<212> TYPE: PRT
<213> ORGANISM: CoV-2
<220> FEATURE:
<223> OTHER INFORMATION: RDRP B15.01_869

<400> SEQUENCE: 510

Leu Thr Lys His Pro Asn Gln Glu Tyr
1               5

<210> SEQ ID NO 511
<211> LENGTH: 9
```

```
<212> TYPE: PRT
<213> ORGANISM: CoV-2
<220> FEATURE:
<223> OTHER INFORMATION: RDRP B15.01_785

<400> SEQUENCE: 511

Val Leu Tyr Tyr Gln Asn Asn Val Phe
1               5

<210> SEQ ID NO 512
<211> LENGTH: 9
<212> TYPE: PRT
<213> ORGANISM: CoV-2
<220> FEATURE:
<223> OTHER INFORMATION: RDRP B15.01_281

<400> SEQUENCE: 512

Lys Leu Phe Asp Arg Tyr Phe Lys Tyr
1               5

<210> SEQ ID NO 513
<211> LENGTH: 9
<212> TYPE: PRT
<213> ORGANISM: CoV-2
<220> FEATURE:
<223> OTHER INFORMATION: RDRP B15.01_360

<400> SEQUENCE: 513

Asn Leu His Ser Ser Arg Leu Ser Phe
1               5

<210> SEQ ID NO 514
<211> LENGTH: 9
<212> TYPE: PRT
<213> ORGANISM: CoV-2
<220> FEATURE:
<223> OTHER INFORMATION: RDRP B15.01_265

<400> SEQUENCE: 514

Tyr Ile Lys Trp Asp Leu Leu Lys Tyr
1               5

<210> SEQ ID NO 515
<211> LENGTH: 9
<212> TYPE: PRT
<213> ORGANISM: CoV-2
<220> FEATURE:
<223> OTHER INFORMATION: RDRP B15.01_318

<400> SEQUENCE: 515

Ser Thr Val Phe Pro Pro Thr Ser Phe
1               5

<210> SEQ ID NO 516
<211> LENGTH: 9
<212> TYPE: PRT
<213> ORGANISM: CoV-2
<220> FEATURE:
<223> OTHER INFORMATION: RDRP B15.01_116

<400> SEQUENCE: 516

Arg Gln Arg Leu Thr Lys Tyr Thr Met
1               5

<210> SEQ ID NO 517
<211> LENGTH: 9
<212> TYPE: PRT
```

```
<213> ORGANISM: CoV-2
<220> FEATURE:
<223> OTHER INFORMATION: RDRP B15.01_587

<400> SEQUENCE: 517

Val Val Ile Gly Thr Ser Lys Phe Tyr
1               5

<210> SEQ ID NO 518
<211> LENGTH: 9
<212> TYPE: PRT
<213> ORGANISM: CoV-2
<220> FEATURE:
<223> OTHER INFORMATION: RDRP B15.01_923

<400> SEQUENCE: 518

Ala Met Tyr Thr Pro His Thr Val Leu
1               5

<210> SEQ ID NO 519
<211> LENGTH: 9
<212> TYPE: PRT
<213> ORGANISM: CoV-2
<220> FEATURE:
<223> OTHER INFORMATION: RDRP B15.01_366

<400> SEQUENCE: 519

Leu Ser Phe Lys Glu Leu Leu Val Tyr
1               5

<210> SEQ ID NO 520
<211> LENGTH: 9
<212> TYPE: PRT
<213> ORGANISM: CoV-2
<220> FEATURE:
<223> OTHER INFORMATION: RDRP B15.01_471

<400> SEQUENCE: 520

Phe Val Val Glu Val Val Asp Lys Tyr
1               5

<210> SEQ ID NO 521
<211> LENGTH: 9
<212> TYPE: PRT
<213> ORGANISM: CoV-2
<220> FEATURE:
<223> OTHER INFORMATION: RDRP B15.01_660

<400> SEQUENCE: 521

Ala Gln Val Leu Ser Glu Met Val Met
1               5

<210> SEQ ID NO 522
<211> LENGTH: 9
<212> TYPE: PRT
<213> ORGANISM: CoV-2
<220> FEATURE:
<223> OTHER INFORMATION: RDRP B15.01_279

<400> SEQUENCE: 522

Arg Leu Lys Leu Phe Asp Arg Tyr Phe
1               5

<210> SEQ ID NO 523
<211> LENGTH: 9
<212> TYPE: PRT
<213> ORGANISM: CoV-2
```

<220> FEATURE:
<223> OTHER INFORMATION: RDRP B15.01_332

<400> SEQUENCE: 523

Lys Ile Phe Val Asp Gly Val Pro Phe
1               5

<210> SEQ ID NO 524
<211> LENGTH: 9
<212> TYPE: PRT
<213> ORGANISM: CoV-2
<220> FEATURE:
<223> OTHER INFORMATION: RDRP B15.01_907

<400> SEQUENCE: 524

Leu Thr Asn Asp Asn Thr Ser Arg Tyr
1               5

<210> SEQ ID NO 525
<211> LENGTH: 9
<212> TYPE: PRT
<213> ORGANISM: CoV-2
<220> FEATURE:
<223> OTHER INFORMATION: RDRP B15.01_681

<400> SEQUENCE: 525

Ser Ser Gly Asp Ala Thr Thr Ala Tyr
1               5

<210> SEQ ID NO 526
<211> LENGTH: 9
<212> TYPE: PRT
<213> ORGANISM: CoV-2
<220> FEATURE:
<223> OTHER INFORMATION: RDRP B15.01_340

<400> SEQUENCE: 526

Phe Val Val Ser Thr Gly Tyr His Phe
1               5

<210> SEQ ID NO 527
<211> LENGTH: 9
<212> TYPE: PRT
<213> ORGANISM: CoV-2
<220> FEATURE:
<223> OTHER INFORMATION: RDRP B15.01_30

<400> SEQUENCE: 527

Val Val Tyr Arg Ala Phe Asp Ile Tyr
1               5

<210> SEQ ID NO 528
<211> LENGTH: 9
<212> TYPE: PRT
<213> ORGANISM: CoV-2
<220> FEATURE:
<223> OTHER INFORMATION: RDRP B15.01_774

<400> SEQUENCE: 528

Gly Leu Val Ala Ser Ile Lys Asn Phe
1               5

<210> SEQ ID NO 529
<211> LENGTH: 9
<212> TYPE: PRT
<213> ORGANISM: CoV-2
<220> FEATURE:

<223> OTHER INFORMATION: RDRP B15.01_762

<400> SEQUENCE: 529

Ala Val Val Cys Phe Asn Ser Thr Tyr
1               5

<210> SEQ ID NO 530
<211> LENGTH: 9
<212> TYPE: PRT
<213> ORGANISM: CoV-2
<220> FEATURE:
<223> OTHER INFORMATION: RDRP B15.01_586

<400> SEQUENCE: 530

Thr Val Val Ile Gly Thr Ser Lys Phe
1               5

<210> SEQ ID NO 531
<211> LENGTH: 9
<212> TYPE: PRT
<213> ORGANISM: CoV-2
<220> FEATURE:
<223> OTHER INFORMATION: RDRP B15.01_114

<400> SEQUENCE: 531

Ile Ser Arg Gln Arg Leu Thr Lys Tyr
1               5

<210> SEQ ID NO 532
<211> LENGTH: 9
<212> TYPE: PRT
<213> ORGANISM: CoV-2
<220> FEATURE:
<223> OTHER INFORMATION: RDRP B15.01_229

<400> SEQUENCE: 532

Ser Gly Val Pro Val Val Asp Ser Tyr
1               5

<210> SEQ ID NO 533
<211> LENGTH: 9
<212> TYPE: PRT
<213> ORGANISM: CoV-2
<220> FEATURE:
<223> OTHER INFORMATION: RDRP B15.01_666

<400> SEQUENCE: 533

Met Val Met Cys Gly Gly Ser Leu Tyr
1               5

<210> SEQ ID NO 534
<211> LENGTH: 9
<212> TYPE: PRT
<213> ORGANISM: CoV-2
<220> FEATURE:
<223> OTHER INFORMATION: RDRP B15.01_859

<400> SEQUENCE: 534

Phe Val Ser Leu Ala Ile Asp Ala Tyr
1               5

<210> SEQ ID NO 535
<211> LENGTH: 9
<212> TYPE: PRT
<213> ORGANISM: CoV-2
<220> FEATURE:
<223> OTHER INFORMATION: RDRP B15.01_748

<400> SEQUENCE: 535

Tyr Leu Arg Lys His Phe Ser Met Met
1               5

<210> SEQ ID NO 536
<211> LENGTH: 9
<212> TYPE: PRT
<213> ORGANISM: CoV-2
<220> FEATURE:
<223> OTHER INFORMATION: RDRP B15.01_854

<400> SEQUENCE: 536

Leu Met Ile Glu Arg Phe Val Ser Leu
1               5

<210> SEQ ID NO 537
<211> LENGTH: 9
<212> TYPE: PRT
<213> ORGANISM: CoV-2
<220> FEATURE:
<223> OTHER INFORMATION: RDRP B15.01_407

<400> SEQUENCE: 537

Phe Gln Thr Val Lys Pro Gly Asn Phe
1               5

<210> SEQ ID NO 538
<211> LENGTH: 9
<212> TYPE: PRT
<213> ORGANISM: CoV-2
<220> FEATURE:
<223> OTHER INFORMATION: RDRP B15.01_534

<400> SEQUENCE: 538

Asn Val Ile Pro Thr Ile Thr Gln Met
1               5

<210> SEQ ID NO 539
<211> LENGTH: 9
<212> TYPE: PRT
<213> ORGANISM: CoV-2
<220> FEATURE:
<223> OTHER INFORMATION: RDRP B15.01_847

<400> SEQUENCE: 539

Ile Val Lys Thr Asp Gly Thr Leu Met
1               5

<210> SEQ ID NO 540
<211> LENGTH: 9
<212> TYPE: PRT
<213> ORGANISM: CoV-2
<220> FEATURE:
<223> OTHER INFORMATION: RDRP B15.01_780

<400> SEQUENCE: 540

Lys Asn Phe Lys Ser Val Leu Tyr Tyr
1               5

<210> SEQ ID NO 541
<211> LENGTH: 9
<212> TYPE: PRT
<213> ORGANISM: CoV-2
<220> FEATURE:
<223> OTHER INFORMATION: RDRP B15.01_538

```
<400> SEQUENCE: 541

Thr Ile Thr Gln Met Asn Leu Lys Tyr
1               5

<210> SEQ ID NO 542
<211> LENGTH: 9
<212> TYPE: PRT
<213> ORGANISM: CoV-2
<220> FEATURE:
<223> OTHER INFORMATION: RDRP B15.01_286

<400> SEQUENCE: 542

Tyr Phe Lys Tyr Trp Asp Gln Thr Tyr
1               5

<210> SEQ ID NO 543
<211> LENGTH: 9
<212> TYPE: PRT
<213> ORGANISM: CoV-2
<220> FEATURE:
<223> OTHER INFORMATION: RDRP B15.01_818

<400> SEQUENCE: 543

Met Leu Val Lys Gln Gly Asp Asp Tyr
1               5

<210> SEQ ID NO 544
<211> LENGTH: 9
<212> TYPE: PRT
<213> ORGANISM: CoV-2
<220> FEATURE:
<223> OTHER INFORMATION: RDRP B15.01_898

<400> SEQUENCE: 544

His Met Leu Asp Met Tyr Ser Val Met
1               5

<210> SEQ ID NO 545
<211> LENGTH: 9
<212> TYPE: PRT
<213> ORGANISM: CoV-2
<220> FEATURE:
<223> OTHER INFORMATION: RDRP B40.01_875

<400> SEQUENCE: 545

Gln Glu Tyr Ala Asp Val Phe His Leu
1               5

<210> SEQ ID NO 546
<211> LENGTH: 9
<212> TYPE: PRT
<213> ORGANISM: CoV-2
<220> FEATURE:
<223> OTHER INFORMATION: RDRP B40.01_82

<400> SEQUENCE: 546

His Glu Glu Thr Ile Tyr Asn Leu Leu
1               5

<210> SEQ ID NO 547
<211> LENGTH: 9
<212> TYPE: PRT
<213> ORGANISM: CoV-2
<220> FEATURE:
<223> OTHER INFORMATION: RDRP B40.01_810

<400> SEQUENCE: 547
```

```
His Glu Phe Cys Ser Gln His Thr Met
1               5

<210> SEQ ID NO 548
<211> LENGTH: 9
<212> TYPE: PRT
<213> ORGANISM: CoV-2
<220> FEATURE:
<223> OTHER INFORMATION: RDRP B40.01_253

<400> SEQUENCE: 548

Ala Glu Ser His Val Asp Thr Asp Leu
1               5

<210> SEQ ID NO 549
<211> LENGTH: 9
<212> TYPE: PRT
<213> ORGANISM: CoV-2
<220> FEATURE:
<223> OTHER INFORMATION: RDRP B40.01_166

<400> SEQUENCE: 549

Val Glu Asn Pro Asp Ile Leu Arg Val
1               5

<210> SEQ ID NO 550
<211> LENGTH: 9
<212> TYPE: PRT
<213> ORGANISM: CoV-2
<220> FEATURE:
<223> OTHER INFORMATION: RDRP B40.01_57

<400> SEQUENCE: 550

Gln Glu Lys Asp Glu Asp Asp Asn Leu
1               5

<210> SEQ ID NO 551
<211> LENGTH: 9
<212> TYPE: PRT
<213> ORGANISM: CoV-2
<220> FEATURE:
<223> OTHER INFORMATION: RDRP B40.01_916

<400> SEQUENCE: 551

Trp Glu Pro Glu Phe Tyr Glu Ala Met
1               5

<210> SEQ ID NO 552
<211> LENGTH: 9
<212> TYPE: PRT
<213> ORGANISM: CoV-2
<220> FEATURE:
<223> OTHER INFORMATION: RDRP B40.01_179

<400> SEQUENCE: 552

Gly Glu Arg Val Arg Gln Ala Leu Leu
1               5

<210> SEQ ID NO 553
<211> LENGTH: 9
<212> TYPE: PRT
<213> ORGANISM: CoV-2
<220> FEATURE:
<223> OTHER INFORMATION: RDRP B58.01_501

<400> SEQUENCE: 553
```

Ser Ala Gly Phe Pro Phe Asn Lys Trp
1               5

<210> SEQ ID NO 554
<211> LENGTH: 9
<212> TYPE: PRT
<213> ORGANISM: CoV-2
<220> FEATURE:
<223> OTHER INFORMATION: RDRP B58.01_433

<400> SEQUENCE: 554

Ser Ser Val Glu Leu Lys His Phe Phe
1               5

<210> SEQ ID NO 555
<211> LENGTH: 9
<212> TYPE: PRT
<213> ORGANISM: CoV-2
<220> FEATURE:
<223> OTHER INFORMATION: RDRP B58.01_366

<400> SEQUENCE: 555

Leu Ser Phe Lys Glu Leu Leu Val Tyr
1               5

<210> SEQ ID NO 556
<211> LENGTH: 9
<212> TYPE: PRT
<213> ORGANISM: CoV-2
<220> FEATURE:
<223> OTHER INFORMATION: RDRP B58.01_96

<400> SEQUENCE: 556

Val Ala Lys His Asp Phe Phe Lys Phe
1               5

<210> SEQ ID NO 557
<211> LENGTH: 9
<212> TYPE: PRT
<213> ORGANISM: CoV-2
<220> FEATURE:
<223> OTHER INFORMATION: RDRP B58.01_624

<400> SEQUENCE: 557

Arg Ala Met Pro Asn Met Leu Arg Ile
1               5

<210> SEQ ID NO 558
<211> LENGTH: 9
<212> TYPE: PRT
<213> ORGANISM: CoV-2
<220> FEATURE:
<223> OTHER INFORMATION: RDRP B58.01_318

<400> SEQUENCE: 558

Ser Thr Val Phe Pro Pro Thr Ser Phe
1               5

<210> SEQ ID NO 559
<211> LENGTH: 9
<212> TYPE: PRT
<213> ORGANISM: CoV-2
<220> FEATURE:
<223> OTHER INFORMATION: RDRP B58.01_590

<400> SEQUENCE: 559

Gly Thr Ser Lys Phe Tyr Gly Gly Trp

```
<210> SEQ ID NO 560
<211> LENGTH: 9
<212> TYPE: PRT
<213> ORGANISM: CoV-2
<220> FEATURE:
<223> OTHER INFORMATION: RDRP B58.01_184

<400> SEQUENCE: 560

Gln Ala Leu Leu Lys Thr Val Gln Phe
1               5

<210> SEQ ID NO 561
<211> LENGTH: 9
<212> TYPE: PRT
<213> ORGANISM: CoV-2
<220> FEATURE:
<223> OTHER INFORMATION: RDRP B58.01_432

<400> SEQUENCE: 561

Gly Ser Ser Val Glu Leu Lys His Phe
1               5

<210> SEQ ID NO 562
<211> LENGTH: 9
<212> TYPE: PRT
<213> ORGANISM: CoV-2
<220> FEATURE:
<223> OTHER INFORMATION: RDRP B58.01_908

<400> SEQUENCE: 562

Thr Asn Asp Asn Thr Ser Arg Tyr Trp
1               5

<210> SEQ ID NO 563
<211> LENGTH: 9
<212> TYPE: PRT
<213> ORGANISM: CoV-2
<220> FEATURE:
<223> OTHER INFORMATION: RDRP B58.01_758

<400> SEQUENCE: 563

Leu Ser Asp Asp Ala Val Val Cys Phe
1               5

<210> SEQ ID NO 564
<211> LENGTH: 9
<212> TYPE: PRT
<213> ORGANISM: CoV-2
<220> FEATURE:
<223> OTHER INFORMATION: RDRP B58.01_27

<400> SEQUENCE: 564

Ser Thr Asp Val Val Tyr Arg Ala Phe
1               5

<210> SEQ ID NO 565
<211> LENGTH: 9
<212> TYPE: PRT
<213> ORGANISM: CoV-2
<220> FEATURE:
<223> OTHER INFORMATION: RDRP B58.01_780

<400> SEQUENCE: 565

Lys Asn Phe Lys Ser Val Leu Tyr Tyr
1               5
```

```
<210> SEQ ID NO 566
<211> LENGTH: 9
<212> TYPE: PRT
<213> ORGANISM: CoV-2
<220> FEATURE:
<223> OTHER INFORMATION: RDRP B58.01_609

<400> SEQUENCE: 566

Val Glu Asn Pro His Leu Met Gly Trp
1               5

<210> SEQ ID NO 567
<211> LENGTH: 9
<212> TYPE: PRT
<213> ORGANISM: CoV-2
<220> FEATURE:
<223> OTHER INFORMATION: RDRP B58.01_281

<400> SEQUENCE: 567

Lys Leu Phe Asp Arg Tyr Phe Lys Tyr
1               5

<210> SEQ ID NO 568
<211> LENGTH: 9
<212> TYPE: PRT
<213> ORGANISM: CoV-2
<220> FEATURE:
<223> OTHER INFORMATION: RDRP B58.01_907

<400> SEQUENCE: 568

Leu Thr Asn Asp Asn Thr Ser Arg Tyr
1               5

<210> SEQ ID NO 569
<211> LENGTH: 9
<212> TYPE: PRT
<213> ORGANISM: CoV-2
<220> FEATURE:
<223> OTHER INFORMATION: RDRP B58.01_869

<400> SEQUENCE: 569

Leu Thr Lys His Pro Asn Gln Glu Tyr
1               5

<210> SEQ ID NO 570
<211> LENGTH: 9
<212> TYPE: PRT
<213> ORGANISM: CoV-2
<220> FEATURE:
<223> OTHER INFORMATION: RDRP B58.01_450

<400> SEQUENCE: 570

Ile Ser Asp Tyr Asp Tyr Tyr Arg Tyr
1               5

<210> SEQ ID NO 571
<211> LENGTH: 9
<212> TYPE: PRT
<213> ORGANISM: CoV-2
<220> FEATURE:
<223> OTHER INFORMATION: RDRP B58.01_563

<400> SEQUENCE: 571

Cys Ser Thr Met Thr Asn Arg Gln Phe
1               5
```

<210> SEQ ID NO 572
<211> LENGTH: 9
<212> TYPE: PRT
<213> ORGANISM: CoV-2
<220> FEATURE:
<223> OTHER INFORMATION: Heli A1.01_56

<400> SEQUENCE: 572

Asp Val Thr Asp Val Thr Gln Leu Tyr
1 5

<210> SEQ ID NO 573
<211> LENGTH: 9
<212> TYPE: PRT
<213> ORGANISM: CoV-2
<220> FEATURE:
<223> OTHER INFORMATION: Heli A1.01_57

<400> SEQUENCE: 573

Val Thr Asp Val Thr Gln Leu Tyr Leu
1 5

<210> SEQ ID NO 574
<211> LENGTH: 9
<212> TYPE: PRT
<213> ORGANISM: CoV-2
<220> FEATURE:
<223> OTHER INFORMATION: Heli A1.01_535

<400> SEQUENCE: 574

Ser Ser Gln Gly Ser Glu Tyr Asp Tyr
1 5

<210> SEQ ID NO 575
<211> LENGTH: 9
<212> TYPE: PRT
<213> ORGANISM: CoV-2
<220> FEATURE:
<223> OTHER INFORMATION: Heli A1.01_347

<400> SEQUENCE: 575

Lys Val Asn Ser Thr Leu Glu Gln Tyr
1 5

<210> SEQ ID NO 576
<211> LENGTH: 9
<212> TYPE: PRT
<213> ORGANISM: CoV-2
<220> FEATURE:
<223> OTHER INFORMATION: Heli A1.01_291

<400> SEQUENCE: 576

Phe Ala Ile Gly Leu Ala Leu Tyr Tyr
1 5

<210> SEQ ID NO 577
<211> LENGTH: 9
<212> TYPE: PRT
<213> ORGANISM: CoV-2
<220> FEATURE:
<223> OTHER INFORMATION: Heli A1.01_238

<400> SEQUENCE: 577

Pro Thr Leu Val Pro Gln Glu His Tyr
1 5

-continued

```
<210> SEQ ID NO 578
<211> LENGTH: 9
<212> TYPE: PRT
<213> ORGANISM: CoV-2
<220> FEATURE:
<223> OTHER INFORMATION: Heli A1.01_316

<400> SEQUENCE: 578

Ala Leu Cys Glu Lys Ala Leu Lys Tyr
1               5

<210> SEQ ID NO 579
<211> LENGTH: 9
<212> TYPE: PRT
<213> ORGANISM: CoV-2
<220> FEATURE:
<223> OTHER INFORMATION: Heli A1.01_533

<400> SEQUENCE: 579

Val Asp Ser Ser Gln Gly Ser Glu Tyr
1               5

<210> SEQ ID NO 580
<211> LENGTH: 9
<212> TYPE: PRT
<213> ORGANISM: CoV-2
<220> FEATURE:
<223> OTHER INFORMATION: Heli A1.01_209

<400> SEQUENCE: 580

Val Val Tyr Arg Gly Thr Thr Thr Tyr
1               5

<210> SEQ ID NO 581
<211> LENGTH: 9
<212> TYPE: PRT
<213> ORGANISM: CoV-2
<220> FEATURE:
<223> OTHER INFORMATION: Heli A1.01_258

<400> SEQUENCE: 581

Ile Ser Asp Glu Phe Ser Ser Asn Val
1               5

<210> SEQ ID NO 582
<211> LENGTH: 9
<212> TYPE: PRT
<213> ORGANISM: CoV-2
<220> FEATURE:
<223> OTHER INFORMATION: Heli A1.01_141

<400> SEQUENCE: 582

Thr Glu Glu Thr Phe Lys Leu Ser Tyr
1               5

<210> SEQ ID NO 583
<211> LENGTH: 9
<212> TYPE: PRT
<213> ORGANISM: CoV-2
<220> FEATURE:
<223> OTHER INFORMATION: Heli A1.01_62

<400> SEQUENCE: 583

Gln Leu Tyr Leu Gly Gly Met Ser Tyr
1               5

<210> SEQ ID NO 584
```

-continued

```
<211> LENGTH: 9
<212> TYPE: PRT
<213> ORGANISM: CoV-2
<220> FEATURE:
<223> OTHER INFORMATION: Heli A1.01_190

<400> SEQUENCE: 584

Asn Ser Lys Val Gln Ile Gly Glu Tyr
1               5

<210> SEQ ID NO 585
<211> LENGTH: 9
<212> TYPE: PRT
<213> ORGANISM: CoV-2
<220> FEATURE:
<223> OTHER INFORMATION: Heli A1.01_574

<400> SEQUENCE: 585

Cys Ile Met Ser Asp Arg Asp Leu Tyr
1               5

<210> SEQ ID NO 586
<211> LENGTH: 9
<212> TYPE: PRT
<213> ORGANISM: CoV-2
<220> FEATURE:
<223> OTHER INFORMATION: Heli A1.01_468

<400> SEQUENCE: 586

Ser Ala Gln Cys Phe Lys Met Phe Tyr
1               5

<210> SEQ ID NO 587
<211> LENGTH: 9
<212> TYPE: PRT
<213> ORGANISM: CoV-2
<220> FEATURE:
<223> OTHER INFORMATION: Heli A2.01_239

<400> SEQUENCE: 587

Thr Leu Val Pro Gln Glu His Tyr Val
1               5

<210> SEQ ID NO 588
<211> LENGTH: 9
<212> TYPE: PRT
<213> ORGANISM: CoV-2
<220> FEATURE:
<223> OTHER INFORMATION: Heli A2.01_146

<400> SEQUENCE: 588

Lys Leu Ser Tyr Gly Ile Ala Thr Val
1               5

<210> SEQ ID NO 589
<211> LENGTH: 9
<212> TYPE: PRT
<213> ORGANISM: CoV-2
<220> FEATURE:
<223> OTHER INFORMATION: Heli A2.01_157

<400> SEQUENCE: 589

Val Leu Ser Asp Arg Glu Leu His Leu
1               5

<210> SEQ ID NO 590
<211> LENGTH: 9
```

```
<212> TYPE: PRT
<213> ORGANISM: CoV-2
<220> FEATURE:
<223> OTHER INFORMATION: Heli A2.01_525

<400> SEQUENCE: 590

Ile Leu Gly Leu Pro Thr Gln Thr Val
1               5

<210> SEQ ID NO 591
<211> LENGTH: 9
<212> TYPE: PRT
<213> ORGANISM: CoV-2
<220> FEATURE:
<223> OTHER INFORMATION: Heli A2.01_218

<400> SEQUENCE: 591

Lys Leu Asn Val Gly Asp Tyr Phe Val
1               5

<210> SEQ ID NO 592
<211> LENGTH: 9
<212> TYPE: PRT
<213> ORGANISM: CoV-2
<220> FEATURE:
<223> OTHER INFORMATION: Heli A2.01_41

<400> SEQUENCE: 592

Leu Val Leu Ser Val Asn Pro Tyr Val
1               5

<210> SEQ ID NO 593
<211> LENGTH: 9
<212> TYPE: PRT
<213> ORGANISM: CoV-2
<220> FEATURE:
<223> OTHER INFORMATION: Heli A2.01_520

<400> SEQUENCE: 593

Ala Val Ala Ser Lys Ile Leu Gly Leu
1               5

<210> SEQ ID NO 594
<211> LENGTH: 9
<212> TYPE: PRT
<213> ORGANISM: CoV-2
<220> FEATURE:
<223> OTHER INFORMATION: Heli A2.01_448

<400> SEQUENCE: 594

Ile Val Asp Thr Val Ser Ala Leu Val
1               5

<210> SEQ ID NO 595
<211> LENGTH: 9
<212> TYPE: PRT
<213> ORGANISM: CoV-2
<220> FEATURE:
<223> OTHER INFORMATION: Heli A2.01_371

<400> SEQUENCE: 595

Val Val Phe Asp Glu Ile Ser Met Ala
1               5

<210> SEQ ID NO 596
<211> LENGTH: 9
<212> TYPE: PRT
```

```
<213> ORGANISM: CoV-2
<220> FEATURE:
<223> OTHER INFORMATION: Heli A2.01_296

<400> SEQUENCE: 596

Ala Leu Tyr Tyr Pro Ser Ala Arg Ile
1               5

<210> SEQ ID NO 597
<211> LENGTH: 9
<212> TYPE: PRT
<213> ORGANISM: CoV-2
<220> FEATURE:
<223> OTHER INFORMATION: Heli A2.01_248

<400> SEQUENCE: 597

Arg Ile Thr Gly Leu Tyr Pro Thr Leu
1               5

<210> SEQ ID NO 598
<211> LENGTH: 9
<212> TYPE: PRT
<213> ORGANISM: CoV-2
<220> FEATURE:
<223> OTHER INFORMATION: Heli A2.01_294

<400> SEQUENCE: 598

Gly Leu Ala Leu Tyr Tyr Pro Ser Ala
1               5

<210> SEQ ID NO 599
<211> LENGTH: 9
<212> TYPE: PRT
<213> ORGANISM: CoV-2
<220> FEATURE:
<223> OTHER INFORMATION: Heli A2.01_403

<400> SEQUENCE: 599

Ala Gln Leu Pro Ala Pro Arg Thr Leu
1               5

<210> SEQ ID NO 600
<211> LENGTH: 9
<212> TYPE: PRT
<213> ORGANISM: CoV-2
<220> FEATURE:
<223> OTHER INFORMATION: Heli A2.01_584

<400> SEQUENCE: 600

Lys Leu Gln Phe Thr Ser Leu Glu Ile
1               5

<210> SEQ ID NO 601
<211> LENGTH: 9
<212> TYPE: PRT
<213> ORGANISM: CoV-2
<220> FEATURE:
<223> OTHER INFORMATION: Heli A2.01_232

<400> SEQUENCE: 601

Val Met Pro Leu Ser Ala Pro Thr Leu
1               5

<210> SEQ ID NO 602
<211> LENGTH: 9
<212> TYPE: PRT
<213> ORGANISM: CoV-2
```

```
<220> FEATURE:
<223> OTHER INFORMATION: Heli A2.01_6

<400> SEQUENCE: 602

Val Leu Cys Asn Ser Gln Thr Ser Leu
1               5

<210> SEQ ID NO 603
<211> LENGTH: 9
<212> TYPE: PRT
<213> ORGANISM: CoV-2
<220> FEATURE:
<223> OTHER INFORMATION: Heli A2.01_362

<400> SEQUENCE: 603

Ala Leu Pro Glu Thr Thr Ala Asp Ile
1               5

<210> SEQ ID NO 604
<211> LENGTH: 9
<212> TYPE: PRT
<213> ORGANISM: CoV-2
<220> FEATURE:
<223> OTHER INFORMATION: Heli A2.01_33

<400> SEQUENCE: 604

His Val Ile Ser Thr Ser His Lys Leu
1               5

<210> SEQ ID NO 605
<211> LENGTH: 9
<212> TYPE: PRT
<213> ORGANISM: CoV-2
<220> FEATURE:
<223> OTHER INFORMATION: Heli A2.01_258

<400> SEQUENCE: 605

Ile Ser Asp Glu Phe Ser Ser Asn Val
1               5

<210> SEQ ID NO 606
<211> LENGTH: 9
<212> TYPE: PRT
<213> ORGANISM: CoV-2
<220> FEATURE:
<223> OTHER INFORMATION: Heli A2.01_430

<400> SEQUENCE: 606

Lys Thr Ile Gly Pro Asp Met Phe Leu
1               5

<210> SEQ ID NO 607
<211> LENGTH: 9
<212> TYPE: PRT
<213> ORGANISM: CoV-2
<220> FEATURE:
<223> OTHER INFORMATION: Heli A2.01_487

<400> SEQUENCE: 607

Ala Ile Asn Arg Pro Gln Ile Gly Val
1               5

<210> SEQ ID NO 608
<211> LENGTH: 9
<212> TYPE: PRT
<213> ORGANISM: CoV-2
<220> FEATURE:
```

-continued

<223> OTHER INFORMATION: Heli A2.01_332

<400> SEQUENCE: 608

Arg Ile Ile Pro Ala Arg Ala Arg Val
1               5

<210> SEQ ID NO 609
<211> LENGTH: 9
<212> TYPE: PRT
<213> ORGANISM: CoV-2
<220> FEATURE:
<223> OTHER INFORMATION: Heli A3.01_131

<400> SEQUENCE: 609

Lys Leu Phe Ala Ala Glu Thr Leu Lys
1               5

<210> SEQ ID NO 610
<211> LENGTH: 9
<212> TYPE: PRT
<213> ORGANISM: CoV-2
<220> FEATURE:
<223> OTHER INFORMATION: Heli A3.01_209

<400> SEQUENCE: 610

Val Val Tyr Arg Gly Thr Thr Thr Tyr
1               5

<210> SEQ ID NO 611
<211> LENGTH: 9
<212> TYPE: PRT
<213> ORGANISM: CoV-2
<220> FEATURE:
<223> OTHER INFORMATION: Heli A3.01_386

<400> SEQUENCE: 611

Val Val Asn Ala Arg Leu Arg Ala Lys
1               5

<210> SEQ ID NO 612
<211> LENGTH: 9
<212> TYPE: PRT
<213> ORGANISM: CoV-2
<220> FEATURE:
<223> OTHER INFORMATION: Heli A3.01_321

<400> SEQUENCE: 612

Ala Leu Lys Tyr Leu Pro Ile Asp Lys
1               5

<210> SEQ ID NO 613
<211> LENGTH: 9
<212> TYPE: PRT
<213> ORGANISM: CoV-2
<220> FEATURE:
<223> OTHER INFORMATION: Heli A3.01_62

<400> SEQUENCE: 613

Gln Leu Tyr Leu Gly Gly Met Ser Tyr
1               5

<210> SEQ ID NO 614
<211> LENGTH: 9
<212> TYPE: PRT
<213> ORGANISM: CoV-2
<220> FEATURE:
<223> OTHER INFORMATION: Heli A3.01_347

```
<400> SEQUENCE: 614

Lys Val Asn Ser Thr Leu Glu Gln Tyr
1               5

<210> SEQ ID NO 615
<211> LENGTH: 9
<212> TYPE: PRT
<213> ORGANISM: CoV-2
<220> FEATURE:
<223> OTHER INFORMATION: Heli A3.01_500

<400> SEQUENCE: 615

Leu Thr Arg Asn Pro Ala Trp Arg Lys
1               5

<210> SEQ ID NO 616
<211> LENGTH: 9
<212> TYPE: PRT
<213> ORGANISM: CoV-2
<220> FEATURE:
<223> OTHER INFORMATION: Heli A3.01_316

<400> SEQUENCE: 616

Ala Leu Cys Glu Lys Ala Leu Lys Tyr
1               5

<210> SEQ ID NO 617
<211> LENGTH: 9
<212> TYPE: PRT
<213> ORGANISM: CoV-2
<220> FEATURE:
<223> OTHER INFORMATION: Heli A3.01_469

<400> SEQUENCE: 617

Ala Gln Cys Phe Lys Met Phe Tyr Lys
1               5

<210> SEQ ID NO 618
<211> LENGTH: 9
<212> TYPE: PRT
<213> ORGANISM: CoV-2
<220> FEATURE:
<223> OTHER INFORMATION: Heli A3.01_280

<400> SEQUENCE: 618

Leu Gln Gly Pro Pro Gly Thr Gly Lys
1               5

<210> SEQ ID NO 619
<211> LENGTH: 9
<212> TYPE: PRT
<213> ORGANISM: CoV-2
<220> FEATURE:
<223> OTHER INFORMATION: Heli A3.01_68

<400> SEQUENCE: 619

Met Ser Tyr Tyr Cys Lys Ser His Lys
1               5

<210> SEQ ID NO 620
<211> LENGTH: 9
<212> TYPE: PRT
<213> ORGANISM: CoV-2
<220> FEATURE:
<223> OTHER INFORMATION: Heli A3.01_194
```

```
<400> SEQUENCE: 620

Gln Ile Gly Glu Tyr Thr Phe Glu Lys
1               5

<210> SEQ ID NO 621
<211> LENGTH: 9
<212> TYPE: PRT
<213> ORGANISM: CoV-2
<220> FEATURE:
<223> OTHER INFORMATION: Heli A3.01_390

<400> SEQUENCE: 621

Arg Leu Arg Ala Lys His Tyr Val Tyr
1               5

<210> SEQ ID NO 622
<211> LENGTH: 9
<212> TYPE: PRT
<213> ORGANISM: CoV-2
<220> FEATURE:
<223> OTHER INFORMATION: Heli A3.01_263

<400> SEQUENCE: 622

Ser Ser Asn Val Ala Asn Tyr Gln Lys
1               5

<210> SEQ ID NO 623
<211> LENGTH: 9
<212> TYPE: PRT
<213> ORGANISM: CoV-2
<220> FEATURE:
<223> OTHER INFORMATION: Heli A3.01_454

<400> SEQUENCE: 623

Ala Leu Val Tyr Asp Asn Lys Leu Lys
1               5

<210> SEQ ID NO 624
<211> LENGTH: 9
<212> TYPE: PRT
<213> ORGANISM: CoV-2
<220> FEATURE:
<223> OTHER INFORMATION: Heli A3.01_147

<400> SEQUENCE: 624

Leu Ser Tyr Gly Ile Ala Thr Val Arg
1               5

<210> SEQ ID NO 625
<211> LENGTH: 9
<212> TYPE: PRT
<213> ORGANISM: CoV-2
<220> FEATURE:
<223> OTHER INFORMATION: Heli A24.02_397

<400> SEQUENCE: 625

Val Tyr Ile Gly Asp Pro Ala Gln Leu
1               5

<210> SEQ ID NO 626
<211> LENGTH: 9
<212> TYPE: PRT
<213> ORGANISM: CoV-2
<220> FEATURE:
<223> OTHER INFORMATION: Heli A24.02_420

<400> SEQUENCE: 626
```

Glu Tyr Phe Asn Ser Val Cys Arg Leu
1               5

<210> SEQ ID NO 627
<211> LENGTH: 9
<212> TYPE: PRT
<213> ORGANISM: CoV-2
<220> FEATURE:
<223> OTHER INFORMATION: Heli A24.02_298

<400> SEQUENCE: 627

Tyr Tyr Pro Ser Ala Arg Ile Val Tyr
1               5

<210> SEQ ID NO 628
<211> LENGTH: 9
<212> TYPE: PRT
<213> ORGANISM: CoV-2
<220> FEATURE:
<223> OTHER INFORMATION: Heli A24.02_297

<400> SEQUENCE: 628

Leu Tyr Tyr Pro Ser Ala Arg Ile Val
1               5

<210> SEQ ID NO 629
<211> LENGTH: 9
<212> TYPE: PRT
<213> ORGANISM: CoV-2
<220> FEATURE:
<223> OTHER INFORMATION: Heli A24.02_232

<400> SEQUENCE: 629

Val Met Pro Leu Ser Ala Pro Thr Leu
1               5

<210> SEQ ID NO 630
<211> LENGTH: 9
<212> TYPE: PRT
<213> ORGANISM: CoV-2
<220> FEATURE:
<223> OTHER INFORMATION: Heli A24.02_192

<400> SEQUENCE: 630

Lys Val Gln Ile Gly Glu Tyr Thr Phe
1               5

<210> SEQ ID NO 631
<211> LENGTH: 9
<212> TYPE: PRT
<213> ORGANISM: CoV-2
<220> FEATURE:
<223> OTHER INFORMATION: Heli A24.02_73

<400> SEQUENCE: 631

Lys Ser His Lys Pro Pro Ile Ser Phe
1               5

<210> SEQ ID NO 632
<211> LENGTH: 9
<212> TYPE: PRT
<213> ORGANISM: CoV-2
<220> FEATURE:
<223> OTHER INFORMATION: Heli A24.02_179

<400> SEQUENCE: 632

Asn Tyr Val Phe Thr Gly Tyr Arg Val
1 5

<210> SEQ ID NO 633
<211> LENGTH: 9
<212> TYPE: PRT
<213> ORGANISM: CoV-2
<220> FEATURE:
<223> OTHER INFORMATION: Heli A24.02_63

<400> SEQUENCE: 633

Leu Tyr Leu Gly Gly Met Ser Tyr Tyr
1 5

<210> SEQ ID NO 634
<211> LENGTH: 9
<212> TYPE: PRT
<213> ORGANISM: CoV-2
<220> FEATURE:
<223> OTHER INFORMATION: Heli A24.02_498

<400> SEQUENCE: 634

Glu Phe Leu Thr Arg Asn Pro Ala Trp
1 5

<210> SEQ ID NO 635
<211> LENGTH: 9
<212> TYPE: PRT
<213> ORGANISM: CoV-2
<220> FEATURE:
<223> OTHER INFORMATION: Heli A24.02_224

<400> SEQUENCE: 635

Tyr Phe Val Leu Thr Ser His Thr Val
1 5

<210> SEQ ID NO 636
<211> LENGTH: 9
<212> TYPE: PRT
<213> ORGANISM: CoV-2
<220> FEATURE:
<223> OTHER INFORMATION: Heli A26.01_56

<400> SEQUENCE: 636

Asp Val Thr Asp Val Thr Gln Leu Tyr
1 5

<210> SEQ ID NO 637
<211> LENGTH: 9
<212> TYPE: PRT
<213> ORGANISM: CoV-2
<220> FEATURE:
<223> OTHER INFORMATION: Heli A26.01_447

<400> SEQUENCE: 637

Glu Ile Val Asp Thr Val Ser Ala Leu
1 5

<210> SEQ ID NO 638
<211> LENGTH: 9
<212> TYPE: PRT
<213> ORGANISM: CoV-2
<220> FEATURE:
<223> OTHER INFORMATION: Heli A26.01_365

<400> SEQUENCE: 638

Glu Thr Thr Ala Asp Ile Val Val Phe

```
1               5

<210> SEQ ID NO 639
<211> LENGTH: 9
<212> TYPE: PRT
<213> ORGANISM: CoV-2
<220> FEATURE:
<223> OTHER INFORMATION: Heli A26.01_209

<400> SEQUENCE: 639

Val Val Tyr Arg Gly Thr Thr Thr Tyr
1               5

<210> SEQ ID NO 640
<211> LENGTH: 9
<212> TYPE: PRT
<213> ORGANISM: CoV-2
<220> FEATURE:
<223> OTHER INFORMATION: Heli A26.01_291

<400> SEQUENCE: 640

Phe Ala Ile Gly Leu Ala Leu Tyr Tyr
1               5

<210> SEQ ID NO 641
<211> LENGTH: 9
<212> TYPE: PRT
<213> ORGANISM: CoV-2
<220> FEATURE:
<223> OTHER INFORMATION: Heli A26.01_33

<400> SEQUENCE: 641

His Val Ile Ser Thr Ser His Lys Leu
1               5

<210> SEQ ID NO 642
<211> LENGTH: 9
<212> TYPE: PRT
<213> ORGANISM: CoV-2
<220> FEATURE:
<223> OTHER INFORMATION: Heli A26.01_261

<400> SEQUENCE: 642

Glu Phe Ser Ser Asn Val Ala Asn Tyr
1               5

<210> SEQ ID NO 643
<211> LENGTH: 9
<212> TYPE: PRT
<213> ORGANISM: CoV-2
<220> FEATURE:
<223> OTHER INFORMATION: Heli A26.01_62

<400> SEQUENCE: 643

Gln Leu Tyr Leu Gly Gly Met Ser Tyr
1               5

<210> SEQ ID NO 644
<211> LENGTH: 9
<212> TYPE: PRT
<213> ORGANISM: CoV-2
<220> FEATURE:
<223> OTHER INFORMATION: Heli A26.01_347

<400> SEQUENCE: 644

Lys Val Asn Ser Thr Leu Glu Gln Tyr
1               5
```

```
<210> SEQ ID NO 645
<211> LENGTH: 9
<212> TYPE: PRT
<213> ORGANISM: CoV-2
<220> FEATURE:
<223> OTHER INFORMATION: Heli A26.01_190

<400> SEQUENCE: 645

Asn Ser Lys Val Gln Ile Gly Glu Tyr
1               5

<210> SEQ ID NO 646
<211> LENGTH: 9
<212> TYPE: PRT
<213> ORGANISM: CoV-2
<220> FEATURE:
<223> OTHER INFORMATION: Heli A26.01_143

<400> SEQUENCE: 646

Glu Thr Phe Lys Leu Ser Tyr Gly Ile
1               5

<210> SEQ ID NO 647
<211> LENGTH: 9
<212> TYPE: PRT
<213> ORGANISM: CoV-2
<220> FEATURE:
<223> OTHER INFORMATION: Heli A26.01_269

<400> SEQUENCE: 647

Tyr Gln Lys Val Gly Met Gln Lys Tyr
1               5

<210> SEQ ID NO 648
<211> LENGTH: 9
<212> TYPE: PRT
<213> ORGANISM: CoV-2
<220> FEATURE:
<223> OTHER INFORMATION: Heli A26.01_290

<400> SEQUENCE: 648

His Phe Ala Ile Gly Leu Ala Leu Tyr
1               5

<210> SEQ ID NO 649
<211> LENGTH: 9
<212> TYPE: PRT
<213> ORGANISM: CoV-2
<220> FEATURE:
<223> OTHER INFORMATION: Heli B7.02_592

<400> SEQUENCE: 649

Ile Pro Arg Arg Asn Val Ala Thr Leu
1               5

<210> SEQ ID NO 650
<211> LENGTH: 9
<212> TYPE: PRT
<213> ORGANISM: CoV-2
<220> FEATURE:
<223> OTHER INFORMATION: Heli B7.02_513

<400> SEQUENCE: 650

Ser Pro Tyr Asn Ser Gln Asn Ala Val
1               5
```

<210> SEQ ID NO 651
<211> LENGTH: 9
<212> TYPE: PRT
<213> ORGANISM: CoV-2
<220> FEATURE:
<223> OTHER INFORMATION: Heli B7.02_503

<400> SEQUENCE: 651

Asn Pro Ala Trp Arg Lys Ala Val Phe
1               5

<210> SEQ ID NO 652
<211> LENGTH: 9
<212> TYPE: PRT
<213> ORGANISM: CoV-2
<220> FEATURE:
<223> OTHER INFORMATION: Heli B7.02_334

<400> SEQUENCE: 652

Ile Pro Ala Arg Ala Arg Val Glu Cys
1               5

<210> SEQ ID NO 653
<211> LENGTH: 9
<212> TYPE: PRT
<213> ORGANISM: CoV-2
<220> FEATURE:
<223> OTHER INFORMATION: Heli B7.02_173

<400> SEQUENCE: 653

Arg Pro Pro Leu Asn Arg Asn Tyr Val
1               5

<210> SEQ ID NO 654
<211> LENGTH: 9
<212> TYPE: PRT
<213> ORGANISM: CoV-2
<220> FEATURE:
<223> OTHER INFORMATION: Heli B7.02_241

<400> SEQUENCE: 654

Val Pro Gln Glu His Tyr Val Arg Ile
1               5

<210> SEQ ID NO 655
<211> LENGTH: 9
<212> TYPE: PRT
<213> ORGANISM: CoV-2
<220> FEATURE:
<223> OTHER INFORMATION: Heli B7.02_233

<400> SEQUENCE: 655

Met Pro Leu Ser Ala Pro Thr Leu Val
1               5

<210> SEQ ID NO 656
<211> LENGTH: 9
<212> TYPE: PRT
<213> ORGANISM: CoV-2
<220> FEATURE:
<223> OTHER INFORMATION: Heli B7.02_405

<400> SEQUENCE: 656

Leu Pro Ala Pro Arg Thr Leu Leu Thr
1               5

```
<210> SEQ ID NO 657
<211> LENGTH: 9
<212> TYPE: PRT
<213> ORGANISM: CoV-2
<220> FEATURE:
<223> OTHER INFORMATION: Heli B7.02_168

<400> SEQUENCE: 657

Glu Val Gly Lys Pro Arg Pro Pro Leu
1               5

<210> SEQ ID NO 658
<211> LENGTH: 9
<212> TYPE: PRT
<213> ORGANISM: CoV-2
<220> FEATURE:
<223> OTHER INFORMATION: Heli B7.02_73

<400> SEQUENCE: 658

Lys Ser His Lys Pro Pro Ile Ser Phe
1               5

<210> SEQ ID NO 659
<211> LENGTH: 9
<212> TYPE: PRT
<213> ORGANISM: CoV-2
<220> FEATURE:
<223> OTHER INFORMATION: Heli B7.02_325

<400> SEQUENCE: 659

Leu Pro Ile Asp Lys Cys Ser Arg Ile
1               5

<210> SEQ ID NO 660
<211> LENGTH: 9
<212> TYPE: PRT
<213> ORGANISM: CoV-2
<220> FEATURE:
<223> OTHER INFORMATION: Heli B7.02_407

<400> SEQUENCE: 660

Ala Pro Arg Thr Leu Leu Thr Lys Gly
1               5

<210> SEQ ID NO 661
<211> LENGTH: 9
<212> TYPE: PRT
<213> ORGANISM: CoV-2
<220> FEATURE:
<223> OTHER INFORMATION: Heli B15.01_269

<400> SEQUENCE: 661

Tyr Gln Lys Val Gly Met Gln Lys Tyr
1               5

<210> SEQ ID NO 662
<211> LENGTH: 9
<212> TYPE: PRT
<213> ORGANISM: CoV-2
<220> FEATURE:
<223> OTHER INFORMATION: Heli B15.01_209

<400> SEQUENCE: 662

Val Val Tyr Arg Gly Thr Thr Thr Tyr
1               5

<210> SEQ ID NO 663
```

```
<211> LENGTH: 9
<212> TYPE: PRT
<213> ORGANISM: CoV-2
<220> FEATURE:
<223> OTHER INFORMATION: Heli B15.01_62

<400> SEQUENCE: 663

Gln Leu Tyr Leu Gly Gly Met Ser Tyr
1               5

<210> SEQ ID NO 664
<211> LENGTH: 9
<212> TYPE: PRT
<213> ORGANISM: CoV-2
<220> FEATURE:
<223> OTHER INFORMATION: Heli B15.01_347

<400> SEQUENCE: 664

Lys Val Asn Ser Thr Leu Glu Gln Tyr
1               5

<210> SEQ ID NO 665
<211> LENGTH: 9
<212> TYPE: PRT
<213> ORGANISM: CoV-2
<220> FEATURE:
<223> OTHER INFORMATION: Heli B15.01_137

<400> SEQUENCE: 665

Thr Leu Lys Ala Thr Glu Glu Thr Phe
1               5

<210> SEQ ID NO 666
<211> LENGTH: 9
<212> TYPE: PRT
<213> ORGANISM: CoV-2
<220> FEATURE:
<223> OTHER INFORMATION: Heli B15.01_390

<400> SEQUENCE: 666

Arg Leu Arg Ala Lys His Tyr Val Tyr
1               5

<210> SEQ ID NO 667
<211> LENGTH: 9
<212> TYPE: PRT
<213> ORGANISM: CoV-2
<220> FEATURE:
<223> OTHER INFORMATION: Heli B15.01_73

<400> SEQUENCE: 667

Lys Ser His Lys Pro Pro Ile Ser Phe
1               5

<210> SEQ ID NO 668
<211> LENGTH: 9
<212> TYPE: PRT
<213> ORGANISM: CoV-2
<220> FEATURE:
<223> OTHER INFORMATION: Heli B15.01_403

<400> SEQUENCE: 668

Ala Gln Leu Pro Ala Pro Arg Thr Leu
1               5

<210> SEQ ID NO 669
<211> LENGTH: 9
```

-continued

```
<212> TYPE: PRT
<213> ORGANISM: CoV-2
<220> FEATURE:
<223> OTHER INFORMATION: Heli B15.01_40

<400> SEQUENCE: 669

Lys Leu Val Leu Ser Val Asn Pro Tyr
1               5

<210> SEQ ID NO 670
<211> LENGTH: 9
<212> TYPE: PRT
<213> ORGANISM: CoV-2
<220> FEATURE:
<223> OTHER INFORMATION: Heli B15.01_316

<400> SEQUENCE: 670

Ala Leu Cys Glu Lys Ala Leu Lys Tyr
1               5

<210> SEQ ID NO 671
<211> LENGTH: 9
<212> TYPE: PRT
<213> ORGANISM: CoV-2
<220> FEATURE:
<223> OTHER INFORMATION: Heli B15.01_491

<400> SEQUENCE: 671

Pro Gln Ile Gly Val Val Arg Glu Phe
1               5

<210> SEQ ID NO 672
<211> LENGTH: 9
<212> TYPE: PRT
<213> ORGANISM: CoV-2
<220> FEATURE:
<223> OTHER INFORMATION: Heli B15.01_291

<400> SEQUENCE: 672

Phe Ala Ile Gly Leu Ala Leu Tyr Tyr
1               5

<210> SEQ ID NO 673
<211> LENGTH: 9
<212> TYPE: PRT
<213> ORGANISM: CoV-2
<220> FEATURE:
<223> OTHER INFORMATION: Heli B15.01_192

<400> SEQUENCE: 673

Lys Val Gln Ile Gly Glu Tyr Thr Phe
1               5

<210> SEQ ID NO 674
<211> LENGTH: 9
<212> TYPE: PRT
<213> ORGANISM: CoV-2
<220> FEATURE:
<223> OTHER INFORMATION: Heli B15.01_190

<400> SEQUENCE: 674

Asn Ser Lys Val Gln Ile Gly Glu Tyr
1               5

<210> SEQ ID NO 675
<211> LENGTH: 9
<212> TYPE: PRT
```

-continued

<213> ORGANISM: CoV-2
<220> FEATURE:
<223> OTHER INFORMATION: Heli B15.01_428

<400> SEQUENCE: 675

Leu Met Lys Thr Ile Gly Pro Asp Met
1               5

<210> SEQ ID NO 676
<211> LENGTH: 9
<212> TYPE: PRT
<213> ORGANISM: CoV-2
<220> FEATURE:
<223> OTHER INFORMATION: Heli B15.01_517

<400> SEQUENCE: 676

Ser Gln Asn Ala Val Ala Ser Lys Ile
1               5

<210> SEQ ID NO 677
<211> LENGTH: 9
<212> TYPE: PRT
<213> ORGANISM: CoV-2
<220> FEATURE:
<223> OTHER INFORMATION: Heli B15.01_225

<400> SEQUENCE: 677

Phe Val Leu Thr Ser His Thr Val Met
1               5

<210> SEQ ID NO 678
<211> LENGTH: 9
<212> TYPE: PRT
<213> ORGANISM: CoV-2
<220> FEATURE:
<223> OTHER INFORMATION: Heli B15.01_33

<400> SEQUENCE: 678

His Val Ile Ser Thr Ser His Lys Leu
1               5

<210> SEQ ID NO 679
<211> LENGTH: 9
<212> TYPE: PRT
<213> ORGANISM: CoV-2
<220> FEATURE:
<223> OTHER INFORMATION: Heli B15.01_507

<400> SEQUENCE: 679

Arg Lys Ala Val Phe Ile Ser Pro Tyr
1               5

<210> SEQ ID NO 680
<211> LENGTH: 9
<212> TYPE: PRT
<213> ORGANISM: CoV-2
<220> FEATURE:
<223> OTHER INFORMATION: Heli B40.01_155

<400> SEQUENCE: 680

Arg Glu Val Leu Ser Asp Arg Glu Leu
1               5

<210> SEQ ID NO 681
<211> LENGTH: 9
<212> TYPE: PRT
<213> ORGANISM: CoV-2

```
<220> FEATURE:
<223> OTHER INFORMATION: Heli B40.01_161

<400> SEQUENCE: 681

Arg Glu Leu His Leu Ser Trp Glu Val
1               5

<210> SEQ ID NO 682
<211> LENGTH: 9
<212> TYPE: PRT
<213> ORGANISM: CoV-2
<220> FEATURE:
<223> OTHER INFORMATION: Heli B40.01_403

<400> SEQUENCE: 682

Ala Gln Leu Pro Ala Pro Arg Thr Leu
1               5

<210> SEQ ID NO 683
<211> LENGTH: 9
<212> TYPE: PRT
<213> ORGANISM: CoV-2
<220> FEATURE:
<223> OTHER INFORMATION: Heli B40.01_446

<400> SEQUENCE: 683

Ala Glu Ile Val Asp Thr Val Ser Ala
1               5

<210> SEQ ID NO 684
<211> LENGTH: 9
<212> TYPE: PRT
<213> ORGANISM: CoV-2
<220> FEATURE:
<223> OTHER INFORMATION: Heli B40.01_417

<400> SEQUENCE: 684

Leu Glu Pro Glu Tyr Phe Asn Ser Val
1               5

<210> SEQ ID NO 685
<211> LENGTH: 9
<212> TYPE: PRT
<213> ORGANISM: CoV-2
<220> FEATURE:
<223> OTHER INFORMATION: Heli B40.01_539

<400> SEQUENCE: 685

Ser Glu Tyr Asp Tyr Val Ile Phe Thr
1               5

<210> SEQ ID NO 686
<211> LENGTH: 9
<212> TYPE: PRT
<213> ORGANISM: CoV-2
<220> FEATURE:
<223> OTHER INFORMATION: Heli B58.01_73

<400> SEQUENCE: 686

Lys Ser His Lys Pro Pro Ile Ser Phe
1               5

<210> SEQ ID NO 687
<211> LENGTH: 9
<212> TYPE: PRT
<213> ORGANISM: CoV-2
<220> FEATURE:
```

```
<223> OTHER INFORMATION: Heli B58.01_467

<400> SEQUENCE: 687

Lys Ser Ala Gln Cys Phe Lys Met Phe
1               5

<210> SEQ ID NO 688
<211> LENGTH: 9
<212> TYPE: PRT
<213> ORGANISM: CoV-2
<220> FEATURE:
<223> OTHER INFORMATION: Heli B58.01_347

<400> SEQUENCE: 688

Lys Val Asn Ser Thr Leu Glu Gln Tyr
1               5

<210> SEQ ID NO 689
<211> LENGTH: 9
<212> TYPE: PRT
<213> ORGANISM: CoV-2
<220> FEATURE:
<223> OTHER INFORMATION: Heli B58.01_192

<400> SEQUENCE: 689

Lys Val Gln Ile Gly Glu Tyr Thr Phe
1               5

<210> SEQ ID NO 690
<211> LENGTH: 9
<212> TYPE: PRT
<213> ORGANISM: CoV-2
<220> FEATURE:
<223> OTHER INFORMATION: Heli B58.01_430

<400> SEQUENCE: 690

Lys Thr Ile Gly Pro Asp Met Phe Leu
1               5

<210> SEQ ID NO 691
<211> LENGTH: 9
<212> TYPE: PRT
<213> ORGANISM: CoV-2
<220> FEATURE:
<223> OTHER INFORMATION: Heli B58.01_139

<400> SEQUENCE: 691

Lys Ala Thr Glu Glu Thr Phe Lys Leu
1               5

<210> SEQ ID NO 692
<211> LENGTH: 9
<212> TYPE: PRT
<213> ORGANISM: CoV-2
<220> FEATURE:
<223> OTHER INFORMATION: Heli B58.01_209

<400> SEQUENCE: 692

Val Val Tyr Arg Gly Thr Thr Thr Tyr
1               5

<210> SEQ ID NO 693
<211> LENGTH: 9
<212> TYPE: PRT
<213> ORGANISM: CoV-2
<220> FEATURE:
<223> OTHER INFORMATION: Heli B58.01_291
```

<400> SEQUENCE: 693

Phe Ala Ile Gly Leu Ala Leu Tyr Tyr
1               5

<210> SEQ ID NO 694
<211> LENGTH: 9
<212> TYPE: PRT
<213> ORGANISM: CoV-2
<220> FEATURE:
<223> OTHER INFORMATION: Heli B58.01_57

<400> SEQUENCE: 694

Val Thr Asp Val Thr Gln Leu Tyr Leu
1               5

<210> SEQ ID NO 695
<211> LENGTH: 9
<212> TYPE: PRT
<213> ORGANISM: CoV-2
<220> FEATURE:
<223> OTHER INFORMATION: Heli B58.01_159

<400> SEQUENCE: 695

Ser Asp Arg Glu Leu His Leu Ser Trp
1               5

<210> SEQ ID NO 696
<211> LENGTH: 9
<212> TYPE: PRT
<213> ORGANISM: CoV-2
<220> FEATURE:
<223> OTHER INFORMATION: Heli B58.01_35

<400> SEQUENCE: 696

Ile Ser Thr Ser His Lys Leu Val Leu
1               5

<210> SEQ ID NO 697
<211> LENGTH: 9
<212> TYPE: PRT
<213> ORGANISM: CoV-2
<220> FEATURE:
<223> OTHER INFORMATION: Heli B58.01_349

<400> SEQUENCE: 697

Asn Ser Thr Leu Glu Gln Tyr Val Phe
1               5

<210> SEQ ID NO 698
<211> LENGTH: 9
<212> TYPE: PRT
<213> ORGANISM: CoV-2
<220> FEATURE:
<223> OTHER INFORMATION: Heli B58.01_365

<400> SEQUENCE: 698

Glu Thr Thr Ala Asp Ile Val Val Phe
1               5

<210> SEQ ID NO 699
<211> LENGTH: 9
<212> TYPE: PRT
<213> ORGANISM: CoV-2
<220> FEATURE:
<223> OTHER INFORMATION: Heli B58.01_414

```
<400> SEQUENCE: 699

Lys Gly Thr Leu Glu Pro Glu Tyr Phe
1               5

<210> SEQ ID NO 700
<211> LENGTH: 9
<212> TYPE: PRT
<213> ORGANISM: CoV-2
<220> FEATURE:
<223> OTHER INFORMATION: ExNuc A1.01_343

<400> SEQUENCE: 700

Gln Ala Asp Val Glu Trp Lys Phe Tyr
1               5

<210> SEQ ID NO 701
<211> LENGTH: 9
<212> TYPE: PRT
<213> ORGANISM: CoV-2
<220> FEATURE:
<223> OTHER INFORMATION: ExNuc A1.01_362

<400> SEQUENCE: 701

Lys Ile Glu Glu Leu Phe Tyr Ser Tyr
1               5

<210> SEQ ID NO 702
<211> LENGTH: 9
<212> TYPE: PRT
<213> ORGANISM: CoV-2
<220> FEATURE:
<223> OTHER INFORMATION: ExNuc A1.01_252

<400> SEQUENCE: 702

Asn Leu Gln Ser Asn His Asp Leu Tyr
1               5

<210> SEQ ID NO 703
<211> LENGTH: 9
<212> TYPE: PRT
<213> ORGANISM: CoV-2
<220> FEATURE:
<223> OTHER INFORMATION: ExNuc A1.01_447

<400> SEQUENCE: 703

Tyr Ser Asp Ser Pro Cys Glu Ser His
1               5

<210> SEQ ID NO 704
<211> LENGTH: 9
<212> TYPE: PRT
<213> ORGANISM: CoV-2
<220> FEATURE:
<223> OTHER INFORMATION: ExNuc A1.01_229

<400> SEQUENCE: 704

His Ser Ile Gly Phe Asp Tyr Val Tyr
1               5

<210> SEQ ID NO 705
<211> LENGTH: 9
<212> TYPE: PRT
<213> ORGANISM: CoV-2
<220> FEATURE:
<223> OTHER INFORMATION: ExNuc A1.01_322

<400> SEQUENCE: 705
```

```
Leu Ala Asp Lys Phe Pro Val Leu His
1               5

<210> SEQ ID NO 706
<211> LENGTH: 9
<212> TYPE: PRT
<213> ORGANISM: CoV-2
<220> FEATURE:
<223> OTHER INFORMATION: ExNuc A1.01_377

<400> SEQUENCE: 706

Phe Thr Asp Gly Val Cys Leu Phe Trp
1               5

<210> SEQ ID NO 707
<211> LENGTH: 9
<212> TYPE: PRT
<213> ORGANISM: CoV-2
<220> FEATURE:
<223> OTHER INFORMATION: ExNuc A1.01_509

<400> SEQUENCE: 707

Trp Val Tyr Lys Gln Phe Asp Thr Tyr
1               5

<210> SEQ ID NO 708
<211> LENGTH: 9
<212> TYPE: PRT
<213> ORGANISM: CoV-2
<220> FEATURE:
<223> OTHER INFORMATION: ExNuc A1.01_373

<400> SEQUENCE: 708

His Ser Asp Lys Phe Thr Asp Gly Val
1               5

<210> SEQ ID NO 709
<211> LENGTH: 9
<212> TYPE: PRT
<213> ORGANISM: CoV-2
<220> FEATURE:
<223> OTHER INFORMATION: ExNuc A1.01_241

<400> SEQUENCE: 709

Met Ile Asp Val Gln Gln Trp Gly Phe
1               5

<210> SEQ ID NO 710
<211> LENGTH: 9
<212> TYPE: PRT
<213> ORGANISM: CoV-2
<220> FEATURE:
<223> OTHER INFORMATION: ExNuc A1.01_438

<400> SEQUENCE: 710

Asn Leu Lys Gln Leu Pro Phe Phe Tyr
1               5

<210> SEQ ID NO 711
<211> LENGTH: 9
<212> TYPE: PRT
<213> ORGANISM: CoV-2
<220> FEATURE:
<223> OTHER INFORMATION: ExNuc A1.01_503

<400> SEQUENCE: 711
```

```
Ser Ala Gly Phe Ser Leu Trp Val Tyr
1               5
```

<210> SEQ ID NO 712
<211> LENGTH: 9
<212> TYPE: PRT
<213> ORGANISM: CoV-2
<220> FEATURE:
<223> OTHER INFORMATION: ExNuc A2.01_321

<400> SEQUENCE: 712

```
Leu Leu Ala Asp Lys Phe Pro Val Leu
1               5
```

<210> SEQ ID NO 713
<211> LENGTH: 9
<212> TYPE: PRT
<213> ORGANISM: CoV-2
<220> FEATURE:
<223> OTHER INFORMATION: ExNuc A2.01_176

<400> SEQUENCE: 713

```
Asn Leu Ser Asp Arg Val Val Phe Val
1               5
```

<210> SEQ ID NO 714
<211> LENGTH: 9
<212> TYPE: PRT
<213> ORGANISM: CoV-2
<220> FEATURE:
<223> OTHER INFORMATION: ExNuc A2.01_184

<400> SEQUENCE: 714

```
Val Leu Trp Ala His Gly Phe Glu Leu
1               5
```

<210> SEQ ID NO 715
<211> LENGTH: 9
<212> TYPE: PRT
<213> ORGANISM: CoV-2
<220> FEATURE:
<223> OTHER INFORMATION: ExNuc A2.01_494

<400> SEQUENCE: 715

```
Tyr Leu Asp Ala Tyr Asn Met Met Ile
1               5
```

<210> SEQ ID NO 716
<211> LENGTH: 9
<212> TYPE: PRT
<213> ORGANISM: CoV-2
<220> FEATURE:
<223> OTHER INFORMATION: ExNuc A2.01_169

<400> SEQUENCE: 716

```
Met Leu Ser Asp Thr Leu Lys Asn Leu
1               5
```

<210> SEQ ID NO 717
<211> LENGTH: 9
<212> TYPE: PRT
<213> ORGANISM: CoV-2
<220> FEATURE:
<223> OTHER INFORMATION: ExNuc A2.01_320

<400> SEQUENCE: 717

```
Ala Leu Leu Ala Asp Lys Phe Pro Val
```

```
<210> SEQ ID NO 718
<211> LENGTH: 9
<212> TYPE: PRT
<213> ORGANISM: CoV-2
<220> FEATURE:
<223> OTHER INFORMATION: ExNuc A2.01_518

<400> SEQUENCE: 718

Asn Leu Trp Asn Thr Phe Thr Arg Leu
1               5

<210> SEQ ID NO 719
<211> LENGTH: 9
<212> TYPE: PRT
<213> ORGANISM: CoV-2
<220> FEATURE:
<223> OTHER INFORMATION: ExNuc A2.01_6

<400> SEQUENCE: 719

Gly Leu Phe Lys Asp Cys Ser Lys Val
1               5

<210> SEQ ID NO 720
<211> LENGTH: 9
<212> TYPE: PRT
<213> ORGANISM: CoV-2
<220> FEATURE:
<223> OTHER INFORMATION: ExNuc A2.01_500

<400> SEQUENCE: 720

Met Met Ile Ser Ala Gly Phe Ser Leu
1               5

<210> SEQ ID NO 721
<211> LENGTH: 9
<212> TYPE: PRT
<213> ORGANISM: CoV-2
<220> FEATURE:
<223> OTHER INFORMATION: ExNuc A2.01_107

<400> SEQUENCE: 721

Leu Gln Leu Gly Phe Ser Thr Gly Val
1               5

<210> SEQ ID NO 722
<211> LENGTH: 9
<212> TYPE: PRT
<213> ORGANISM: CoV-2
<220> FEATURE:
<223> OTHER INFORMATION: ExNuc A2.01_21

<400> SEQUENCE: 722

Thr Gln Ala Pro Thr His Leu Ser Val
1               5

<210> SEQ ID NO 723
<211> LENGTH: 9
<212> TYPE: PRT
<213> ORGANISM: CoV-2
<220> FEATURE:
<223> OTHER INFORMATION: ExNuc A2.01_156

<400> SEQUENCE: 723

Gly Leu Pro Trp Asn Val Val Arg Ile
1               5
```

```
<210> SEQ ID NO 724
<211> LENGTH: 9
<212> TYPE: PRT
<213> ORGANISM: CoV-2
<220> FEATURE:
<223> OTHER INFORMATION: ExNuc A2.01_37

<400> SEQUENCE: 724

Gly Leu Cys Val Asp Ile Pro Gly Ile
1               5

<210> SEQ ID NO 725
<211> LENGTH: 9
<212> TYPE: PRT
<213> ORGANISM: CoV-2
<220> FEATURE:
<223> OTHER INFORMATION: ExNuc A2.01_492

<400> SEQUENCE: 725

Arg Leu Tyr Leu Asp Ala Tyr Asn Met
1               5

<210> SEQ ID NO 726
<211> LENGTH: 9
<212> TYPE: PRT
<213> ORGANISM: CoV-2
<220> FEATURE:
<223> OTHER INFORMATION: ExNuc A3.01_53

<400> SEQUENCE: 726

Arg Leu Ile Ser Met Met Gly Phe Lys
1               5

<210> SEQ ID NO 727
<211> LENGTH: 9
<212> TYPE: PRT
<213> ORGANISM: CoV-2
<220> FEATURE:
<223> OTHER INFORMATION: ExNuc A3.01_328

<400> SEQUENCE: 727

Val Leu His Asp Ile Gly Asn Pro Lys
1               5

<210> SEQ ID NO 728
<211> LENGTH: 9
<212> TYPE: PRT
<213> ORGANISM: CoV-2
<220> FEATURE:
<223> OTHER INFORMATION: ExNuc A3.01_56

<400> SEQUENCE: 728

Ser Met Met Gly Phe Lys Met Asn Tyr
1               5

<210> SEQ ID NO 729
<211> LENGTH: 9
<212> TYPE: PRT
<213> ORGANISM: CoV-2
<220> FEATURE:
<223> OTHER INFORMATION: ExNuc A3.01_61

<400> SEQUENCE: 729

Lys Met Asn Tyr Gln Val Asn Gly Tyr
1               5
```

<210> SEQ ID NO 730
<211> LENGTH: 9
<212> TYPE: PRT
<213> ORGANISM: CoV-2
<220> FEATURE:
<223> OTHER INFORMATION: ExNuc A3.01_504

<400> SEQUENCE: 730

Ala Gly Phe Ser Leu Trp Val Tyr Lys
1               5

<210> SEQ ID NO 731
<211> LENGTH: 9
<212> TYPE: PRT
<213> ORGANISM: CoV-2
<220> FEATURE:
<223> OTHER INFORMATION: ExNuc A3.01_368

<400> SEQUENCE: 731

Tyr Ser Tyr Ala Thr His Ser Asp Lys
1               5

<210> SEQ ID NO 732
<211> LENGTH: 9
<212> TYPE: PRT
<213> ORGANISM: CoV-2
<220> FEATURE:
<223> OTHER INFORMATION: ExNuc A3.01_281

<400> SEQUENCE: 732

Ala Val His Glu Cys Phe Val Lys Arg
1               5

<210> SEQ ID NO 733
<211> LENGTH: 9
<212> TYPE: PRT
<213> ORGANISM: CoV-2
<220> FEATURE:
<223> OTHER INFORMATION: ExNuc A3.01_26

<400> SEQUENCE: 733

His Leu Ser Val Asp Thr Lys Phe Lys
1               5

<210> SEQ ID NO 734
<211> LENGTH: 9
<212> TYPE: PRT
<213> ORGANISM: CoV-2
<220> FEATURE:
<223> OTHER INFORMATION: ExNuc A3.01_39

<400> SEQUENCE: 734

Cys Val Asp Ile Pro Gly Ile Pro Lys
1               5

<210> SEQ ID NO 735
<211> LENGTH: 9
<212> TYPE: PRT
<213> ORGANISM: CoV-2
<220> FEATURE:
<223> OTHER INFORMATION: ExNuc A3.01_188

<400> SEQUENCE: 735

His Gly Phe Glu Leu Thr Ser Met Lys
1               5

```
<210> SEQ ID NO 736
<211> LENGTH: 9
<212> TYPE: PRT
<213> ORGANISM: CoV-2
<220> FEATURE:
<223> OTHER INFORMATION: ExNuc A3.01_270

<400> SEQUENCE: 736

Ala Ser Cys Asp Ala Ile Met Thr Arg
1               5

<210> SEQ ID NO 737
<211> LENGTH: 9
<212> TYPE: PRT
<213> ORGANISM: CoV-2
<220> FEATURE:
<223> OTHER INFORMATION: ExNuc A3.01_192

<400> SEQUENCE: 737

Leu Thr Ser Met Lys Tyr Phe Val Lys
1               5

<210> SEQ ID NO 738
<211> LENGTH: 9
<212> TYPE: PRT
<213> ORGANISM: CoV-2
<220> FEATURE:
<223> OTHER INFORMATION: ExNuc A24.02_369

<400> SEQUENCE: 738

Ser Tyr Ala Thr His Ser Asp Lys Phe
1               5

<210> SEQ ID NO 739
<211> LENGTH: 9
<212> TYPE: PRT
<213> ORGANISM: CoV-2
<220> FEATURE:
<223> OTHER INFORMATION: ExNuc A24.02_223

<400> SEQUENCE: 739

Thr Tyr Ala Cys Trp His His Ser Ile
1               5

<210> SEQ ID NO 740
<211> LENGTH: 9
<212> TYPE: PRT
<213> ORGANISM: CoV-2
<220> FEATURE:
<223> OTHER INFORMATION: ExNuc A24.02_493

<400> SEQUENCE: 740

Leu Tyr Leu Asp Ala Tyr Asn Met Met
1               5

<210> SEQ ID NO 741
<211> LENGTH: 9
<212> TYPE: PRT
<213> ORGANISM: CoV-2
<220> FEATURE:
<223> OTHER INFORMATION: ExNuc A24.02_376

<400> SEQUENCE: 741

Lys Phe Thr Asp Gly Val Cys Leu Phe
1               5

<210> SEQ ID NO 742
```

```
<211> LENGTH: 9
<212> TYPE: PRT
<213> ORGANISM: CoV-2
<220> FEATURE:
<223> OTHER INFORMATION: ExNuc A

```
<212> TYPE: PRT
<213> ORGANISM: CoV-2
<220> FEATURE:
<223> OTHER INFORMATION: ExNuc A24.02_295

<400> SEQUENCE: 748

Glu Tyr Pro Ile Ile Gly Asp Glu Leu
1               5

<210> SEQ ID NO 749
<211> LENGTH: 9
<212> TYPE: PRT
<213> ORGANISM: CoV-2
<220> FEATURE:
<223> OTHER INFORMATION: ExNuc A24.02_359

<400> SEQUENCE: 749

Lys Ala Tyr Lys Ile Glu Glu Leu Phe
1               5

<210> SEQ ID NO 750
<211> LENGTH: 9
<212> TYPE: PRT
<213> ORGANISM: CoV-2
<220> FEATURE:
<223> OTHER INFORMATION: ExNuc A24.02_50

<400> SEQUENCE: 750

Thr Tyr Arg Arg Leu Ile Ser Met Met
1               5

<210> SEQ ID NO 751
<211> LENGTH: 9
<212> TYPE: PRT
<213> ORGANISM: CoV-2
<220> FEATURE:
<223> OTHER INFORMATION: ExNuc A24.02_423

<400> SEQUENCE: 751

Lys His Ala Phe His Thr Pro Ala Phe
1               5

<210> SEQ ID NO 752
<211> LENGTH: 9
<212> TYPE: PRT
<213> ORGANISM: CoV-2
<220> FEATURE:
<223> OTHER INFORMATION: ExNuc A24.02_418

<400> SEQUENCE: 752

Ser Leu Tyr Val Asn Lys His Ala Phe
1               5

<210> SEQ ID NO 753
<211> LENGTH: 9
<212> TYPE: PRT
<213> ORGANISM: CoV-2
<220> FEATURE:
<223> OTHER INFORMATION: ExNuc A26.01_515

<400> SEQUENCE: 753

Asp Thr Tyr Asn Leu Trp Asn Thr Phe
1               5

<210> SEQ ID NO 754
<211> LENGTH: 9
<212> TYPE: PRT
```

```
<213> ORGANISM: CoV-2
<220> FEATURE:
<223> OTHER INFORMATION: ExNuc A26.01_509

<400> SEQUENCE: 754

Trp Val Tyr Lys Gln Phe Asp Thr Tyr
1               5

<210> SEQ ID NO 755
<211> LENGTH: 9
<212> TYPE: PRT
<213> ORGANISM: CoV-2
<220> FEATURE:
<223> OTHER INFORMATION: ExNuc A26.01_116

<400> SEQUENCE: 755

Asn Leu Val Ala Val Pro Thr Gly Tyr
1               5

<210> SEQ ID NO 756
<211> LENGTH: 9
<212> TYPE: PRT
<213> ORGANISM: CoV-2
<220> FEATURE:
<223> OTHER INFORMATION: ExNuc A26.01_229

<400> SEQUENCE: 756

His Ser Ile Gly Phe Asp Tyr Val Tyr
1               5

<210> SEQ ID NO 757
<211> LENGTH: 9
<212> TYPE: PRT
<213> ORGANISM: CoV-2
<220> FEATURE:
<223> OTHER INFORMATION: ExNuc A26.01_49

<400> SEQUENCE: 757

Met Thr Tyr Arg Arg Leu Ile Ser Met
1               5

<210> SEQ ID NO 758
<211> LENGTH: 9
<212> TYPE: PRT
<213> ORGANISM: CoV-2
<220> FEATURE:
<223> OTHER INFORMATION: ExNuc A26.01_65

<400> SEQUENCE: 758

Gln Val Asn Gly Tyr Pro Asn Met Phe
1               5

<210> SEQ ID NO 759
<211> LENGTH: 9
<212> TYPE: PRT
<213> ORGANISM: CoV-2
<220> FEATURE:
<223> OTHER INFORMATION: ExNuc A26.01_78

<400> SEQUENCE: 759

Glu Ala Ile Arg His Val Arg Ala Trp
1               5

<210> SEQ ID NO 760
<211> LENGTH: 9
<212> TYPE: PRT
<213> ORGANISM: CoV-2
```

```
<220> FEATURE:
<223> OTHER INFORMATION: ExNuc A26.01_56

<400> SEQUENCE: 760

Ser Met Met Gly Phe Lys Met Asn Tyr
1               5

<210> SEQ ID NO 761
<211> LENGTH: 9
<212> TYPE: PRT
<213> ORGANISM: CoV-2
<220> FEATURE:
<223> OTHER INFORMATION: ExNuc A26.01_438

<400> SEQUENCE: 761

Asn Leu Lys Gln Leu Pro Phe Phe Tyr
1               5

<210> SEQ ID NO 762
<211> LENGTH: 9
<212> TYPE: PRT
<213> ORGANISM: CoV-2
<220> FEATURE:
<223> OTHER INFORMATION: ExNuc B07.02_19

<400> SEQUENCE: 762

His Pro Thr Gln Ala Pro Thr His Leu
1               5

<210> SEQ ID NO 763
<211> LENGTH: 9
<212> TYPE: PRT
<213> ORGANISM: CoV-2
<220> FEATURE:
<223> OTHER INFORMATION: ExNuc B07.02_428

<400> SEQUENCE: 763

Thr Pro Ala Phe Asp Lys Ser Ala Phe
1               5

<210> SEQ ID NO 764
<211> LENGTH: 9
<212> TYPE: PRT
<213> ORGANISM: CoV-2
<220> FEATURE:
<223> OTHER INFORMATION: ExNuc B07.02_466

<400> SEQUENCE: 764

Val Pro Leu Lys Ser Ala Thr Cys Ile
1               5

<210> SEQ ID NO 765
<211> LENGTH: 9
<212> TYPE: PRT
<213> ORGANISM: CoV-2
<220> FEATURE:
<223> OTHER INFORMATION: ExNuc B07.02_487

<400> SEQUENCE: 765

His Ala Asn Glu Tyr Arg Leu Tyr Leu
1               5

<210> SEQ ID NO 766
<211> LENGTH: 9
<212> TYPE: PRT
<213> ORGANISM: CoV-2
<220> FEATURE:
```

```
<223> OTHER INFORMATION: ExNuc B07.02_161

<400> SEQUENCE: 766

Val Val Arg Ile Lys Ile Val Gln Met
1               5

<210> SEQ ID NO 767
<211> LENGTH: 9
<212> TYPE: PRT
<213> ORGANISM: CoV-2
<220> FEATURE:
<223> OTHER INFORMATION: ExNuc B07.02_411

<400> SEQUENCE: 767

Leu Pro Gly Cys Asp Gly Gly Ser Leu
1               5

<210> SEQ ID NO 768
<211> LENGTH: 9
<212> TYPE: PRT
<213> ORGANISM: CoV-2
<220> FEATURE:
<223> OTHER INFORMATION: ExNuc B15.01_418

<400> SEQUENCE: 768

Ser Leu Tyr Val Asn Lys His Ala Phe
1               5

<210> SEQ ID NO 769
<211> LENGTH: 9
<212> TYPE: PRT
<213> ORGANISM: CoV-2
<220> FEATURE:
<223> OTHER INFORMATION: ExNuc B15.01_56

<400> SEQUENCE: 769

Ser Met Met Gly Phe Lys Met Asn Tyr
1               5

<210> SEQ ID NO 770
<211> LENGTH: 9
<212> TYPE: PRT
<213> ORGANISM: CoV-2
<220> FEATURE:
<223> OTHER INFORMATION: ExNuc B15.01_61

<400> SEQUENCE: 770

Lys Met Asn Tyr Gln Val Asn Gly Tyr
1               5

<210> SEQ ID NO 771
<211> LENGTH: 9
<212> TYPE: PRT
<213> ORGANISM: CoV-2
<220> FEATURE:
<223> OTHER INFORMATION: ExNuc B15.01_509

<400> SEQUENCE: 771

Trp Val Tyr Lys Gln Phe Asp Thr Tyr
1               5

<210> SEQ ID NO 772
<211> LENGTH: 9
<212> TYPE: PRT
<213> ORGANISM: CoV-2
<220> FEATURE:
<223> OTHER INFORMATION: ExNuc B15.01_457
```

```
<400> SEQUENCE: 772

Lys Gln Val Val Ser Asp Ile Asp Tyr
1               5

<210> SEQ ID NO 773
<211> LENGTH: 9
<212> TYPE: PRT
<213> ORGANISM: CoV-2
<220> FEATURE:
<223> OTHER INFORMATION: ExNuc B15.01_353

<400> SEQUENCE: 773

Ala Gln Pro Cys Ser Asp Lys Ala Tyr
1               5

<210> SEQ ID NO 774
<211> LENGTH: 9
<212> TYPE: PRT
<213> ORGANISM: CoV-2
<220> FEATURE:
<223> OTHER INFORMATION: ExNuc B15.01_116

<400> SEQUENCE: 774

Asn Leu Val Ala Val Pro Thr Gly Tyr
1               5

<210> SEQ ID NO 775
<211> LENGTH: 9
<212> TYPE: PRT
<213> ORGANISM: CoV-2
<220> FEATURE:
<223> OTHER INFORMATION: ExNuc B15.01_512

<400> SEQUENCE: 775

Lys Gln Phe Asp Thr Tyr Asn Leu Trp
1               5

<210> SEQ ID NO 776
<211> LENGTH: 9
<212> TYPE: PRT
<213> ORGANISM: CoV-2
<220> FEATURE:
<223> OTHER INFORMATION: ExNuc B15.01_362

<400> SEQUENCE: 776

Lys Ile Glu Glu Leu Phe Tyr Ser Tyr
1               5

<210> SEQ ID NO 777
<211> LENGTH: 9
<212> TYPE: PRT
<213> ORGANISM: CoV-2
<220> FEATURE:
<223> OTHER INFORMATION: ExNuc B15.01_438

<400> SEQUENCE: 777

Asn Leu Lys Gln Leu Pro Phe Phe Tyr
1               5

<210> SEQ ID NO 778
<211> LENGTH: 9
<212> TYPE: PRT
<213> ORGANISM: CoV-2
<220> FEATURE:
<223> OTHER INFORMATION: ExNuc B15.01_64
```

```
<400> SEQUENCE: 778

Tyr Gln Val Asn Gly Tyr Pro Asn Met
1               5

<210> SEQ ID NO 779
<211> LENGTH: 9
<212> TYPE: PRT
<213> ORGANISM: CoV-2
<220> FEATURE:
<223> OTHER INFORMATION: ExNuc B15.01_21

<400> SEQUENCE: 779

Thr Gln Ala Pro Thr His Leu Ser Val
1               5

<210> SEQ ID NO 780
<211> LENGTH: 9
<212> TYPE: PRT
<213> ORGANISM: CoV-2
<220> FEATURE:
<223> OTHER INFORMATION: ExNuc B15.01_229

<400> SEQUENCE: 780

His Ser Ile Gly Phe Asp Tyr Val Tyr
1               5

<210> SEQ ID NO 781
<211> LENGTH: 9
<212> TYPE: PRT
<213> ORGANISM: CoV-2
<220> FEATURE:
<223> OTHER INFORMATION: ExNuc B15.01_436

<400> SEQUENCE: 781

Phe Val Asn Leu Lys Gln Leu Pro Phe
1               5

<210> SEQ ID NO 782
<211> LENGTH: 9
<212> TYPE: PRT
<213> ORGANISM: CoV-2
<220> FEATURE:
<223> OTHER INFORMATION: ExNuc B15.01_359

<400> SEQUENCE: 782

Lys Ala Tyr Lys Ile Glu Glu Leu Phe
1               5

<210> SEQ ID NO 783
<211> LENGTH: 9
<212> TYPE: PRT
<213> ORGANISM: CoV-2
<220> FEATURE:
<223> OTHER INFORMATION: ExNuc B15.01_65

<400> SEQUENCE: 783

Gln Val Asn Gly Tyr Pro Asn Met Phe
1               5

<210> SEQ ID NO 784
<211> LENGTH: 9
<212> TYPE: PRT
<213> ORGANISM: CoV-2
<220> FEATURE:
<223> OTHER INFORMATION: ExNuc B15.01_500

<400> SEQUENCE: 784
```

```
Met Met Ile Ser Ala Gly Phe Ser Leu
1               5

<210> SEQ ID NO 785
<211> LENGTH: 9
<212> TYPE: PRT
<213> ORGANISM: CoV-2
<220> FEATURE:
<223> OTHER INFORMATION: ExNuc B15.01_321

<400> SEQUENCE: 785

Leu Leu Ala Asp Lys Phe Pro Val Leu
1               5

<210> SEQ ID NO 786
<211> LENGTH: 9
<212> TYPE: PRT
<213> ORGANISM: CoV-2
<220> FEATURE:
<223> OTHER INFORMATION: ExNuc B15.01_161

<400> SEQUENCE: 786

Val Val Arg Ile Lys Ile Val Gln Met
1               5

<210> SEQ ID NO 787
<211> LENGTH: 9
<212> TYPE: PRT
<213> ORGANISM: CoV-2
<220> FEATURE:
<223> OTHER INFORMATION: ExNuc B15.01_146

<400> SEQUENCE: 787

Phe Lys His Leu Ile Pro Leu Met Tyr
1               5

<210> SEQ ID NO 788
<211> LENGTH: 9
<212> TYPE: PRT
<213> ORGANISM: CoV-2
<220> FEATURE:
<223> OTHER INFORMATION: ExNuc B40.01_190

<400> SEQUENCE: 788

Phe Glu Leu Thr Ser Met Lys Tyr Phe
1               5

<210> SEQ ID NO 789
<211> LENGTH: 9
<212> TYPE: PRT
<213> ORGANISM: CoV-2
<220> FEATURE:
<223> OTHER INFORMATION: ExNuc B40.01_452

<400> SEQUENCE: 789

Cys Glu Ser His Gly Lys Gln Val Val
1               5

<210> SEQ ID NO 790
<211> LENGTH: 9
<212> TYPE: PRT
<213> ORGANISM: CoV-2
<220> FEATURE:
<223> OTHER INFORMATION: ExNuc B58.01_359

<400> SEQUENCE: 790
```

```
Lys Ala Tyr Lys Ile Glu Glu Leu Phe
1               5

<210> SEQ ID NO 791
<211> LENGTH: 9
<212> TYPE: PRT
<213> ORGANISM: CoV-2
<220> FEATURE:
<223> OTHER INFORMATION: ExNuc B58.01_501

<400> SEQUENCE: 791

Met Ile Ser Ala Gly Phe Ser Leu Trp
1               5

<210> SEQ ID NO 792
<211> LENGTH: 9
<212> TYPE: PRT
<213> ORGANISM: CoV-2
<220> FEATURE:
<223> OTHER INFORMATION: ExNuc B58.01_219

<400> SEQUENCE: 792

Thr Ala Ser Asp Thr Tyr Ala Cys Trp
1               5

<210> SEQ ID NO 793
<211> LENGTH: 9
<212> TYPE: PRT
<213> ORGANISM: CoV-2
<220> FEATURE:
<223> OTHER INFORMATION: ExNuc B58.01_512

<400> SEQUENCE: 793

Lys Gln Phe Asp Thr Tyr Asn Leu Trp
1               5

<210> SEQ ID NO 794
<211> LENGTH: 9
<212> TYPE: PRT
<213> ORGANISM: CoV-2
<220> FEATURE:
<223> OTHER INFORMATION: ExNuc B58.01_377

<400> SEQUENCE: 794

Phe Thr Asp Gly Val Cys Leu Phe Trp
1               5

<210> SEQ ID NO 795
<211> LENGTH: 9
<212> TYPE: PRT
<213> ORGANISM: CoV-2
<220> FEATURE:
<223> OTHER INFORMATION: ExNuc B58.01_318

<400> SEQUENCE: 795

Lys Ala Ala Leu Leu Ala Asp Lys Phe
1               5

<210> SEQ ID NO 796
<211> LENGTH: 9
<212> TYPE: PRT
<213> ORGANISM: CoV-2
<220> FEATURE:
<223> OTHER INFORMATION: ExNuc B58.01_78

<400> SEQUENCE: 796

Glu Ala Ile Arg His Val Arg Ala Trp
```

```
<210> SEQ ID NO 797
<211> LENGTH: 9
<212> TYPE: PRT
<213> ORGANISM: CoV-2
<220> FEATURE:
<223> OTHER INFORMATION: ExNuc B58.01_229

<400> SEQUENCE: 797

His Ser Ile Gly Phe Asp Tyr Val Tyr
1               5

<210> SEQ ID NO 798
<211> LENGTH: 9
<212> TYPE: PRT
<213> ORGANISM: CoV-2
<220> FEATURE:
<223> OTHER INFORMATION: ExNuc B58.01_506

<400> SEQUENCE: 798

Phe Ser Leu Trp Val Tyr Lys Gln Phe
1               5

<210> SEQ ID NO 799
<211> LENGTH: 9
<212> TYPE: PRT
<213> ORGANISM: CoV-2
<220> FEATURE:
<223> OTHER INFORMATION: ExNuc B58.01_177

<400> SEQUENCE: 799

Leu Ser Asp Arg Val Val Phe Val Leu
1               5

<210> SEQ ID NO 800
<211> LENGTH: 9
<212> TYPE: PRT
<213> ORGANISM: CoV-2
<220> FEATURE:
<223> OTHER INFORMATION: ExNuc B58.01_340

<400> SEQUENCE: 800

Cys Val Pro Gln Ala Asp Val Glu Trp
1               5

<210> SEQ ID NO 801
<211> LENGTH: 9
<212> TYPE: PRT
<213> ORGANISM: CoV-2
<220> FEATURE:
<223> OTHER INFORMATION: ExNuc B58.01_49

<400> SEQUENCE: 801

Met Thr Tyr Arg Arg Leu Ile Ser Met
1               5

<210> SEQ ID NO 802
<211> LENGTH: 9
<212> TYPE: PRT
<213> ORGANISM: CoV-2
<220> FEATURE:
<223> OTHER INFORMATION: ExNuc B58.01_193

<400> SEQUENCE: 802

Thr Ser Met Lys Tyr Phe Val Lys Ile
1               5
```

<210> SEQ ID NO 803
<211> LENGTH: 9
<212> TYPE: PRT
<213> ORGANISM: CoV-2
<220> FEATURE:
<223> OTHER INFORMATION: ExNuc B58.01_278

<400> SEQUENCE: 803

Arg Cys Leu Ala Val His Glu Cys Phe
1 5

<210> SEQ ID NO 804
<211> LENGTH: 9
<212> TYPE: PRT
<213> ORGANISM: CoV-2
<220> FEATURE:
<223> OTHER INFORMATION: EndoRNA A1.01_217

<400> SEQUENCE: 804

Ala Met Asp Glu Phe Ile Glu Arg Tyr
1 5

<210> SEQ ID NO 805
<211> LENGTH: 9
<212> TYPE: PRT
<213> ORGANISM: CoV-2
<220> FEATURE:
<223> OTHER INFORMATION: EndoRNA A1.01_270

<400> SEQUENCE: 805

Pro Met Asp Ser Thr Val Lys Asn Tyr
1 5

<210> SEQ ID NO 806
<211> LENGTH: 9
<212> TYPE: PRT
<213> ORGANISM: CoV-2
<220> FEATURE:
<223> OTHER INFORMATION: EndoRNA A1.01_185

<400> SEQUENCE: 806

Val Val Gln Gln Leu Pro Glu Thr Tyr
1 5

<210> SEQ ID NO 807
<211> LENGTH: 9
<212> TYPE: PRT
<213> ORGANISM: CoV-2
<220> FEATURE:
<223> OTHER INFORMATION: EndoRNA A1.01_126

<400> SEQUENCE: 807

Arg Val Asp Gly Gln Val Asp Leu Phe
1 5

<210> SEQ ID NO 808
<211> LENGTH: 9
<212> TYPE: PRT
<213> ORGANISM: CoV-2
<220> FEATURE:
<223> OTHER INFORMATION: EndoRNA A1.01_80

<400> SEQUENCE: 808

Ala Ala Asn Thr Val Ile Trp Asp Tyr
1 5

```
<210> SEQ ID NO 809
<211> LENGTH: 9
<212> TYPE: PRT
<213> ORGANISM: CoV-2
<220> FEATURE:
<223> OTHER INFORMATION: EndoRNA A1.01_324

<400> SEQUENCE: 809

Tyr Thr Glu Ile Ser Phe Met Leu Trp
1               5

<210> SEQ ID NO 810
<211> LENGTH: 9
<212> TYPE: PRT
<213> ORGANISM: CoV-2
<220> FEATURE:
<223> OTHER INFORMATION: EndoRNA A1.01_24

<400> SEQUENCE: 810

Val Ser Ile Ile Asn Asn Thr Val Tyr
1               5

<210> SEQ ID NO 811
<211> LENGTH: 9
<212> TYPE: PRT
<213> ORGANISM: CoV-2
<220> FEATURE:
<223> OTHER INFORMATION: EndoRNA A1.01_170

<400> SEQUENCE: 811

Glu Ala Val Lys Thr Gln Phe Asn Tyr
1               5

<210> SEQ ID NO 812
<211> LENGTH: 9
<212> TYPE: PRT
<213> ORGANISM: CoV-2
<220> FEATURE:
<223> OTHER INFORMATION: EndoRNA A1.01_321

<400> SEQUENCE: 812

Thr Ile Asp Tyr Thr Glu Ile Ser Phe
1               5

<210> SEQ ID NO 813
<211> LENGTH: 9
<212> TYPE: PRT
<213> ORGANISM: CoV-2
<220> FEATURE:
<223> OTHER INFORMATION: EndoRNA A1.01_171

<400> SEQUENCE: 813

Ala Val Lys Thr Gln Phe Asn Tyr Tyr
1               5

<210> SEQ ID NO 814
<211> LENGTH: 9
<212> TYPE: PRT
<213> ORGANISM: CoV-2
<220> FEATURE:
<223> OTHER INFORMATION: EndoRNA A2.01_297

<400> SEQUENCE: 814

Leu Leu Leu Asp Asp Phe Val Glu Ile
1               5
```

```
<210> SEQ ID NO 815
<211> LENGTH: 9
<212> TYPE: PRT
<213> ORGANISM: CoV-2
<220> FEATURE:
<223> OTHER INFORMATION: EndoRNA A2.01_181

<400> SEQUENCE: 815

Lys Val Asp Gly Val Val Gln Gln Leu
1               5

<210> SEQ ID NO 816
<211> LENGTH: 9
<212> TYPE: PRT
<213> ORGANISM: CoV-2
<220> FEATURE:
<223> OTHER INFORMATION: EndoRNA A2.01_312

<400> SEQUENCE: 816

Ser Val Val Ser Lys Val Val Lys Val
1               5

<210> SEQ ID NO 817
<211> LENGTH: 9
<212> TYPE: PRT
<213> ORGANISM: CoV-2
<220> FEATURE:
<223> OTHER INFORMATION: EndoRNA A2.01_243

<400> SEQUENCE: 817

Ser Gln Leu Gly Gly Leu His Leu Leu
1               5

<210> SEQ ID NO 818
<211> LENGTH: 9
<212> TYPE: PRT
<213> ORGANISM: CoV-2
<220> FEATURE:
<223> OTHER INFORMATION: EndoRNA A2.01_298

<400> SEQUENCE: 818

Leu Leu Asp Asp Phe Val Glu Ile Ile
1               5

<210> SEQ ID NO 819
<211> LENGTH: 9
<212> TYPE: PRT
<213> ORGANISM: CoV-2
<220> FEATURE:
<223> OTHER INFORMATION: EndoRNA A2.01_34

<400> SEQUENCE: 819

Lys Val Asp Gly Val Asp Val Glu Leu
1               5

<210> SEQ ID NO 820
<211> LENGTH: 9
<212> TYPE: PRT
<213> ORGANISM: CoV-2
<220> FEATURE:
<223> OTHER INFORMATION: EndoRNA A2.01_1

<400> SEQUENCE: 820

Ser Leu Glu Asn Val Ala Phe Asn Val
1               5

<210> SEQ ID NO 821
```

```
<211> LENGTH: 9
<212> TYPE: PRT
<213> ORGANISM: CoV-2
<220> FEATURE:
<223> OTHER INFORMATION: EndoRNA A2.01_30

<400> SEQUENCE: 821

Thr Val Tyr Thr Lys Val Asp Gly Val
1               5

<210> SEQ ID NO 822
<211> LENGTH: 9
<212> TYPE: PRT
<213> ORGANISM: CoV-2
<220> FEATURE:
<223> OTHER INFORMATION: EndoRNA A2.01_41

<400> SEQUENCE: 822

Glu Leu Phe Glu Asn Lys Thr Thr Leu
1               5

<210> SEQ ID NO 823
<211> LENGTH: 9
<212> TYPE: PRT
<213> ORGANISM: CoV-2
<220> FEATURE:
<223> OTHER INFORMATION: EndoRNA A2.01_18

<400> SEQUENCE: 823

Gln Gln Gly Glu Val Pro Val Ser Ile
1               5

<210> SEQ ID NO 824
<211> LENGTH: 9
<212> TYPE: PRT
<213> ORGANISM: CoV-2
<220> FEATURE:
<223> OTHER INFORMATION: EndoRNA A2.01_147

<400> SEQUENCE: 824

Ser Val Lys Gly Leu Gln Pro Ser Val
1               5

<210> SEQ ID NO 825
<211> LENGTH: 9
<212> TYPE: PRT
<213> ORGANISM: CoV-2
<220> FEATURE:
<223> OTHER INFORMATION: EndoRNA A2.01_244

<400> SEQUENCE: 825

Gln Leu Gly Gly Leu His Leu Leu Ile
1               5

<210> SEQ ID NO 826
<211> LENGTH: 9
<212> TYPE: PRT
<213> ORGANISM: CoV-2
<220> FEATURE:
<223> OTHER INFORMATION: EndoRNA A3.01_26

<400> SEQUENCE: 826

Ile Ile Asn Asn Thr Val Tyr Thr Lys
1               5

<210> SEQ ID NO 827
<211> LENGTH: 9
```

```
<212> TYPE: PRT
<213> ORGANISM: CoV-2
<220> FEATURE:
<223> OTHER INFORMATION: EndoRNA A3.01_150

<400> SEQUENCE: 827

Gly Leu Gln Pro Ser Val Gly Pro Lys
1               5

<210> SEQ ID NO 828
<211> LENGTH: 9
<212> TYPE: PRT
<213> ORGANISM: CoV-2
<220> FEATURE:
<223> OTHER INFORMATION: EndoRNA A3.01_173

<400> SEQUENCE: 828

Lys Thr Gln Phe Asn Tyr Tyr Lys Lys
1               5

<210> SEQ ID NO 829
<211> LENGTH: 9
<212> TYPE: PRT
<213> ORGANISM: CoV-2
<220> FEATURE:
<223> OTHER INFORMATION: EndoRNA A3.01_308

<400> SEQUENCE: 829

Ser Gln Asp Leu Ser Val Val Ser Lys
1               5

<210> SEQ ID NO 830
<211> LENGTH: 9
<212> TYPE: PRT
<213> ORGANISM: CoV-2
<220> FEATURE:
<223> OTHER INFORMATION: EndoRNA A3.01_316

<400> SEQUENCE: 830

Lys Val Val Lys Val Thr Ile Asp Tyr
1               5

<210> SEQ ID NO 831
<211> LENGTH: 9
<212> TYPE: PRT
<213> ORGANISM: CoV-2
<220> FEATURE:
<223> OTHER INFORMATION: EndoRNA A3.01_141

<400> SEQUENCE: 831

Val Leu Ile Thr Glu Gly Ser Val Lys
1               5

<210> SEQ ID NO 832
<211> LENGTH: 9
<212> TYPE: PRT
<213> ORGANISM: CoV-2
<220> FEATURE:
<223> OTHER INFORMATION: EndoRNA A3.01_4

<400> SEQUENCE: 832

Asn Val Ala Phe Asn Val Val Asn Lys
1               5

<210> SEQ ID NO 833
<211> LENGTH: 9
<212> TYPE: PRT
```

```
<213> ORGANISM: CoV-2
<220> FEATURE:
<223> OTHER INFORMATION: EndoRNA A3.01_171

<400> SEQUENCE: 833

Ala Val Lys Thr Gln Phe Asn Tyr Tyr
1               5

<210> SEQ ID NO 834
<211> LENGTH: 9
<212> TYPE: PRT
<213> ORGANISM: CoV-2
<220> FEATURE:
<223> OTHER INFORMATION: EndoRNA A3.01_62

<400> SEQUENCE: 834

Asn Ile Lys Pro Val Pro Glu Val Lys
1               5

<210> SEQ ID NO 835
<211> LENGTH: 9
<212> TYPE: PRT
<213> ORGANISM: CoV-2
<220> FEATURE:
<223> OTHER INFORMATION: EndoRNA A24.02_224

<400> SEQUENCE: 835

Arg Tyr Lys Leu Glu Gly Tyr Ala Phe
1               5

<210> SEQ ID NO 836
<211> LENGTH: 9
<212> TYPE: PRT
<213> ORGANISM: CoV-2
<220> FEATURE:
<223> OTHER INFORMATION: EndoRNA A24.02_192

<400> SEQUENCE: 836

Thr Tyr Phe Thr Gln Ser Arg Asn Leu
1               5

<210> SEQ ID NO 837
<211> LENGTH: 9
<212> TYPE: PRT
<213> ORGANISM: CoV-2
<220> FEATURE:
<223> OTHER INFORMATION: EndoRNA A24.02_257

<400> SEQUENCE: 837

Arg Phe Lys Glu Ser Pro Phe Glu Leu
1               5

<210> SEQ ID NO 838
<211> LENGTH: 9
<212> TYPE: PRT
<213> ORGANISM: CoV-2
<220> FEATURE:
<223> OTHER INFORMATION: EndoRNA A24.02_323

<400> SEQUENCE: 838

Asp Tyr Thr Glu Ile Ser Phe Met Leu
1               5

<210> SEQ ID NO 839
<211> LENGTH: 9
<212> TYPE: PRT
<213> ORGANISM: CoV-2
```

```
<220> FEATURE:
<223> OTHER INFORMATION: EndoRNA A24.02_195

<400> SEQUENCE: 839

Thr Gln Ser Arg Asn Leu Gln Glu Phe
1               5

<210> SEQ ID NO 840
<211> LENGTH: 9
<212> TYPE: PRT
<213> ORGANISM: CoV-2
<220> FEATURE:
<223> OTHER INFORMATION: EndoRNA A26.01_170

<400> SEQUENCE: 840

Glu Ala Val Lys Thr Gln Phe Asn Tyr
1               5

<210> SEQ ID NO 841
<211> LENGTH: 9
<212> TYPE: PRT
<213> ORGANISM: CoV-2
<220> FEATURE:
<223> OTHER INFORMATION: EndoRNA A26.01_171

<400> SEQUENCE: 841

Ala Val Lys Thr Gln Phe Asn Tyr Tyr
1               5

<210> SEQ ID NO 842
<211> LENGTH: 9
<212> TYPE: PRT
<213> ORGANISM: CoV-2
<220> FEATURE:
<223> OTHER INFORMATION: EndoRNA A26.01_47

<400> SEQUENCE: 842

Thr Thr Leu Pro Val Asn Val Ala Phe
1               5

<210> SEQ ID NO 843
<211> LENGTH: 9
<212> TYPE: PRT
<213> ORGANISM: CoV-2
<220> FEATURE:
<223> OTHER INFORMATION: EndoRNA A26.01_312

<400> SEQUENCE: 843

Ser Val Val Ser Lys Val Val Lys Val
1               5

<210> SEQ ID NO 844
<211> LENGTH: 9
<212> TYPE: PRT
<213> ORGANISM: CoV-2
<220> FEATURE:
<223> OTHER INFORMATION: EndoRNA A26.01_41

<400> SEQUENCE: 844

Glu Leu Phe Glu Asn Lys Thr Thr Leu
1               5

<210> SEQ ID NO 845
<211> LENGTH: 9
<212> TYPE: PRT
<213> ORGANISM: CoV-2
<220> FEATURE:
```

```
<223> OTHER INFORMATION: EndoRNA A26.01_78

<400> SEQUENCE: 845

Asp Ile Ala Ala Asn Thr Val Ile Trp
1               5

<210> SEQ ID NO 846
<211> LENGTH: 9
<212> TYPE: PRT
<213> ORGANISM: CoV-2
<220> FEATURE:
<223> OTHER INFORMATION: EndoRNA A26.01_217

<400> SEQUENCE: 846

Ala Met Asp Glu Phe Ile Glu Arg Tyr
1               5

<210> SEQ ID NO 847
<211> LENGTH: 9
<212> TYPE: PRT
<213> ORGANISM: CoV-2
<220> FEATURE:
<223> OTHER INFORMATION: EndoRNA A26.01_185

<400> SEQUENCE: 847

Val Val Gln Gln Leu Pro Glu Thr Tyr
1               5

<210> SEQ ID NO 848
<211> LENGTH: 9
<212> TYPE: PRT
<213> ORGANISM: CoV-2
<220> FEATURE:
<223> OTHER INFORMATION: EndoRNA A07.02_64

<400> SEQUENCE: 848

Lys Pro Val Pro Glu Val Lys Ile Leu
1               5

<210> SEQ ID NO 849
<211> LENGTH: 9
<212> TYPE: PRT
<213> ORGANISM: CoV-2
<220> FEATURE:
<223> OTHER INFORMATION: EndoRNA A07.02_154

<400> SEQUENCE: 849

Ser Val Gly Pro Lys Gln Ala Ser Leu
1               5

<210> SEQ ID NO 850
<211> LENGTH: 9
<212> TYPE: PRT
<213> ORGANISM: CoV-2
<220> FEATURE:
<223> OTHER INFORMATION: EndoRNA A07.02_49

<400> SEQUENCE: 850

Leu Pro Val Asn Val Ala Phe Glu Leu
1               5

<210> SEQ ID NO 851
<211> LENGTH: 9
<212> TYPE: PRT
<213> ORGANISM: CoV-2
<220> FEATURE:
<223> OTHER INFORMATION: EndoRNA A07.02_152
```

-continued

```
<400> SEQUENCE: 851

Gln Pro Ser Val Gly Pro Lys Gln Ala
1               5

<210> SEQ ID NO 852
<211> LENGTH: 9
<212> TYPE: PRT
<213> ORGANISM: CoV-2
<220> FEATURE:
<223> OTHER INFORMATION: EndoRNA A15.01_195

<400> SEQUENCE: 852

Thr Gln Ser Arg Asn Leu Gln Glu Phe
1               5

<210> SEQ ID NO 853
<211> LENGTH: 9
<212> TYPE: PRT
<213> ORGANISM: CoV-2
<220> FEATURE:
<223> OTHER INFORMATION: EndoRNA A15.01_185

<400> SEQUENCE: 853

Val Val Gln Gln Leu Pro Glu Thr Tyr
1               5

<210> SEQ ID NO 854
<211> LENGTH: 9
<212> TYPE: PRT
<213> ORGANISM: CoV-2
<220> FEATURE:
<223> OTHER INFORMATION: EndoRNA A15.01_186

<400> SEQUENCE: 854

Val Gln Gln Leu Pro Glu Thr Tyr Phe
1               5

<210> SEQ ID NO 855
<211> LENGTH: 9
<212> TYPE: PRT
<213> ORGANISM: CoV-2
<220> FEATURE:
<223> OTHER INFORMATION: EndoRNA A15.01_171

<400> SEQUENCE: 855

Ala Val Lys Thr Gln Phe Asn Tyr Tyr
1               5

<210> SEQ ID NO 856
<211> LENGTH: 9
<212> TYPE: PRT
<213> ORGANISM: CoV-2
<220> FEATURE:
<223> OTHER INFORMATION: EndoRNA A15.01_316

<400> SEQUENCE: 856

Lys Val Val Lys Val Thr Ile Asp Tyr
1               5

<210> SEQ ID NO 857
<211> LENGTH: 9
<212> TYPE: PRT
<213> ORGANISM: CoV-2
<220> FEATURE:
<223> OTHER INFORMATION: EndoRNA A15.01_24
```

<400> SEQUENCE: 857

Val Ser Ile Ile Asn Asn Thr Val Tyr
1               5

<210> SEQ ID NO 858
<211> LENGTH: 9
<212> TYPE: PRT
<213> ORGANISM: CoV-2
<220> FEATURE:
<223> OTHER INFORMATION: EndoRNA A15.01_217

<400> SEQUENCE: 858

Ala Met Asp Glu Phe Ile Glu Arg Tyr
1               5

<210> SEQ ID NO 859
<211> LENGTH: 9
<212> TYPE: PRT
<213> ORGANISM: CoV-2
<220> FEATURE:
<223> OTHER INFORMATION: EndoRNA A15.01_114

<400> SEQUENCE: 859

Thr Ile Cys Ala Pro Leu Thr Val Phe
1               5

<210> SEQ ID NO 860
<211> LENGTH: 9
<212> TYPE: PRT
<213> ORGANISM: CoV-2
<220> FEATURE:
<223> OTHER INFORMATION: EndoRNA A15.01_250

<400> SEQUENCE: 860

Leu Leu Ile Gly Leu Ala Lys Arg Phe
1               5

<210> SEQ ID NO 861
<211> LENGTH: 9
<212> TYPE: PRT
<213> ORGANISM: CoV-2
<220> FEATURE:
<223> OTHER INFORMATION: EndoRNA A15.01_243

<400> SEQUENCE: 861

Ser Gln Leu Gly Gly Leu His Leu Leu
1               5

<210> SEQ ID NO 862
<211> LENGTH: 9
<212> TYPE: PRT
<213> ORGANISM: CoV-2
<220> FEATURE:
<223> OTHER INFORMATION: EndoRNA A15.01_47

<400> SEQUENCE: 862

Thr Thr Leu Pro Val Asn Val Ala Phe
1               5

<210> SEQ ID NO 863
<211> LENGTH: 9
<212> TYPE: PRT
<213> ORGANISM: CoV-2
<220> FEATURE:
<223> OTHER INFORMATION: EndoRNA A40.01_201

<400> SEQUENCE: 863

```
Gln Glu Phe Lys Pro Arg Ser Gln Met
1               5

<210> SEQ ID NO 864
<211> LENGTH: 9
<212> TYPE: PRT
<213> ORGANISM: CoV-2
<220> FEATURE:
<223> OTHER INFORMATION: EndoRNA A40.01_303

<400> SEQUENCE: 864

Val Glu Ile Ile Lys Ser Gln Asp Leu
1               5

<210> SEQ ID NO 865
<211> LENGTH: 9
<212> TYPE: PRT
<213> ORGANISM: CoV-2
<220> FEATURE:
<223> OTHER INFORMATION: EndoRNA A40.01_263

<400> SEQUENCE: 865

Phe Glu Leu Glu Asp Phe Ile Pro Met
1               5

<210> SEQ ID NO 866
<211> LENGTH: 9
<212> TYPE: PRT
<213> ORGANISM: CoV-2
<220> FEATURE:
<223> OTHER INFORMATION: EndoRNA A40.01_219

<400> SEQUENCE: 866

Asp Glu Phe Ile Glu Arg Tyr Lys Leu
1               5

<210> SEQ ID NO 867
<211> LENGTH: 9
<212> TYPE: PRT
<213> ORGANISM: CoV-2
<220> FEATURE:
<223> OTHER INFORMATION: EndoRNA A40.01_243

<400> SEQUENCE: 867

Ser Gln Leu Gly Gly Leu His Leu Leu
1               5

<210> SEQ ID NO 868
<211> LENGTH: 9
<212> TYPE: PRT
<213> ORGANISM: CoV-2
<220> FEATURE:
<223> OTHER INFORMATION: EndoRNA A40.01_43

<400> SEQUENCE: 868

Phe Glu Asn Lys Thr Thr Leu Pro Val
1               5

<210> SEQ ID NO 869
<211> LENGTH: 9
<212> TYPE: PRT
<213> ORGANISM: CoV-2
<220> FEATURE:
<223> OTHER INFORMATION: EndoRNA A40.01_2

<400> SEQUENCE: 869
```

Leu Glu Asn Val Ala Phe Asn Val Val
1 5

<210> SEQ ID NO 870
<211> LENGTH: 9
<212> TYPE: PRT
<213> ORGANISM: CoV-2
<220> FEATURE:
<223> OTHER INFORMATION: EndoRNA A40.01_67

<400> SEQUENCE: 870

Pro Glu Val Lys Ile Leu Asn Asn Leu
1 5

<210> SEQ ID NO 871
<211> LENGTH: 9
<212> TYPE: PRT
<213> ORGANISM: CoV-2
<220> FEATURE:
<223> OTHER INFORMATION: EndoRNA A40.01_55

<400> SEQUENCE: 871

Phe Glu Leu Trp Ala Lys Arg Asn Ile
1 5

<210> SEQ ID NO 872
<211> LENGTH: 9
<212> TYPE: PRT
<213> ORGANISM: CoV-2
<220> FEATURE:
<223> OTHER INFORMATION: EndoRNA A58.01_324

<400> SEQUENCE: 872

Tyr Thr Glu Ile Ser Phe Met Leu Trp
1 5

<210> SEQ ID NO 873
<211> LENGTH: 9
<212> TYPE: PRT
<213> ORGANISM: CoV-2
<220> FEATURE:
<223> OTHER INFORMATION: EndoRNA A58.01_47

<400> SEQUENCE: 873

Thr Thr Leu Pro Val Asn Val Ala Phe
1 5

<210> SEQ ID NO 874
<211> LENGTH: 9
<212> TYPE: PRT
<213> ORGANISM: CoV-2
<220> FEATURE:
<223> OTHER INFORMATION: EndoRNA A58.01_115

<400> SEQUENCE: 874

Ile Cys Ala Pro Leu Thr Val Phe Phe
1 5

<210> SEQ ID NO 875
<211> LENGTH: 9
<212> TYPE: PRT
<213> ORGANISM: CoV-2
<220> FEATURE:
<223> OTHER INFORMATION: EndoRNA A58.01_24

<400> SEQUENCE: 875

Val Ser Ile Ile Asn Asn Thr Val Tyr

```
<210> SEQ ID NO 876
<211> LENGTH: 9
<212> TYPE: PRT
<213> ORGANISM: CoV-2
<220> FEATURE:
<223> OTHER INFORMATION: EndoRNA A58.01_50

<400> SEQUENCE: 876

Pro Val Asn Val Ala Phe Glu Leu Trp
1               5

<210> SEQ ID NO 877
<211> LENGTH: 9
<212> TYPE: PRT
<213> ORGANISM: CoV-2
<220> FEATURE:
<223> OTHER INFORMATION: EndoRNA A58.01_185

<400> SEQUENCE: 877

Val Val Gln Gln Leu Pro Glu Thr Tyr
1               5

<210> SEQ ID NO 878
<211> LENGTH: 9
<212> TYPE: PRT
<213> ORGANISM: CoV-2
<220> FEATURE:
<223> OTHER INFORMATION: EndoRNA A58.01_316

<400> SEQUENCE: 878

Lys Val Val Lys Val Thr Ile Asp Tyr
1               5

<210> SEQ ID NO 879
<211> LENGTH: 9
<212> TYPE: PRT
<213> ORGANISM: CoV-2
<220> FEATURE:
<223> OTHER INFORMATION: EndoRNA A58.01_181

<400> SEQUENCE: 879

Lys Val Asp Gly Val Val Gln Gln Leu
1               5

<210> SEQ ID NO 880
<211> LENGTH: 9
<212> TYPE: PRT
<213> ORGANISM: CoV-2
<220> FEATURE:
<223> OTHER INFORMATION: EndoRNA A58.01_80

<400> SEQUENCE: 880

Ala Ala Asn Thr Val Ile Trp Asp Tyr
1               5

<210> SEQ ID NO 881
<211> LENGTH: 9
<212> TYPE: PRT
<213> ORGANISM: CoV-2
<220> FEATURE:
<223> OTHER INFORMATION: EndoRNA A58.01_126

<400> SEQUENCE: 881

Arg Val Asp Gly Gln Val Asp Leu Phe
1               5
```

```
<210> SEQ ID NO 882
<211> LENGTH: 9
<212> TYPE: PRT
<213> ORGANISM: CoV-2
<220> FEATURE:
<223> OTHER INFORMATION: EndoRNA A58.01_107

<400> SEQUENCE: 882

Ile Ala Lys Lys Pro Thr Glu Thr Ile
1               5

<210> SEQ ID NO 883
<211> LENGTH: 9
<212> TYPE: PRT
<213> ORGANISM: CoV-2
<220> FEATURE:
<223> OTHER INFORMATION: MthlTrns A1.01_143

<400> SEQUENCE: 883

Asp Ser Lys Glu Gly Phe Phe Thr Tyr
1               5

<210> SEQ ID NO 884
<211> LENGTH: 9
<212> TYPE: PRT
<213> ORGANISM: CoV-2
<220> FEATURE:
<223> OTHER INFORMATION: MthlTrns A1.01_55

<400> SEQUENCE: 884

Asn Thr Leu Thr Leu Ala Val Pro Tyr
1               5

<210> SEQ ID NO 885
<211> LENGTH: 9
<212> TYPE: PRT
<213> ORGANISM: CoV-2
<220> FEATURE:
<223> OTHER INFORMATION: MthlTrns A1.01_103

<400> SEQUENCE: 885

Val Ser Asp Ala Asp Ser Thr Leu Ile
1               5

<210> SEQ ID NO 886
<211> LENGTH: 9
<212> TYPE: PRT
<213> ORGANISM: CoV-2
<220> FEATURE:
<223> OTHER INFORMATION: MthlTrns A2.01_53

<400> SEQUENCE: 886

Tyr Leu Asn Thr Leu Thr Leu Ala Val
1               5

<210> SEQ ID NO 887
<211> LENGTH: 9
<212> TYPE: PRT
<213> ORGANISM: CoV-2
<220> FEATURE:
<223> OTHER INFORMATION: MthlTrns A2.01_109

<400> SEQUENCE: 887

Thr Leu Ile Gly Asp Cys Ala Thr Val
1               5
```

<210> SEQ ID NO 888
<211> LENGTH: 9
<212> TYPE: PRT
<213> ORGANISM: CoV-2
<220> FEATURE:
<223> OTHER INFORMATION: MthlTrns A2.01_265

<400> SEQUENCE: 888

Gln Ile Asn Asp Met Ile Leu Ser Leu
1 5

<210> SEQ ID NO 889
<211> LENGTH: 9
<212> TYPE: PRT
<213> ORGANISM: CoV-2
<220> FEATURE:
<223> OTHER INFORMATION: MthlTrns A2.01_87

<400> SEQUENCE: 889

Trp Leu Pro Thr Gly Thr Leu Leu Val
1 5

<210> SEQ ID NO 890
<211> LENGTH: 9
<212> TYPE: PRT
<213> ORGANISM: CoV-2
<220> FEATURE:
<223> OTHER INFORMATION: MthlTrns A2.01_102

<400> SEQUENCE: 890

Phe Val Ser Asp Ala Asp Ser Thr Leu
1 5

<210> SEQ ID NO 891
<211> LENGTH: 9
<212> TYPE: PRT
<213> ORGANISM: CoV-2
<220> FEATURE:
<223> OTHER INFORMATION: MthlTrns A2.01_169

<400> SEQUENCE: 891

Lys Ile Thr Glu His Ser Trp Asn Ala
1 5

<210> SEQ ID NO 892
<211> LENGTH: 9
<212> TYPE: PRT
<213> ORGANISM: CoV-2
<220> FEATURE:
<223> OTHER INFORMATION: MthlTrns A2.01_76

<400> SEQUENCE: 892

Lys Val Ala Pro Gly Thr Ala Val Leu
1 5

<210> SEQ ID NO 893
<211> LENGTH: 9
<212> TYPE: PRT
<213> ORGANISM: CoV-2
<220> FEATURE:
<223> OTHER INFORMATION: MthlTrns A2.01_210

<400> SEQUENCE: 893

Tyr Leu Gly Lys Pro Arg Glu Gln Ile
1 5

```
<210> SEQ ID NO 894
<211> LENGTH: 9
<212> TYPE: PRT
<213> ORGANISM: CoV-2
<220> FEATURE:
<223> OTHER INFORMATION: MthlTrns A2.01_49

<400> SEQUENCE: 894

Gln Leu Cys Gln Tyr Leu Asn Thr Leu
1               5

<210> SEQ ID NO 895
<211> LENGTH: 9
<212> TYPE: PRT
<213> ORGANISM: CoV-2
<220> FEATURE:
<223> OTHER INFORMATION: MthlTrns A3.01_8

<400> SEQUENCE: 895

Gly Val Ala Met Pro Asn Leu Tyr Lys
1               5

<210> SEQ ID NO 896
<211> LENGTH: 9
<212> TYPE: PRT
<213> ORGANISM: CoV-2
<220> FEATURE:
<223> OTHER INFORMATION: MthlTrns A3.01_16

<400> SEQUENCE: 896

Lys Met Gln Arg Met Leu Leu Glu Lys
1               5

<210> SEQ ID NO 897
<211> LENGTH: 9
<212> TYPE: PRT
<213> ORGANISM: CoV-2
<220> FEATURE:
<223> OTHER INFORMATION: MthlTrns A3.01_161

<400> SEQUENCE: 897

Ala Leu Gly Gly Ser Val Ala Ile Lys
1               5

<210> SEQ ID NO 898
<211> LENGTH: 9
<212> TYPE: PRT
<213> ORGANISM: CoV-2
<220> FEATURE:
<223> OTHER INFORMATION: MthlTrns A3.01_173

<400> SEQUENCE: 898

His Ser Trp Asn Ala Asp Leu Tyr Lys
1               5

<210> SEQ ID NO 899
<211> LENGTH: 9
<212> TYPE: PRT
<213> ORGANISM: CoV-2
<220> FEATURE:
<223> OTHER INFORMATION: MthlTrns A3.01_151

<400> SEQUENCE: 899

Tyr Ile Cys Gly Phe Ile Gln Gln Lys
1               5

<210> SEQ ID NO 900
```

```
<211> LENGTH: 9
<212> TYPE: PRT
<213> ORGANISM: CoV-2
<220> FEATURE:
<223> OTHER INFORMATION: MthlTrns A3.01_254

<400> SEQUENCE: 900

Arg Gly Thr Ala Val Met Ser Leu Lys
1               5

<210> SEQ ID NO 901
<211> LENGTH: 9
<212> TYPE: PRT
<213> ORGANISM: CoV-2
<220> FEATURE:
<223> OTHER INFORMATION: MthlTrns A3.01_165

<400> SEQUENCE: 901

Ser Val Ala Ile Lys Ile Thr Glu His
1               5

<210> SEQ ID NO 902
<211> LENGTH: 9
<212> TYPE: PRT
<213> ORGANISM: CoV-2
<220> FEATURE:
<223> OTHER INFORMATION: MthlTrns A24.02_46

<400> SEQUENCE: 902

Lys Tyr Thr Gln Leu Cys Gln Tyr Leu
1               5

<210> SEQ ID NO 903
<211> LENGTH: 9
<212> TYPE: PRT
<213> ORGANISM: CoV-2
<220> FEATURE:
<223> OTHER INFORMATION: MthlTrns A24.02_62

<400> SEQUENCE: 903

Pro Tyr Asn Met Arg Val Ile His Phe
1               5

<210> SEQ ID NO 904
<211> LENGTH: 9
<212> TYPE: PRT
<213> ORGANISM: CoV-2
<220> FEATURE:
<223> OTHER INFORMATION: MthlTrns A24.02_236

<400> SEQUENCE: 904

Ile Gln Leu Ser Ser Tyr Ser Leu Phe
1               5

<210> SEQ ID NO 905
<211> LENGTH: 9
<212> TYPE: PRT
<213> ORGANISM: CoV-2
<220> FEATURE:
<223> OTHER INFORMATION: MthlTrns A24.02_86

<400> SEQUENCE: 905

Gln Trp Leu Pro Thr Gly Thr Leu Leu
1               5

<210> SEQ ID NO 906
<211> LENGTH: 9
```

```
<212> TYPE: PRT
<213> ORGANISM: CoV-2
<220> FEATURE:
<223> OTHER INFORMATION: MthlTrns A24.02_130

<400> SEQUENCE: 906

Met Tyr Asp Pro Lys Thr Lys Asn Val
1               5

<210> SEQ ID NO 907
<211> LENGTH: 9
<212> TYPE: PRT
<213> ORGANISM: CoV-2
<220> FEATURE:
<223> OTHER INFORMATION: MthlTrns A24.02_174

<400> SEQUENCE: 907

Ser Trp Asn Ala Asp Leu Tyr Lys Leu
1               5

<210> SEQ ID NO 908
<211> LENGTH: 9
<212> TYPE: PRT
<213> ORGANISM: CoV-2
<220> FEATURE:
<223> OTHER INFORMATION: MthlTrns A24.02_222

<400> SEQUENCE: 908

Val Met His Ala Asn Tyr Ile Phe Trp
1               5

<210> SEQ ID NO 909
<211> LENGTH: 9
<212> TYPE: PRT
<213> ORGANISM: CoV-2
<220> FEATURE:
<223> OTHER INFORMATION: MthlTrns A24.02_14

<400> SEQUENCE: 909

Leu Tyr Lys Met Gln Arg Met Leu Leu
1               5

<210> SEQ ID NO 910
<211> LENGTH: 9
<212> TYPE: PRT
<213> ORGANISM: CoV-2
<220> FEATURE:
<223> OTHER INFORMATION: MthlTrns A24.02_221

<400> SEQUENCE: 910

Tyr Val Met His Ala Asn Tyr Ile Phe
1               5

<210> SEQ ID NO 911
<211> LENGTH: 9
<212> TYPE: PRT
<213> ORGANISM: CoV-2
<220> FEATURE:
<223> OTHER INFORMATION: MthlTrns A24.02_220

<400> SEQUENCE: 911

Gly Tyr Val Met His Ala Asn Tyr Ile
1               5

<210> SEQ ID NO 912
<211> LENGTH: 9
<212> TYPE: PRT
```

```
<213> ORGANISM: CoV-2
<220> FEATURE:
<223> OTHER INFORMATION: MthlTrns A24.02_181

<400> SEQUENCE: 912

Lys Leu Met Gly His Phe Ala Trp Trp
1               5

<210> SEQ ID NO 913
<211> LENGTH: 9
<212> TYPE: PRT
<213> ORGANISM: CoV-2
<220> FEATURE:
<223> OTHER INFORMATION: MthlTrns A26.01_143

<400> SEQUENCE: 913

Asp Ser Lys Glu Gly Phe Phe Thr Tyr
1               5

<210> SEQ ID NO 914
<211> LENGTH: 9
<212> TYPE: PRT
<213> ORGANISM: CoV-2
<220> FEATURE:
<223> OTHER INFORMATION: MthlTrns A26.01_202

<400> SEQUENCE: 914

Glu Ala Phe Leu Ile Gly Cys Asn Tyr
1               5

<210> SEQ ID NO 915
<211> LENGTH: 9
<212> TYPE: PRT
<213> ORGANISM: CoV-2
<220> FEATURE:
<223> OTHER INFORMATION: MthlTrns A26.01_178

<400> SEQUENCE: 915

Asp Leu Tyr Lys Leu Met Gly His Phe
1               5

<210> SEQ ID NO 916
<211> LENGTH: 9
<212> TYPE: PRT
<213> ORGANISM: CoV-2
<220> FEATURE:
<223> OTHER INFORMATION: MthlTrns A26.01_55

<400> SEQUENCE: 916

Asn Thr Leu Thr Leu Ala Val Pro Tyr
1               5

<210> SEQ ID NO 917
<211> LENGTH: 9
<212> TYPE: PRT
<213> ORGANISM: CoV-2
<220> FEATURE:
<223> OTHER INFORMATION: MthlTrns A26.01_39

<400> SEQUENCE: 917

Gly Ile Met Met Asn Val Ala Lys Tyr
1               5

<210> SEQ ID NO 918
<211> LENGTH: 9
<212> TYPE: PRT
<213> ORGANISM: CoV-2
```

-continued

<220> FEATURE:
<223> OTHER INFORMATION: MthlTrns A26.01_221

<400> SEQUENCE: 918

Tyr Val Met His Ala Asn Tyr Ile Phe
1               5

<210> SEQ ID NO 919
<211> LENGTH: 9
<212> TYPE: PRT
<213> ORGANISM: CoV-2
<220> FEATURE:
<223> OTHER INFORMATION: MthlTrns A26.01_265

<400> SEQUENCE: 919

Gln Ile Asn Asp Met Ile Leu Ser Leu
1               5

<210> SEQ ID NO 920
<211> LENGTH: 9
<212> TYPE: PRT
<213> ORGANISM: CoV-2
<220> FEATURE:
<223> OTHER INFORMATION: MthlTrns A26.01_3

<400> SEQUENCE: 920

Gln Ala Trp Gln Pro Gly Val Ala Met
1               5

<210> SEQ ID NO 921
<211> LENGTH: 9
<212> TYPE: PRT
<213> ORGANISM: CoV-2
<220> FEATURE:
<223> OTHER INFORMATION: MthlTrns B07.02_76

<400> SEQUENCE: 921

Lys Val Ala Pro Gly Thr Ala Val Leu
1               5

<210> SEQ ID NO 922
<211> LENGTH: 9
<212> TYPE: PRT
<213> ORGANISM: CoV-2
<220> FEATURE:
<223> OTHER INFORMATION: MthlTrns B07.02_36

<400> SEQUENCE: 922

Leu Pro Lys Gly Ile Met Met Asn Val
1               5

<210> SEQ ID NO 923
<211> LENGTH: 9
<212> TYPE: PRT
<213> ORGANISM: CoV-2
<220> FEATURE:
<223> OTHER INFORMATION: MthlTrns B07.02_249

<400> SEQUENCE: 923

Phe Pro Leu Lys Leu Arg Gly Thr Ala
1               5

<210> SEQ ID NO 924
<211> LENGTH: 9
<212> TYPE: PRT
<213> ORGANISM: CoV-2
<220> FEATURE:

```
<223> OTHER INFORMATION: MthlTrns B07.02_6

<400> SEQUENCE: 924

Gln Pro Gly Val Ala Met Pro Asn Leu
1               5

<210> SEQ ID NO 925
<211> LENGTH: 9
<212> TYPE: PRT
<213> ORGANISM: CoV-2
<220> FEATURE:
<223> OTHER INFORMATION: MthlTrns B07.02_3

<400> SEQUENCE: 925

Gln Ala Trp Gln Pro Gly Val Ala Met
1               5

<210> SEQ ID NO 926
<211> LENGTH: 9
<212> TYPE: PRT
<213> ORGANISM: CoV-2
<220> FEATURE:
<223> OTHER INFORMATION: MthlTrns B07.02_213

<400> SEQUENCE: 926

Lys Pro Arg Glu Gln Ile Asp Gly Tyr
1               5

<210> SEQ ID NO 927
<211> LENGTH: 9
<212> TYPE: PRT
<213> ORGANISM: CoV-2
<220> FEATURE:
<223> OTHER INFORMATION: MthlTrns B15.01_236

<400> SEQUENCE: 927

Ile Gln Leu Ser Ser Tyr Ser Leu Phe
1               5

<210> SEQ ID NO 928
<211> LENGTH: 9
<212> TYPE: PRT
<213> ORGANISM: CoV-2
<220> FEATURE:
<223> OTHER INFORMATION: MthlTrns B15.01_85

<400> SEQUENCE: 928

Arg Gln Trp Leu Pro Thr Gly Thr Leu
1               5

<210> SEQ ID NO 929
<211> LENGTH: 9
<212> TYPE: PRT
<213> ORGANISM: CoV-2
<220> FEATURE:
<223> OTHER INFORMATION: MthlTrns B15.01_39

<400> SEQUENCE: 929

Gly Ile Met Met Asn Val Ala Lys Tyr
1               5

<210> SEQ ID NO 930
<211> LENGTH: 9
<212> TYPE: PRT
<213> ORGANISM: CoV-2
<220> FEATURE:
<223> OTHER INFORMATION: MthlTrns B15.01_76
```

```
<400> SEQUENCE: 930

Lys Val Ala Pro Gly Thr Ala Val Leu
1               5

<210> SEQ ID NO 931
<211> LENGTH: 9
<212> TYPE: PRT
<213> ORGANISM: CoV-2
<220> FEATURE:
<223> OTHER INFORMATION: MthlTrns B15.01_51

<400> SEQUENCE: 931

Cys Gln Tyr Leu Asn Thr Leu Thr Leu
1               5

<210> SEQ ID NO 932
<211> LENGTH: 9
<212> TYPE: PRT
<213> ORGANISM: CoV-2
<220> FEATURE:
<223> OTHER INFORMATION: MthlTrns B15.01_221

<400> SEQUENCE: 932

Tyr Val Met His Ala Asn Tyr Ile Phe
1               5

<210> SEQ ID NO 933
<211> LENGTH: 9
<212> TYPE: PRT
<213> ORGANISM: CoV-2
<220> FEATURE:
<223> OTHER INFORMATION: MthlTrns B15.01_143

<400> SEQUENCE: 933

Asp Ser Lys Glu Gly Phe Phe Thr Tyr
1               5

<210> SEQ ID NO 934
<211> LENGTH: 9
<212> TYPE: PRT
<213> ORGANISM: CoV-2
<220> FEATURE:
<223> OTHER INFORMATION: MthlTrns B15.01_45

<400> SEQUENCE: 934

Ala Lys Tyr Thr Gln Leu Cys Gln Tyr
1               5

<210> SEQ ID NO 935
<211> LENGTH: 9
<212> TYPE: PRT
<213> ORGANISM: CoV-2
<220> FEATURE:
<223> OTHER INFORMATION: MthlTrns B15.01_3

<400> SEQUENCE: 935

Gln Ala Trp Gln Pro Gly Val Ala Met
1               5

<210> SEQ ID NO 936
<211> LENGTH: 9
<212> TYPE: PRT
<213> ORGANISM: CoV-2
<220> FEATURE:
<223> OTHER INFORMATION: MthlTrns B15.01_167
```

```
<400> SEQUENCE: 936

Ala Ile Lys Ile Thr Glu His Ser Trp
1               5

<210> SEQ ID NO 937
<211> LENGTH: 9
<212> TYPE: PRT
<213> ORGANISM: CoV-2
<220> FEATURE:
<223> OTHER INFORMATION: MthlTrns B40.01_215

<400> SEQUENCE: 937

Arg Glu Gln Ile Asp Gly Tyr Val Met
1               5

<210> SEQ ID NO 938
<211> LENGTH: 9
<212> TYPE: PRT
<213> ORGANISM: CoV-2
<220> FEATURE:
<223> OTHER INFORMATION: MthlTrns B40.01_140

<400> SEQUENCE: 938

Lys Glu Asn Asp Ser Lys Glu Gly Phe
1               5

<210> SEQ ID NO 939
<211> LENGTH: 9
<212> TYPE: PRT
<213> ORGANISM: CoV-2
<220> FEATURE:
<223> OTHER INFORMATION: MthlTrns B40.01_171

<400> SEQUENCE: 939

Thr Glu His Ser Trp Asn Ala Asp Leu
1               5

<210> SEQ ID NO 940
<211> LENGTH: 9
<212> TYPE: PRT
<213> ORGANISM: CoV-2
<220> FEATURE:
<223> OTHER INFORMATION: MthlTrns B40.01_262

<400> SEQUENCE: 940

Lys Glu Gly Gln Ile Asn Asp Met Ile
1               5

<210> SEQ ID NO 941
<211> LENGTH: 9
<212> TYPE: PRT
<213> ORGANISM: CoV-2
<220> FEATURE:
<223> OTHER INFORMATION: MthlTrns B40.01_85

<400> SEQUENCE: 941

Arg Gln Trp Leu Pro Thr Gly Thr Leu
1               5

<210> SEQ ID NO 942
<211> LENGTH: 9
<212> TYPE: PRT
<213> ORGANISM: CoV-2
<220> FEATURE:
<223> OTHER INFORMATION: MthlTrns B58.01_115

<400> SEQUENCE: 942
```

Ala Thr Val His Thr Ala Asn Lys Trp
1               5

<210> SEQ ID NO 943
<211> LENGTH: 9
<212> TYPE: PRT
<213> ORGANISM: CoV-2
<220> FEATURE:
<223> OTHER INFORMATION: MthlTrns B58.01_167

<400> SEQUENCE: 943

Ala Ile Lys Ile Thr Glu His Ser Trp
1               5

<210> SEQ ID NO 944
<211> LENGTH: 9
<212> TYPE: PRT
<213> ORGANISM: CoV-2
<220> FEATURE:
<223> OTHER INFORMATION: MthlTrns B58.01_181

<400> SEQUENCE: 944

Lys Leu Met Gly His Phe Ala Trp Trp
1               5

<210> SEQ ID NO 945
<211> LENGTH: 9
<212> TYPE: PRT
<213> ORGANISM: CoV-2
<220> FEATURE:
<223> OTHER INFORMATION: MthlTrns B58.01_241

<400> SEQUENCE: 945

Tyr Ser Leu Phe Asp Met Ser Lys Phe
1               5

<210> SEQ ID NO 946
<211> LENGTH: 9
<212> TYPE: PRT
<213> ORGANISM: CoV-2
<220> FEATURE:
<223> OTHER INFORMATION: MthlTrns B58.01_222

<400> SEQUENCE: 946

Val Met His Ala Asn Tyr Ile Phe Trp
1               5

<210> SEQ ID NO 947
<211> LENGTH: 9
<212> TYPE: PRT
<213> ORGANISM: CoV-2
<220> FEATURE:
<223> OTHER INFORMATION: MthlTrns B58.01_9

<400> SEQUENCE: 947

Val Ala Met Pro Asn Leu Tyr Lys Met
1               5

<210> SEQ ID NO 948
<211> LENGTH: 9
<212> TYPE: PRT
<213> ORGANISM: CoV-2
<220> FEATURE:
<223> OTHER INFORMATION: MthlTrns B58.01_57

<400> SEQUENCE: 948

Leu Thr Leu Ala Val Pro Tyr Asn Met
1               5

<210> SEQ ID NO 949
<211> LENGTH: 9
<212> TYPE: PRT
<213> ORGANISM: CoV-2
<220> FEATURE:
<223> OTHER INFORMATION: MthlTrns B58.01_79

<400> SEQUENCE: 949

Pro Gly Thr Ala Val Leu Arg Gln Trp
1               5

<210> SEQ ID NO 950
<211> LENGTH: 9
<212> TYPE: PRT
<213> ORGANISM: CoV-2
<220> FEATURE:
<223> OTHER INFORMATION: MthlTrns B58.01_221

<400> SEQUENCE: 950

Tyr Val Met His Ala Asn Tyr Ile Phe
1               5

<210> SEQ ID NO 951
<211> LENGTH: 9
<212> TYPE: PRT
<213> ORGANISM: CoV-2
<220> FEATURE:
<223> OTHER INFORMATION: MthlTrns B58.01_198

<400> SEQUENCE: 951

Ala Ser Ser Ser Glu Ala Phe Leu Ile
1               5

<210> SEQ ID NO 952
<211> LENGTH: 9
<212> TYPE: PRT
<213> ORGANISM: CoV-2
<220> FEATURE:
<223> OTHER INFORMATION: MthlTrns B58.01_34

<400> SEQUENCE: 952

Ala Thr Leu Pro Lys Gly Ile Met Met
1               5

<210> SEQ ID NO 953
<211> LENGTH: 9
<212> TYPE: PRT
<213> ORGANISM: CoV-2
<220> FEATURE:
<223> OTHER INFORMATION: MthlTrns B58.01_76

<400> SEQUENCE: 953

Lys Val Ala Pro Gly Thr Ala Val Leu
1               5

<210> SEQ ID NO 954
<211> LENGTH: 9
<212> TYPE: PRT
<213> ORGANISM: CoV-2
<220> FEATURE:
<223> OTHER INFORMATION: Mem A1.01_171

<400> SEQUENCE: 954

Ala Thr Ser Arg Thr Leu Ser Tyr Tyr

```
1               5

<210> SEQ ID NO 955
<211> LENGTH: 9
<212> TYPE: PRT
<213> ORGANISM: CoV-2
<220> FEATURE:
<223> OTHER INFORMATION: Mem A1.01_39

<400> SEQUENCE: 955

Tyr Ala Asn Arg Asn Arg Phe Leu Tyr
1               5

<210> SEQ ID NO 956
<211> LENGTH: 9
<212> TYPE: PRT
<213> ORGANISM: CoV-2
<220> FEATURE:
<223> OTHER INFORMATION: Mem A1.01_188

<400> SEQUENCE: 956

Ala Gly Asp Ser Gly Phe Ala Ala Tyr
1               5

<210> SEQ ID NO 957
<211> LENGTH: 9
<212> TYPE: PRT
<213> ORGANISM: CoV-2
<220> FEATURE:
<223> OTHER INFORMATION: Mem A1.01_213

<400> SEQUENCE: 957

Ser Ser Asp Asn Ile Ala Leu Leu Val
1               5

<210> SEQ ID NO 958
<211> LENGTH: 9
<212> TYPE: PRT
<213> ORGANISM: CoV-2
<220> FEATURE:
<223> OTHER INFORMATION: Mem A1.01_170

<400> SEQUENCE: 958

Val Ala Thr Ser Arg Thr Leu Ser Tyr
1               5

<210> SEQ ID NO 959
<211> LENGTH: 9
<212> TYPE: PRT
<213> ORGANISM: CoV-2
<220> FEATURE:
<223> OTHER INFORMATION: Mem A2.01_15

<400> SEQUENCE: 959

Lys Leu Leu Glu Gln Trp Asn Leu Val
1               5

<210> SEQ ID NO 960
<211> LENGTH: 9
<212> TYPE: PRT
<213> ORGANISM: CoV-2
<220> FEATURE:
<223> OTHER INFORMATION: Mem A2.01_65

<400> SEQUENCE: 960

Phe Val Leu Ala Ala Val Tyr Arg Ile
1               5
```

```
<210> SEQ ID NO 961
<211> LENGTH: 9
<212> TYPE: PRT
<213> ORGANISM: CoV-2
<220> FEATURE:
<223> OTHER INFORMATION: Mem A2.01_108

<400> SEQUENCE: 961

Ser Met Trp Ser Phe Asn Pro Glu Thr
1               5

<210> SEQ ID NO 962
<211> LENGTH: 9
<212> TYPE: PRT
<213> ORGANISM: CoV-2
<220> FEATURE:
<223> OTHER INFORMATION: Mem A2.01_89

<400> SEQUENCE: 962

Gly Leu Met Trp Leu Ser Tyr Phe Ile
1               5

<210> SEQ ID NO 963
<211> LENGTH: 9
<212> TYPE: PRT
<213> ORGANISM: CoV-2
<220> FEATURE:
<223> OTHER INFORMATION: Mem A2.01_56

<400> SEQUENCE: 963

Leu Leu Trp Pro Val Thr Leu Ala Cys
1               5

<210> SEQ ID NO 964
<211> LENGTH: 9
<212> TYPE: PRT
<213> ORGANISM: CoV-2
<220> FEATURE:
<223> OTHER INFORMATION: Mem A2.01_55

<400> SEQUENCE: 964

Trp Leu Leu Trp Pro Val Thr Leu Ala
1               5

<210> SEQ ID NO 965
<211> LENGTH: 9
<212> TYPE: PRT
<213> ORGANISM: CoV-2
<220> FEATURE:
<223> OTHER INFORMATION: Mem A2.01_101

<400> SEQUENCE: 965

Arg Leu Phe Ala Arg Thr Arg Ser Met
1               5

<210> SEQ ID NO 966
<211> LENGTH: 9
<212> TYPE: PRT
<213> ORGANISM: CoV-2
<220> FEATURE:
<223> OTHER INFORMATION: Mem A3.01_150

<400> SEQUENCE: 966

Arg Ile Ala Gly His His Leu Gly Arg
1               5
```

```
<210> SEQ ID NO 967
<211> LENGTH: 9
<212> TYPE: PRT
<213> ORGANISM: CoV-2
<220> FEATURE:
<223> OTHER INFORMATION: Mem A3.01_171

<400> SEQUENCE: 967

Ala Thr Ser Arg Thr Leu Ser Tyr Tyr
1               5

<210> SEQ ID NO 968
<211> LENGTH: 9
<212> TYPE: PRT
<213> ORGANISM: CoV-2
<220> FEATURE:
<223> OTHER INFORMATION: Mem A3.01_172

<400> SEQUENCE: 968

Thr Ser Arg Thr Leu Ser Tyr Tyr Lys
1               5

<210> SEQ ID NO 969
<211> LENGTH: 9
<212> TYPE: PRT
<213> ORGANISM: CoV-2
<220> FEATURE:
<223> OTHER INFORMATION: Mem A3.01_6

<400> SEQUENCE: 969

Gly Thr Ile Thr Val Glu Glu Leu Lys
1               5

<210> SEQ ID NO 970
<211> LENGTH: 9
<212> TYPE: PRT
<213> ORGANISM: CoV-2
<220> FEATURE:
<223> OTHER INFORMATION: Mem A3.01_93

<400> SEQUENCE: 970

Leu Ser Tyr Phe Ile Ala Ser Phe Arg
1               5

<210> SEQ ID NO 971
<211> LENGTH: 9
<212> TYPE: PRT
<213> ORGANISM: CoV-2
<220> FEATURE:
<223> OTHER INFORMATION: Mem A3.01_138

<400> SEQUENCE: 971

Leu Val Ile Gly Ala Val Ile Leu Arg
1               5

<210> SEQ ID NO 972
<211> LENGTH: 9
<212> TYPE: PRT
<213> ORGANISM: CoV-2
<220> FEATURE:
<223> OTHER INFORMATION: Mem A24.02_95

<400> SEQUENCE: 972

Tyr Phe Ile Ala Ser Phe Arg Leu Phe
1               5
```

```
<210> SEQ ID NO 973
<211> LENGTH: 9
<212> TYPE: PRT
<213> ORGANISM: CoV-2
<220> FEATURE:
<223> OTHER INFORMATION: Mem A24.02_94

<400> SEQUENCE: 973

Ser Tyr Phe Ile Ala Ser Phe Arg Leu
1               5

<210> SEQ ID NO 974
<211> LENGTH: 9
<212> TYPE: PRT
<213> ORGANISM: CoV-2
<220> FEATURE:
<223> OTHER INFORMATION: Mem A24.02_46

<400> SEQUENCE: 974

Leu Tyr Ile Ile Lys Leu Ile Phe Leu
1               5

<210> SEQ ID NO 975
<211> LENGTH: 9
<212> TYPE: PRT
<213> ORGANISM: CoV-2
<220> FEATURE:
<223> OTHER INFORMATION: Mem A24.02_198

<400> SEQUENCE: 975

Arg Tyr Arg Ile Gly Asn Tyr Lys Leu
1               5

<210> SEQ ID NO 976
<211> LENGTH: 9
<212> TYPE: PRT
<213> ORGANISM: CoV-2
<220> FEATURE:
<223> OTHER INFORMATION: Mem A24.02_54

<400> SEQUENCE: 976

Leu Trp Leu Leu Trp Pro Val Thr Leu
1               5

<210> SEQ ID NO 977
<211> LENGTH: 9
<212> TYPE: PRT
<213> ORGANISM: CoV-2
<220> FEATURE:
<223> OTHER INFORMATION: Mem A24.02_57

<400> SEQUENCE: 977

Leu Trp Pro Val Thr Leu Ala Cys Phe
1               5

<210> SEQ ID NO 978
<211> LENGTH: 9
<212> TYPE: PRT
<213> ORGANISM: CoV-2
<220> FEATURE:
<223> OTHER INFORMATION: Mem A24.02_111

<400> SEQUENCE: 978

Ser Phe Asn Pro Glu Thr Asn Ile Leu
1               5

<210> SEQ ID NO 979
```

```
<211> LENGTH: 9
<212> TYPE: PRT
<213> ORGANISM: CoV-2
<220> FEATURE:
<223> OTHER INFORMATION: Mem A24.02_38

<400> SEQUENCE: 979

Ala Tyr Ala Asn Arg Asn Arg Phe Leu
1               5

<210> SEQ ID NO 980
<211> LENGTH: 9
<212> TYPE: PRT
<213> ORGANISM: CoV-2
<220> FEATURE:
<223> OTHER INFORMATION: Mem A24.02_102

<400> SEQUENCE: 980

Leu Phe Ala Arg Thr Arg Ser Met Trp
1               5

<210> SEQ ID NO 981
<211> LENGTH: 9
<212> TYPE: PRT
<213> ORGANISM: CoV-2
<220> FEATURE:
<223> OTHER INFORMATION: Mem A24.02_44

<400> SEQUENCE: 981

Arg Phe Leu Tyr Ile Ile Lys Leu Ile
1               5

<210> SEQ ID NO 982
<211> LENGTH: 9
<212> TYPE: PRT
<213> ORGANISM: CoV-2
<220> FEATURE:
<223> OTHER INFORMATION: Mem A26.01_171

<400> SEQUENCE: 982

Ala Thr Ser Arg Thr Leu Ser Tyr Tyr
1               5

<210> SEQ ID NO 983
<211> LENGTH: 9
<212> TYPE: PRT
<213> ORGANISM: CoV-2
<220> FEATURE:
<223> OTHER INFORMATION: Mem A26.01_170

<400> SEQUENCE: 983

Val Ala Thr Ser Arg Thr Leu Ser Tyr
1               5

<210> SEQ ID NO 984
<211> LENGTH: 9
<212> TYPE: PRT
<213> ORGANISM: CoV-2
<220> FEATURE:
<223> OTHER INFORMATION: Mem A26.01_196

<400> SEQUENCE: 984

Tyr Ser Arg Tyr Arg Ile Gly Asn Tyr
1               5

<210> SEQ ID NO 985
<211> LENGTH: 9
```

<212> TYPE: PRT
<213> ORGANISM: CoV-2
<220> FEATURE:
<223> OTHER INFORMATION: Mem A26.01_39

<400> SEQUENCE: 985

Tyr Ala Asn Arg Asn Arg Phe Leu Tyr
1 5

<210> SEQ ID NO 986
<211> LENGTH: 9
<212> TYPE: PRT
<213> ORGANISM: CoV-2
<220> FEATURE:
<223> OTHER INFORMATION: Mem A26.01_37

<400> SEQUENCE: 986

Phe Ala Tyr Ala Asn Arg Asn Arg Phe
1 5

<210> SEQ ID NO 987
<211> LENGTH: 9
<212> TYPE: PRT
<213> ORGANISM: CoV-2
<220> FEATURE:
<223> OTHER INFORMATION: Mem B7.02_164

<400> SEQUENCE: 987

Leu Pro Lys Glu Ile Thr Val Ala Thr
1 5

<210> SEQ ID NO 988
<211> LENGTH: 9
<212> TYPE: PRT
<213> ORGANISM: CoV-2
<220> FEATURE:
<223> OTHER INFORMATION: Mem B7.02_148

<400> SEQUENCE: 988

His Leu Arg Ile Ala Gly His His Leu
1 5

<210> SEQ ID NO 989
<211> LENGTH: 9
<212> TYPE: PRT
<213> ORGANISM: CoV-2
<220> FEATURE:
<223> OTHER INFORMATION: Mem B7.02_101

<400> SEQUENCE: 989

Arg Leu Phe Ala Arg Thr Arg Ser Met
1 5

<210> SEQ ID NO 990
<211> LENGTH: 9
<212> TYPE: PRT
<213> ORGANISM: CoV-2
<220> FEATURE:
<223> OTHER INFORMATION: Mem B15.01_101

<400> SEQUENCE: 990

Arg Leu Phe Ala Arg Thr Arg Ser Met
1 5

<210> SEQ ID NO 991
<211> LENGTH: 9
<212> TYPE: PRT

```
<213> ORGANISM: CoV-2
<220> FEATURE:
<223> OTHER INFORMATION: Mem B15.01_170

<400> SEQUENCE: 991

Val Ala Thr Ser Arg Thr Leu Ser Tyr
1               5

<210> SEQ ID NO 992
<211> LENGTH: 9
<212> TYPE: PRT
<213> ORGANISM: CoV-2
<220> FEATURE:
<223> OTHER INFORMATION: Mem B15.01_171

<400> SEQUENCE: 992

Ala Thr Ser Arg Thr Leu Ser Tyr Tyr
1               5

<210> SEQ ID NO 993
<211> LENGTH: 9
<212> TYPE: PRT
<213> ORGANISM: CoV-2
<220> FEATURE:
<223> OTHER INFORMATION: Mem B15.01_37

<400> SEQUENCE: 993

Phe Ala Tyr Ala Asn Arg Asn Arg Phe
1               5

<210> SEQ ID NO 994
<211> LENGTH: 9
<212> TYPE: PRT
<213> ORGANISM: CoV-2
<220> FEATURE:
<223> OTHER INFORMATION: Mem B15.01_191

<400> SEQUENCE: 994

Ser Gly Phe Ala Ala Tyr Ser Arg Tyr
1               5

<210> SEQ ID NO 995
<211> LENGTH: 9
<212> TYPE: PRT
<213> ORGANISM: CoV-2
<220> FEATURE:
<223> OTHER INFORMATION: Mem B15.01_39

<400> SEQUENCE: 995

Tyr Ala Asn Arg Asn Arg Phe Leu Tyr
1               5

<210> SEQ ID NO 996
<211> LENGTH: 9
<212> TYPE: PRT
<213> ORGANISM: CoV-2
<220> FEATURE:
<223> OTHER INFORMATION: Mem B15.01_196

<400> SEQUENCE: 996

Tyr Ser Arg Tyr Arg Ile Gly Asn Tyr
1               5

<210> SEQ ID NO 997
<211> LENGTH: 9
<212> TYPE: PRT
<213> ORGANISM: CoV-2
```

```
<220> FEATURE:
<223> OTHER INFORMATION: Mem B15.01_148

<400> SEQUENCE: 997

His Leu Arg Ile Ala Gly His His Leu
1               5

<210> SEQ ID NO 998
<211> LENGTH: 9
<212> TYPE: PRT
<213> ORGANISM: CoV-2
<220> FEATURE:
<223> OTHER INFORMATION: Mem B15.01_18

<400> SEQUENCE: 998

Glu Gln Trp Asn Leu Val Ile Gly Phe
1               5

<210> SEQ ID NO 999
<211> LENGTH: 9
<212> TYPE: PRT
<213> ORGANISM: CoV-2
<220> FEATURE:
<223> OTHER INFORMATION: Mem B15.01_45

<400> SEQUENCE: 999

Phe Leu Tyr Ile Ile Lys Leu Ile Phe
1               5

<210> SEQ ID NO 1000
<211> LENGTH: 9
<212> TYPE: PRT
<213> ORGANISM: CoV-2
<220> FEATURE:
<223> OTHER INFORMATION: Mem B40.01_136

<400> SEQUENCE: 1000

Ser Glu Leu Val Ile Gly Ala Val Ile
1               5

<210> SEQ ID NO 1001
<211> LENGTH: 9
<212> TYPE: PRT
<213> ORGANISM: CoV-2
<220> FEATURE:
<223> OTHER INFORMATION: Mem B58.01_84

<400> SEQUENCE: 1001

Met Ala Cys Leu Val Gly Leu Met Trp
1               5

<210> SEQ ID NO 1002
<211> LENGTH: 9
<212> TYPE: PRT
<213> ORGANISM: CoV-2
<220> FEATURE:
<223> OTHER INFORMATION: Mem B58.01_67

<400> SEQUENCE: 1002

Leu Ala Ala Val Tyr Arg Ile Asn Trp
1               5

<210> SEQ ID NO 1003
<211> LENGTH: 9
<212> TYPE: PRT
<213> ORGANISM: CoV-2
<220> FEATURE:
```

-continued

```
<223> OTHER INFORMATION: Mem B58.01_47

<400> SEQUENCE: 1003

Tyr Ile Ile Lys Leu Ile Phe Leu Trp
1               5

<210> SEQ ID NO 1004
<211> LENGTH: 9
<212> TYPE: PRT
<213> ORGANISM: CoV-2
<220> FEATURE:
<223> OTHER INFORMATION: Mem B58.01_39

<400> SEQUENCE: 1004

Tyr Ala Asn Arg Asn Arg Phe Leu Tyr
1               5

<210> SEQ ID NO 1005
<211> LENGTH: 9
<212> TYPE: PRT
<213> ORGANISM: CoV-2
<220> FEATURE:
<223> OTHER INFORMATION: Mem B58.01_171

<400> SEQUENCE: 1005

Ala Thr Ser Arg Thr Leu Ser Tyr Tyr
1               5

<210> SEQ ID NO 1006
<211> LENGTH: 9
<212> TYPE: PRT
<213> ORGANISM: CoV-2
<220> FEATURE:
<223> OTHER INFORMATION: Mem B58.01_23

<400> SEQUENCE: 1006

Val Ile Gly Phe Leu Phe Leu Thr Trp
1               5

<210> SEQ ID NO 1007
<211> LENGTH: 9
<212> TYPE: PRT
<213> ORGANISM: CoV-2
<220> FEATURE:
<223> OTHER INFORMATION: Mem B58.01_12

<400> SEQUENCE: 1007

Glu Leu Lys Lys Leu Leu Glu Gln Trp
1               5

<210> SEQ ID NO 1008
<211> LENGTH: 9
<212> TYPE: PRT
<213> ORGANISM: CoV-2
<220> FEATURE:
<223> OTHER INFORMATION: Mem B58.01_50

<400> SEQUENCE: 1008

Lys Leu Ile Phe Leu Trp Leu Leu Trp
1               5

<210> SEQ ID NO 1009
<211> LENGTH: 9
<212> TYPE: PRT
<213> ORGANISM: CoV-2
<220> FEATURE:
<223> OTHER INFORMATION: Mem B58.01_170
```

```
<400> SEQUENCE: 1009

Val Ala Thr Ser Arg Thr Leu Ser Tyr
1               5

<210> SEQ ID NO 1010
<211> LENGTH: 9
<212> TYPE: PRT
<213> ORGANISM: CoV-2
<220> FEATURE:
<223> OTHER INFORMATION: Mem B58.01_168

<400> SEQUENCE: 1010

Ile Thr Val Ala Thr Ser Arg Thr Leu
1               5

<210> SEQ ID NO 1011
<211> LENGTH: 9
<212> TYPE: PRT
<213> ORGANISM: CoV-2
<220> FEATURE:
<223> OTHER INFORMATION: Mem B58.01_102

<400> SEQUENCE: 1011

Leu Phe Ala Arg Thr Arg Ser Met Trp
1               5

<210> SEQ ID NO 1012
<211> LENGTH: 9
<212> TYPE: PRT
<213> ORGANISM: CoV-2
<220> FEATURE:
<223> OTHER INFORMATION: Mem B58.01_37

<400> SEQUENCE: 1012

Phe Ala Tyr Ala Asn Arg Asn Arg Phe
1               5

<210> SEQ ID NO 1013
<211> LENGTH: 9
<212> TYPE: PRT
<213> ORGANISM: CoV-2
<220> FEATURE:
<223> OTHER INFORMATION: Mem B58.01_29

<400> SEQUENCE: 1013

Leu Thr Trp Ile Cys Leu Leu Gln Phe
1               5

<210> SEQ ID NO 1014
<211> LENGTH: 9
<212> TYPE: PRT
<213> ORGANISM: CoV-2
<220> FEATURE:
<223> OTHER INFORMATION: Mem B58.01_8

<400> SEQUENCE: 1014

Ile Thr Val Glu Glu Leu Lys Lys Leu
1               5

<210> SEQ ID NO 1015
<211> LENGTH: 9
<212> TYPE: PRT
<213> ORGANISM: CoV-2
<220> FEATURE:
<223> OTHER INFORMATION: Evlp A1.01_49
```

```
<400> SEQUENCE: 1015

Val Ser Leu Val Lys Pro Ser Phe Tyr
1               5

<210> SEQ ID NO 1016
<211> LENGTH: 9
<212> TYPE: PRT
<213> ORGANISM: CoV-2
<220> FEATURE:
<223> OTHER INFORMATION: Evlp A1.01_34

<400> SEQUENCE: 1016

Leu Thr Ala Leu Arg Leu Cys Ala Tyr
1               5

<210> SEQ ID NO 1017
<211> LENGTH: 9
<212> TYPE: PRT
<213> ORGANISM: CoV-2
<220> FEATURE:
<223> OTHER INFORMATION: Evlp A1.01_51

<400> SEQUENCE: 1017

Leu Val Lys Pro Ser Phe Tyr Val Tyr
1               5

<210> SEQ ID NO 1018
<211> LENGTH: 9
<212> TYPE: PRT
<213> ORGANISM: CoV-2
<220> FEATURE:
<223> OTHER INFORMATION: Evlp A2.01_50

<400> SEQUENCE: 1018

Ser Leu Val Lys Pro Ser Phe Tyr Val
1               5

<210> SEQ ID NO 1019
<211> LENGTH: 9
<212> TYPE: PRT
<213> ORGANISM: CoV-2
<220> FEATURE:
<223> OTHER INFORMATION: Evlp A2.01_57

<400> SEQUENCE: 1019

Tyr Val Tyr Ser Arg Val Lys Asn Leu
1               5

<210> SEQ ID NO 1020
<211> LENGTH: 9
<212> TYPE: PRT
<213> ORGANISM: CoV-2
<220> FEATURE:
<223> OTHER INFORMATION: Evlp A2.01_20

<400> SEQUENCE: 1020

Phe Leu Ala Phe Val Val Phe Leu Leu
1               5

<210> SEQ ID NO 1021
<211> LENGTH: 9
<212> TYPE: PRT
<213> ORGANISM: CoV-2
<220> FEATURE:
<223> OTHER INFORMATION: Evlp A2.01_13

<400> SEQUENCE: 1021
```

```
Ile Val Asn Ser Val Leu Leu Phe Leu
1               5

<210> SEQ ID NO 1022
<211> LENGTH: 9
<212> TYPE: PRT
<213> ORGANISM: CoV-2
<220> FEATURE:
<223> OTHER INFORMATION: Evlp A2.01_11

<400> SEQUENCE: 1022

Thr Leu Ile Val Asn Ser Val Leu Leu
1               5

<210> SEQ ID NO 1023
<211> LENGTH: 9
<212> TYPE: PRT
<213> ORGANISM: CoV-2
<220> FEATURE:
<223> OTHER INFORMATION: Evlp A2.01_4

<400> SEQUENCE: 1023

Phe Val Ser Glu Glu Thr Gly Thr Leu
1               5

<210> SEQ ID NO 1024
<211> LENGTH: 9
<212> TYPE: PRT
<213> ORGANISM: CoV-2
<220> FEATURE:
<223> OTHER INFORMATION: Evlp A2.01_26

<400> SEQUENCE: 1024

Phe Leu Leu Val Thr Leu Ala Ile Leu
1               5

<210> SEQ ID NO 1025
<211> LENGTH: 9
<212> TYPE: PRT
<213> ORGANISM: CoV-2
<220> FEATURE:
<223> OTHER INFORMATION: Evlp A2.01_16

<400> SEQUENCE: 1025

Ser Val Leu Leu Phe Leu Ala Phe Val
1               5

<210> SEQ ID NO 1026
<211> LENGTH: 9
<212> TYPE: PRT
<213> ORGANISM: CoV-2
<220> FEATURE:
<223> OTHER INFORMATION: Evlp A3.01_61

<400> SEQUENCE: 1026

Arg Val Lys Asn Leu Asn Ser Ser Arg
1               5

<210> SEQ ID NO 1027
<211> LENGTH: 9
<212> TYPE: PRT
<213> ORGANISM: CoV-2
<220> FEATURE:
<223> OTHER INFORMATION: Evlp A3.01_45

<400> SEQUENCE: 1027
```

Asn Ile Val Asn Val Ser Leu Val Lys
1               5

<210> SEQ ID NO 1028
<211> LENGTH: 9
<212> TYPE: PRT
<213> ORGANISM: CoV-2
<220> FEATURE:
<223> OTHER INFORMATION: Evlp A26.01_51

<400> SEQUENCE: 1028

Leu Val Lys Pro Ser Phe Tyr Val Tyr
1               5

<210> SEQ ID NO 1029
<211> LENGTH: 9
<212> TYPE: PRT
<213> ORGANISM: CoV-2
<220> FEATURE:
<223> OTHER INFORMATION: Evlp A26.01_57

<400> SEQUENCE: 1029

Tyr Val Tyr Ser Arg Val Lys Asn Leu
1               5

<210> SEQ ID NO 1030
<211> LENGTH: 9
<212> TYPE: PRT
<213> ORGANISM: CoV-2
<220> FEATURE:
<223> OTHER INFORMATION: Evlp A26.01_48

<400> SEQUENCE: 1030

Asn Val Ser Leu Val Lys Pro Ser Phe
1               5

<210> SEQ ID NO 1031
<211> LENGTH: 9
<212> TYPE: PRT
<213> ORGANISM: CoV-2
<220> FEATURE:
<223> OTHER INFORMATION: Evlp A26.01_4

<400> SEQUENCE: 1031

Phe Val Ser Glu Glu Thr Gly Thr Leu
1               5

<210> SEQ ID NO 1032
<211> LENGTH: 9
<212> TYPE: PRT
<213> ORGANISM: CoV-2
<220> FEATURE:
<223> OTHER INFORMATION: Evlp A26.01_34

<400> SEQUENCE: 1032

Leu Thr Ala Leu Arg Leu Cys Ala Tyr
1               5

<210> SEQ ID NO 1033
<211> LENGTH: 9
<212> TYPE: PRT
<213> ORGANISM: CoV-2
<220> FEATURE:
<223> OTHER INFORMATION: Evlp A26.01_12

<400> SEQUENCE: 1033

Leu Ile Val Asn Ser Val Leu Leu Phe

```
1               5

<210> SEQ ID NO 1034
<211> LENGTH: 9
<212> TYPE: PRT
<213> ORGANISM: CoV-2
<220> FEATURE:
<223> OTHER INFORMATION: Evlp B07.02_57

<400> SEQUENCE: 1034

Tyr Val Tyr Ser Arg Val Lys Asn Leu
1               5

<210> SEQ ID NO 1035
<211> LENGTH: 9
<212> TYPE: PRT
<213> ORGANISM: CoV-2
<220> FEATURE:
<223> OTHER INFORMATION: Evlp B15.01_51

<400> SEQUENCE: 1035

Leu Val Lys Pro Ser Phe Tyr Val Tyr
1               5

<210> SEQ ID NO 1036
<211> LENGTH: 9
<212> TYPE: PRT
<213> ORGANISM: CoV-2
<220> FEATURE:
<223> OTHER INFORMATION: Evlp B15.01_12

<400> SEQUENCE: 1036

Leu Ile Val Asn Ser Val Leu Leu Phe
1               5

<210> SEQ ID NO 1037
<211> LENGTH: 9
<212> TYPE: PRT
<213> ORGANISM: CoV-2
<220> FEATURE:
<223> OTHER INFORMATION: Evlp B15.01_18

<400> SEQUENCE: 1037

Leu Leu Phe Leu Ala Phe Val Val Phe
1               5

<210> SEQ ID NO 1038
<211> LENGTH: 9
<212> TYPE: PRT
<213> ORGANISM: CoV-2
<220> FEATURE:
<223> OTHER INFORMATION: Evlp B15.01_34

<400> SEQUENCE: 1038

Leu Thr Ala Leu Arg Leu Cys Ala Tyr
1               5

<210> SEQ ID NO 1039
<211> LENGTH: 9
<212> TYPE: PRT
<213> ORGANISM: CoV-2
<220> FEATURE:
<223> OTHER INFORMATION: Evlp B15.01_49

<400> SEQUENCE: 1039

Val Ser Leu Val Lys Pro Ser Phe Tyr
1               5
```

```
<210> SEQ ID NO 1040
<211> LENGTH: 9
<212> TYPE: PRT
<213> ORGANISM: CoV-2
<220> FEATURE:
<223> OTHER INFORMATION: Evlp B40.01_6

<400> SEQUENCE: 1040

Ser Glu Glu Thr Gly Thr Leu Ile Val
1 5

<210> SEQ ID NO 1041
<211> LENGTH: 9
<212> TYPE: PRT
<213> ORGANISM: CoV-2
<220> FEATURE:
<223> OTHER INFORMATION: Evlp B58.01_49

<400> SEQUENCE: 1041

Val Ser Leu Val Lys Pro Ser Phe Tyr
1 5

<210> SEQ ID NO 1042
<211> LENGTH: 9
<212> TYPE: PRT
<213> ORGANISM: CoV-2
<220> FEATURE:
<223> OTHER INFORMATION: Evlp B58.01_51

<400> SEQUENCE: 1042

Leu Val Lys Pro Ser Phe Tyr Val Tyr
1 5

<210> SEQ ID NO 1043
<211> LENGTH: 9
<212> TYPE: PRT
<213> ORGANISM: CoV-2
<220> FEATURE:
<223> OTHER INFORMATION: Evlp B58.01_12

<400> SEQUENCE: 1043

Leu Ile Val Asn Ser Val Leu Leu Phe
1 5

<210> SEQ ID NO 1044
<211> LENGTH: 9
<212> TYPE: PRT
<213> ORGANISM: CoV-2
<220> FEATURE:
<223> OTHER INFORMATION: Evlp B58.01_29

<400> SEQUENCE: 1044

Val Thr Leu Ala Ile Leu Thr Ala Leu
1 5

<210> SEQ ID NO 1045
<211> LENGTH: 9
<212> TYPE: PRT
<213> ORGANISM: CoV-2
<220> FEATURE:
<223> OTHER INFORMATION: ORF3a A1.01_207

<400> SEQUENCE: 1045

Phe Thr Ser Asp Tyr Tyr Gln Leu Tyr
1 5

<210> SEQ ID NO 1046
<211> LENGTH: 9
<212> TYPE: PRT
<213> ORGANISM: CoV-2
<220> FEATURE:
<223> OTHER INFORMATION: ORF3a A1.01_204

<400> SEQUENCE: 1046

His Ser Tyr Phe Thr Ser Asp Tyr Tyr
1               5

<210> SEQ ID NO 1047
<211> LENGTH: 9
<212> TYPE: PRT
<213> ORGANISM: CoV-2
<220> FEATURE:
<223> OTHER INFORMATION: ORF3a A1.01_176

<400> SEQUENCE: 1047

Thr Ser Pro Ile Ser Glu His Asp Tyr
1               5

<210> SEQ ID NO 1048
<211> LENGTH: 9
<212> TYPE: PRT
<213> ORGANISM: CoV-2
<220> FEATURE:
<223> OTHER INFORMATION: ORF3a A1.01_220

<400> SEQUENCE: 1048

Ser Thr Asp Thr Gly Val Glu His Val
1               5

<210> SEQ ID NO 1049
<211> LENGTH: 9
<212> TYPE: PRT
<213> ORGANISM: CoV-2
<220> FEATURE:
<223> OTHER INFORMATION: ORF3a A1.01_101

<400> SEQUENCE: 1049

Leu Glu Ala Pro Phe Leu Tyr Leu Tyr
1               5

<210> SEQ ID NO 1050
<211> LENGTH: 9
<212> TYPE: PRT
<213> ORGANISM: CoV-2
<220> FEATURE:
<223> OTHER INFORMATION: ORF3a A1.01_146

<400> SEQUENCE: 1050

Phe Leu Cys Trp His Thr Asn Cys Tyr
1               5

<210> SEQ ID NO 1051
<211> LENGTH: 9
<212> TYPE: PRT
<213> ORGANISM: CoV-2
<220> FEATURE:
<223> OTHER INFORMATION: ORF3a A2.01_139

<400> SEQUENCE: 1051

Leu Leu Tyr Asp Ala Asn Tyr Phe Leu
1               5

```
<210> SEQ ID NO 1052
<211> LENGTH: 9
<212> TYPE: PRT
<213> ORGANISM: CoV-2
<220> FEATURE:
<223> OTHER INFORMATION: ORF3a A2.01_72

<400> SEQUENCE: 1052

Ala Leu Ser Lys Gly Val His Phe Val
1               5

<210> SEQ ID NO 1053
<211> LENGTH: 9
<212> TYPE: PRT
<213> ORGANISM: CoV-2
<220> FEATURE:
<223> OTHER INFORMATION: ORF3a A2.01_89

<400> SEQUENCE: 1053

Thr Val Tyr Ser His Leu Leu Leu Val
1               5

<210> SEQ ID NO 1054
<211> LENGTH: 9
<212> TYPE: PRT
<213> ORGANISM: CoV-2
<220> FEATURE:
<223> OTHER INFORMATION: ORF3a A2.01_107

<400> SEQUENCE: 1054

Tyr Leu Tyr Ala Leu Val Tyr Phe Leu
1               5

<210> SEQ ID NO 1055
<211> LENGTH: 9
<212> TYPE: PRT
<213> ORGANISM: CoV-2
<220> FEATURE:
<223> OTHER INFORMATION: ORF3a A2.01_236

<400> SEQUENCE: 1055

Ile Val Asp Glu Pro Glu Glu His Val
1               5

<210> SEQ ID NO 1056
<211> LENGTH: 9
<212> TYPE: PRT
<213> ORGANISM: CoV-2
<220> FEATURE:
<223> OTHER INFORMATION: ORF3a A2.01_110

<400> SEQUENCE: 1056

Ala Leu Val Tyr Phe Leu Gln Ser Ile
1               5

<210> SEQ ID NO 1057
<211> LENGTH: 9
<212> TYPE: PRT
<213> ORGANISM: CoV-2
<220> FEATURE:
<223> OTHER INFORMATION: ORF3a A2.01_51

<400> SEQUENCE: 1057

Ala Leu Leu Ala Val Phe Gln Ser Ala
1               5

<210> SEQ ID NO 1058
```

```
<211> LENGTH: 9
<212> TYPE: PRT
<213> ORGANISM: CoV-2
<220> FEATURE:
<223> OTHER INFORMATION: ORF3a A2.01_100

<400> SEQUENCE: 1058

Gly Leu Glu Ala Pro Phe Leu Tyr Leu
1               5

<210> SEQ ID NO 1059
<211> LENGTH: 9
<212> TYPE: PRT
<213> ORGANISM: CoV-2
<220> FEATURE:
<223> OTHER INFORMATION: ORF3a A2.01_82

<400> SEQUENCE: 1059

Asn Leu Leu Leu Leu Phe Val Thr Val
1               5

<210> SEQ ID NO 1060
<211> LENGTH: 9
<212> TYPE: PRT
<213> ORGANISM: CoV-2
<220> FEATURE:
<223> OTHER INFORMATION: ORF3a A2.01_33

<400> SEQUENCE: 1060

Ala Thr Ile Pro Ile Gln Ala Ser Leu
1               5

<210> SEQ ID NO 1061
<211> LENGTH: 9
<212> TYPE: PRT
<213> ORGANISM: CoV-2
<220> FEATURE:
<223> OTHER INFORMATION: ORF3a A2.01_87

<400> SEQUENCE: 1061

Phe Val Thr Val Tyr Ser His Leu Leu
1               5

<210> SEQ ID NO 1062
<211> LENGTH: 9
<212> TYPE: PRT
<213> ORGANISM: CoV-2
<220> FEATURE:
<223> OTHER INFORMATION: ORF3a A2.01_45

<400> SEQUENCE: 1062

Trp Leu Ile Val Gly Val Ala Leu Leu
1               5

<210> SEQ ID NO 1063
<211> LENGTH: 9
<212> TYPE: PRT
<213> ORGANISM: CoV-2
<220> FEATURE:
<223> OTHER INFORMATION: ORF3a A2.01_247

<400> SEQUENCE: 1063

His Thr Ile Asp Gly Ser Ser Gly Val
1               5

<210> SEQ ID NO 1064
<211> LENGTH: 9
```

```
<212> TYPE: PRT
<213> ORGANISM: CoV-2
<220> FEATURE:
<223> OTHER INFORMATION: ORF3a A2.01_220

<400> SEQUENCE: 1064

Ser Thr Asp Thr Gly Val Glu His Val
1               5

<210> SEQ ID NO 1065
<211> LENGTH: 9
<212> TYPE: PRT
<213> ORGANISM: CoV-2
<220> FEATURE:
<223> OTHER INFORMATION: ORF3a A3.01_58

<400> SEQUENCE: 1065

Ser Ala Ser Lys Ile Ile Thr Leu Lys
1               5

<210> SEQ ID NO 1066
<211> LENGTH: 9
<212> TYPE: PRT
<213> ORGANISM: CoV-2
<220> FEATURE:
<223> OTHER INFORMATION: ORF3a A3.01_59

<400> SEQUENCE: 1066

Ala Ser Lys Ile Ile Thr Leu Lys Lys
1               5

<210> SEQ ID NO 1067
<211> LENGTH: 9
<212> TYPE: PRT
<213> ORGANISM: CoV-2
<220> FEATURE:
<223> OTHER INFORMATION: ORF3a A3.01_8

<400> SEQUENCE: 1067

Phe Thr Ile Gly Thr Val Thr Leu Lys
1               5

<210> SEQ ID NO 1068
<211> LENGTH: 9
<212> TYPE: PRT
<213> ORGANISM: CoV-2
<220> FEATURE:
<223> OTHER INFORMATION: ORF3a A3.01_227

<400> SEQUENCE: 1068

His Val Thr Phe Phe Ile Tyr Asn Lys
1               5

<210> SEQ ID NO 1069
<211> LENGTH: 9
<212> TYPE: PRT
<213> ORGANISM: CoV-2
<220> FEATURE:
<223> OTHER INFORMATION: ORF3a A3.01_184

<400> SEQUENCE: 1069

Tyr Gln Ile Gly Gly Tyr Thr Glu Lys
1               5

<210> SEQ ID NO 1070
<211> LENGTH: 9
<212> TYPE: PRT
```

```
<213> ORGANISM: CoV-2
<220> FEATURE:
<223> OTHER INFORMATION: ORF3a A3.01_13

<400> SEQUENCE: 1070

Val Thr Leu Lys Gln Gly Glu Ile Lys
1               5

<210> SEQ ID NO 1071
<211> LENGTH: 9
<212> TYPE: PRT
<213> ORGANISM: CoV-2
<220> FEATURE:
<223> OTHER INFORMATION: ORF3a A24.02_112

<400> SEQUENCE: 1071

Val Tyr Phe Leu Gln Ser Ile Asn Phe
1               5

<210> SEQ ID NO 1072
<211> LENGTH: 9
<212> TYPE: PRT
<213> ORGANISM: CoV-2
<220> FEATURE:
<223> OTHER INFORMATION: ORF3a A24.02_211

<400> SEQUENCE: 1072

Tyr Tyr Gln Leu Tyr Ser Thr Gln Leu
1               5

<210> SEQ ID NO 1073
<211> LENGTH: 9
<212> TYPE: PRT
<213> ORGANISM: CoV-2
<220> FEATURE:
<223> OTHER INFORMATION: ORF3a A24.02_106

<400> SEQUENCE: 1073

Leu Tyr Leu Tyr Ala Leu Val Tyr Phe
1               5

<210> SEQ ID NO 1074
<211> LENGTH: 9
<212> TYPE: PRT
<213> ORGANISM: CoV-2
<220> FEATURE:
<223> OTHER INFORMATION: ORF3a A24.02_159

<400> SEQUENCE: 1074

Pro Tyr Asn Ser Val Thr Ser Ser Ile
1               5

<210> SEQ ID NO 1075
<211> LENGTH: 9
<212> TYPE: PRT
<213> ORGANISM: CoV-2
<220> FEATURE:
<223> OTHER INFORMATION: ORF3a A24.02_206

<400> SEQUENCE: 1075

Tyr Phe Thr Ser Asp Tyr Tyr Gln Leu
1               5

<210> SEQ ID NO 1076
<211> LENGTH: 9
<212> TYPE: PRT
<213> ORGANISM: CoV-2
```

```
<220> FEATURE:
<223> OTHER INFORMATION: ORF3a A24.02_7

<400> SEQUENCE: 1076

Ile Phe Thr Ile Gly Thr Val Thr Leu
1               5

<210> SEQ ID NO 1077
<211> LENGTH: 9
<212> TYPE: PRT
<213> ORGANISM: CoV-2
<220> FEATURE:
<223> OTHER INFORMATION: ORF3a A24.02_86

<400> SEQUENCE: 1077

Leu Phe Val Thr Val Tyr Ser His Leu
1               5

<210> SEQ ID NO 1078
<211> LENGTH: 9
<212> TYPE: PRT
<213> ORGANISM: CoV-2
<220> FEATURE:
<223> OTHER INFORMATION: ORF3a A24.02_37

<400> SEQUENCE: 1078

Ile Gln Ala Ser Leu Pro Phe Gly Trp
1               5

<210> SEQ ID NO 1079
<211> LENGTH: 9
<212> TYPE: PRT
<213> ORGANISM: CoV-2
<220> FEATURE:
<223> OTHER INFORMATION: ORF3a A24.02_119

<400> SEQUENCE: 1079

Asn Phe Val Arg Ile Ile Met Arg Leu
1               5

<210> SEQ ID NO 1080
<211> LENGTH: 9
<212> TYPE: PRT
<213> ORGANISM: CoV-2
<220> FEATURE:
<223> OTHER INFORMATION: ORF3a A24.02_55

<400> SEQUENCE: 1080

Val Phe Gln Ser Ala Ser Lys Ile Ile
1               5

<210> SEQ ID NO 1081
<211> LENGTH: 9
<212> TYPE: PRT
<213> ORGANISM: CoV-2
<220> FEATURE:
<223> OTHER INFORMATION: ORF3a A26.01_207

<400> SEQUENCE: 1081

Phe Thr Ser Asp Tyr Tyr Gln Leu Tyr
1               5

<210> SEQ ID NO 1082
<211> LENGTH: 9
<212> TYPE: PRT
<213> ORGANISM: CoV-2
<220> FEATURE:
```

```
<223> OTHER INFORMATION: ORF3a A26.01_247

<400> SEQUENCE: 1082

His Thr Ile Asp Gly Ser Ser Gly Val
1               5

<210> SEQ ID NO 1083
<211> LENGTH: 9
<212> TYPE: PRT
<213> ORGANISM: CoV-2
<220> FEATURE:
<223> OTHER INFORMATION: ORF3a A26.01_33

<400> SEQUENCE: 1083

Ala Thr Ile Pro Ile Gln Ala Ser Leu
1               5

<210> SEQ ID NO 1084
<211> LENGTH: 9
<212> TYPE: PRT
<213> ORGANISM: CoV-2
<220> FEATURE:
<223> OTHER INFORMATION: ORF3a A26.01_204

<400> SEQUENCE: 1084

His Ser Tyr Phe Thr Ser Asp Tyr Tyr
1               5

<210> SEQ ID NO 1085
<211> LENGTH: 9
<212> TYPE: PRT
<213> ORGANISM: CoV-2
<220> FEATURE:
<223> OTHER INFORMATION: ORF3a A26.01_89

<400> SEQUENCE: 1085

Thr Val Tyr Ser His Leu Leu Leu Val
1               5

<210> SEQ ID NO 1086
<211> LENGTH: 9
<212> TYPE: PRT
<213> ORGANISM: CoV-2
<220> FEATURE:
<223> OTHER INFORMATION: ORF3a B07.02_35

<400> SEQUENCE: 1086

Ile Pro Ile Gln Ala Ser Leu Pro Phe
1               5

<210> SEQ ID NO 1087
<211> LENGTH: 9
<212> TYPE: PRT
<213> ORGANISM: CoV-2
<220> FEATURE:
<223> OTHER INFORMATION: ORF3a B07.02_103

<400> SEQUENCE: 1087

Ala Pro Phe Leu Tyr Leu Tyr Ala Leu
1               5

<210> SEQ ID NO 1088
<211> LENGTH: 9
<212> TYPE: PRT
<213> ORGANISM: CoV-2
<220> FEATURE:
<223> OTHER INFORMATION: ORF3a B07.02_33
```

```
<400> SEQUENCE: 1088

Ala Thr Ile Pro Ile Gln Ala Ser Leu
1               5

<210> SEQ ID NO 1089
<211> LENGTH: 9
<212> TYPE: PRT
<213> ORGANISM: CoV-2
<220> FEATURE:
<223> OTHER INFORMATION: ORF3a B15.01_207

<400> SEQUENCE: 1089

Phe Thr Ser Asp Tyr Tyr Gln Leu Tyr
1               5

<210> SEQ ID NO 1090
<211> LENGTH: 9
<212> TYPE: PRT
<213> ORGANISM: CoV-2
<220> FEATURE:
<223> OTHER INFORMATION: ORF3a B15.01_204

<400> SEQUENCE: 1090

His Ser Tyr Phe Thr Ser Asp Tyr Tyr
1               5

<210> SEQ ID NO 1091
<211> LENGTH: 9
<212> TYPE: PRT
<213> ORGANISM: CoV-2
<220> FEATURE:
<223> OTHER INFORMATION: ORF3a B15.01_105

<400> SEQUENCE: 1091

Phe Leu Tyr Leu Tyr Ala Leu Val Tyr
1               5

<210> SEQ ID NO 1092
<211> LENGTH: 9
<212> TYPE: PRT
<213> ORGANISM: CoV-2
<220> FEATURE:
<223> OTHER INFORMATION: ORF3a B15.01_71

<400> SEQUENCE: 1092

Leu Ala Leu Ser Lys Gly Val His Phe
1               5

<210> SEQ ID NO 1093
<211> LENGTH: 9
<212> TYPE: PRT
<213> ORGANISM: CoV-2
<220> FEATURE:
<223> OTHER INFORMATION: ORF3a B15.01_146

<400> SEQUENCE: 1093

Phe Leu Cys Trp His Thr Asn Cys Tyr
1               5

<210> SEQ ID NO 1094
<211> LENGTH: 9
<212> TYPE: PRT
<213> ORGANISM: CoV-2
<220> FEATURE:
<223> OTHER INFORMATION: ORF3a B15.01_33
```

```
<400> SEQUENCE: 1094

Ala Thr Ile Pro Ile Gln Ala Ser Leu
1               5

<210> SEQ ID NO 1095
<211> LENGTH: 9
<212> T

Ala Ser Leu Pro Phe Gly Trp Leu Ile
1               5

<210> SEQ ID NO 1101
<211> LENGTH: 9
<212> TYPE: PRT
<213> ORGANISM: CoV-2
<220> FEATURE:
<223> OTHER INFORMATION: ORF3a B58.01_185

<400> SEQUENCE: 1101

Gln Ile Gly Gly Tyr Thr Glu Lys Trp
1               5

<210> SEQ ID NO 1102
<211> LENGTH: 9
<212> TYPE: PRT
<213> ORGANISM: CoV-2
<220> FEATURE:
<223> OTHER INFORMATION: ORF3a B58.01_33

<400> SEQUENCE: 1102

Ala Thr Ile Pro Ile Gln Ala Ser Leu
1               5

<210> SEQ ID NO 1103
<211> LENGTH: 9
<212> TYPE: PRT
<213> ORGANISM: CoV-2
<220> FEATURE:
<223> OTHER INFORMATION: ORF3a B58.01_71

<400> SEQUENCE: 1103

Leu Ala Leu Ser Lys Gly Val His Phe
1               5

<210> SEQ ID NO 1104
<211> LENGTH: 9
<212> TYPE: PRT
<213> ORGANISM: CoV-2
<220> FEATURE:
<223> OTHER INFORMATION: ORF3a B58.01_207

<400> SEQUENCE: 1104

Phe Thr Ser Asp Tyr Tyr Gln Leu Tyr
1               5

<210> SEQ ID NO 1105
<211> LENGTH: 9
<212> TYPE: PRT
<213> ORGANISM: CoV-2
<220> FEATURE:
<223> OTHER INFORMATION: ORF3a B58.01_63

<400> SEQUENCE: 1105

Ile Thr Leu Lys Lys Arg Trp Gln Leu
1               5

<210> SEQ ID NO 1106
<211> LENGTH: 9
<212> TYPE: PRT
<213> ORGANISM: CoV-2
<220> FEATURE:
<223> OTHER INFORMATION: ORF3a B58.01_57

<400> SEQUENCE: 1106

Gln Ser Ala Ser Lys Ile Ile Thr Leu
1               5

<210> SEQ ID NO 1107
<211> LENGTH: 9
<212> TYPE: PRT
<213> ORGANISM: CoV-2
<220> FEATURE:
<223> OTHER INFORMATION: ORF3a B58.01_120

<400> SEQUENCE: 1107

Phe Val Arg Ile Ile Met Arg Leu Trp
1               5

<210> SEQ ID NO 1108
<211> LENGTH: 9
<212> TYPE: PRT
<213> ORGANISM: CoV-2
<220> FEATURE:
<223> OTHER INFORMATION: ORF3a B58.01_123

<400> SEQUENCE: 1108

Ile Ile Met Arg Leu Trp Leu Cys Trp
1               5

<210> SEQ ID NO 1109
<211> LENGTH: 9
<212> TYPE: PRT
<213> ORGANISM: CoV-2
<220> FEATURE:
<223> OTHER INFORMATION: ORF3a B58.01_204

<400> SEQUENCE: 1109

His Ser Tyr Phe Thr Ser Asp Tyr Tyr
1               5

<210> SEQ ID NO 1110
<211> LENGTH: 9
<212> TYPE: PRT
<213> ORGANISM: CoV-2
<220> FEATURE:
<223> OTHER INFORMATION: ORF3a B58.01_99

<400> SEQUENCE: 1110

Ala Gly Leu Glu Ala Pro Phe Leu Tyr
1               5

<210> SEQ ID NO 1111
<211> LENGTH: 9
<212> TYPE: PRT
<213> ORGANISM: CoV-2
<220> FEATURE:
<223> OTHER INFORMATION: ORF3a B58.01_88

<400> SEQUENCE: 1111

Val Thr Val Tyr Ser His Leu Leu Leu
1               5

<210> SEQ ID NO 1112
<211> LENGTH: 9
<212> TYPE: PRT
<213> ORGANISM: CoV-2
<220> FEATURE:
<223> OTHER INFORMATION: ORF3a B58.01_79

<400> SEQUENCE: 1112

Phe Val Cys Asn Leu Leu Leu Leu Phe

<210> SEQ ID NO 1113
<211> LENGTH: 9
<212> TYPE: PRT
<213> ORGANISM: CoV-2
<220> FEATURE:
<223> OTHER INFORMATION: ORF6 A1.01_23

<400> SEQUENCE: 1113

Lys Val Ser Ile Trp Asn Leu Asp Tyr
1               5

<210> SEQ ID NO 1114
<211> LENGTH: 9
<212> TYPE: PRT
<213> ORGANISM: CoV-2
<220> FEATURE:
<223> OTHER INFORMATION: ORF6 A2.01_3

<400> SEQUENCE: 1114

His Leu Val Asp Phe Gln Val Thr Ile
1               5

<210> SEQ ID NO 1115
<211> LENGTH: 9
<212> TYPE: PRT
<213> ORGANISM: CoV-2
<220> FEATURE:
<223> OTHER INFORMATION: ORF6 A2.01_28

<400> SEQUENCE: 1115

Asn Leu Asp Tyr Ile Ile Asn Leu Ile
1               5

<210> SEQ ID NO 1116
<211> LENGTH: 9
<212> TYPE: PRT
<213> ORGANISM: CoV-2
<220> FEATURE:
<223> OTHER INFORMATION: ORF6 A2.01_10

<400> SEQUENCE: 1116

Thr Ile Ala Glu Ile Leu Leu Ile Ile
1               5

<210> SEQ ID NO 1117
<211> LENGTH: 9
<212> TYPE: PRT
<213> ORGANISM: CoV-2
<220> FEATURE:
<223> OTHER INFORMATION: ORF6 A2.01_16

<400> SEQUENCE: 1117

Leu Ile Ile Met Arg Thr Phe Lys Val
1               5

<210> SEQ ID NO 1118
<211> LENGTH: 9
<212> TYPE: PRT
<213> ORGANISM: CoV-2
<220> FEATURE:
<223> OTHER INFORMATION: ORF6 A3.01_15

<400> SEQUENCE: 1118

Leu Leu Ile Ile Met Arg Thr Phe Lys
1               5

```
<210> SEQ ID NO 1119
<211> LENGTH: 9
<212> TYPE: PRT
<213> ORGANISM: CoV-2
<220> FEATURE:
<223> OTHER INFORMATION: ORF6 A3.01_34

<400> SEQUENCE: 1119

Asn Leu Ile Ile Lys Asn Leu Ser Lys
1               5

<210> SEQ ID NO 1120
<211> LENGTH: 9
<212> TYPE: PRT
<213> ORGANISM: CoV-2
<220> FEATURE:
<223> OTHER INFORMATION: ORF6 A3.01_23

<400> SEQUENCE: 1120

Lys Val Ser Ile Trp Asn Leu Asp Tyr
1               5

<210> SEQ ID NO 1121
<211> LENGTH: 9
<212> TYPE: PRT
<213> ORGANISM: CoV-2
<220> FEATURE:
<223> OTHER INFORMATION: ORF6 A24.02_21

<400> SEQUENCE: 1121

Thr Phe Lys Val Ser Ile Trp Asn Leu
1               5

<210> SEQ ID NO 1122
<211> LENGTH: 9
<212> TYPE: PRT
<213> ORGANISM: CoV-2
<220> FEATURE:
<223> OTHER INFORMATION: ORF6 B07.01_36

<400> SEQUENCE: 1122

Ile Ile Lys Asn Leu Ser Lys Ser Leu
1               5

<210> SEQ ID NO 1123
<211> LENGTH: 9
<212> TYPE: PRT
<213> ORGANISM: CoV-2
<220> FEATURE:
<223> OTHER INFORMATION: ORF6 B15.01_50

<400> SEQUENCE: 1123

Ser Gln Leu Asp Glu Glu Gln Pro Met
1               5

<210> SEQ ID NO 1124
<211> LENGTH: 9
<212> TYPE: PRT
<213> ORGANISM: CoV-2
<220> FEATURE:
<223> OTHER INFORMATION: ORF6 B15.01_23

<400> SEQUENCE: 1124

Lys Val Ser Ile Trp Asn Leu Asp Tyr
1               5
```

<210> SEQ ID NO 1125
<211> LENGTH: 9
<212> TYPE: PRT
<213> ORGANISM: CoV-2
<220> FEATURE:
<223> OTHER INFORMATION: ORF6 B58.01_9

<400> SEQUENCE: 1125

Val Thr Ile Ala Glu Ile Leu Leu Ile
1               5

<210> SEQ ID NO 1126
<211> LENGTH: 9
<212> TYPE: PRT
<213> ORGANISM: CoV-2
<220> FEATURE:
<223> OTHER INFORMATION: ORF7 A2.01_13

<400> SEQUENCE: 1126

Phe Leu Ala Phe Leu Leu Phe Leu Val
1               5

<210> SEQ ID NO 1127
<211> LENGTH: 9
<212> TYPE: PRT
<213> ORGANISM: CoV-2
<220> FEATURE:
<223> OTHER INFORMATION: ORF7 A2.01_26

<400> SEQUENCE: 1127

Ile Ile Phe Trp Phe Ser Leu Glu Leu
1               5

<210> SEQ ID NO 1128
<211> LENGTH: 9
<212> TYPE: PRT
<213> ORGANISM: CoV-2
<220> FEATURE:
<223> OTHER INFORMATION: ORF7 A2.01_10

<400> SEQUENCE: 1128

Tyr Leu Cys Phe Leu Ala Phe Leu Leu
1               5

<210> SEQ ID NO 1129
<211> LENGTH: 9
<212> TYPE: PRT
<213> ORGANISM: CoV-2
<220> FEATURE:
<223> OTHER INFORMATION: ORF7 A2.01_3

<400> SEQUENCE: 1129

Glu Leu Ser Leu Ile Asp Phe Tyr Leu
1               5

<210> SEQ ID NO 1130
<211> LENGTH: 9
<212> TYPE: PRT
<213> ORGANISM: CoV-2
<220> FEATURE:
<223> OTHER INFORMATION: ORF7 A2.01_17

<400> SEQUENCE: 1130

Leu Leu Phe Leu Val Leu Ile Met Leu
1               5

-continued

```
<210> SEQ ID NO 1131
<211> LENGTH: 9
<212> TYPE: PRT
<213> ORGANISM: CoV-2
<220> FEATURE:
<223> OTHER INFORMATION: ORF7 A24.02_5

<400> SEQUENCE: 1131

Ser Leu Ile Asp Phe Tyr Leu Cys Phe
1               5

<210> SEQ ID NO 1132
<211> LENGTH: 9
<212> TYPE: PRT
<213> ORGANISM: CoV-2
<220> FEATURE:
<223> OTHER INFORMATION: ORF7 A24.02_9

<400> SEQUENCE: 1132

Phe Tyr Leu Cys Phe Leu Ala Phe Leu
1               5

<210> SEQ ID NO 1133
<211> LENGTH: 9
<212> TYPE: PRT
<213> ORGANISM: CoV-2
<220> FEATURE:
<223> OTHER INFORMATION: ORF7 A26.01_5

<400> SEQUENCE: 1133

Ser Leu Ile Asp Phe Tyr Leu Cys Phe
1               5

<210> SEQ ID NO 1134
<211> LENGTH: 9
<212> TYPE: PRT
<213> ORGANISM: CoV-2
<220> FEATURE:
<223> OTHER INFORMATION: ORF7 B15.01_5

<400> SEQUENCE: 1134

Ser Leu Ile Asp Phe Tyr Leu Cys Phe
1               5

<210> SEQ ID NO 1135
<211> LENGTH: 9
<212> TYPE: PRT
<213> ORGANISM: CoV-2
<220> FEATURE:
<223> OTHER INFORMATION: ORF7 B58.01_21

<400> SEQUENCE: 1135

Val Leu Ile Met Leu Ile Ile Phe Trp
1               5

<210> SEQ ID NO 1136
<211> LENGTH: 9
<212> TYPE: PRT
<213> ORGANISM: CoV-2
<220> FEATURE:
<223> OTHER INFORMATION: ORF8 A1.01_23

<400> SEQUENCE: 1136

Gln Ser Cys Thr Gln His Gln Pro Tyr
1               5

<210> SEQ ID NO 1137
```

```
<211> LENGTH: 9
<212> TYPE: PRT
<213> ORGANISM: CoV-2
<220> FEATURE:
<223> OTHER INFORMATION: ORF8 A1.01_65

<400> SEQUENCE: 1137

Ala Gly Ser Lys Ser Pro Ile Gln Tyr
1               5

<210> SEQ ID NO 1138
<211> LENGTH: 9
<212> TYPE: PRT
<213> ORGANISM: CoV-2
<220> FEATURE:
<223> OTHER INFORMATION: ORF8 A1.01_102

<400> SEQUENCE: 1138

Ser Phe Tyr Glu Asp Phe Leu Glu Tyr
1               5

<210> SEQ ID NO 1139
<211> LENGTH: 9
<212> TYPE: PRT
<213> ORGANISM: CoV-2
<220> FEATURE:
<223> OTHER INFORMATION: ORF8 A1.01_32

<400> SEQUENCE: 1139

Val Val Asp Asp Pro Cys Pro Ile His
1               5

<210> SEQ ID NO 1140
<211> LENGTH: 9
<212> TYPE: PRT
<213> ORGANISM: CoV-2
<220> FEATURE:
<223> OTHER INFORMATION: ORF8 A1.01_33

<400> SEQUENCE: 1140

Val Asp Asp Pro Cys Pro Ile His Phe
1               5

<210> SEQ ID NO 1141
<211> LENGTH: 9
<212> TYPE: PRT
<213> ORGANISM: CoV-2
<220> FEATURE:
<223> OTHER INFORMATION: ORF8 A1.01_96

<400> SEQUENCE: 1141

Ser Leu Val Val Arg Cys Ser Phe Tyr
1               5

<210> SEQ ID NO 1142
<211> LENGTH: 9
<212> TYPE: PRT
<213> ORGANISM: CoV-2
<220> FEATURE:
<223> OTHER INFORMATION: ORF8 A2.01_107

<400> SEQUENCE: 1142

Phe Leu Glu Tyr His Asp Val Arg Val
1               5

<210> SEQ ID NO 1143
<211> LENGTH: 9
```

<212> TYPE: PRT
<213> ORGANISM: CoV-2
<220> FEATURE:
<223> OTHER INFORMATION: ORF8 A2.01_93

<400> SEQUENCE: 1143

Lys Leu Gly Ser Leu Val Val Arg Cys
1               5

<210> SEQ ID NO 1144
<211> LENGTH: 9
<212> TYPE: PRT
<213> ORGANISM: CoV-2
<220> FEATURE:
<223> OTHER INFORMATION: ORF8 A2.01_31

<400> SEQUENCE: 1144

Tyr Val Val Asp Asp Pro Cys Pro Ile
1               5

<210> SEQ ID NO 1145
<211> LENGTH: 9
<212> TYPE: PRT
<213> ORGANISM: CoV-2
<220> FEATURE:
<223> OTHER INFORMATION: ORF8 A2.01_6

<400> SEQUENCE: 1145

Phe Leu Gly Ile Ile Thr Thr Val Ala
1               5

<210> SEQ ID NO 1146
<211> LENGTH: 9
<212> TYPE: PRT
<213> ORGANISM: CoV-2
<220> FEATURE:
<223> OTHER INFORMATION: ORF8 A2.01_5

<400> SEQUENCE: 1146

Val Phe Leu Gly Ile Ile Thr Thr Val
1               5

<210> SEQ ID NO 1147
<211> LENGTH: 9
<212> TYPE: PRT
<213> ORGANISM: CoV-2
<220> FEATURE:
<223> OTHER INFORMATION: ORF8 A2.01_72

<400> SEQUENCE: 1147

Gln Tyr Ile Asp Ile Asn Tyr Thr Val
1               5

<210> SEQ ID NO 1148
<211> LENGTH: 9
<212> TYPE: PRT
<213> ORGANISM: CoV-2
<220> FEATURE:
<223> OTHER INFORMATION: ORF8 A3.01_102

<400> SEQUENCE: 1148

Ser Phe Tyr Glu Asp Phe Leu Glu Tyr
1               5

<210> SEQ ID NO 1149
<211> LENGTH: 9
<212> TYPE: PRT

```
<213> ORGANISM: CoV-2
<220> FEATURE:
<223> OTHER INFORMATION: ORF8 A24.02_72

<400> SEQUENCE: 1149

Gln Tyr Ile Asp Ile Asn Tyr Thr Val
1               5

<210> SEQ ID NO 1150
<211> LENGTH: 9
<212> TYPE: PRT
<213> ORGANISM: CoV-2
<220> FEATURE:
<223> OTHER INFORMATION: ORF8 A24.02_109

<400> SEQUENCE: 1150

Glu Tyr His Asp Val Arg Val Val Leu
1               5

<210> SEQ ID NO 1151
<211> LENGTH: 9
<212> TYPE: PRT
<213> ORGANISM: CoV-2
<220> FEATURE:
<223> OTHER INFORMATION: ORF8 A24.02_41

<400> SEQUENCE: 1151

Phe Tyr Ser Lys Trp Tyr Ile Arg Val
1               5

<210> SEQ ID NO 1152
<211> LENGTH: 9
<212> TYPE: PRT
<213> ORGANISM: CoV-2
<220> FEATURE:
<223> OTHER INFORMATION: ORF8 A24.02_77

<400> SEQUENCE: 1152

Asn Tyr Thr Val Ser Cys Leu Pro Phe
1               5

<210> SEQ ID NO 1153
<211> LENGTH: 9
<212> TYPE: PRT
<213> ORGANISM: CoV-2
<220> FEATURE:
<223> OTHER INFORMATION: ORF8 A24.02_102

<400> SEQUENCE: 1153

Ser Phe Tyr Glu Asp Phe Leu Glu Tyr
1               5

<210> SEQ ID NO 1154
<211> LENGTH: 9
<212> TYPE: PRT
<213> ORGANISM: CoV-2
<220> FEATURE:
<223> OTHER INFORMATION: ORF8 A24.02_5

<400> SEQUENCE: 1154

Val Phe Leu Gly Ile Ile Thr Thr Val
1               5

<210> SEQ ID NO 1155
<211> LENGTH: 9
<212> TYPE: PRT
<213> ORGANISM: CoV-2
```

```
<220> FEATURE:
<223> OTHER INFORMATION: ORF8 A26.01_102

<400> SEQUENCE: 1155

Ser Phe Tyr Glu Asp Phe Leu Glu Tyr
1               5

<210> SEQ ID NO 1156
<211> LENGTH: 9
<212> TYPE: PRT
<213> ORGANISM: CoV-2
<220> FEATURE:
<223> OTHER INFORMATION: ORF8 A26.01_8

<400> SEQUENCE: 1156

Gly Ile Ile Thr Thr Val Ala Ala Phe
1               5

<210> SEQ ID NO 1157
<211> LENGTH: 9
<212> TYPE: PRT
<213> ORGANISM: CoV-2
<220> FEATURE:
<223> OTHER INFORMATION: ORF8 A26.01_75

<400> SEQUENCE: 1157

Asp Ile Asn Tyr Thr Val Ser Cys Leu
1               5

<210> SEQ ID NO 1158
<211> LENGTH: 9
<212> TYPE: PRT
<213> ORGANISM: CoV-2
<220> FEATURE:
<223> OTHER INFORMATION: ORF8 A26.01_34

<400> SEQUENCE: 1158

Asp Asp Pro Cys Pro Ile His Phe Tyr
1               5

<210> SEQ ID NO 1159
<211> LENGTH: 9
<212> TYPE: PRT
<213> ORGANISM: CoV-2
<220> FEATURE:
<223> OTHER INFORMATION: ORF8 B07.02_91

<400> SEQUENCE: 1159

Glu Pro Lys Leu Gly Ser Leu Val Val
1               5

<210> SEQ ID NO 1160
<211> LENGTH: 9
<212> TYPE: PRT
<213> ORGANISM: CoV-2
<220> FEATURE:
<223> OTHER INFORMATION: ORF8 B15.01_8

<400> SEQUENCE: 1160

Gly Ile Ile Thr Thr Val Ala Ala Phe
1               5

<210> SEQ ID NO 1161
<211> LENGTH: 9
<212> TYPE: PRT
<213> ORGANISM: CoV-2
<220> FEATURE:
```

```
<223> OTHER INFORMATION: ORF8 B15.01_102

<400> SEQUENCE: 1161

Ser Phe Tyr Glu Asp Phe Leu Glu Tyr
1               5

<210> SEQ ID NO 1162
<211> LENGTH: 9
<212> TYPE: PRT
<213> ORGANISM: CoV-2
<220> FEATURE:
<223> OTHER INFORMATION: ORF8 B15.01_65

<400> SEQUENCE: 1162

Ala Gly Ser Lys Ser Pro Ile Gln Tyr
1               5

<210> SEQ ID NO 1163
<211> LENGTH: 9
<212> TYPE: PRT
<213> ORGANISM: CoV-2
<220> FEATURE:
<223> OTHER INFORMATION: ORF8 B15.01_96

<400> SEQUENCE: 1163

Ser Leu Val Val Arg Cys Ser Phe Tyr
1               5

<210> SEQ ID NO 1164
<211> LENGTH: 9
<212> TYPE: PRT
<213> ORGANISM: CoV-2
<220> FEATURE:
<223> OTHER INFORMATION: ORF8 B15.01_23

<400> SEQUENCE: 1164

Gln Ser Cys Thr Gln His Gln Pro Tyr
1               5

<210> SEQ ID NO 1165
<211> LENGTH: 9
<212> TYPE: PRT
<213> ORGANISM: CoV-2
<220> FEATURE:
<223> OTHER INFORMATION: ORF8 B15.01_89

<400> SEQUENCE: 1165

Cys Gln Glu Pro Lys Leu Gly Ser Leu
1               5

<210> SEQ ID NO 1166
<211> LENGTH: 9
<212> TYPE: PRT
<213> ORGANISM: CoV-2
<220> FEATURE:
<223> OTHER INFORMATION: ORF8 B40.01_108

<400> SEQUENCE: 1166

Leu Glu Tyr His Asp Val Arg Val Val
1               5

<210> SEQ ID NO 1167
<211> LENGTH: 9
<212> TYPE: PRT
<213> ORGANISM: CoV-2
<220> FEATURE:
<223> OTHER INFORMATION: ORF8 B40.01_90
```

```
<400> SEQUENCE: 1167

Gln Glu Pro Lys Leu Gly Ser Leu Val
1               5

<210> SEQ ID NO 1168
<211> LENGTH: 9
<212> TYPE: PRT
<213> ORGANISM: CoV-2
<220> FEATURE:
<223> OTHER INFORMATION: ORF8 B40.01_52

<400> SEQUENCE: 1168

Arg Lys Ser Ala Pro Leu Ile Glu Leu
1               5

<210> SEQ ID NO 1169
<211> LENGTH: 9
<212> TYPE: PRT
<213> ORGANISM: CoV-2
<220> FEATURE:
<223> OTHER INFORMATION: ORF8 B58.01_53

<400> SEQUENCE: 1169

Lys Ser Ala Pro Leu Ile Glu Leu Cys
1               5

<210> SEQ ID NO 1170
<211> LENGTH: 9
<212> TYPE: PRT
<213> ORGANISM: CoV-2
<220> FEATURE:
<223> OTHER INFORMATION: ORF8 B58.01_95

<400> SEQUENCE: 1170

Gly Ser Leu Val Val Arg Cys Ser Phe
1               5

<210> SEQ ID NO 1171
<211> LENGTH: 9
<212> TYPE: PRT
<213> ORGANISM: CoV-2
<220> FEATURE:
<223> OTHER INFORMATION: ORF8 B58.01_65

<400> SEQUENCE: 1171

Ala Gly Ser Lys Ser Pro Ile Gln Tyr
1               5

<210> SEQ ID NO 1172
<211> LENGTH: 9
<212> TYPE: PRT
<213> ORGANISM: CoV-2
<220> FEATURE:
<223> OTHER INFORMATION: ORF8 B58.01_37

<400> SEQUENCE: 1172

Cys Pro Ile His Phe Tyr Ser Lys Trp
1               5

<210> SEQ ID NO 1173
<211> LENGTH: 9
<212> TYPE: PRT
<213> ORGANISM: CoV-2
<220> FEATURE:
<223> OTHER INFORMATION: ORF8 B58.01_66
```

<400> SEQUENCE: 1173

Gly Ser Lys Ser Pro Ile Gln Tyr Ile
1               5

<210> SEQ ID NO 1174
<211> LENGTH: 9
<212> TYPE: PRT
<213> ORGANISM: CoV-2
<220> FEATURE:
<223> OTHER INFORMATION: ORF8 B58.01_23

<400> SEQUENCE: 1174

Gln Ser Cys Thr Gln His Gln Pro Tyr
1               5

<210> SEQ ID NO 1175
<211> LENGTH: 853
<212> TYPE: DNA
<213> ORGANISM: Homo sapiens
<220> FEATURE:
<223> OTHER INFORMATION: MutRNA 1

<400> SEQUENCE: 1175

```
ctggtaccgc caccatcgag tggcggcgga ggatccatgt ggctgcagaa tttacttttc    60
ctgggcattg tggtctacag cctctcagca cccacccgct cacccatcac tgtcacccgg   120
ccttggaagc atgtagaggc catcaaagaa gccctgaacc tcctggatga catgcctgtc   180
acgttgaatg aagaggtaga agtcgtctct aacgagttct ccttcaagaa gctaacatgt   240
gtgcagaccc gcctgaagat attcgagcag ggtctacggg gcaatttcac caaactcaag   300
ggcgccttga acatgacagc cagctactac agacatact gccccccaac tccggaaacg   360
gactgtgaaa cacaagttac cacctatgcg gatttcatag acagccttaa aacctttctg   420
actgatatcc cctttgaatg caaaaaacca ggccaaaaat aaagctcgct tcttgctgt    480
ccaatttcta ttaaaggttc ctttgttccc taagtccaac tactaaactg ggggatatta   540
tgaagggcct tgagcatctg gattctgcct aataaaaaac atttattttc attgcagctc   600
gctttcttgc tgtccaattt ctattaaagg ttcctttgtt ccctaagtcc aactactaaa   660
ctggggata ttatgaaggg ccttgagcat ctggattctg cctaataaaa aacatttatt   720
ttcattgcaa aaaaaaaaa aaaaaaaaaa aaaaaaagc atatgactaa aaaaaaaaa     780
aaaaaaaaa aaaaaaaaa aaaaaaaaa aaaaaaaaa aaaaaaaaa aaaaaaaga        840
agagctctag atg                                                     853
```

<210> SEQ ID NO 1176
<211> LENGTH: 1284
<212> TYPE: DNA
<213> ORGANISM: Homo sapiens
<220> FEATURE:
<223> OTHER INFORMATION: MutRNA 1 - Complete

<400> SEQUENCE: 1176

```
ctggtaccgc caccatgcag gttcagctgg ttgaaagtgg cggcggcagc gttcaggccg    60
gcggtagctt acgcctgagt tgtgccgcaa gcggttatac ctttagtagc tatccgatgg   120
gttggtatcg tcaggccccg ggtaaagaat gtgaactggt gagcaaccac agcacaagaa   180
aggaggagaa gcagagaaac ggcacccctga cagtgacaag cacactgcct gcaaattatg   240
ccggcagcgt taaggtcgt tttaccatta gtcgcgataa tgccaaaaat accgcctatc   300
tgcagatgga tagcctgaaa ccggaagata ccgccgttta ttattgcgca gcagaaacct   360
```

```
atcagtgccg tgttacccat ccgcatctgc cgcgcgccct gatgagtacc accaaatggg      420
gccagggcac ccaggttacc gttagcagta gtggcggcgg aggatccatg tggctgcaga      480
atttactttt cctgggcatt gtggtctaca gcctctcagc acccacccgc tcacccatca      540
ctgtcacccg gccttggaag catgtagagg ccatcaaaga agccctgaac ctcctggatg      600
acatgcctgt cacgttgaat gaagaggtag aagtcgtctc taacgagttc tccttcaaga      660
agctaacatg tgtgcagacc cgcctgaaga tattcgagca gggtctacgg ggcaatttca      720
ccaaactcaa gggcgccttg aacatgacag ccagctacta ccagacatac tgcccccaa      780 ctccggaaac ggactgtgaa acacaagtta ccacctatgc ggatttcata gacagcctta      840
aaacctttct gactgatatc ccctttgaat gcaaaaaacc aggccaaaaa taaagctcgc      900
tttcttgctg tccaatttct attaaaggtt cctttgttcc ctaagtccaa ctactaaact      960
gggggatatt atgaagggcc ttgagcatct ggattctgcc taataaaaaa catttatttt     1020
cattgcagct cgctttcttg ctgtccaatt tctattaaag gttcctttgt tccctaagtc     1080
caactactaa actgggggat attatgaagg gccttgagca tctggattct gcctaataaa     1140
aaacatttat tttcattgca aaaaaaaaa aaaaaaaaa aaaaaaaag catatgacta     1200 aaaaaaaaa aaaaaaaaa aaaaaaaaa aaaaaaaaa aaaaaaaaa aaaaaaaaa     1260 aaaaaaaaag aagagctcta gatg     1284

<210> SEQ ID NO 1177
<211> LENGTH: 553
<212> TYPE: DNA
<213> ORGANISM: Homo sapiens
<220> FEATURE:
<223> OTHER INFORMATION: MutRNA 2

<400> SEQUENCE: 1177
ctggtacctc tcaacacaac atatacaaaa caaacgaatc tcaagcaatc aagcattcta       60
cttctattgc agcaatttaa atcatttctt ttaaagcaaa agcaattttc tgaaaatttt      120
caccatttac gaacgatagc ctggtactgc atgcacgcaa tgctagctgc ccctttcccg      180
tcctgggtac cccgagtctc ccccgacctc gggtcccagg tatgctccca cctccacctg      240
ccccactcac cacctctgct agttccagac acctcccaag cacgcagcaa tgcagctcaa      300
aacgcttagc ctagccacac ccccacggga acagcagtg attaaccttt agcaataaac      360
gaaagtttaa ctaagctata ctaaccccag ggtggtcaat ttcgtgccag ccacaccctc      420
gagctagcaa aaaaaaaaa aaaaaaaaa aaaaaaagc atatgactaa aaaaaaaaa      480 aaaaaaaaa aaaaaaaaa aaaaaaaaa aaaaaaaaa aaaaaaaaa aaaaaaaga      540 agagctctag atg     553

<210> SEQ ID NO 1178
<211> LENGTH: 995
<212> TYPE: DNA
<213> ORGANISM: Homo sapiens
<220> FEATURE:
<223> OTHER INFORMATION: MutRNA 2 - Complete

<400> SEQUENCE: 1178
ctggtacctc tcaacacaac atatacaaaa caaacgaatc tcaagcaatc aagcattcta       60
cttctattgc agcaatttaa atcatttctt ttaaagcaaa agcaattttc tgaaaatttt      120
caccatttac gaacgatagc gccaccatgg ccaccatggg ccaggttcag ctggttgaaa      180
```

```
gtggcggcgg cagcgttcag gccggcggta gcttacgcct gagttgtgcc gcaagcggtt    240
atacctttag tagctatccg atgggttggt atcgtcaggc cccgggtaaa gaatgtgaac    300
tggtgagcta ccagtgcagg gtgacccacc ccgtggacct ggcacccgcc ctcatgcggt    360
ccacggcaaa ttatgccggc agcgttaaag gtcgttttac cattagtcgc gataatgcca    420
aaaataccgc ctatctgcag atggatagcc tgaaaccgga agataccgcc gtttattatt    480
gcgcagcata ccagtgcagg gtgacccacc ccaacccgag aggggtgagc gccctcatgc    540
ggtccacgtg gggccagggc acccaggtta ccgttagcag tctggtactg catgcacgca    600
atgctagctg ccccttttccc gtcctgggta ccccgagtct cccccgacct cgggtcccag    660
gtatgctccc acctccacct gccccactca ccacctctgc tagttccaga cacctcccaa    720
gcacgcagca atgcagctca aaacgcttag cctagccaca ccccacgggg aaacagcagt    780
gattaacctt tagcaataaa cgaaagttta actaagctat actaacccca gggttggtca    840
atttcgtgcc agccacaccc tcgagctagc aaaaaaaaaa aaaaaaaaaa aaaaaaaaaa    900
gcatatgact aaaaaaaaaa aaaaaaaaaa aaaaaaaaaa aaaaaaaaaa aaaaaaaaaa    960
aaaaaaaaaa aaaaaaaaaa gaagagctct agatg                              995

<210> SEQ ID NO 1179
<211> LENGTH: 1093
<212> TYPE: DNA
<213> ORGANISM: Homo sapiens
<220> FEATURE:
<223> OTHER INFORMATION: SP1-2-A32-mRNA

<400> SEQUENCE: 1179
ctggtaccgc caccatggga atgcaggtgc agatccagag cctgtttctg ctcctcctgt     60 gggtgccccgg gtccagagga gccaagttcg tggctgcctg gaccctgaag gctgccgcta    120
tttcgatctc cgagatcaag ggagtcatcg tgcacaaaat cgagaccatc ctcttccatc    180
atcatcatca ccattgagga agcggagcca cgaacttctc tctgttaaag caagcaggag    240
atgttgaaga aaaccccggg cctatgtggc tgcagaattt acttttcctg ggcattgtgg    300
tctacagcct ctcagcaccc acccgctcac ccatcactgt cacccggcct tggaagcatg    360
tagaggccat caaagaagcc ctgaacctcc tggatgacat gcctgtcacg ttgaatgaag    420
aggtagaagt cgtctctaac gagttctcct tcaagaagct aacatgtgtg cagacccgcc    480
tgaagatatt cgagcagggt ctacggggca atttcaccaa actcaagggc gccttgaaca    540
tgacagccag ctactaccag acatactgcc ccccaactcc ggaaacggac tgtgaaacac    600
aagttaccac ctatgcggat ttcatagaca gccttaaaac ctttctgact gatatcccct    660
ttgaatgcaa aaaccaggc caaaaatgac ggaattccgt aaagctcgct ttcttgctgt    720
ccaatttcta ttaaaggttc ctttgttccc taagtccaac tactaaactg ggggatatta    780
tgaagggcct tgagcatctg gattctgcct aataaaaaac attattttc attgcagctc    840 gctttcttgc tgtccaattt ctattaaagg ttcctttgtt ccctaagtcc aactactaaa    900 ctggggata ttatgaaggg ccttgagcat ctggattctg cctaataaaa acatttatt    960 ttcattgcaa aaaaaaaaaa aaaaaaaaaa aaaaaaagc atatgactaa aaaaaaaaa    1020 aaaaaaaaaa aaaaaaaaaa aaaaaaaaaa aaaaaaaaaa aaaaaaaaaa aaaaaaaaga   1080
agagctctag atg                                                    1093

<210> SEQ ID NO 1180
<211> LENGTH: 1177
```

<212> TYPE: DNA
<213> ORGANISM: Homo sapiens
<220> FEATURE:
<223> OTHER INFORMATION: SP1-2-A32-mRNA - Complete

<400> SEQUENCE: 1180

```
ctggtaccgc caccatggga atgcaggtgc agatccagag cctgtttctg ctcctcctgt      60
gggtgcccgg gtccagagga aacccgagag gggtgagcgc ctacctagcc aagttcgtgg     120
ctgcctggac cctgaaggct gccgctcacc cccacctgcc cagggccctc atgatttcga     180
tctccgagat caagggagtc atcgtgcaca aaatcgagac catcctcttc gtgactctgg     240
gctgcctggc cacgggctac catcatcatc atcaccattg aggaagcgga gccacgaact     300
tctctctgtt aaagcaagca ggagatgttg aagaaaaccc cgggcctatg tggctgcaga     360
atttactttt cctgggcatt gtggtctaca gcctctcagc acccacccgc tcacccatca     420
ctgtcacccg gccttggaag catgtagagg ccatcaaaga agccctgaac ctcctggatg     480
acatgcctgt cacgttgaat gaagaggtag aagtcgtctc taacgagttc tccttcaaga     540
agctaacatg tgtgcagacc cgcctgaaga tattcgagca gggtctacgg ggcaatttca     600
ccaaactcaa gggcgccttg aacatgacag ccagctacta ccagacatac tgccccccaa     660
ctccggaaac ggactgtgaa acacaagtta ccacctatgc ggatttcata gacagcctta     720
aaacctttct gactgatatc ccctttgaat gcaaaaaacc aggccaaaaa tgacggaatt     780
ccgtaaagct cgctttcttg ctgtccaatt tctattaaag gttcctttgt tccctaagtc     840
caactactaa actgggggat attatgaagg gccttgagca tctggattct gcctaataaa     900
aaacatttat tttcattgca gctcgctttc ttgctgtcca atttctatta aaggttcctt     960
tgttccctaa gtccaactac taaactgggg gatattatga agggccttga gcatctggat    1020
tctgcctaat aaaaaacatt tattttcatt gcaaaaaaaa aaaaaaaaaa aaaaaaaaaa    1080
aagcatatga ctaaaaaaaa aaaaaaaaaa aaaaaaaaaa aaaaaaaaaa aaaaaaaaaa    1140
aaaaaaaaaa aaaaaaaaaa aagaagagct ctagatg                             1177
```

The invention claimed is:

1. A composition comprising recombinant B cell antigenic epitopes chemically modified from the CoV-2 surface spike protein (S) (SEQ ID NO: 1243), comprising and not limited to NTD (SEQ ID NO: 1 to SEQ ID NO: 10, SEQ ID NO: 1244), RBD/RBE (SEQ ID NO: 11 to SEQ ID NO:17, SEQ ID NO: 37 to SEQ ID NO: 42, SEQ ID NO: 1215 to SEQ ID NO: 1220) and S1-S2 furin junction (SEQ ID NO: 18 to SEQ ID NO: 36, SEQ ID NO: 1221 to SEQ ID NO: 1223, SEQ ID NO: 1252 to SEQ ID NO: 1254), wherein said chemically modified recombinant antigenic B cell epitopes are in protein scaffolds comprising but not limited to CDRs of camelid VHH (SEQ ID NO: 1255, SEQ ID NO: 1260), lipocalin (SEQ ID NO: 1258, SEQ ID NO:1263), GFP (SEQ ID NO: 1257, SEQ ID NO: 1262), fibronectin (SEQ ID NO: 1281, SEQ ID NO: 1282), ankyrin repeat (SEQ ID NO: 1256, SEQ ID NO: 1261), VH3 (SEQ ID NO: 1259, SEQ ID NO: 1264), and wherein said chemically modified recombinant B cell antigenic epitopes of CoV-2 S protein in said protein scaffolds as chemically modified recombinant vaccine products, whereby said chemically modified combinatory recombinant vaccine products are employed to vaccinate human population to prevent CoV-2 infection.

2. The composition according to claim 1, wherein the chemically modified recombinant RBD and Spike protein S1 (SEQ ID NO: 43 to SEQ ID NO: 51, SEQ ID NO: 281 to SEQ ID NO: 292, SEQ ID NO: 279 to SEQ ID NO: 309, SEQ ID NO: 313) are at N- and C-terminus of said recombinant protein scaffolds (SEQ ID NO: 1255 to SEQ ID NO: 1264, SEQ ID NO: 1281, SEQ ID NO: 1282), whereby said chemically modified recombinant RBD and S1 with said recombinant protein scaffolds are employed as chemically modified combinatory recombinant vaccine products to prevent CoV-2 infection.

3. The composition according to claim 1, wherein recombinant open reading frame proteins are chemically modified in said recombinant protein scaffolds (SEQ ID NO: 1255 to SEQ ID NO: 1264, SEQ ID NO: 1281 to SEQ ID NO: 1282), wherein chemically modified recombinant open reading frame proteins consist of leader protein (SEQ ID NO: 1228), nsp-2 (SEQ ID NO: 1229), nsp-3 (SEQ ID NO: 1230), nsp-4 (SEQ ID NO: 1231), 3C-like proteinase (SEQ ID NO: 1232), nsp-5 (SEQ ID NO: 1232), nsp-6 (SEQ ID NO: 1233), nsp-7 (SEQ ID NO: 1234), nsp-8 (SEQ ID NO: 1235), nsp-9 (SEQ ID NO: 1236), nsp-10 (SEQ ID NO: 1237), RNA-dependent RNA polymerase (SEQ ID NO: 1238), helicase (SEQ ID NO: 1239), 3→5' exonuclease (SEQ ID NO: 1240), endoRNAse (SEQ ID NO: 1241), 2-O' ribose methyltransferase (SEQ ID NO: 1242), Spike Glycoprotein (S) (SEQ ID NO: 1243), ORF-3a (SEQ ID NO:

1244), E (SEQ ID NO: 1245), M (SEQ ID NO: 1246), ORF-6 (SEQ ID NO: 1247), N (SEQ ID NO: 1251), ORF-7a (SEQ ID NO: 1248), ORF-7b (SEQ ID NO: 1249), ORF-8 (SEQ ID NO: 1250), nucleocapsid (NC) (SEQ ID NO: 1251), and wherein said chemically modified recombinant open reading frame proteins (SEQ ID NO: 1228 to SEQ ID NO: 1251) is at N-, C-terminus of said recombinant protein scaffolds (SEQ ID NO: 1255 to SEQ ID NO: 1264, SEQ ID NO: 1281, SEQ ID NO: 1282) as chemically modified combinatory recombinant vaccine products, whereby CoV-2 infection is prevented in population vaccinated with said vaccine products.

4. The composition according to claim 1, wherein chemically modified recombinatory B cell antigenic epitopes of the CoV-2 open reading frames are in said recombinant protein scaffolds (SEQ ID NO: 1255 to SEQ ID NO: 1264, SEQ ID NO: 1281 to SEQ ID NO: 1282), consisting of leader protein (SEQ ID NO: 1228), nsp-2 (SEQ ID NO: 1229), nsp-3 (SEQ ID NO: 1230), nsp-4 (SEQ ID NO: 1231), 3C-like proteinase (SEQ ID NO: 1232), nsp-5 (SEQ ID NO: 1232), nsp-6 (SEQ ID NO: 1233), nsp-7 (SEQ ID NO: 1234), nsp-8 (SEQ ID NO: 1235), nsp-9 (SEQ ID NO: 1236), nsp-10 (SEQ ID NO: 1237), RNA-dependent RNA polymerase (SEQ ID NO: 1238), helicase (SEQ ID NO: 1239), 3→5' exonuclease (SEQ ID NO: 1240), endoRNAse (SEQ ID NO: 1241), 2-O' ribose methyltransferase (SEQ ID NO: 1242), Spike Glycoprotein (S) (SEQ ID NO: 1243), ORF-3a (SEQ ID NO: 1244), E (SEQ ID NO: 1245), M (SEQ ID NO: 1246), ORF-6 (SEQ ID NO: 1247), N (SEQ ID NO: 1251), ORF-7a (SEQ ID NO: 1248), ORF-7b (SEQ ID NO: 1249), ORF-8 (SEQ ID NO: 1250), nucleocapsid (NC) (SEQ ID NO: 1251), and wherein chemically modified B cell antigenic epitopes of said open reading frame proteins (SEQ ID NO: 1228 to SEQ ID NO: 1251) in said recombinant protein scaffolds (SEQ ID NO: 1255 to SEQ ID NO: 1264, SEQ ID NO: 1281, SEQ ID NO: 1282) are chemically modified combinatory recombinatory vaccine products, whereby CoV-2 infection is prevented in population vaccinated with said chemically modified vaccine products.

5. The composition according to claim 1, wherein chemically modified antigenic B cell epitopes of RBD/RBE (SEQ ID NO: 11 to SEQ ID NO:17, SEQ ID NO: 37 to SEQ ID NO: 42, SEQ ID NO: 1215 to SEQ ID NO: 1220) in VHH (SEQ ID NO: 1255, SEQ ID NO: 1260), are selected for binding to ACE2 on solid phase via ribosome display, wherein the selected chemically modified antigenic B cell epitopes are used as chemically modified vaccines, whereby vaccinated population is protected from emerging CoV-2 infection.

6. The composition according to claim 1, wherein the chemically modified helper T cell epitopes (SEQ ID NO: 1265 to SEQ ID NO: 1271) are in the said protein scaffolds (SEQ ID NO: 1255, SEQ ID NO: 1264) containing said chemically modified antigenic B cell epitopes of RBD/RBE (SEQ ID NO: 11 to SEQ ID NO: 17, SEQ ID NO: 37 to SEQ ID NO: 42, SEQ ID NO: 1215 to SEQ ID NO: 1220) and S1-S2 furin junction (SEQ ID NO: 18 to SEQ ID NO: 36, SEQ ID NO: 1221 to SEQ ID NO: 1223, SEQ ID NO: 1252 to SEQ ID NO: 1254), whereby chemically modified vaccines are enhanced.

7. A composition comprising chemically modified recombinant nonameric peptides (+1/−1) into recombinant CDR1, CDR2 and CDR3 of VHH (SEQ ID NO: 1255, SEQ ID NO: 1260), chemically derived from CoV-2 open reading frame proteins, comprising spike protein (SEQ ID: 60 to SEQ ID: 235); NC protein (SEQ ID: 236 to SEQ ID: 280); ORF1a (SEQ ID: 314 to SEQ ID: 395), rdrp protein (SEQ ID: 396 to SEQ ID: 571); helicase protein (SEQ ID: 572 to SEQ ID: 699); Exonuclease 5>3 (SEQ ID: 700 to SEQ ID: 803); endoRNAse (SEQ ID: 804 to SEQ ID: 882); methyltransferase protein (SEQ ID: 883 to SEQ ID: 953); membrane protein (SEQ ID: 954 to SEQ ID: 1014); envelope protein (SEQ ID: 1015 to SEQ ID: 1044); ORF-3a protein (SEQ ID: 1045 to SEQ ID: 1112); ORF-6 protein (SEQ ID: 1113 to SEQ ID: 1125); ORF-7 protein (SEQ ID: 1126 to SEQ ID: 1135); ORF-8 protein (SEQ ID: 1136 to SEQ ID: 1174), wherein said chemically modified recombinant nonamers of said CoV-2 open reading frame proteins are used ad as recombinant nonameric VHH (SEQ ID NO: 1255, SEQ ID NO: 1260) recombinant vaccine products, whereby said chemically modified recombinant vaccines elicit cytotoxic T lymphocytes, preventing CoV-2 infection in vaccinated population.

8. The composition according to claim 7, wherein said chemically modified recombinant nonameric peptides (+1/−1) are in recombinant protein scaffolds of lipocalin (SEQ ID NO: 1258, SEQ ID NO:1263), GFP (SEQ ID NO: 1257, SEQ ID NO: 1262), fibronectin (SEQ ID NO: 1281, SEQ ID NO: 1282), ankyrin repeat (SEQ ID NO: 1256, SEQ ID NO: 1261), VH3 (SEQ ID NO: 1259, SEQ ID NO: 1264).

9. The composition according to claim 7, wherein chemically modified recombinant chemical helper T cell epitopes (SEQ ID NO: 1265 to SEQ ID NO: 1271) are in recombinant protein scaffolds of camelid VHH (SEQ ID NO: 1255, SEQ ID NO: 1260), lipocalin (SEQ ID NO: 1258, SEQ ID NO:1263), GFP (SEQ ID NO: 1257, SEQ ID NO: 1262), fibronectin (SEQ ID NO: 1281, SEQ ID NO: 1282), ankyrin repeat (SEQ ID NO: 1256, SEQ ID NO: 1261), VH3 (SEQ ID NO: 1259, SEQ ID NO: 1264), wherein said nonameric peptides (+1/−1) in said recombinant protein scaffolds with said recombinant chemical helper T cell epitopes are employed as chemically modified recombinant vaccines, whereby cytotoxic T lymphocytes to CoV-2 infection is enhanced in vaccinated population.

10. A composition comprising mRNA vaccines, wherein the chemically modified CoV-2 open reading frame genes (SEQ ID NO: 1228 to SEQ ID NO: 1251) and chemically modified nonamer (+1/−1) to spike protein (SEQ ID: 60 to SEQ ID: 235); NC protein (SEQ ID: 236 to SEQ ID: 280); ORF1a (SEQ ID: 314 to SEQ ID: 395), rdrp protein (SEQ ID: 396 to SEQ ID: 571); helicase protein (SEQ ID: 572 to SEQ ID: 699); Exonuclease 5>3 (SEQ ID: 700 to SEQ ID: 803); endoRNAse (SEQ ID: 804 to SEQ ID: 882); methyltransferase protein (SEQ ID: 883 to SEQ ID: 953); membrane protein (SEQ ID: 954 to SEQ ID: 1014); envelope protein (SEQ ID: 1015 to SEQ ID: 1044); ORF-3a protein (SEQ ID: 1045 to SEQ ID: 1112); ORF-6 protein (SEQ ID: 1113 to SEQ ID: 1125); ORF-7 protein (SEQ ID: 1126 to SEQ ID: 1135); ORF-8 protein (SEQ ID: 1136 to SEQ ID: 1174), are chemically modified to motifs of mRNA vaccines (SEQ ID NO: 1175 to SEQ ID NO: 1180), and wherein said mRNA vaccines are employed as CoV-2 vaccines, whereby immune protection and suppression for cytokine storms are ensured.

11. The composition according to claim 10, wherein said chemically modified CoV-2 open reading frame genes and said chemically modified nonamer (+1/−1) are in an mRNA motif (SEQ ID NO: 1178) as vaccines, wherein GM-CSF is included for immune stimulation, whereby immune responses are elicited in population vaccinated with said chemically modified mRNA vaccines.

12. The composition according to claim 10, wherein said CoV-2 chemically modified open reading frame genes and said chemically modified nonamer (+1/−1) are in an mRNA motif (SEQ ID NO: 1177) as vaccines, wherein GM-CSF is not included for immune stimulation, whereby immune suppression is elicited to prevent cytokine storm in population vaccinated with said chemically modified mRNA vaccines.

13. The composition according to claim 10, wherein said chemically modified nonameric peptides (+1/−1) are in chemically modified mRNA motif (SEQ ID NO: 1180) as vaccines, wherein chemically modified helper peptides (SEQ ID NO: 1265 to SEQ ID NO: 1271) are included for immune stimulation, whereby cell-mediated CTLs are elicited in population vaccinated with said chemically modified mRNA vaccines.

14. The composition according to claim 1, wherein said CoV-2 said chemically modified nonameric peptides (+1/−1) are in an mRNA motif (SEQ ID NO: 1179) as mRNA vaccines, wherein chemically modified helper peptides are not included for immune stimulation, whereby immune suppression is elicited to prevent cytokine storm in population vaccinated with said chemically modified mRNA vaccines.

* * * * *